United States Patent
Zhang et al.

(10) Patent No.: US 10,287,611 B2
(45) Date of Patent: May 14, 2019

(54) ENGINEERING THE PATHWAY FOR SUCCINATE PRODUCTION

(71) Applicant: UNIVERSITY OF FLORIDA RESEARCH FOUNDATION, INCORPORATED, Gainesville, FL (US)

(72) Inventors: Xueli Zhang, Tianjin (CN); Kaemwich Jantama, Chiang Mai (TH); Jonathan C. Moore, Encinitas, CA (US); Laura R. Jarboe, Ames, IA (US); Keelnatham T. Shanmugam, Gainesville, FL (US); Lonnie O'Neal Ingram, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 15 days.

(21) Appl. No.: 14/705,011

(22) Filed: May 6, 2015

(65) Prior Publication Data

US 2015/0284746 A1    Oct. 8, 2015

Related U.S. Application Data

(63) Continuation of application No. 13/256,460, filed as application No. PCT/US2010/029728 on Apr. 2, 2010, now abandoned, which is a continuation-in-part of application No. 12/529,826, filed as application No. PCT/US2008/057439 on Mar. 19, 2008, now Pat. No. 8,691,539.

(60) Provisional application No. 61/166,093, filed on Apr. 2, 2009, provisional application No. 60/895,806, filed on Mar. 20, 2007.

(51) Int. Cl.
  *C12P 7/46*  (2006.01)
  *C12N 9/88*  (2006.01)
  *C12N 9/00*  (2006.01)

(52) U.S. Cl.
  CPC .............. *C12P 7/46* (2013.01); *C12N 9/88* (2013.01); *C12N 9/93* (2013.01); *C12Y 401/01* (2013.01); *C12Y 604/01001* (2013.01)

(58) Field of Classification Search
  CPC .... C12N 9/88; C12N 9/93; C12P 7/46; C12Y 401/01; C12Y 604/01001
  See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,162,516 A | 11/1992 | Ingram et al. |
| 5,583,278 A | 12/1996 | Alt et al. |
| 5,723,322 A | 3/1998 | Guettler et al. |
| 5,869,301 A | 2/1999 | Nghiem et al. |
| 6,159,738 A | 12/2000 | Donnelly et al. |
| 6,358,714 B1 | 3/2002 | Fotheringham et al. |
| 6,607,885 B1 | 8/2003 | Larossa et al. |
| 6,911,329 B2 | 6/2005 | Dusch et al. |
| 7,098,009 B2 | 8/2006 | Shanmugam et al. |
| 7,145,058 B2 | 12/2006 | Sandal et al. |
| 7,223,567 B2 | 5/2007 | Ka-Yiu et al. |
| 7,629,162 B2 | 12/2009 | Zhou et al. |
| 7,977,075 B2 | 7/2011 | Causey et al. |
| 2004/0152159 A1 | 8/2004 | Causey et al. |

(Continued)

FOREIGN PATENT DOCUMENTS

| | | |
|---|---|---|
| EP | 2241630 | 10/2010 |
| JP | 2007-535926 | 12/2007 |

(Continued)

OTHER PUBLICATIONS

Zhang et al., PNAS 106(48):20180-20185, Dec. 1, 2009.*

(Continued)

*Primary Examiner* — Delia M Ramirez

(74) *Attorney, Agent, or Firm* — Saliwanchik, Lloyd & Eisenschenk

(57) ABSTRACT

This invention relates to biocatalysts for the efficient production of succinic acid and/or other products from renewable biological feedstocks. The biocatalysts have a very high efficiency for the growth-coupled production of succinic acid and/or other products from carbohydrate feed stocks as a result of both genetic manipulation and metabolic evolution. More specifically, certain biocatalysts of the present invention produce succinic acid at high titers and yields in mineral salts media during simple pH-controlled batch fermentation without the addition of any exogenous genetic material. The genetic manipulations of the present invention are concerned with energy-conserving strategies coupled with the elimination of alternative routes for NADH oxidation other than the routes for succinic acid production. The biocatalysts contain glucose-repressed gluconeogenic phosphoenolpyruvate carboxykinase (pck) derepressed by genetic modifications and a genetically-inactivated phosphotransferase system. In terms of succinic acid production efficiency, the biocatalysts of the present invention are functionally equivalent to succinate producing rumen bacteria such as *Actinobacillus succinogens* and *Mannheimia succiniproducens*, with one difference: that the biocatalysts are able to achieve this high level of succinic acid production in a minimal salt medium with carbohydrate source, as opposed to the requirement for a rich medium for succinic acid production by rumen bacteria.

9 Claims, 27 Drawing Sheets

Specification includes a Sequence Listing.

(56) References Cited

U.S. PATENT DOCUMENTS

| | | |
|---|---|---|
| 2005/0170482 A1 | 8/2005 | Ka-Yiu et al. |
| 2006/0035348 A1 | 2/2006 | Gulevich et al. |
| 2007/0037265 A1 | 2/2007 | Zhou et al. |
| 2007/0072279 A1 | 3/2007 | Meynial-Salles et al. |
| 2007/0072280 A1 | 3/2007 | Cirino et al. |
| 2007/0154999 A1 | 7/2007 | Fukui et al. |
| 2009/0148914 A1 | 6/2009 | Causey et al. |
| 2010/0159544 A1 | 6/2010 | Lee et al. |
| 2010/0184171 A1 | 7/2010 | Jantama et al. |
| 2010/0203602 A1 | 8/2010 | Zhou et al. |
| 2012/0129231 A1 | 5/2012 | Wang et al. |

FOREIGN PATENT DOCUMENTS

| | | |
|---|---|---|
| WO | WO 2004/043881 | 5/2004 |
| WO | WO 2005/073364 | 8/2005 |
| WO | WO 2005/113745 | 12/2005 |
| WO | WO 2005/116227 | 12/2005 |
| WO | WO 2008/115958 | 9/2008 |
| WO | WO 2008/119009 | 10/2008 |
| WO | WO 2012/071392 | 5/2012 |

OTHER PUBLICATIONS

Iverson, T. M. et al. "Crystallographic Studies of the *Escherichia coli* Quinol-Fumarate Reductase with Inhibitors Bound to the Quinol-binding Site" *The Journal of Biological Chemistry*, May 3, 2002, pp. 16124-16130, vol. 277, No. 18.

Jantama, K. et al. "Combining Metabolic Engineering and Metabolic Evolution to Develop Nonrecombinant Strains of *Escherichia coli* C That Produce Succinate and Malate" *Biotechnology and Bioengineering*, Apr. 1, 2008, pp. 1140-1153, vol. 99, No. 5.

Jarboe, L. R. et al. "Determination of the *Escherichia coli* S-Nitrosoglutathione Response Network Using Integrated Biochemical and Systems Analysis" *The Journal of Biological Chemistry*, Feb. 22, 2008, pp. 5148-5157, vol. 283, No. 8.

Andersson, C. et al. "Effect of Different Carbon Sources on the Production of Succinic Acid Using Metabolically Engineered *Escherichia coli*" *Biotechnol Prog.*, 2007, pp. 381-388, vol. 23, No. 2.

Ajl, S. J. et al. "Enzymatic Fixation of Carbon Dioxide in α-KETO-Glutaric Acid" *Proceedings of the National Academy of Sciences*, Nov. 15, 1948, pp. 491-498, vol. 34, No. 11.

Asghari, A. et al. "Ethanol production from hemicellulose hydrolysates of agricultural residues using genetically engineered *Escherichia coli* strain KO11" *Journal of Industrial Microbiology*, 1996, pp. 42-47, vol. 16.

Kao, K. C. et al. "A Global Regulatory Role of Gluconeogenic Genes in *Escherichia coli* Revealed by Transcriptome Network Analysis" *The Journal of Biological Chemistry*, Oct. 28, 2005, pp. 36079-36087, vol. 280, No. 43.

Delbaere, L.T.J. et al. "Structure/function studies of phosphoryl transfer by phosphoenolpyruvate carboxykinase" *Biochimica et Biophysica ACTA 1697*, 2004, pp. 271-278.

De Graef, M. R. et al. "The Steady-State Internal Redox State (NADH/NAD) Reflects the External Redox State and Is Correlated with Catabolic Adaptation in *Escherichia coli*" *Journal of Bacteriology*, Apr. 1999, pp. 2351-2357, vol. 181, No. 8.

Chao, Y. et al. "Alteration of Growth Yield by Overexpression of Phosphoenolpyruvate Carboxylase and Phosphoenolpyruvate Carboxykinase in *Escherichia coli*" *Applied and Environmental Microbiology*, Dec. 1993, pp. 4261-4265, vol. 59, No. 12.

Cox, S. J. et al. "Development of a metabolic network design and optimization framework incorporating implementation constraints: A succinate production case study" *Metabolic Engineering*, 2006, pp. 46-57, vol. 8.

Datsenko, K. A. et al. "One-step inactivation of chromosomal genes in *Escherichia coli* K-12 using PCR products" *PNAS*, Jun. 6, 2000, pp. 6640-6645, vol. 97, No. 12.

Chatterjee, R. et al. "Mutation of the ptsG Gene Results in Increased Production of Succinate in Fermentation of Glucose by *Escherichia coli*" *Applied and Environmental Microbiology*, Jan. 2001, pp. 148-154, vol. 67, No. 1.

Canovas, J. L. et al. "Phosphoenolpyruvate Carboxylase from *Escherichia coli*" *Methods in Enzymology*, 1969, pp. 288-292, vol. 13.

Chang, Y. et al. "Conversion of *Escherichia coli* pyruvate oxidase to an 'α-ketobutyrate oxidase'" *Biochem. J.*, 2000, pp. 717-724, vol. 352.

Causey, T. B. et al. "Engineering *Escherichia coli* for efficient conversion of glucose to pyruvate" *PNAS*, Feb. 24, 2004, pp. 2235-2240, vol. 101, No. 8.

Hopper, D. J. et al. "The Regulation of *Escherichia coli* Methylglyoxal Synthase; A New Control Site in Glycolysis?" *FEBS Letters*, Mar. 1971, pp. 213-216, vol. 13, No. 4.

Goldie, A. H. et al. "Allosteric Control by Calcium and Mechanism of Desensitization of Phosphoenolpyruvate Carboxykinase of *Escherichia coli*" *The Journal of Biological Chemistry*, Feb. 25, 1980, pp. 1399-1405, vol. 255, No. 4.

Grabar, T. B. et al. "Methylglyoxal bypass identified as source of chiral contamination in L(+) and D(−)-lactate fermentations by recombinant *Escherichia coli*" *Biotechnol Lett*, 2006, pp. 1527-1535, vol. 28.

Gokarn, R. R. et al. "Metabolic Analysis of *Escherichia coli* in the Presence and Absence of the Carboxylating Enzymes Phosphoenolpyruvate Carboxylase and Pyruvate Carboxylase" *Applied and Environmental Microbiology*, May 2000, pp. 1844-1850, vol. 66, No. 5.

Farmer, W. R. et al. "Reduction of Aerobic Acetate Production by *Escherichia coli*" *Applied and Environmental Microbiology*, Aug. 1997, pp. 3205-3210, vol. 63, No. 8.

Goldie, A. H. et al. "Genetic and Physiological Characterization of *Escherichia coli* Mutants Deficient in Phosphoenolpyruvate Carboxykinase Activity" *Journal of Bacteriology*, Mar. 1980, pp. 1115-1121, vol. 141, No. 3.

Heßlinger, C. et al. "Novel keto acid formate-lyase and propionate kinase enzymes are components of an anaerobic pathway in *Escherichia coli* that degrades L-threonine to propionate" *Molecular Microbiology*, 1998, pp. 477-492, vol. 27, No. 2.

Fraenkel, D. G. (1996) Section A, Class I Reactions: Generation of Precursor Metabolites and Energy, Glycolysis, Chapter 14, Böck, R. Curtiss III, J. B. Kaper, F. C. Neidhardt, T. Nyström, K. E. Rudd, and C. L. Squires (ed.), EcoSal—*Escherichia coli* and *Salmonella*: Cellular and Molecular Biology. [Online.] http://www.ecosal.org. ASM Press, Washington, D.C.

Egyud, L. G. et al. "On the Regulation of Cell Division" *Biochemistry*, 1966, pp. 203-207, vol. 56.

Du, C. et al. "Succinic acid production from wheat using a biorefining strategy" *Appl Microbiol Biotechnol*, 2007, pp. 1263-1270, vol. 76.

Laivenieks, M. et al. "Cloning, Sequencing, and Overexpression of the *Anaerobiospirillum succiniciproducens* Phosphoenolpyruvate Carboxykinase (pckA) Gene" *Applied and Environmental Microbiology*, Jun. 1997, pp. 2273-2280, vol. 63, No. 6.

Kim, P. et al. "Effect of Overexpression of *Actinobacillus succinogenes* Phosphoenolpyruvate Carboxykinase on Succinate Production in *Escherichia coli*" *Applied and Environmental Microbiology*, Feb. 2004, pp. 1238-1241, vol. 70, No. 2.

Kulla, H. et al. "Energy-Dependent Inactivation of Citrate Lyase in *Enterobacter aerogenes*" *Journal of Bacteriology*, Dec. 1977, pp. 764-770, vol. 132, No. 3.

Kessler, D. et al. "Anaerobic dissimilation of pyruvate" Neidhardt FC, Curtiss III R, Ingraham JL, Lin ECC, Low KB, Magasanik B, Reznikoff WS, Riley M, Schaechter M, Umbarger HE, editors. *Escherichia coli* and *Salmonella*: Cellular and Molecular Biology. ASM Press, Washington, D.C., 1996, pp. 199-205.

Lee, S. Y. et al. "Fermentative Production of Chemicals That Can Be Used for Polymer Synthesis" *Macromolecular Bioscience*, 2004, pp. 157-164, vol. 4.

Lee, S. J. et al. "Metabolic Engineering of *Escherichia coli* for Enhanced Production of Succinic Acid, Based on Genome Com-

(56) References Cited

OTHER PUBLICATIONS parison and In Silico Gene Knockout Simulation" *Applied and Environmental Microbiology*, Dec. 2005, pp. 7880-7887, vol. 71, No. 12.

Lee, S. J. et al. "Genome-Based Metabolic Engineering of *Mannheimia succiniciproducens* for Succinic Acid Production" *Applied and Environmental Microbiology*, Mar. 2006, pp. 1939-1948, vol. 72, No. 3.

Lin, H. et al. "Metabolic engineering of aerobic succinate production systems in *Escherichia coli* to improve process productivity and achieve the maximum theoretical succinate yield" *Metabolic Engineering*, 2005, pp. 116-127, vol. 7.

Lee, E. et al. "A Highly Efficient *Escherichia coli*-Based Chromosome Engineering System Adapted for Recombinogenic Targeting and Subcloning of BAC DNA" *Genomics*, 2001, pp. 56-65, vol. 73.

Lin, H. et al. "Chemostat culture characterization of *Escherichia coli* mutant strains metabolically engineered for aerobic succinate production: A study of the modified metabolic network based on metabolite profile, enzyme activity, and gene expression profile" *Metabolic Engineering*, 2005, pp. 337-352, vol. 7.

Nilekani, S. et al. "Purification and Properties of Citrate Lyase from *Escherichia coli*" *Biochemistry*, 1983, pp. 4657-4663, vol. 22.

Martinez, A. et al. "Low salt medium for lactate and ethanol production by recombinant *Escherichia coli* B" *Biotechnol Lett*, 2007, pp. 397-404, vol. 29.

Meynial-Salles, I. et al. "A New Process for the Continuous Production of Succinic Acid from Glucose at High Yield, Titer, and Productivity" *Biotechnology and Bioengineering*, Jan. 1, 2008, pp. 129-135, vol. 99, No. 1.

McKinlay, J. B. et al. "Prospects for a bio-based succinate industry" *Applied Microbiol Biotechnol*, 2007, pp. 1-14.

Oh, M.-K. et al. "Global Expression Profiling of Acetate-grown *Escherichia coli*" *The Journal of Biological Chemistry*, Apr. 12, 2002, pp. 13175-13183, vol. 277, No. 15.

Millard, C. S. et al. "Enhanced Production of Succinic Acid by Overexpression of Phosphoenolpyruvate Carboxylase in *Escherichia coli*" *Applied and Environmental Microbiology*, May 1996, pp. 1808-1810, vol. 62, No. 5.

Lin, H. et al. "Effect of carbon sources differing in oxidation state and transport route on succinate production in metabolically engineered *Escherichia coli*," *J. Ind. Microbiol Biotechnol*, 2005, pp. 87-93, vol. 32.

McKinlay, J. B. et al. "$^{13}$C-metabolic flux analysis of *Actinobacillus succinogenes* fermentative metabolism at different $NaHCO_3$ and $H_2$ concentrations" *Metabolic Engineering*, 2008, pp. 55-68, vol. 10.

Martinez-Morales, F. et al. "Chromosomal Integration of Heterologous DNA in *Escherichia coli* with Precise Removal of Markers and Replicons Used during Construction" *Journal of Bacteriology*, Nov. 1999, pp. 7143-7148, vol. 181, No. 22.

Moniruzzaman, M. et al. "Extracellular Melibiose and Fructose Are Intermediates in Raffinose Catabolism during Fermentation to Ethanol by Engineered Enteric Bacteria" *Journal of Bacteriology*, Mar. 1997, pp. 1880-1886, vol. 179, No. 6.

McKinlay, J. B. et al. "Insights into *Actinobacillus succinogenes* Fermentative Metabolism in a Chemically Defined Growth Medium" *Applied and Environmental Microbiology*, Nov. 2005, pp. 6651-6656, vol. 71, No. 11.

Posfai, G. et al. "Versatile Insertion Plasmids for Targeted Genome Manipulations in Bacteria: Isolation, Deletion, and Rescue of the Pathogenicity Island LEE of the *Escherichia coli* O157:H7 Genome" *Journal of Bacteriology*, Jul. 1997, pp. 4426-4428, vol. 179, No. 13.

Quentmeier, A. et al. "Reevaluation of citrate lyase from *Escherichia coli*" *Biochimica et Biophysica Acta*, 1987, pp. 60-65, vol. 913.

Reed, J. L. et al. "An expanded genome-scale model of *Escherichia coli* K-12 (iJR904 GSM/GPR)" *Genome Biology*, 2003, pp. R54-R54.12, vol. 4, Issue 9, Article R54.

Keseler, I. M. et al. "EcoCyc: a comprehensive database resource for *Escherichia coli*" *Nucleic Acids Research*, 2005, pp. D334-D337, vol. 33.

Okino, S. et al. "Production of organic acids by *Corynebacterium glutamicum* under oxygen deprivation" *Appl Microbiol Biotechnol*, 2005, pp. 475-480, vol. 68.

Stols, L. et al. "Production of Succinic Acid through Overexpression of $NAD^{+-Dependent\ Malic\ Enzyme\ in\ an}$ *Escherichia coli* Mutant" *Applied and Environmental Microbiology*, Jul. 1997, pp. 2695-2701, vol. 63, No. 7.

Zeikus, J. G. et al. "Biotechnology of succinic acid production and markets for derived industrial products" *Appl Microbiol Biotechnol*, 1999, pp. 545-552, vol. 51.

Zhou, S. et al. "Betaine tripled the volumetric productivity of D(−)-lactate by *Escherichia coli* strain SZ132 in mineral salts medium" *Biotechnology Letters*, 2006, pp. 671-676, vol. 28.

Underwood, S. A. et al. "Genetic Changes to Optimize Carbon Partitioning between Ethanol and Biosynthesis in Ethanologenic *Escherichia coli*" *Applied and Environmental Microbiology*, Dec. 2002, pp. 6263-6272, vol. 68, No. 12.

Zhang, X. et al. "Production of L-aianine by metabolically engineered *Escherichia coli*" *Appl Microbiol Biotechnol*, 2007, pp. 355-366, vol. 77.

Reitzer, L. Chapter 3.6.1.3, Biosynthesis of Glutamate, Aspartate, Asparagine, L-Alanine, and D-Alanine, A. Böck, R. Curtiss III, J. B. Kaper, F. C. Neidhardt, T. Nyström, K. E. Rudd, and C. L. Squires (ed.), EcoSal—*Escherichia coli* and *Salmonella*: Cellular and Molecular Biology. [Online.] http://www.ecosal.org. ASM Press, Washington, D.C., Jul. 6, 2004, posting date.

Unden, G. et al. "$C_4$-Dicarboxylate Degradation in Aerobic and Anaerobic Growth" *EcoSal Module 3.4.5*, 2006, pp. 1-15, ASM Press.

Sawers, G. et al. "Anaerobic Regulation of Pyruvate Formate-Lyase from *Escherichia coli* K-12" *Journal of Bacteriology*, Nov. 1988, pp. 5330-5336, vol. 170, No. 11.

Sanwal, B. D. "Regulatory Mechanisms Involving Nicotinamide Adenine Nucleotides as Allosteric Effectors" *The Journal of Biological Chemistry*, Apr. 10, 1969, pp. 1831-1837, vol. 244, No. 7.

Storici, F. et al. "A μm DNA-Based Marker Recycling System for Multiple Gene Disruption in the Yeast *Saccharomyces cerevisiae*" *Yeast*, 1999, pp. 271-283, vol. 15.

Sanwal, B. D. "Regulatory Characteristics of the Diphosphopyridine Nucleotide-specific Malic Enzyme of *Escherichia coli*" *The Journal of Biological Chemistry*, Mar. 10, 1970, pp. 1212-1216, vol. 245, No. 5.

Sanwal, B. D. "Allosteric Controls of Amphibolic Pathways in Bacteria" *Bacteriological Reviews*, Mar. 1970, pp. 20-39, vol. 34, No. 1.

Sanwal, B. D. et al. "Malic Enzyme of *Escherichia coli*: Diversity of the Effectors Controlling Enzyme Activity" *The Journal of Biological Chemistry*, Apr. 10, 1969, pp. 1817-1823, vol. 244, No. 7.

Sanchez, A. M. et al. "Batch culture characterization and metabolic flux analysis of succinate-producing *Escherichia coli* strains" *Metabolic Engineering*, 2006, pp. 209-226, vol. 8.

Sanchez, A. M. et al. "Novel pathway engineering design of the anaerobic central metabolic pathway in *Escherichia coli* to increase succinate yield and productivity" *Metabolic Engineering*, 2005, pp. 229-239, vol. 7.

Sanchez, A. M. et al. "Efficient Succinic Acid Production from Glucose through Overexpression of Pyruvate Carboxylase in an *Escherichia coli* Alcohol Dehydrogenase and Lactate Dehydrogenase Mutant" *Biotechnol. Prog.*, 2005, pp. 358-365, vol. 21.

Samuelov, N. S. et al. "Influence of $CO_2$-$HCO_3^-$ Levels and pH on Growth, Succinate Production, and Enzyme Activities of *Anaerobiospirillum succiniciproducens*" *Applied and Environmental Microbiology*, Oct. 1991, pp. 3013-3019, vol. 57, No. 10.

Yun, N.-R. et al. "Enhancement of lactate and succinate formation in adhE or pta-ackA mutants of NADH dehydrogenase-deficient *Escherichia coli*" *Journal of Applied Microbiology*, 2005, pp. 1404-1412, vol. 99.

Wright, J. A. et al. "Regulatory Mechanisms Involving Nicotinamide Adenine Nucleotides as Allosteric Effectors" *The Journal of Biological Chemistry*, Apr. 10, 1969, pp. 1838-1845, vol. 244, No. 7.

Wood, B. E. et al. "Development of Industrial-Medium-Required Elimination of the 2,3-Butanediol Fermentation Pathway to Main-

(56) References Cited

OTHER PUBLICATIONS tain Ethanol Yield in an Ethanologenic Strain of *Klebsiella oxytoca*" *Biotechnol. Prog.*, 2005, pp. 1366-1372, vol. 21.

Vemuri, G. N. et al. "Effects of Growth Mode and Pyruvate Carboxylase on Succinic Acid Production by Metabolically Engineered Strains of *Escherichia coli*" *Applied and Environmental Microbiology*, Apr. 2002, pp. 1715-1727, vol. 68, No. 4.

Vemuri, G. N. et al. "Succinate production in dual-phase *Escherichia coli* fermentations depends on the time of transition from aerobic to anaerobic conditions" *Journal of Industrial Microbiology & Biotechnology*, 2002, pp. 325-332, vol. 28.

Wendisch, V. F. "Metabolic engineering of *Escherichia coli* and *Corynebacterium glutamicum* for biotechnological production of organic acids and amino acids" *Current Opinion in Microbiology*, 2006, pp. 268-274, vol. 9.

Van Der Werf, M. J. "Environmental and physiological factors affecting the succinate product ratio during carbohydrate fermentation by *Actinobacillus* sp. 130Z" *Arch Microbiol*, 1997, pp. 332-342, vol. 167.

Song, H. et al. "Effects of Dissolved $CO_2$ Levels on the Growth of *Mannheimia succiniciproducens* and Succinic Acid Production" *Biotechnology and Bioengineering*, Dec. 15, 2007, pp. 1296-1304, vol. 98, No. 6.

Underwood, S. A. et al. "Lack of Protective Osmolytes Limits Final Cell Density and Volumetric Productivity of Ethanologenic *Escherichia coli* KO11 during Xylose Fermentation" *Applied and Environmental Microbiology*, May 2004, pp. 2734-2740, vol. 70, No. 5.

Thomason, L. et al. "Recombineering: Genetic Engineering in Bacteria Using Homologous Recombination" *Current Protocols in Molecular Biology*, 2007, pp. 1.16.1-1.16.24, Supplement 78.

Krebs, A. et al. "The kinetic properties of phosphoenolpyruvate carboxykinase of *Escherichia coli*" *Can. J. Biochem.*, 1979, pp. 309-318, vol. 58.

Izui, K. et al. "Regulation of *Escherichia coli* Phosphoenolpyruvate Carboxylase by Multiple Effectors In Vivo. II. Kinetic Studies with a Reaction System Containing Physiological Concentration of Ligands" *J. Biochem.*, 1981, pp. 1321-1331, vol. 90.

Gottschalk, G., Bacterial Metabolism, 1985, 2nd ed. Springer-Verlag, New York.

Causey, T. B. et al. "Engineering the metabolism of *Escherichia coli* W3110 for the conversion of sugar to redox-neutral and oxidized products: Homoacetate production" *PNAS*, Feb. 4, 2003, pp. 825-832, vol. 100, No. 3.

Zhou, S. et al. "Production of Optically Pure D-Lactic Acid in Mineral Salts Medium by Metabolically Engineered *Escherichia coli* W3110" *Applied and Environmental Microbiology*, Jan. 2003, pp. 399-407, vol. 69, No. 1.

Karp, P. D. et al. "Multidimensional annotation of the *Escherichia coli* K-12 genome" *Nucleic Acids Research*, 2007, pp. 7577-7590, vol. 35, No. 22.

Sanwal, B. D. et al. "Malic Enzyme of *Escherichia coli*: Possible Mechanism for Allosteric Effects" *The Journal of Biological Chemistry*, Apr. 10, 1969, pp. 1824-1830, vol. 244, No. 7.

Written Opinion in International Application No. PCT/US2008/057439, dated Dec. 18, 2008, pp. 1-5.

Meyer, M. et al. "In Vitro Binding of the Response Regulator CitB and of its Carboxy-terminal Domain to A + T-rich DNA Target Sequences in the Control Region of the Divergent citC and citS Operons of *Klebsiella pneumoniae*" *J. Mol. Biol.*, Jul. 27, 1997, pp. 719-731, vol. 269, No. 5 XP-004453842.

Kim, Y. et al. "Construction of an *Escherichia coli* K-12 Mutant for Homoethanologenic Fermentation of Glucose or Xylose without Foreign Genes" *Applied and Environmental Microbiology*, Mar. 1, 2007, pp. 1766-1771, vol. 73, No. 6, XP-008102027.

Jantama, K. et al. "Eliminating Side Products and Increasing Succinate Yields in Engineered Strains of *Escherichia coli* C" *Biotechnology and Bioengineering*, Jun. 4, 2008, pp. 881-893, vol. 101, No. 5, XP-002551943.

Office Action dated Jun. 5, 2012 in U.S. Appl. No. 12/529,826.

Zhou, S. et al. "Functional Replacement of the *Escherichia coli* D-(−)-Lactate Dehydrogenase Gene (ldhA) with the L-(+)-Lactate Dehydrogenase Gene (ldhL) from *Pediococcus acidilactici*" *Applied and Environmental Microbiology*, Apr. 2003, pp. 2237-2244, vol. 69, No. 4.

Kwon, Y. et al. "A Physiology Study of *Escherichia coli* Overexpressing Phosphoenolpyruvate Carboxykinase" *Biosci. Biotechnol. Biochem.*, 2008, pp. 1138-1141, vol. 72, No. 4.

Lin, H. et al. "Fed-Batch Culture of a Metabolically Engineered *Escherichia coli* Strain Designed for High-Level Succinate Production and Yield Under Aerobic Conditions" *Biotechnology and Bioengineering*, Jun. 20, 2005, pp. 775-779, vol. 90, No. 6.

Wang, Q. et al. "Genome-scale in silico aided metabolic analysis and flux comparisons of *Escherichia coli* to improve succinate production" *Appl. Microbiol. Biotechnol.*, 2006, pp. 887-894, vol. 73.

Wang, Q. et al. "Expression of glactose permease and pyruvate carboxylase in *Escherichia coli* ptsG mutant increases the growth rate and succinate yield under anaerobic conditions" *Biotechnology Letters*, 2006, pp. 89-93, vol. 28.

Wu, H. et al. "Improved Succinic Acid Production in the Anaerobic Culture of an *Escherichia coli* pflB ldhA Double Mutant as a Result of Enhanced Anaplerotic Activities in the Preceding Aerobic Culture" *Appl. Environ. Microbiol.*, 2007, pp. 7837-7843, vol. 73, No. 24.

Written Opinion in International Application No. PCT/US2010/029728, dated Jan. 18, 2011, pp. 1-6.

Hasona, et al. "Pyruvate Formate Lyase and Acetate Kinase Are Essential for Anaerobic Growth of *Escherichia coli* on Xylose" *Journal of Bacteriology*, Nov. 2004, pp. 7593-7600, vol. 186, No. 22.

Kwon, Y. et al. "Influence of Gluconeogenic Phosphoenolpyruvate Carboxykinase (PCK) Expression on Succinic Acid Fermentation in *Escherichia coli* Under High Bicarbonate Condition" *J Microbial. Biotechnol.*, 2006, pp. 1148-1452, vol. 16. No. 9.

Onuffer, J. et al. "Redesign of the substrate specificity of *Escherichia coli* aspartate aminotransferase to that of *Escherichia coli* tyrosine aminotransferase by homology modeling and site-directed mutagenesis" *Protein Science*, 1995, pp. 1750-1757, vol. 4.

Gosset, G. "Improvement of *Escherichia coli* production strains by modification of the phosphoenolpyruvate:sugar phosphotransferase system" *Microbial Cell Factories*, 2005, pp. 1-11, vol. 4, No. 14.

Zhou, D. et al. "Global analysis of gene transcription regulation in prokaryotes" *Cellular and Molecular Life Sciences*, 2006, 2260-2290, vol. 63.

Kozak, M. "Initiation of translation in prokaryotes and eukaryotes" *Gene*, 1999, pp. 187-208, vol. 234.

Sousa, S. et al. "The AR04 gene of *Candida albicans* encodes a tyrosine-sensitive DAHP synthase: evolution, functional conservation and phenotype of Aro3p-, Aro4p-deficient mutants" *Microbiology*, 2002, pp. 1291-1303, vol. 148.

* cited by examiner

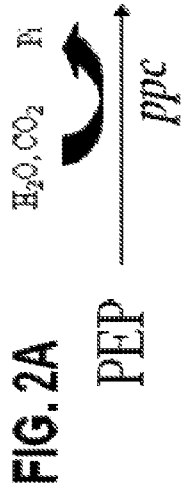
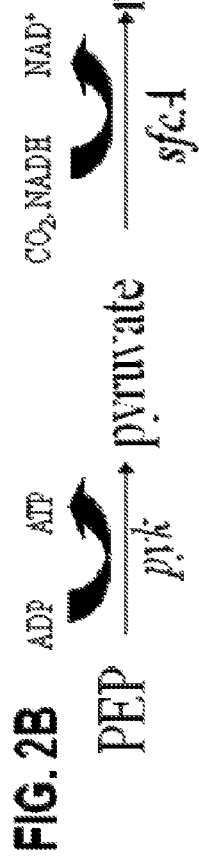
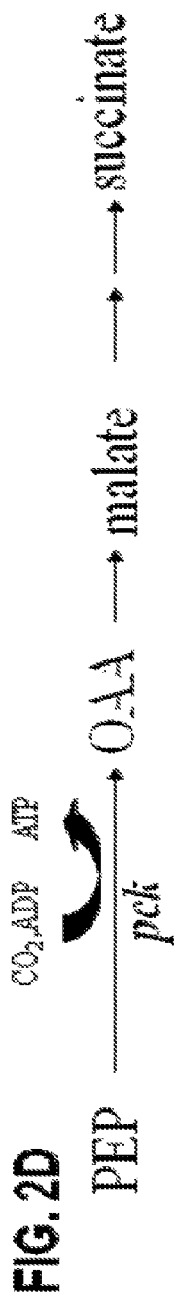
FIG. 2A
FIG. 2B
FIG. 2C
FIG. 2D

Construction of pLOI4162

SEQUENCE LISTING

<160> NUMBER OF SEQ ID NOS: 194

<210> SEQ ID NO 1
<211> LENGTH: 18
<212> TYPE: DNA
<213> ORGANISM: Artificial sequence
<220> FEATURE:
<223> OTHER INFORMATION: translational stop sequence

<400> SEQUENCE: 1
gcctaattaa ttaatccc                                                 18

<210> SEQ ID NO 2
<211> LENGTH: 65
<212> TYPE: DNA
<213> ORGANISM: Artificial sequence
<220> FEATURE:
<223> OTHER INFORMATION: Primer set for ldhA

<400> SEQUENCE: 2
atgaactcgc cgtttttatag cacaaaacag tacgacaaga agtacgtgta ggctggagct    60
gcttc                                                               65

<210> SEQ ID NO 3
<211> LENGTH: 65
<212> TYPE: DNA
<213> ORGANISM: Artificial sequence
<220> FEATURE:
<223> OTHER INFORMATION: Primer set for ldhA

<400> SEQUENCE: 3
ttaaaccagt tcgttcgggc aggtttcgcc tttttccaga ttgctcatat gaatatcctc    60
cttag                                                               65

<210> SEQ ID NO 4
<211> LENGTH: 65
<212> TYPE: DNA
<213> ORGANISM: Artificial sequence
<220> FEATURE:
<223> OTHER INFORMATION: Primer set for adhE

<400> SEQUENCE: 4
atggctgtta ctaatgtcgc tgaacttaac gcactcgtag agcgtgtgta ggctggagct    60
gcttc                                                               65

<210> SEQ ID NO 5
<211> LENGTH: 65
<212> TYPE: DNA
<213> ORGANISM: Artificial sequence
<220> FEATURE:
<223> OTHER INFORMATION: Primer set for adhE

<400> SEQUENCE: 5
ttaagcggat tttttcgctt ttttctcagc tttagccgga gcagccatat gaatatcctc    60
cttag                                                               65

<210> SEQ ID NO 6
<211> LENGTH: 65
<212> TYPE: DNA
<213> ORGANISM: Artificial sequence
<220> FEATURE:
<223> OTHER INFORMATION: Primer set for ackA

<400> SEQUENCE: 6

```
atgtcgagta agttagtact ggttctgaac tgcggtagtt cttcagtgta ggctggagct    60
gcttc                                                                65

<210> SEQ ID NO 7
<211> LENGTH: 65
<212> TYPE: DNA
<213> ORGANISM: Artificial sequence
<220> FEATURE:
<223> OTHER INFORMATION: Primer set for ackA

<400> SEQUENCE: 7
tcaggcagtc aggcggctcg cgtcttgcgc gataaccagt tcttccatat gaatatcctc    60
cttag                                                                65

<210> SEQ ID NO 8
<211> LENGTH: 65
<212> TYPE: DNA
<213> ORGANISM: Artificial sequence
<220> FEATURE:
<223> OTHER INFORMATION: Primer set for focA-plfB

<400> SEQUENCE: 8
ttactccgta tttgcataaa aaccatgcga gttacgggcc tataagtgta ggctggagct    60
gcttc                                                                65

<210> SEQ ID NO 9
<211> LENGTH: 65
<212> TYPE: DNA
<213> ORGANISM: Artificial sequence
<220> FEATURE:
<223> OTHER INFORMATION: Primer set for focA-plfB

<400> SEQUENCE: 9
atagattgag tgaaggtacg agtaataacg tcctgctgct gttctcatat gaatatcctc    60
cttag                                                                65

<210> SEQ ID NO 10
<211> LENGTH: 30
<212> TYPE: DNA
<213> ORGANISM: Artificial sequence
<220> FEATURE:
<223> OTHER INFORMATION: Primer set for JMcatsacB

<400> SEQUENCE: 10
ttagctagca tgtgacggaa gatcacttcg                                     30

<210> SEQ ID NO 11
<211> LENGTH: 31
<212> TYPE: DNA
<213> ORGANISM: Artificial sequence
<220> FEATURE:
<223> OTHER INFORMATION: Primer JMcatsacB

<400> SEQUENCE: 11
ccgctagcat caaagggaaa actgtccata t                                   31

<210> SEQ ID NO 12
<211> LENGTH: 32
<212> TYPE: DNA
<213> ORGANISM: Artificial sequence
<220> FEATURE:
<223> OTHER INFORMATION: Primer set for cat-up2/sacB-down2
```

```
<400> SEQUENCE: 12
agagaggata tctgtgacgg aagatcactt cg                              32

<210> SEQ ID NO 13
<211> LENGTH: 32
<212> TYPE: DNA
<213> ORGANISM: Artificial sequence
<220> FEATURE:
<223> OTHER INFORMATION: Primer set for cat-up2/sacB-down2

<400> SEQUENCE: 13
agagaggata tcgaattgat ccggtggatg ac                              32

<210> SEQ ID NO 14
<211> LENGTH: 20
<212> TYPE: DNA
<213> ORGANISM: Artificial sequence
<220> FEATURE:
<223> OTHER INFORMATION: Primer set for mgsA-up/down

<400> SEQUENCE: 14
cagctcatca accaggtcaa                                            20

<210> SEQ ID NO 15
<211> LENGTH: 20
<212> TYPE: DNA
<213> ORGANISM: Artificial sequence
<220> FEATURE:
<223> OTHER INFORMATION: Primer set for mgsA-up/down

<400> SEQUENCE: 15
aaaagccgtc acgttattgg                                            20

<210> SEQ ID NO 16
<211> LENGTH: 20
<212> TYPE: DNA
<213> ORGANISM: Artificial sequence
<220> FEATURE:
<223> OTHER INFORMATION: Primer set for mgsA-1/2

<400> SEQUENCE: 16
agcgttatct cgcggaccgt                                            20

<210> SEQ ID NO 17
<211> LENGTH: 20
<212> TYPE: DNA
<213> ORGANISM: Artificial sequence
<220> FEATURE:
<223> OTHER INFORMATION: Primer set for mgsA-1/2

<400> SEQUENCE: 17
aagtgcgagt cgtcagttcc                                            20

<210> SEQ ID NO 18
<211> LENGTH: 20
<212> TYPE: DNA
<213> ORGANISM: Artificial sequence
<220> FEATURE:
<223> OTHER INFORMATION: Primer set for poxB-up/down

<400> SEQUENCE: 18
aagcaataac gttccggttg                                            20

<210> SEQ ID NO 19
<211> LENGTH: 20
```

```
<212> TYPE: DNA
<213> ORGANISM: Artificial sequence
<220> FEATURE:
<223> OTHER INFORMATION: Primer set for poxB-up/down

<400> SEQUENCE: 19
ccactttatc cagcggtagc                                              20

<210> SEQ ID NO 20
<211> LENGTH: 19
<212> TYPE: DNA
<213> ORGANISM: Artificial sequence
<220> FEATURE:
<223> OTHER INFORMATION: Primer set for poxB-1/2

<400> SEQUENCE: 20
gacgcggtga tgaagtgat                                               19

<210> SEQ ID NO 21
<211> LENGTH: 20
<212> TYPE: DNA
<213> ORGANISM: Artificial sequence
<220> FEATURE:
<223> OTHER INFORMATION: Primer set for poxB-1/2

<400> SEQUENCE: 21
tttggcgata taagctgcaa                                              20

<210> SEQ ID NO 22
<211> LENGTH: 29
<212> TYPE: DNA
<213> ORGANISM: Artificial sequence
<220> FEATURE:
<223> OTHER INFORMATION: Primer set for pck-F/R

<400> SEQUENCE: 22
ttggctaagg agcagtgaaa tgcgcgtta                                    29

<210> SEQ ID NO 23
<211> LENGTH: 25
<212> TYPE: DNA
<213> ORGANISM: Artificial sequence
<220> FEATURE:
<223> OTHER INFORMATION: Primer set for pck-F/R

<400> SEQUENCE: 23
cacgacaaaa gaagggtaaa taaac                                        25

<210> SEQ ID NO 24
<211> LENGTH: 20
<212> TYPE: DNA
<213> ORGANISM: Artificial sequence
<220> FEATURE:
<223> OTHER INFORMATION: Primer set for pck-2/3

<400> SEQUENCE: 24
ttgttaacgc gcatttcact                                              20

<210> SEQ ID NO 25
<211> LENGTH: 20
<212> TYPE: DNA
<213> ORGANISM: Artificial sequence
<220> FEATURE:
<223> OTHER INFORMATION: Primer set for pck-2/3

<400> SEQUENCE: 25
```

```
gcgatagcgg ctactgtcat                                               20
```

```
<210> SEQ ID NO 26
<211> LENGTH: 18
<212> TYPE: DNA
<213> ORGANISM: Artificial sequence
<220> FEATURE:
<223> OTHER INFORMATION: Primer set for pck (RT-PCR)

<400> SEQUENCE: 26
gacgatacca ctcgcgat                                                 18
```

```
<210> SEQ ID NO 27
<211> LENGTH: 19
<212> TYPE: DNA
<213> ORGANISM: Artificial sequence
<220> FEATURE:
<223> OTHER INFORMATION: Primer set for pck (RT-PCR)

<400> SEQUENCE: 27
gtcgacaacg aacagacgt                                                19
```

```
<210> SEQ ID NO 28
<211> LENGTH: 17
<212> TYPE: DNA
<213> ORGANISM: Artificial sequence
<220> FEATURE:
<223> OTHER INFORMATION: Primer set for birA (RT-PCR)

<400> SEQUENCE: 28
atcgtgatgg cggaagt                                                  17
```

```
<210> SEQ ID NO 29
<211> LENGTH: 19
<212> TYPE: DNA
<213> ORGANISM: Artificial sequence
<220> FEATURE:
<223> OTHER INFORMATION: Primer set for birA (RT-PCR)

<400> SEQUENCE: 29
cttgcgatcc tgcagatag                                                19
```

```
<210> SEQ ID NO 30
<211> LENGTH: 32
<212> TYPE: DNA
<213> ORGANISM: Artificial sequence
<220> FEATURE:
<223> OTHER INFORMATION: Primer set for JM4161 sense/comp

<400> SEQUENCE: 30
accgcatcag gcgcctaatt aattaatccc gg                                 32
```

```
<210> SEQ ID NO 31
<211> LENGTH: 32
<212> TYPE: DNA
<213> ORGANISM: Artificial sequence
<220> FEATURE:
<223> OTHER INFORMATION: Primer set for JM4161 sense/comp

<400> SEQUENCE: 31
ccgggattaa ttaattaggc gcctgatgcg gt                                 32
```

```
<210> SEQ ID NO 32
<211> LENGTH: 30
<212> TYPE: DNA
<213> ORGANISM: Artificial sequence
```

```
<220> FEATURE:
<223> OTHER INFORMATION: Primer set for JMpEL04F1/R1

<400> SEQUENCE: 32
cagcagatct aagtaaatcg cgcgggtttg                                     30

<210> SEQ ID NO 33
<211> LENGTH: 30
<212> TYPE: DNA
<213> ORGANISM: Artificial sequence
<220> FEATURE:
<223> OTHER INFORMATION: Primer set for JMpEL04F1/R1

<400> SEQUENCE: 33
cagcagatct agcggctatt taacgaccct                                     30

<210> SEQ ID NO 34
<211> LENGTH: 20
<212> TYPE: DNA
<213> ORGANISM: Artificial sequence
<220> FEATURE:
<223> OTHER INFORMATION: Primer set for JMackA-F1/R1

<400> SEQUENCE: 34
gcctgaaggc ctaagtagta                                                20

<210> SEQ ID NO 35
<211> LENGTH: 20
<212> TYPE: DNA
<213> ORGANISM: Artificial sequence
<220> FEATURE:
<223> OTHER INFORMATION: Primer set for JMackA-F1/R1

<400> SEQUENCE: 35
gcacgatagt cgtagtctga                                                20

<210> SEQ ID NO 36
<211> LENGTH: 20
<212> TYPE: DNA
<213> ORGANISM: Artificial sequence
<220> FEATURE:
<223> OTHER INFORMATION: Primer set for JMackA up1/down1

<400> SEQUENCE: 36
gttgagcgct tcgctgtgag                                                20

<210> SEQ ID NO 37
<211> LENGTH: 20
<212> TYPE: DNA
<213> ORGANISM: Artificial sequence
<220> FEATURE:
<223> OTHER INFORMATION: Primer set for JMackA up1/down1

<400> SEQUENCE: 37
gccgcaatgg ttcgtgaact                                                20

<210> SEQ ID NO 38
<211> LENGTH: 31
<212> TYPE: DNA
<213> ORGANISM: Artificial sequence
<220> FEATURE:
<223> OTHER INFORMATION: Primer set for JMcatsacB up3/down3

<400> SEQUENCE: 38
ctcacctcga gtgtgacgga agatcacttc g                                   31
```

<210> SEQ ID NO 39
<211> LENGTH: 34
<212> TYPE: DNA
<213> ORGANISM: Artificial sequence
<220> FEATURE:
<223> OTHER INFORMATION: Primer set for JmcatsacB up3/down3

<400> SEQUENCE: 39
gtgcaggatc catcaaaggg aaaactgtcc atat                         34

<210> SEQ ID NO 40
<211> LENGTH: 59
<212> TYPE: DNA
<213> ORGANISM: Artificial sequence
<220> FEATURE:
<223> OTHER INFORMATION: Primer set for SfPBXPS sense/comp

<400> SEQUENCE: 40
atgtaggcgc cattaattaa tggatccact atctcgagat taattaatcc cgggactat    59

<210> SEQ ID NO 41
<211> LENGTH: 59
<212> TYPE: DNA
<213> ORGANISM: Artificial sequence
<220> FEATURE:
<223> OTHER INFORMATION: Primer set for SfPBXPS sense/comp

<400> SEQUENCE: 41
atagtcccgg gattaattaa tctcgagata gtggatccat taattaatgg cgcctacat    59

<210> SEQ ID NO 42
<211> LENGTH: 65
<212> TYPE: DNA
<213> ORGANISM: Artificial sequence
<220> FEATURE:
<223> OTHER INFORMATION: Primer set for WMadhE A/C

<400> SEQUENCE: 42
atggctgtta ctaatgtcgc tgaacttaac gcactcgtag agcgtcggca cgtaagaggt    60
tccaa                                                                65

<210> SEQ ID NO 43
<211> LENGTH: 65
<212> TYPE: DNA
<213> ORGANISM: Artificial sequence
<220> FEATURE:
<223> OTHER INFORMATION: Primer set for WMadhE A/C

<400> SEQUENCE: 43
ttaagcggat tttttcgctt ttttctcagc tttagccgga gcagcacact gcttccggta    60
gtcaa                                                                65

<210> SEQ ID NO 44
<211> LENGTH: 64
<212> TYPE: DNA
<213> ORGANISM: Artificial sequence
<220> FEATURE:
<223> OTHER INFORMATION: Primer set for WMldhA A/C

<400> SEQUENCE: 44
atgaaactcg ccgtttatag cacaaaacag tacgacaaga agtacggcac gtaagaggtt    60
ccaa                                                                 64

```
<210> SEQ ID NO 45
<211> LENGTH: 65
<212> TYPE: DNA
<213> ORGANISM: Artificial sequence
<220> FEATURE:
<223> OTHER INFORMATION: Primer set for WMldhA A/C

<400> SEQUENCE: 45
ttaaaccagt tcgttcgggc aggtttcgcc ttttccaga ttgctacact gcttccggta    60
gtcaa                                                               65

<210> SEQ ID NO 46
<211> LENGTH: 65
<212> TYPE: DNA
<213> ORGANISM: Artificial sequence
<220> FEATURE:
<223> OTHER INFORMATION: Primer set for WMpflB A/C

<400> SEQUENCE: 46
ttactccgta tttgcataaa aaccatgcga gttacgggcc tataacggca cgtaagaggt    60
tccaa                                                               65

<210> SEQ ID NO 47
<211> LENGTH: 69
<212> TYPE: DNA
<213> ORGANISM: Artificial sequence
<220> FEATURE:
<223> OTHER INFORMATION: Primer set for WMpflB A/C

<400> SEQUENCE: 47
ttacatagat tgagtgaagg tacgagtaat aacgtcctgc tgctgttcta cactgcttcc    60
ggtagtcaa                                                           69

<210> SEQ ID NO 48
<211> LENGTH: 20
<212> TYPE: DNA
<213> ORGANISM: Artificial sequence
<220> FEATURE:
<223> OTHER INFORMATION: Primer set for tdcDE-up/down

<400> SEQUENCE: 48
cgccgacaga gtaataggtt                                               20

<210> SEQ ID NO 49
<211> LENGTH: 20
<212> TYPE: DNA
<213> ORGANISM: Artificial sequence
<220> FEATURE:
<223> OTHER INFORMATION: Primer set for tdcDE-up/down

<400> SEQUENCE: 49
tgatgagcta cctggtatgg                                               20

<210> SEQ ID NO 50
<211> LENGTH: 20
<212> TYPE: DNA
<213> ORGANISM: Artificial sequence
<220> FEATURE:
<223> OTHER INFORMATION: Primer set for tdcDE-F7/R7

<400> SEQUENCE: 50
cgatgcggtg gccaattaag                                               20

<210> SEQ ID NO 51
```

```
<211> LENGTH: 20
<212> TYPE: DNA
<213> ORGANISM: Artificial sequence
<220> FEATURE:
<223> OTHER INFORMATION: Primer set for tdcDE-F7/R7

<400> SEQUENCE: 51
gacgacgtgc tggattacga                                               20

<210> SEQ ID NO 52
<211> LENGTH: 20
<212> TYPE: DNA
<213> ORGANISM: Artificial sequence
<220> FEATURE:
<223> OTHER INFORMATION: Primer set for citF-up2/down2

<400> SEQUENCE: 52
gggtattcag gcgttcgata                                               20

<210> SEQ ID NO 53
<211> LENGTH: 20
<212> TYPE: DNA
<213> ORGANISM: Artificial sequence
<220> FEATURE:
<223> OTHER INFORMATION: Primer set for citF-up2/down2

<400> SEQUENCE: 53
gcccgagagg atgactatgt                                               20

<210> SEQ ID NO 54
<211> LENGTH: 20
<212> TYPE: DNA
<213> ORGANISM: Artificial sequence
<220> FEATURE:
<223> OTHER INFORMATION: Primer set for citF-2/3

<400> SEQUENCE: 54
ggtgatcgat gttgtgcatc                                               20

<210> SEQ ID NO 55
<211> LENGTH: 20
<212> TYPE: DNA
<213> ORGANISM: Artificial sequence
<220> FEATURE:
<223> OTHER INFORMATION: Primer set for citF-2/3

<400> SEQUENCE: 55
cccgttcttg tcgttgagat                                               20

<210> SEQ ID NO 56
<211> LENGTH: 20
<212> TYPE: DNA
<213> ORGANISM: Artificial sequence
<220> FEATURE:
<223> OTHER INFORMATION: Primer set for IO-adhE-up/down

<400> SEQUENCE: 56
gctgctccgg ctaaagctga                                               20

<210> SEQ ID NO 57
<211> LENGTH: 20
<212> TYPE: DNA
<213> ORGANISM: Artificial sequence
<220> FEATURE:
<223> OTHER INFORMATION: Primer set for IO-adhE-up/down

<400> SEQUENCE: 57
```
acgctctacg agtgcgttaa                                            20

<210> SEQ ID NO 58
<211> LENGTH: 20
<212> TYPE: DNA
<213> ORGANISM: Artificial sequence
<220> FEATURE:
<223> OTHER INFORMATION: Primer set for up-focA/Mid-pflB

<400> SEQUENCE: 58
agatcgccag ccgctgcaat                                            20

<210> SEQ ID NO 59
<211> LENGTH: 20
<212> TYPE: DNA
<213> ORGANISM: Artificial sequence
<220> FEATURE:
<223> OTHER INFORMATION: Primer set for up-focA/Mid-pflB

<400> SEQUENCE: 59
aaccgttggt gtccagacag                                            20

<210> SEQ ID NO 60
<211> LENGTH: 20
<212> TYPE: DNA
<213> ORGANISM: Artificial sequence
<220> FEATURE:
<223> OTHER INFORMATION: Primer set for IO-ycaO-up/IO-midpflB-down

<400> SEQUENCE: 60
gcctacattg cgtaggctat                                            20

<210> SEQ ID NO 61
<211> LENGTH: 20
<212> TYPE: DNA
<213> ORGANISM: Artificial sequence
<220> FEATURE:
<223> OTHER INFORMATION: Primer set for IO-ycaO-up/IO-midpflB-down

<400> SEQUENCE: 61
gcagcaggac gttattactc                                            20

<210> SEQ ID NO 62
<211> LENGTH: 20
<212> TYPE: DNA
<213> ORGANISM: Artificial sequence
<220> FEATURE:
<223> OTHER INFORMATION: Primer set for ldhA-A/C

<400> SEQUENCE: 62
atgaaactcg ccgtttatag                                            20

<210> SEQ ID NO 63
<211> LENGTH: 19
<212> TYPE: DNA
<213> ORGANISM: Artificial sequence
<220> FEATURE:
<223> OTHER INFORMATION: Primer set for ldhA-A/C

<400> SEQUENCE: 63
ttaaaccagt tcgttgccc                                             19

<210> SEQ ID NO 64
<211> LENGTH: 20
<212> TYPE: DNA

```
<213> ORGANISM: Artificial sequence
<220> FEATURE:
<223> OTHER INFORMATION: Primer set for IO/ldhA-up/down

<400> SEQUENCE: 64
cgttcgatcc gtatccaagt                                            20

<210> SEQ ID NO 65
<211> LENGTH: 20
<212> TYPE: DNA
<213> ORGANISM: Artificial sequence
<220> FEATURE:
<223> OTHER INFORMATION: Primer set for IO-ldhA-up/down

<400> SEQUENCE: 65
aggctggaac tcggactact                                            20

<210> SEQ ID NO 66
<211> LENGTH: 20
<212> TYPE: DNA
<213> ORGANISM: Artificial sequence
<220> FEATURE:
<223> OTHER INFORMATION: Primer set for aspC-up/down

<400> SEQUENCE: 66
tccatcgctt acaccaaatc                                            20

<210> SEQ ID NO 67
<211> LENGTH: 20
<212> TYPE: DNA
<213> ORGANISM: Artificial sequence
<220> FEATURE:
<223> OTHER INFORMATION: Primer set for aspC-up/down

<400> SEQUENCE: 67
tgggggatga cgtgatattt                                            20

<210> SEQ ID NO 68
<211> LENGTH: 20
<212> TYPE: DNA
<213> ORGANISM: Artificial sequence
<220> FEATURE:
<223> OTHER INFORMATION: Primer set for aspC-1/2

<400> SEQUENCE: 68
agataacatg gctccgctgt                                            20

<210> SEQ ID NO 69
<211> LENGTH: 19
<212> TYPE: DNA
<213> ORGANISM: Artificial sequence
<220> FEATURE:
<223> OTHER INFORMATION: Primer set for aspC-1/2

<400> SEQUENCE: 69
aggagcggcg gtaatgttc                                             19

<210> SEQ ID NO 70
<211> LENGTH: 20
<212> TYPE: DNA
<213> ORGANISM: Artificial sequence
<220> FEATURE:
<223> OTHER INFORMATION: Primer set for sfcA-up/down

<400> SEQUENCE: 70
ctatgcttga tcggcaacct                                            20
```

<210> SEQ ID NO 71
<211> LENGTH: 20
<212> TYPE: DNA
<213> ORGANISM: Artificial sequence
<220> FEATURE:
<223> OTHER INFORMATION: Primer set for sfcA-up/down

<400> SEQUENCE: 71
acgatcgcct ggttttaatg                                        20

<210> SEQ ID NO 72
<211> LENGTH: 20
<212> TYPE: DNA
<213> ORGANISM: Artificial sequence
<220> FEATURE:
<223> OTHER INFORMATION: Primer set for sfcA-1/2

<400> SEQUENCE: 72
taccgccgta cctccatcta                                        20

<210> SEQ ID NO 73
<211> LENGTH: 22
<212> TYPE: DNA
<213> ORGANISM: Artificial sequence
<220> FEATURE:
<223> OTHER INFORMATION: Primer set for sfcA-1/2

<400> SEQUENCE: 73
cgtaagggat ataaagcgaa cg                                     22

<210> SEQ ID NO 74
<211> LENGTH: 20
<212> TYPE: DNA
<213> ORGANISM: Artificial sequence
<220> FEATURE:
<223> OTHER INFORMATION: Primer set for ackA-up/pta-down

<400> SEQUENCE: 74
cgggacaacg ttcaaaacat                                        20

<210> SEQ ID NO 75
<211> LENGTH: 20
<212> TYPE: DNA
<213> ORGANISM: Artificial sequence
<220> FEATURE:
<223> OTHER INFORMATION: Primer set for ackA-up/pta-down

<400> SEQUENCE: 75
attgcccatc ttcttgttgg                                        20

<210> SEQ ID NO 76
<211> LENGTH: 21
<212> TYPE: DNA
<213> ORGANISM: Artificial sequence
<220> FEATURE:
<223> OTHER INFORMATION: Primer set for ackA-2/pta-2

<400> SEQUENCE: 76
aactaccgca gttcagaacc a                                      21

<210> SEQ ID NO 77
<211> LENGTH: 20
<212> TYPE: DNA
<213> ORGANISM: Artificial sequence
<220> FEATURE:

<223> OTHER INFORMATION: Primer set for ackA-2/pta-2

<400> SEQUENCE: 77
tctgaacacc ggtaacacca                                               20

<210> SEQ ID NO 78
<211> LENGTH: 20
<212> TYPE: DNA
<213> ORGANISM: Artificial sequence
<220> FEATURE:
<223> OTHER INFORMATION: pck-Pro-up

<400> SEQUENCE: 78
cacggtagca acaacattgc                                               20

<210> SEQ ID NO 79
<211> LENGTH: 20
<212> TYPE: DNA
<213> ORGANISM: Artificial Sequence
<220> FEATURE:
<223> OTHER INFORMATION: pck-Pro-down

<400> SEQUENCE: 79
agaaagcgtc gacaacgaac                                               20

<210> SEQ ID NO 80
<211> LENGTH: 20
<212> TYPE: DNA
<213> ORGANISM: Artificial Sequence
<220> FEATURE:
<223> OTHER INFORMATION: pck-Pro-1

<400> SEQUENCE: 80
atgcgcgtta acaatggttt                                               20

<210> SEQ ID NO 81
<211> LENGTH: 20
<212> TYPE: DNA
<213> ORGANISM: Artificial Sequence
<220> FEATURE:
<223> OTHER INFORMATION: pck-Pro-2

<400> SEQUENCE: 81
atggataacg ttgaactttc                                               20

<210> SEQ ID NO 82
<211> LENGTH: 20
<212> TYPE: DNA
<213> ORGANISM: Artificial Sequence
<220> FEATURE:
<223> OTHER INFORMATION: ptsI-D-up

<400> SEQUENCE: 82
cgcattatgt tcccgatgat                                               20

<210> SEQ ID NO 83
<211> LENGTH: 20
<212> TYPE: DNA
<213> ORGANISM: Artificial Sequence
<220> FEATURE:
<223> OTHER INFORMATION: ptsI-D-down

<400> SEQUENCE: 83
gcctttcagt tcaacggtgt                                               20

```
<210> SEQ ID NO 84
<211> LENGTH: 20
<212> TYPE: DNA
<213> ORGANISM: Artificial Sequence
<220> FEATURE:
<223> OTHER INFORMATION: ptsI-D-1

<400> SEQUENCE: 84
cggcccaatt tactgcttag                                              20

<210> SEQ ID NO 85
<211> LENGTH: 20
<212> TYPE: DNA
<213> ORGANISM: Artificial Sequence
<220> FEATURE:
<223> OTHER INFORMATION: ptsI-D-2

<400> SEQUENCE: 85
atccccagca acagaagtgt                                              20

<210> SEQ ID NO 86
<211> LENGTH: 29
<212> TYPE: DNA
<213> ORGANISM: Artificial Sequence
<220> FEATURE:
<223> OTHER INFORMATION: pck-F

<400> SEQUENCE: 86
ttggctaagg agcagtgaaa tgcgcgtta                                    29

<210> SEQ ID NO 87
<211> LENGTH: 25
<212> TYPE: DNA
<213> ORGANISM: Artificial Sequence
<220> FEATURE:
<223> OTHER INFORMATION: pck-R

<400> SEQUENCE: 87
cacgacaaaa gaagggtaaa taaac                                        25

<210> SEQ ID NO 88
<211> LENGTH: 20
<212> TYPE: DNA
<213> ORGANISM: Artificial Sequence
<220> FEATURE:
<223> OTHER INFORMATION: pck-2

<400> SEQUENCE: 88
ttgttaacgc gcatttcact                                              20

<210> SEQ ID NO 89
<211> LENGTH: 20
<212> TYPE: DNA
<213> ORGANISM: Artificial Sequence
<220> FEATURE:
<223> OTHER INFORMATION: pck-3

<400> SEQUENCE: 89
gcgatagcgg ctactgtcat                                              20

<210> SEQ ID NO 90
<211> LENGTH: 20
<212> TYPE: DNA
<213> ORGANISM: Artificial Sequence
<220> FEATURE:
<223> OTHER INFORMATION: sfcA-up
```

<400> SEQUENCE: 90
ctatgcttga tcggcaacct                                           20

<210> SEQ ID NO 91
<211> LENGTH: 20
<212> TYPE: DNA
<213> ORGANISM: Artificial Sequence
<220> FEATURE:
<223> OTHER INFORMATION: sfcA-down

<400> SEQUENCE: 91
acgatcgcct ggttttaatg                                           20

<210> SEQ ID NO 92
<211> LENGTH: 20
<212> TYPE: DNA
<213> ORGANISM: Artificial Sequence
<220> FEATURE:
<223> OTHER INFORMATION: sfcA-1

<400> SEQUENCE: 92
taccgccgta cctccatcta                                           20

<210> SEQ ID NO 93
<211> LENGTH: 22
<212> TYPE: DNA
<213> ORGANISM: Artificial Sequence
<220> FEATURE:
<223> OTHER INFORMATION: sfcA-2

<400> SEQUENCE: 93
cgtaagggat ataaagcgaa cg                                        22

<210> SEQ ID NO 94
<211> LENGTH: 20
<212> TYPE: DNA
<213> ORGANISM: Artificial Sequence
<220> FEATURE:
<223> OTHER INFORMATION: ppc-up

<400> SEQUENCE: 94
tcaaacgatg cccaactgta                                           20

<210> SEQ ID NO 95
<211> LENGTH: 20
<212> TYPE: DNA
<213> ORGANISM: Artificial Sequence
<220> FEATURE:
<223> OTHER INFORMATION: ppc-down

<400> SEQUENCE: 95
tttaatccgc ttcggaaaga                                           20

<210> SEQ ID NO 96
<211> LENGTH: 20
<212> TYPE: DNA
<213> ORGANISM: Artificial Sequence
<220> FEATURE:
<223> OTHER INFORMATION: ppc-1

<400> SEQUENCE: 96
gtcactattg ccgggattgc                                           20

<210> SEQ ID NO 97
<211> LENGTH: 20

```
<212> TYPE: DNA
<213> ORGANISM: Artificial Sequence
<220> FEATURE:
<223> OTHER INFORMATION: ppc-2

<400> SEQUENCE: 97
caatgcggaa tattgttcgt                                            20

<210> SEQ ID NO 98
<211> LENGTH: 20
<212> TYPE: DNA
<213> ORGANISM: Artificial Sequence
<220> FEATURE:
<223> OTHER INFORMATION: pck-up

<400> SEQUENCE: 98
tccgggcagt agtattttgc                                            20

<210> SEQ ID NO 99
<211> LENGTH: 20
<212> TYPE: DNA
<213> ORGANISM: Artificial Sequence
<220> FEATURE:
<223> OTHER INFORMATION: pck-down

<400> SEQUENCE: 99
atggctggat caaagtcagc                                            20

<210> SEQ ID NO 100
<211> LENGTH: 20
<212> TYPE: DNA
<213> ORGANISM: Artificial Sequence
<220> FEATURE:
<223> OTHER INFORMATION: pck-1

<400> SEQUENCE: 100
cctggcgaaa ctgtttatcg                                            20

<210> SEQ ID NO 101
<211> LENGTH: 20
<212> TYPE: DNA
<213> ORGANISM: Artificial Sequence
<220> FEATURE:
<223> OTHER INFORMATION: pck-2

<400> SEQUENCE: 101
ttgttaacgc gcatttcact                                            20

<210> SEQ ID NO 102
<211> LENGTH: 20
<212> TYPE: DNA
<213> ORGANISM: Artificial Sequence
<220> FEATURE:
<223> OTHER INFORMATION: maeB-up

<400> SEQUENCE: 102
gcatcctggg gatgataatg                                            20

<210> SEQ ID NO 103
<211> LENGTH: 20
<212> TYPE: DNA
<213> ORGANISM: Artificial Sequence
<220> FEATURE:
<223> OTHER INFORMATION: maeB-down

<400> SEQUENCE: 103
```
tttcttcgcc agttcctcac                                         20

<210> SEQ ID NO 104
<211> LENGTH: 21
<212> TYPE: DNA
<213> ORGANISM: Artificial Sequence
<220> FEATURE:
<223> OTHER INFORMATION: maeB-1

<400> SEQUENCE: 104
aacccaaccg ctgtaatttt t                                       21

<210> SEQ ID NO 105
<211> LENGTH: 20
<212> TYPE: DNA
<213> ORGANISM: Artificial Sequence
<220> FEATURE:
<223> OTHER INFORMATION: maeB-2

<400> SEQUENCE: 105
ctggaactgg aaattcatgg                                         20

<210> SEQ ID NO 106
<211> LENGTH: 20
<212> TYPE: DNA
<213> ORGANISM: Artificial Sequence
<220> FEATURE:
<223> OTHER INFORMATION: pck-Pro-up

<400> SEQUENCE: 106
cacggtagca acaacattgc                                         20

<210> SEQ ID NO 107
<211> LENGTH: 20
<212> TYPE: DNA
<213> ORGANISM: Artificial Sequence
<220> FEATURE:
<223> OTHER INFORMATION: pck-Pro-down

<400> SEQUENCE: 107
agaaagcgtc gacaacgaac                                         20

<210> SEQ ID NO 108
<211> LENGTH: 20
<212> TYPE: DNA
<213> ORGANISM: Artificial Sequence
<220> FEATURE:
<223> OTHER INFORMATION: pck-Pro-1

<400> SEQUENCE: 108
atgcgcgtta acaatggttt                                         20

<210> SEQ ID NO 109
<211> LENGTH: 20
<212> TYPE: DNA
<213> ORGANISM: Artificial Sequence
<220> FEATURE:
<223> OTHER INFORMATION: pck-Pro-2

<400> SEQUENCE: 109
atggataacg ttgaactttc                                         20

<210> SEQ ID NO 110
<211> LENGTH: 20
<212> TYPE: DNA
<213> ORGANISM: Artificial Sequence

```
<220> FEATURE:
<223> OTHER INFORMATION: ptsI-D-up

<400> SEQUENCE: 110
cgcattatgt tcccgatgat                                                    20

<210> SEQ ID NO 111
<211> LENGTH: 20
<212> TYPE: DNA
<213> ORGANISM: Artificial Sequence
<220> FEATURE:
<223> OTHER INFORMATION: ptsI-D-down

<400> SEQUENCE: 111
gcctttcagt tcaacggtgt                                                    20

<210> SEQ ID NO 112
<211> LENGTH: 20
<212> TYPE: DNA
<213> ORGANISM: Artificial Sequence
<220> FEATURE:
<223> OTHER INFORMATION: ptsI-D-1

<400> SEQUENCE: 112
cggcccaatt tactgcttag                                                    20

<210> SEQ ID NO 113
<211> LENGTH: 20
<212> TYPE: DNA
<213> ORGANISM: Artificial Sequence
<220> FEATURE:
<223> OTHER INFORMATION: ptsI-D-2

<400> SEQUENCE: 113
atccccagca acagaagtgt                                                    20

<210> SEQ ID NO 114
<211> LENGTH: 29
<212> TYPE: DNA
<213> ORGANISM: Artificial Sequence
<220> FEATURE:
<223> OTHER INFORMATION: pck-F

<400> SEQUENCE: 114
ttggctaagg agcagtgaaa tgcgcgtta                                          29

<210> SEQ ID NO 115
<211> LENGTH: 25
<212> TYPE: DNA
<213> ORGANISM: Artificial Sequence
<220> FEATURE:
<223> OTHER INFORMATION: pck-R

<400> SEQUENCE: 115
cacgacaaaa gaagggtaaa taaac                                              25

<210> SEQ ID NO 116
<211> LENGTH: 20
<212> TYPE: DNA
<213> ORGANISM: Artificial Sequence
<220> FEATURE:
<223> OTHER INFORMATION: pck-2

<400> SEQUENCE: 116
ttgttaacgc gcatttcact                                                    20
```

```
<210> SEQ ID NO 117
<211> LENGTH: 20
<212> TYPE: DNA
<213> ORGANISM: Artificial Sequence
<220> FEATURE:
<223> OTHER INFORMATION: pck-3

<400> SEQUENCE: 117
gcgatagcgg ctactgtcat                                               20

<210> SEQ ID NO 118
<211> LENGTH: 20
<212> TYPE: DNA
<213> ORGANISM: Artificial Sequence
<220> FEATURE:
<223> OTHER INFORMATION: cra-up

<400> SEQUENCE: 118
gcggtaagct tgatgcattt                                               20

<210> SEQ ID NO 119
<211> LENGTH: 20
<212> TYPE: DNA
<213> ORGANISM: Artificial Sequence
<220> FEATURE:
<223> OTHER INFORMATION: cra-down

<400> SEQUENCE: 119
cttccccggt taacagtcct                                               20

<210> SEQ ID NO 120
<211> LENGTH: 20
<212> TYPE: DNA
<213> ORGANISM: Artificial Sequence
<220> FEATURE:
<223> OTHER INFORMATION: ptsHI-up1

<400> SEQUENCE: 120
tcatcgggtg agcgttattt                                               20

<210> SEQ ID NO 121
<211> LENGTH: 20
<212> TYPE: DNA
<213> ORGANISM: Artificial Sequence
<220> FEATURE:
<223> OTHER INFORMATION: ptsHI-down1

<400> SEQUENCE: 121
tgaccgtcca gcgtaatagc                                               20

<210> SEQ ID NO 122
<211> LENGTH: 20
<212> TYPE: DNA
<213> ORGANISM: Artificial Sequence
<220> FEATURE:
<223> OTHER INFORMATION: ptsHI-up2

<400> SEQUENCE: 122
catcctgggc ctgaagatta                                               20

<210> SEQ ID NO 123
<211> LENGTH: 20
<212> TYPE: DNA
<213> ORGANISM: Artificial Sequence
<220> FEATURE:
<223> OTHER INFORMATION: ptsHI-down2
```

<400> SEQUENCE: 123
agcaatacca tcaccaacga                                                20

<210> SEQ ID NO 124
<211> LENGTH: 20
<212> TYPE: DNA
<213> ORGANISM: Artificial Sequence
<220> FEATURE:
<223> OTHER INFORMATION: crr-up

<400> SEQUENCE: 124
cccgcgcatt aagaagatta                                                20

<210> SEQ ID NO 125
<211> LENGTH: 20
<212> TYPE: DNA
<213> ORGANISM: Artificial Sequence
<220> FEATURE:
<223> OTHER INFORMATION: crr-down

<400> SEQUENCE: 125
ctcatcagtg gcttgctgaa                                                20

<210> SEQ ID NO 126
<211> LENGTH: 20
<212> TYPE: DNA
<213> ORGANISM: Artificial Sequence
<220> FEATURE:
<223> OTHER INFORMATION: ptsG-up

<400> SEQUENCE: 126
gaagaactgg cgcaggtaac                                                20

<210> SEQ ID NO 127
<211> LENGTH: 20
<212> TYPE: DNA
<213> ORGANISM: Artificial Sequence
<220> FEATURE:
<223> OTHER INFORMATION: ptsG-down

<400> SEQUENCE: 127
aaggaaacgc cgttaatcct                                                20

<210> SEQ ID NO 128
<211> LENGTH: 20
<212> TYPE: DNA
<213> ORGANISM: Artificial Sequence
<220> FEATURE:
<223> OTHER INFORMATION: cyaA-up

<400> SEQUENCE: 128
tcgccatcaa cttgtctttg                                                20

<210> SEQ ID NO 129
<211> LENGTH: 20
<212> TYPE: DNA
<213> ORGANISM: Artificial Sequence
<220> FEATURE:
<223> OTHER INFORMATION: cyaA-down

<400> SEQUENCE: 129
aaaggcgatg agtggatttg                                                20

<210> SEQ ID NO 130

```
<211> LENGTH: 20
<212> TYPE: DNA
<213> ORGANISM: Artificial Sequence
<220> FEATURE:
<223> OTHER INFORMATION: crp-S-up

<400> SEQUENCE: 130
tgagttgccg tccattaaaa                                                20

<210> SEQ ID NO 131
<211> LENGTH: 20
<212> TYPE: DNA
<213> ORGANISM: Artificial Sequence
<220> FEATURE:
<223> OTHER INFORMATION: crp-S-down

<400> SEQUENCE: 131
aatcgtaatt cgccaagcat                                                20

<210> SEQ ID NO 132
<211> LENGTH: 20
<212> TYPE: DNA
<213> ORGANISM: Artificial Sequence
<220> FEATURE:
<223> OTHER INFORMATION: cpdA-S-up

<400> SEQUENCE: 132
gaagtgtgtt caagccagca                                                20

<210> SEQ ID NO 133
<211> LENGTH: 20
<212> TYPE: DNA
<213> ORGANISM: Artificial Sequence
<220> FEATURE:
<223> OTHER INFORMATION: cpdA-S-down

<400> SEQUENCE: 133
aggacaatgg attccagcag                                                20

<210> SEQ ID NO 134
<211> LENGTH: 20
<212> TYPE: DNA
<213> ORGANISM: Artificial Sequence
<220> FEATURE:
<223> OTHER INFORMATION: ygiF-S-up

<400> SEQUENCE: 134
atcagtgtcg ctacgcaaag                                                20

<210> SEQ ID NO 135
<211> LENGTH: 20
<212> TYPE: DNA
<213> ORGANISM: Artificial Sequence
<220> FEATURE:
<223> OTHER INFORMATION: ygiF-S-down

<400> SEQUENCE: 135
gctgtcctgc acaaaatcac                                                20

<210> SEQ ID NO 136
<211> LENGTH: 20
<212> TYPE: DNA
<213> ORGANISM: Artificial Sequence
<220> FEATURE:
<223> OTHER INFORMATION: sxy-S-up

<400> SEQUENCE: 136
```
tttacttgct gcggatgaga                                              20

<210> SEQ ID NO 137
<211> LENGTH: 20
<212> TYPE: DNA
<213> ORGANISM: Artificial Sequence
<220> FEATURE:
<223> OTHER INFORMATION: sxy-S-down

<400> SEQUENCE: 137
tatctcagcc ctcggtgctc                                              20

<210> SEQ ID NO 138
<211> LENGTH: 20
<212> TYPE: DNA
<213> ORGANISM: Artificial Sequence
<220> FEATURE:
<223> OTHER INFORMATION: csrA-up

<400> SEQUENCE: 138
cagcgttagc cagtgtgaaa                                              20

<210> SEQ ID NO 139
<211> LENGTH: 20
<212> TYPE: DNA
<213> ORGANISM: Artificial Sequence
<220> FEATURE:
<223> OTHER INFORMATION: csrA-down

<400> SEQUENCE: 139
acgcctctta cgagtgcttc                                              20

<210> SEQ ID NO 140
<211> LENGTH: 20
<212> TYPE: DNA
<213> ORGANISM: Artificial Sequence
<220> FEATURE:
<223> OTHER INFORMATION: csrB-S-up

<400> SEQUENCE: 140
ctgtaggaga tcgccaggaa                                              20

<210> SEQ ID NO 141
<211> LENGTH: 20
<212> TYPE: DNA
<213> ORGANISM: Artificial Sequence
<220> FEATURE:
<223> OTHER INFORMATION: csrB-S-down

<400> SEQUENCE: 141
tctaacaaat cgtgcattcg                                              20

<210> SEQ ID NO 142
<211> LENGTH: 20
<212> TYPE: DNA
<213> ORGANISM: Artificial Sequence
<220> FEATURE:
<223> OTHER INFORMATION: csrC-S-up

<400> SEQUENCE: 142
gccatacgct ttgtgagaca                                              20

<210> SEQ ID NO 143
<211> LENGTH: 20
<212> TYPE: DNA

```
<213> ORGANISM: Artificial Sequence
<220> FEATURE:
<223> OTHER INFORMATION: csrC-S-down

<400> SEQUENCE: 143
agtcacgccc aatggaatag                                               20

<210> SEQ ID NO 144
<211> LENGTH: 20
<212> TYPE: DNA
<213> ORGANISM: Artificial Sequence
<220> FEATURE:
<223> OTHER INFORMATION: csrD-S-up1

<400> SEQUENCE: 144
atgtgcatga tggattggaa                                               20

<210> SEQ ID NO 145
<211> LENGTH: 20
<212> TYPE: DNA
<213> ORGANISM: Artificial Sequence
<220> FEATURE:
<223> OTHER INFORMATION: csrD-S-down1

<400> SEQUENCE: 145
cggtatcctg accactacgc                                               20

<210> SEQ ID NO 146
<211> LENGTH: 20
<212> TYPE: DNA
<213> ORGANISM: Artificial Sequence
<220> FEATURE:
<223> OTHER INFORMATION: csrD-S-up2

<400> SEQUENCE: 146
gtgattttgc tgcgctgtta                                               20

<210> SEQ ID NO 147
<211> LENGTH: 20
<212> TYPE: DNA
<213> ORGANISM: Artificial Sequence
<220> FEATURE:
<223> OTHER INFORMATION: csrD-S-down2

<400> SEQUENCE: 147
acaaggcgca aaaatcatct                                               20

<210> SEQ ID NO 148
<211> LENGTH: 20
<212> TYPE: DNA
<213> ORGANISM: Artificial Sequence
<220> FEATURE:
<223> OTHER INFORMATION: uvrY-s-up1

<400> SEQUENCE: 148
cctcgtcatg ttgcaatgaa                                               20

<210> SEQ ID NO 149
<211> LENGTH: 20
<212> TYPE: DNA
<213> ORGANISM: Artificial Sequence
<220> FEATURE:
<223> OTHER INFORMATION: uvrY-s-down1

<400> SEQUENCE: 149
tatcatcgcg tagcaaaacg                                               20
```

<210> SEQ ID NO 150
<211> LENGTH: 20
<212> TYPE: DNA
<213> ORGANISM: Artificial Sequence
<220> FEATURE:
<223> OTHER INFORMATION: barA-s-up1

<400> SEQUENCE: 150
ttttgcttcg ctgctgtaaa                                               20

<210> SEQ ID NO 151
<211> LENGTH: 20
<212> TYPE: DNA
<213> ORGANISM: Artificial Sequence
<220> FEATURE:
<223> OTHER INFORMATION: barA-s-down1

<400> SEQUENCE: 151
tcaggcacgt cgcttttaat                                               20

<210> SEQ ID NO 152
<211> LENGTH: 20
<212> TYPE: DNA
<213> ORGANISM: Artificial Sequence
<220> FEATURE:
<223> OTHER INFORMATION: barA-s-up2

<400> SEQUENCE: 152
cgcgatcacc tgaatacgat                                               20

<210> SEQ ID NO 153
<211> LENGTH: 20
<212> TYPE: DNA
<213> ORGANISM: Artificial Sequence
<220> FEATURE:
<223> OTHER INFORMATION: barA-s-down2

<400> SEQUENCE: 153
ctggctggac gttcgataac                                               20

<210> SEQ ID NO 154
<211> LENGTH: 20
<212> TYPE: DNA
<213> ORGANISM: Artificial Sequence
<220> FEATURE:
<223> OTHER INFORMATION: barA-s-up3

<400> SEQUENCE: 154
tggcctatgt cgaaccaaac                                               20

<210> SEQ ID NO 155
<211> LENGTH: 20
<212> TYPE: DNA
<213> ORGANISM: Artificial Sequence
<220> FEATURE:
<223> OTHER INFORMATION: mlc-s-up1

<400> SEQUENCE: 155
ctggcaaata acccgaatgt                                               20

<210> SEQ ID NO 156
<211> LENGTH: 20
<212> TYPE: DNA
<213> ORGANISM: Artificial Sequence
<220> FEATURE:

<223> OTHER INFORMATION: mlc-s-down1

<400> SEQUENCE: 156
ccagggcatc tttattacgc                                           20

<210> SEQ ID NO 157
<211> LENGTH: 20
<212> TYPE: DNA
<213> ORGANISM: Artificial Sequence
<220> FEATURE:
<223> OTHER INFORMATION: mlc-s-up2

<400> SEQUENCE: 157
tgaaactgaa gcctggcact                                           20

<210> SEQ ID NO 158
<211> LENGTH: 20
<212> TYPE: DNA
<213> ORGANISM: Artificial Sequence
<220> FEATURE:
<223> OTHER INFORMATION: XZ-ldhA-up

<400> SEQUENCE: 158
gataacggag atcgggaatg                                           20

<210> SEQ ID NO 159
<211> LENGTH: 20
<212> TYPE: DNA
<213> ORGANISM: Artificial Sequence
<220> FEATURE:
<223> OTHER INFORMATION: XZ-ldhA-down

<400> SEQUENCE: 159
ctttggctgt cagttcacca                                           20

<210> SEQ ID NO 160
<211> LENGTH: 20
<212> TYPE: DNA
<213> ORGANISM: Artificial Sequence
<220> FEATURE:
<223> OTHER INFORMATION: XZ-ldhA-1

<400> SEQUENCE: 160
tctggaaaaa ggcgaaacct                                           20

<210> SEQ ID NO 161
<211> LENGTH: 21
<212> TYPE: DNA
<213> ORGANISM: Artificial Sequence
<220> FEATURE:
<223> OTHER INFORMATION: XZ-ldhA-2

<400> SEQUENCE: 161
tttgtgctat aaacggcgag t                                         21

<210> SEQ ID NO 162
<211> LENGTH: 22
<212> TYPE: DNA
<213> ORGANISM: Artificial Sequence
<220> FEATURE:
<223> OTHER INFORMATION: PflB-up2

<400> SEQUENCE: 162
tgtccgagct taatgaaaag tt                                        22

```
<210> SEQ ID NO 163
<211> LENGTH: 22
<212> TYPE: DNA
<213> ORGANISM: Artificial Sequence
<220> FEATURE:
<223> OTHER INFORMATION: PflB-down2

<400> SEQUENCE: 163
cgagtaataa cgtcctgctg ct                                              22

<210> SEQ ID NO 164
<211> LENGTH: 20
<212> TYPE: DNA
<213> ORGANISM: Artificial Sequence
<220> FEATURE:
<223> OTHER INFORMATION: PflB-5

<400> SEQUENCE: 164
aaacgggtaa caccccagac                                                 20

<210> SEQ ID NO 165
<211> LENGTH: 20
<212> TYPE: DNA
<213> ORGANISM: Artificial Sequence
<220> FEATURE:
<223> OTHER INFORMATION: PflB-6

<400> SEQUENCE: 165
cggagtgtaa acgtcgaaca                                                 20

<210> SEQ ID NO 166
<211> LENGTH: 21
<212> TYPE: DNA
<213> ORGANISM: Artificial Sequence
<220> FEATURE:
<223> OTHER INFORMATION: adhE-up

<400> SEQUENCE: 166
catgctaatg tagccaccaa a                                               21

<210> SEQ ID NO 167
<211> LENGTH: 20
<212> TYPE: DNA
<213> ORGANISM: Artificial Sequence
<220> FEATURE:
<223> OTHER INFORMATION: adhE-down

<400> SEQUENCE: 167
ttgcaccacc atccagataa                                                 20

<210> SEQ ID NO 168
<211> LENGTH: 20
<212> TYPE: DNA
<213> ORGANISM: Artificial Sequence
<220> FEATURE:
<223> OTHER INFORMATION: adhE-1

<400> SEQUENCE: 168
tccggctaaa gctgagaaaa                                                 20

<210> SEQ ID NO 169
<211> LENGTH: 20
<212> TYPE: DNA
<213> ORGANISM: Artificial Sequence
<220> FEATURE:
<223> OTHER INFORMATION: adhE-2
```

```
<400> SEQUENCE: 169
gtgcgttaag ttcagcgaca                                               20

<210> SEQ ID NO 170
<211> LENGTH: 20
<212> TYPE: DNA
<213> ORGANISM: Artificial Sequence
<220> FEATURE:
<223> OTHER INFORMATION: pck-Pro-up

<400> SEQUENCE: 170
cacggtagca acaacattgc                                               20

<210> SEQ ID NO 171
<211> LENGTH: 20
<212> TYPE: DNA
<213> ORGANISM: Artificial Sequence
<220> FEATURE:
<223> OTHER INFORMATION: pck-Pro-down

<400> SEQUENCE: 171
agaaagcgtc gacaacgaac                                               20

<210> SEQ ID NO 172
<211> LENGTH: 20
<212> TYPE: DNA
<213> ORGANISM: Artificial Sequence
<220> FEATURE:
<223> OTHER INFORMATION: pck-Pro-1

<400> SEQUENCE: 172
atgcgcgtta acaatggttt                                               20

<210> SEQ ID NO 173
<211> LENGTH: 20
<212> TYPE: DNA
<213> ORGANISM: Artificial Sequence
<220> FEATURE:
<223> OTHER INFORMATION: pck-Pro-2

<400> SEQUENCE: 173
atggataacg ttgaactttc                                               20

<210> SEQ ID NO 174
<211> LENGTH: 20
<212> TYPE: DNA
<213> ORGANISM: Artificial Sequence
<220> FEATURE:
<223> OTHER INFORMATION: pck-P-2

<400> SEQUENCE: 174
ttcactgctc cttagccaat                                               20

<210> SEQ ID NO 175
<211> LENGTH: 20
<212> TYPE: DNA
<213> ORGANISM: Artificial Sequence
<220> FEATURE:
<223> OTHER INFORMATION: ptsI-D-up

<400> SEQUENCE: 175
cgcattatgt tcccgatgat                                               20

<210> SEQ ID NO 176
<211> LENGTH: 20
```

```
<212> TYPE: DNA
<213> ORGANISM: Artificial Sequence
<220> FEATURE:
<223> OTHER INFORMATION: ptsI-D-down

<400> SEQUENCE: 176
gcctttcagt tcaacggtgt                                               20

<210> SEQ ID NO 177
<211> LENGTH: 20
<212> TYPE: DNA
<213> ORGANISM: Artificial Sequence
<220> FEATURE:
<223> OTHER INFORMATION: ptsI-D-1

<400> SEQUENCE: 177
cggcccaatt tactgcttag                                               20

<210> SEQ ID NO 178
<211> LENGTH: 20
<212> TYPE: DNA
<213> ORGANISM: Artificial Sequence
<220> FEATURE:
<223> OTHER INFORMATION: ptsI-D-2

<400> SEQUENCE: 178
atccccagca acagaagtgt                                               20

<210> SEQ ID NO 179
<211> LENGTH: 20
<212> TYPE: DNA
<213> ORGANISM: Artificial Sequence
<220> FEATURE:
<223> OTHER INFORMATION: ptsG-up

<400> SEQUENCE: 179
gaagaactgg cgcaggtaac                                               20

<210> SEQ ID NO 180
<211> LENGTH: 20
<212> TYPE: DNA
<213> ORGANISM: Artificial Sequence
<220> FEATURE:
<223> OTHER INFORMATION: ptsG-down

<400> SEQUENCE: 180
aaggaaacgc cgttaatcct                                               20

<210> SEQ ID NO 181
<211> LENGTH: 20
<212> TYPE: DNA
<213> ORGANISM: Artificial Sequence
<220> FEATURE:
<223> OTHER INFORMATION: ptsG-1

<400> SEQUENCE: 181
cctgaaaacc gagatggatg                                               20

<210> SEQ ID NO 182
<211> LENGTH: 20
<212> TYPE: DNA
<213> ORGANISM: Artificial Sequence
<220> FEATURE:
<223> OTHER INFORMATION: ptsG-2

<400> SEQUENCE: 182
```
catcagcgat ttaccgacct 20

<210> SEQ ID NO 183
<211> LENGTH: 65
<212> TYPE: DNA
<213> ORGANISM: Artificial Sequence
<220> FEATURE:
<223> OTHER INFORMATION: ptsH-D-up

<400> SEQUENCE: 183
atgttccagc aagaagttac cattaccgct ccgaacggtc tgcacgtgta ggctggagct 60
gcttc 65

<210> SEQ ID NO 184
<211> LENGTH: 65
<212> TYPE: DNA
<213> ORGANISM: Artificial Sequence
<220> FEATURE:
<223> OTHER INFORMATION: ptsH-D-down

<400> SEQUENCE: 184
ttactcgagt tccgccatca gtttaaccag atgttcaacc gctttcatat gaatatcctc 60
cttag 65

<210> SEQ ID NO 185
<211> LENGTH: 65
<212> TYPE: DNA
<213> ORGANISM: Artificial Sequence
<220> FEATURE:
<223> OTHER INFORMATION: ptsI-D-up

<400> SEQUENCE: 185
atgatttcag gcattttagc atccccgggt atcgctttcg gtaaagtgta ggctggagct 60
gcttc 65

<210> SEQ ID NO 186
<211> LENGTH: 65
<212> TYPE: DNA
<213> ORGANISM: Artificial Sequence
<220> FEATURE:
<223> OTHER INFORMATION: ptsI-D-down

<400> SEQUENCE: 186
ttagcagatt gttttttctt caatgaactt gttaaccagc gtcatcatat gaatatcctc 60
cttag 65

<210> SEQ ID NO 187
<211> LENGTH: 20
<212> TYPE: DNA
<213> ORGANISM: Artificial Sequence
<220> FEATURE:
<223> OTHER INFORMATION: gldA-up

<400> SEQUENCE: 187
tgtatatagc gccgcacaag 20

<210> SEQ ID NO 188
<211> LENGTH: 20
<212> TYPE: DNA
<213> ORGANISM: Artificial Sequence
<220> FEATURE:
<223> OTHER INFORMATION: gldA-down

<400> SEQUENCE: 188

-continued gatggcaagg ttggtattgg                                              20

<210> SEQ ID NO 189
<211> LENGTH: 20
<212> TYPE: DNA
<213> ORGANISM: Artificial Sequence
<220> FEATURE:
<223> OTHER INFORMATION: gldA-1

<400> SEQUENCE: 189
accagtacgg tcagcgtttc                                              20

<210> SEQ ID NO 190
<211> LENGTH: 20
<212> TYPE: DNA
<213> ORGANISM: Artificial Sequence
<220> FEATURE:
<223> OTHER INFORMATION: gldA-2

<400> SEQUENCE: 190
acccggtgat tgaataatgc                                              20

<210> SEQ ID NO 191
<211> LENGTH: 64
<212> TYPE: DNA
<213> ORGANISM: Artificial Sequence
<220> FEATURE:
<223> OTHER INFORMATION: dhaKL-D-up

<400> SEQUENCE: 191
atgaaaaaat tgatcaatga tgtgcaagac gtactggacg aacaatgtag gctggagctg   60
cttc                                                               64

<210> SEQ ID NO 192
<211> LENGTH: 65
<212> TYPE: DNA
<213> ORGANISM: Artificial Sequence
<220> FEATURE:
<223> OTHER INFORMATION: dhaKL-D-down

<400> SEQUENCE: 192
ttactctttt gcggctaacg ccaacatttg catcataaac atcaccatat gaatatcctc   60
cttag                                                              65

<210> SEQ ID NO 193
<211> LENGTH: 64
<212> TYPE: DNA
<213> ORGANISM: Artificial Sequence
<220> FEATURE:
<223> OTHER INFORMATION: dhaM-D-up

<400> SEQUENCE: 193
gtgatggtaa acctggtcat agtttcacat agcagccgac tgggatgtag gctggagctg   60
cttc                                                               64

<210> SEQ ID NO 194
<211> LENGTH: 64
<212> TYPE: DNA
<213> ORGANISM: Artificial Sequence
<220> FEATURE:
<223> OTHER INFORMATION: dhaM-D-down

<400> SEQUENCE: 194

```
ttaaccctga cggttgaaac gttgcgtttt aacgtccagc gttagatatg aatatcctcc    60
ttag                                                                64
```

ENGINEERING THE PATHWAY FOR SUCCINATE PRODUCTION

CROSS-REFERENCE TO RELATED APPLICATIONS

This application is a continuation of U.S. Ser. No. 13/256,460, filed Nov. 2, 2011, now abandoned, which is the U.S. national stage application of International Patent Application No. PCT/US2010/029728, filed Apr. 2, 2010, which claims the priority of U.S. Provisional Application Ser. No. 61/166,093, filed Apr. 2, 2009, which is a continuation-in-part of U.S. application Ser. No. 12/529,826, filed Mar. 24, 2010, now U.S. Pat. No. 8,691,539, which is the U.S. national stage application of PCT/US2008/057439, filed Mar. 19, 2008, which claims the benefit of U.S. Provisional Application Ser. No. 60/895,806, filed Mar. 20, 2007, the disclosure of each of which is hereby incorporated by reference in its entirety, including all figures, tables and amino acid or nucleic acid sequences.

GOVERNMENT SUPPORT

This invention was made with government support under a grant awarded from the Department of Energy under grant number USDOE-DE FG02-96ER20222 and the Department of Energy in conjunction with the United States Department of Agriculture under grant number USDA and DOE Biomass RDI DE FG36-04GO14019. The government has certain rights in the invention.

The Sequence Listing for this application is labeled "Seq-List.txt", which was created on Nov. 1, 2011 and is 38 KB. The entire content of the sequence listing is incorporated herein by reference in its entirety.

BACKGROUND OF THE INVENTION

The present invention is in the field of production of succinic acid from renewable biological feedstocks using microbial biocatalysts. This invention discloses the genetic modifications to the biocatalysts that are useful in achieving high efficiency for succinic acid production. More specifically, this invention provides genetically modified biocatalysts that are suitable for the production of succinic acid from renewable feedstocks in commercially significant quantities.

A 2004 U.S. Department of Energy report entitled "Top value added chemicals from biomass" has identified twelve building block chemicals that can be produced from renewable feed stocks. The twelve sugar-based building blocks are 1,4-diacids (succinic, fumaric and maleic), 2,5-furan dicarboxylic acid, 3-hydroxy propionic acid, aspartic acid, glucaric acid, glutamic acid, itaconic acid, levulinic acid, 3-hydroxybutyrolactone, glycerol, sorbitol, and xylitol/arabinitol. The fermentative production of these building block chemicals from renewable feedstocks will become increasingly competitive as petroleum prices increase.

These building block chemicals are molecules with multiple functional groups that possess the potential to be transformed into new families of useful molecules. These twelve building block chemicals can be subsequently converted to a number of high-value bio-based chemicals or materials. For example, succinate can serve as a substrate for transformation into plastics, solvents, and other chemicals currently made from petroleum (Lee et al., 2004; Lee et al., 2005; McKinlay et al., 2007; Wendisch et al., 2006; Zeikus et al., 1999). Many bacteria have been described with the natural ability to produce succinate as a major fermentation product (Table 1). However, complex processes, expensive growth media and long incubation times are often required to produce succinic acid from these naturally occurring succinic acid producing microorganisms.

A variety of genetic approaches have previously been used to engineer *Escherichia coli* strains for succinate production with varying degrees of success (Table 1). In most studies, titers achieved were low and complex medium ingredients such as yeast extract or corn steep liquor was required. *E. coli* strain NZN111 produced 108 mM succinate with a molar yield of 0.98 mol succinate per mol of metabolized glucose (Chatterjee et al., 2001; Millard et al., 1996; Stols and Donnelly, 1997). This strain was engineered by inactivating two genes (pflB encoding pyruvate-formate lyase and ldhA encoding lactate dehydrogenase), and over-expressing two *E. coli* genes, malate dehydrogenase (mdh) and phosphoenol pyruvate carboxylase (ppc), from multicopy plasmids. *E. coli* strain HL27659k was engineered by mutating succinate dehydrogenase (sdhAB), phosphate acetyltransferase (pta), acetate kinase (ackA), pyruvate oxidase (poxB), glucose transporter (ptsG), and isocitrate lyase repressor (iclR). This strain produced less than 100 mM succinate and required oxygen-limited fermentation conditions (Cox et al., 2006; Lin et al., 2005a, 2005b, 2005c; Yun et al., 2005). Analysis of metabolism in silico has been used to design gene knockouts to create a pathway in *E. coli* that is analogous to the native succinate pathway in *Mannheimia succiniciproducens* (Lee et al., 2005, 2006). The resulting strain, however, produced very little succinate. Andersson et al. (2007) have reported the highest levels of succinate production by engineered *E. coli* (339 mM) containing only native genes.

Other researchers have pursued alternative approaches that express heterologous genes in *E. coli*. The *Rhizobium eteloti* pyruvate carboxylase (pyc) was over-expressed from a multicopy plasmid to direct carbon flow to succinate (Gokarn et al., 2000; Vemuri et al., 2002a, 2002b). Strain SBS550MG was constructed by inactivating the isocitrate lyase repressor (iclR), adhE, ldhA, and ackA, and over-expressing the *Bacillus subtilis* citZ (citrate synthase) and *R. etli* pyc from a multi-copy plasmid (Sanchez et al., 2005a). With this strain, 160 mM succinate was produced from glucose with a molar yield of 1.6.

More complex processes have also been investigated for succinate production (Table 1). Many of these processes include an aerobic growth phase followed by an anaerobic production phase. The anaerobic phase is often supplied with carbon dioxide, hydrogen, or both (Andersson et al., 2007; Sanchez et al., 2005a, 2005b; Sanchez et al., 2006; U.S. Pat. No. 5,869,301; Vemuri et al., 2002a, 2002b). In a recent study with a native succinate producer, *A. succiniciproducens*, electrodialysis, sparging with $CO_2$, cell recycling, and batch feeding were combined for the production of succinic acid from glucose at high yield, titer and productivity (Meynial-Salles et al., 2007).

The majority by far of scientific knowledge of *E. coli* is derived from investigations in complex medium such as Luria broth rather than mineral salts medium, using low concentrations of sugar substrates (typically 0.2% w/v; 11 mM) rather than the 5% (w/v) glucose (278 mM) and 10% (w/v) glucose (555 mM) used in the studies reported herein. Large amounts of sugar are required to produce commercially significant levels of product. Previous researchers have described the construction of many *E. coli* derivatives for succinate production in complex medium (Table 1). With complex medium, rational design based on primary pathways has been reasonably successful for academic demonstrations of metabolic engineering. However, the use of complex nutrients for production of bacterial fermentation products increases the cost of materials, the cost of purification, and the cost associated with waste disposal. Use of mineral salts medium without complex media components should be much more cost-effective.

E. coli C grows well in NBS mineral salts medium containing glucose and produces a mixture of lactate, acetate, ethanol and succinate as fermentation products (FIG. 1A; Table 4). In contrast to other studies with E. coli (Table 1), the studies reported herein have focused on the development of strains that are able to convert high level of sugars into succinate using mineral salts medium to minimize the costs of materials, succinate purification, and waste disposal.

One aspect of the invention provides various strains of E. coli that produce succinate at high titers and yields in mineral salts media during simple, pH-controlled, batch fermentations without the need for heterologous genes or plasmids. The inventors have surprisingly identified a number of target genes useful in genetic manipulation of biocatalysts for achieving high efficiency of succinic acid production.

BRIEF SUMMARY OF THE INVENTION

It is an objective of the present invention to provide a method for obtaining a biocatalyst for manufacturing succinic acid using biological feedstocks. The method for obtaining the biocatalysts for succinic acid production from biological feedstocks combines rational genetic manipulations and the process of metabolic evolution.

In generating a biocatalyst for succinic acid production from biological feedstocks, using a rational design derived from our existing knowledge about the microbial metabolic pathways, a set of genes within the bacterial chromosome are inactivated followed by the process of metabolic evolution to select a strain with desirable phenotype.

In one aspect of the present invention, the mutation of the genes in the bacterial chromosome is accomplished without introducing any exogenous genetic material.

In another aspect of the present invention the mutation of the endogenous genes is accomplished either by introducing point mutation or by introducing a stop codon in the open reading frame of the endogenous gene.

In another aspect of the present invention the entire open reading frame of the endogenous gene is deleted from the chromosomal DNA.

In certain preferred embodiments of the invention, the expression of certain endogenous genes is significantly increased. In one aspect of the present invention, the transcription of the endogenous gene is increased by means of introducing certain mutations in the promoter regions of the endogenous genes. In another aspect of the invention, the transcription of the endogenous gene is enhanced by means of relieving the repressive control of the target gene.

In certain aspect of the present invention, an exogenous nucleotide sequence may be introduced to inactivate a target gene for the purpose of selecting a bacterial strain with a mutated gene with desirable phenotype. In the most preferred aspect of the present invention, the exogenous nucleotide sequence introduced into the microbial genome is subsequently removed in a seamless fashion without leaving behind any residual exogenous nucleotide sequence.

The rationally designed genetic manipulations can all be done in a single stage or in multiple stages in which a single genetic change is accomplished at one time. The microbial strain resulting from genetic manipulations may be subjected to metabolic evolution in order to improve the yield, titer and volumetric productivity of the desired organic acid. In the most preferred aspect of the present invention, the rational genetic manipulations are done in stages and the process of metabolic evolution is carried out in between the stages of genetic manipulation.

In one embodiment of the present invention, the spontaneous mutations that occur during the metabolic evolution are identified through sequencing appropriate regions of the chromosomal DNA. In yet another embodiment of the present invention, the mutations that occur during the metabolic evolution are identified by measuring the activities of suspect enzymes.

In one embodiment of the present invention, based on rational designing, one or more of the genes coding for the proteins known to function in the fermentative pathways are inactivated through one or more mutations.

In yet another aspect of the present invention, the genes which are functional homologues of the genes coding for the proteins functioning in the fermentative pathway are inactivated beside the genes coding for the proteins directly involved in the fermentative pathway.

In one embodiment of the present invention the genes functioning within the TCA cycle are genetically manipulated so that there is an increased flow of carbon towards succinic acid production. In one aspect of the present invention, the carbon flow through reductive arm of the TCA cycle is enhanced. In another aspect of the present invention, the carbon flow through oxidative arm of the TCA cycle is genetically manipulated. In another aspect of the present invention, the carbon flow to succinic acid is improved through genetic manipulation of the glyoxalate bypass pathway closely associated with the TCA cycle.

In yet another embodiment of the present invention, the carbon flow from TCA to other metabolic pathways within the cell is blocked so that the carbon pool within the cell is funneled towards succinic acid production.

In another embodiment of the present invention, the carbon flow into the TCA cycle is enhanced through genetic manipulation leading to one or more carboxylating enzymes within the cell. In one aspect of the present invention, the expression of one or more carboxylating enzymes is achieved through the genetic manipulation of the promoter region or by relieving the repression of the gene expression.

In another embodiment of the present invention, the phosphoenol pyruvate pool within the cell is conserved by mutating those genes involved in the carbon uptake pathway requiring phosphoenol pyruvate. In one aspect of the present invention, the phosphotransferase system for carbon uptake is inactivated in order to conserve the phosphoenol pyruvate available for the operation of the TCA cycle.

The present invention illustrates a number of targets that can be genetically manipulated to achieve increased succinic acid production. All these various targets described in the present invention can be genetically manipulated to achieve improved succinic acid production. In the most preferred embodiment, a minimum number of targets are selected for genetic manipulation to achieve a desirable rate of succinic acid production.

In the preferred embodiment of the present invention, the biocatalysts are selected for their ability to produce succinic acid at high titer, yield and volumetric productivity. In the most preferred aspect of the present invention, a biocatalyst capable of producing at least 1.0 mole of succinic acid for every one mole of carbon source consumed is preferred.

In another most preferred embodiment of the present invention, the biocatalyst is selected during metabolic evolution for its ability to produce at least 1.0 mole of succinic acid for every mole of carbon source consumed in a mineral salt medium and coupling the succinic acid production to microbial growth.

In yet another embodiment of the present invention, biocatalysts capable of producing succinic acid using glycerol as a feed stock are provided.

Additional advantages of this invention will become readily apparent from the ensuing detailed description of the invention and the examples provided.

BRIEF DESCRIPTION OF THE DRAWINGS

FIG. 1A shows the standard pathway for fermentation of glucose by E. coli. This pathway has been redrawn from Unden and Kleefeld (2004). Bold arrows represent central fermentative pathways. Crosses represent the gene deletions performed in this study to engineer KJ012 (ldhA, adhE, ackA). Genes and enzymes: ldhA, lactate dehydrogenase; pflB, pyruvate-formate lyase; focA, formate transporter; pta, phosphate acetyltransferase; ackA, acetate kinase; adhE, alcohol dehydrogenase; ppc, phosphoenolpyruvate carboxylase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; icd, isocitrate dehydrogenase; acs, acetyl-CoA synthetase; mgsA, methylglyoxal synthase; poxB, pyruvate oxidase; aldA, aldehyde dehydrogenase; and aldB, aldehyde dehydrogenase. FIG. 1B shows the coupling of ATP production and growth to succinate production in engineered strains of E. coli for a standard pathway for glucose fermentation. Solid arrows connect NADH pools. Dotted arrows connect NAD$^+$ pools. During glycolysis under anaerobic conditions, growth is obligately coupled to the production of ATP and the oxidation of NADH.

FIGS. 2A-2D. Potential carboxylation pathways for succinate production by E. coli. Genes encoding key carboxylating enzymes are shown in bold. FIG. 2A shows the reaction catalyzed by phosphoenolpyruvate (PEP) carboxylase enzyme (PPC). No ATP is produced from the carboxylation of phosphoenolpyruvate (PEP) by the PPC enzyme. This is regarded as the primary route for succinate production by E. coli during glucose fermentation. FIG. 2B shows the NADH-dependent malic enzyme. Energy is conserved during the production of ATP from ADP and PEP by pyruvate kinase (pykA or pykF). Malic enzyme (sfcA) catalyzes an NADH-linked, reductive carboxylation to produce malate. FIG. 2C shows the NADPH-dependent malic enzyme. Energy is conserved during the production of ATP from ADP and PEP by pyruvate kinase (pykA or pykF). Malic enzyme (maeB) catalyzes an NADPH-linked, reductive carboxylation to produce malate. FIG. 2D shows the reaction catalyzed by PEP carboxykinase (PCK). Energy is conserved by the production of ATP during the carboxylation of PEP to produce oxaloacetic acid.

FIG. 7A shows succinate production by KJ060 in AM1 medium. FIG. 7B shows succinate production by KJ073 in AM1 medium. FIG. 7C shows production of malate by KJ071 in NB S medium. Fermentations were inoculated at a level of 33 mg DCW $1^{-1}$. Symbols for FIG. 7A-7C: ○, glucose; ●, succinate; ■, malate; Δ, cell mass.

FIG. 12A shows the relative abundance of transcripts for the genes pck, ppc, sfcA and maeB in the ATCC8739, KJ012, KJ017, KJ060, KJ071 and KJ073 strains of $E.$ $coli.$ FIG. 12B shows the relative abundance of transcripts for the genes related to glucose utilization, namely cyaA, crp, ptsG, galP and glk in the ATCC8739, KJ012, KJ017, KJ060, KJ071 and KJ073 strains of $E.$ $coli.$ FIG. 12C shows the relative abundance of transcripts for the genes ptsI and crr gene in the ATCC8739, KJ012, KJ017, KJ060, KJ071 and KJ073 strains of $E.$ $coli.$ FIG. 13. Anaerobic metabolism of $E.$ $coli$ using the mixed acid fermentation pathway (Bock and Sawers, 1996). The native mixed acid pathway is shown with black arrows. Additional reactions for glucose uptake, carboxylation, and acetyl-CoA synthesis are shown with dotted arrows. Dotted bold arrows indicate new metabolic steps that have been recruited for succinate production in $E.$ $coli$ mutants. Reactions that have been blocked by gene deletions or point mutations are marked with an X. The pck* indicates a novel mutation that de-repressed phosphoenolpyruvate carboxykinase, increasing activity and allowing this enzyme to serve as the primary route for oxaloacetate production. Pyruvate (boxed) appears at two sites in this diagram but exists as a single intracellular pool.

DETAILED DESCRIPTION OF THE PREFERRED EMBODIMENTS

Figure 1A:
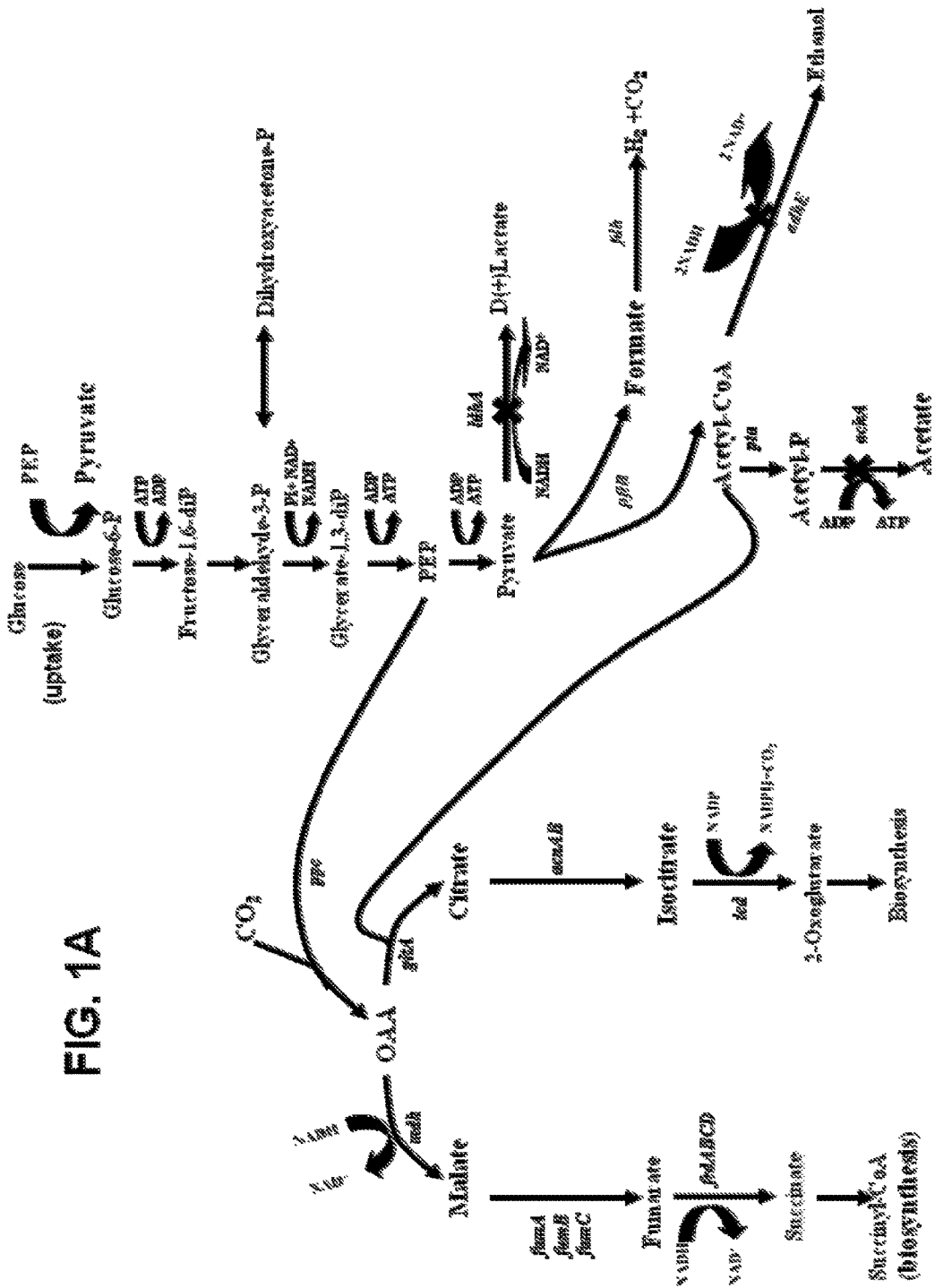
FIGS. 1A-1B. Fermentation of glucose to succinate.

As used in the present invention, the term "titer" means the molar concentration of a particular compound in the fermentation broth. Thus, in the fermentation process for the production of succinic acid according to the present invention, a succinic acid titer of 100 mM would mean that the fermentation broth at the time of measurement contained 100 mMoles of succinic acid per liter of the fermentation broth.

As used in the present invention, the term "yield" refers to the moles of a particular compound produced per mole of the feedstock consumed during the fermentation process. Thus, in the fermentative process for the production of succinic acid using glucose as the feedstock, the term "yield" refers to the number of moles of succinic acid produced per mole of glucose consumed.

As used in the present invention, the term "volumetric productivity" refers to the amount of a particular compound in grams produced per unit of volume per unit of time. Thus a volumetric productivity value of 0.9 g L$^{-1}$ h$^{-1}$ for succinic acid would mean that 0.9 gram succinic acid is accumulated in one liter of fermentation broth during an hour of growth.

The terms "titer," "yield," and "volumetric productivity" as used in this invention also include "normalized titer," "normalized yield," and "normalized volumetric productivity." In the determination of the normalized titer, normalized yield, and normalized volumetric productivity, the volume of the neutralizing reagents added to the fermentation vessel in order to maintain the pH of the growth medium is also taken into consideration.

The terms "genetically engineered" or "genetically modified" as used herein refer to the practice of altering the expression of one or more enzymes in the microorganisms through manipulating the genomic DNA of the microorganisms.

The present invention provides a process for the production of succinic acid in commercially significant quantities from carbon compounds by genetically modified bacterial strains (GMBS). Disclosed in the present invention are the microorganisms suitable for the production of succinic acid through fermentative process.

As used in the present invention, the term "gene" includes the open reading frame of the gene as well as the upstream and downstream regulatory sequences. The upstream regulatory region is also referred as the promoter region of the gene. The downstream regulatory region is also referred as the terminator sequence region.

As used in the present invention, the term "mutation" refers to genetic modifications done to the gene, including the open reading frame, upstream regulatory region and downstream regulatory region. The gene mutations result either an up-regulation or a down-regulation or complete inhibition of the transcription of the open reading frame of the gene. The gene mutations are achieved either by deleting the entire coding region of the gene or a portion of the coding nucleotide sequence or by introducing a frame shift mutation, a missense mutation, and insertion, or by introducing a stop codon or combinations thereof.

As used in this invention, the term "exogenous" is intended to mean that a molecule or an activity derived from outside of a cell is introduced into the host microbial organism. In the case that an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred to as homologous DNA. If the nucleic acid derived from a different microbial species, it is referred to as heterologous DNA. Irrespective of the nature of the DNA, whether it is homologous or heterologous, when introduced into a host cell, the DNA as well as the activity derived from that introduced DNA are referred as exogenous. Therefore, exogenous expression of an encoding nucleic acid of the invention can utilize either or both heterologous and homologous encoding nucleic acid.

The present invention provides GMBS showing impressive titers, high yield and significant volumetric productivity for succinic acid when grown under fermentative conditions in minimal salt medium containing a carbon source as the substrate for fermentation process. The microorganisms of the subject invention can be employed in a single-step production process using various sugars such as hexoses, pentoses, and disaccharides and other carbon compounds such as glycerol.

In the present invention, unique and advantageous combinations of gene mutations have been employed to direct the carbon flow to succinic acid production. In addition, the succinic acid production is coupled with microbial growth which in turn is coupled to cellular ATP level and redox balance.

The term "redox balance" refers to the ability of the cell to maintain the appropriate ratio of NADH to NAD$^+$. In other words, the cells are able to oxidize the NADH so that there is enough NAD$^+$ to oxidize the carbohydrate substrates during the anaerobic fermentative growth. During aerobic growth, the NAD$^+$ pool is regenerated through oxidative phosphorylation involving NADH. However, under anaerobic growth conditions the regeneration of NAD$^+$ pool is achieved only by means of manipulating the flow of carbon through various metabolic pathways inside the cell which could oxidize NADH.

In one embodiment of the present invention, the genetic modifications involve only the manipulation of genes within the native genome of the microorganisms. In that embodiment of the present invention, no exogenous genetic material, such as plasmid-bearing antibiotic resistance genes or any other exogenous nucleotide sequences coding for certain enzyme proteins, is introduced into the bacterial strains used as biocatalysts for succinic acid production.

The recombinant microorganisms suitable for the present invention are derived from a number of bacterial families, preferably from the Enterobacteriaceae family. The suitable microorganisms are selected from the genera *Escherichia, Erwinia, Providencia*, and *Serratia*. The genus *Escherichia* is particularly preferred. Within the genus *Escherichia*, the species *Escherichia coli* is particularly preferred. Any strain of *E. coli* such as *E. coli* B, *E. coli* C, *E. coli* W, or the like is useful for the present invention.

*E. coli* strains capable of producing organic acids in significant quantities are well-known in the art. For example, U.S. Patent Application Publication No. 2009/0148914 provides strains of *E. coli* as biocatalysts for the production of chemically pure acetate and/or pyruvate. U.S. Patent Application Publication No. 2007/0037265 and U.S. Pat. No. 7,629,162 provide derivatives of *E. coli* strain K011 constructed for the production of lactic acid. International Patent Application published under the Patent Cooperation Treaty No. WO 2008/115958 provides a microorganism engineered to produce succinate and malate in minimal mineral salt medium containing glucose as a source of carbon in pH-controlled batch fermentation.

In some other embodiments of the invention, bacteria that can be modified according to the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthro-* bacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Envinia herbicola, Envinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus subtilis, Bacillus licheniformis, Bacillus amyloliqyefaciens, Bacillus coagulans, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri and so forth.

The microorganisms suitable for the practice of present invention can be grown aerobically (in the presence of oxygen) or anaerobically (in the complete absence of oxygen) or microaerobically (with a minimal amount of oxygen supply). In the preferred embodiment of the present invention, the microorganism selected for the production of succinic acid is grown in an anaerobic condition. Alternatively, the microorganisms suitable for the present invention can be grown in a dual-phase growth regime, wherein the microorganism is initially grown in aerobic growth condition to reach a certain level of cell growth before transferring it to the anaerobic growth condition to achieve the production succinic acid in commercially significant quantities. During the dual-phase growth for the production of succinic acid by the microorganisms of the present invention, production and accumulation of the succinic acid occurs during the anaerobic fermentative growth phase.

The present invention combines the technique of specific genetic modifications with the process of metabolic evolution to obtain strains showing high yield, titer and volumetric productivity for succinic acid production under anaerobic growth condition in the mineral salt medium with a carbohydrate substrate.

The microbial strains obtained from genetic manipulations would have the expected genotype for the production of succinic acids. However, their growth rate in the minimal mineral salt medium or the their ability to produce succinic acid at the required yield, titer and volumetric productivity may not allow us to use these genetically modified microorganisms as a biocatalyst for the commercial production of succinic acid through large-scale fermentation processes. Therefore, the genetically modified microbial strains obtained from genetic modifications are subsequently grown in mineral salt medium with a carbohydrate source for several generations to select a clone with very high yield for succinic acid production. This process for the growth-based selection of a clone with the most preferred phenotype is referred to as metabolic evolution. During the metabolic evolution, the genetically modified strain is repeatedly transferred into fresh minimal medium for a period of time to obtain a clone in which the spontaneous mutations that occurred during metabolic evolution result in a clone that exhibits fast cell growth, rapid consumption of different carbon sources, ability to use multiple sugars simultaneously, ability to tolerate toxic chemicals in the carbon source and high production yield and productivity of the desired organic acid coupled with low production of other organic acids.

During the metabolic evolution, attention is paid to select the clones with the desirable phenotypes. A clone resulting from the metabolic evolution showing a very good growth rate in mineral medium supplemented with a carbon source, but that has not improved in the yield of the desired organic acid, is not a desirable clone.

During the process of metabolic evolution using certain selective pressure to force the organism to acquire certain desirable phenotypes, two possible changes could occur. The organism could simply adapt itself to the selective pressure and show a changed phenotype. Alternatively, the organism might undergo certain genetic changes under selective pressure and exhibit a changed phenotype permanently. When there was only an adaptation and there is no genetic change, the organism reverts back to its original phenotype once the selection pressure is relieved. These organisms are referred to as "adapted" organisms. These "adapted" microorganisms would revert back to their original phenotype when the selection pressure is removed. The "adapted" microorganisms have to undergo another fresh round of metabolic evolution under selection pressure to show a changed phenotype. On the other hand, when there is an accompanying genetic change, the changed phenotype will continue to exist even when there is no selection pressure. Metabolic evolution accompanied by a certain genetic change is desirable. The microorganism acquiring a stable genetic change during metabolic evolution can be easily identified by means of growing the microorganism in the original growth medium without any selection pressure for some time before transferring it to the fresh medium with the selection pressure. If these organisms are able to show good growth and the expected phenotype without any lag period, the organism is considered to have acquired a changed genotype during metabolic evolution.

The basis of genetic change gained during the metabolic evolution can be determined by sequencing appropriate regions within the chromosomal DNA of the organism and comparing the sequence data with that of the parent strain. The DNA sequence data can be obtained by means of following the techniques well-known in the art. For example, appropriate regions of the chromosomal DNA of the metabolically evolved strain can be obtained through polymerase chain reaction and the product obtained through polymerase chain reaction can be sequenced by using appropriate sequencing primers.

The wild-type *E. coli* strains obtained from culture collections such as the ATCC (American Type Culture Collection) can be genetically engineered and subsequently metabolically evolved to obtain a strain with an enhanced ability to produce succinic acid in commercially significant amounts.

The genetic manipulations can be done in several different stages accompanied by metabolic evolution in between the stages of genetic manipulations. The genomic manipulations involve either altering the endogenous DNA sequences or completely removing specific DNA sequences from the genomic DNA. The genetic manipulations may also involve inserting a foreign DNA sequence within the genomic DNA sequence of the microorganism. In certain embodiments of the present invention, the genetic manipulations are accomplished by means of removing specific DNA sequences from the genomic DNA of the microorganisms without introducing any foreign DNA. Certain genetic manipulations necessary to inactivate the expression of a gene coding for a particular protein product require an insertion of a foreign DNA sequence into the genome of the microorganism to select a clone with the desired genetic modification. For example, exogenous antibiotic marker genes can be used to insertionally inactivate the endogenous genes and to select the clone with the desired genotype. In one embodiment of the present invention, the introduced exogenous DNA sequences are ultimately removed from the genomic DNA of the microorganism so that the microorganism at the end of the genetic engineering process would have no exogenous DNA in its original genomic DNA. Various genetic engineering techniques necessary for accomplishing the objectives of the preferred embodiment of the present invention have been described in detail in two different scientific publications (Jantama et al., 2008a; Jantama et al., 2008b). Published U.S. Patent Applications US 2007/0037265 and US 2009/0148914 and International patent application No. WO 2008/115958 published under the Patent Cooperation Treaty also describe the genetic engineering techniques useful in practicing various embodiments of this present invention. These scientific publications and patent documents are herein incorporated by reference for the purpose of providing the details for genetic engineering techniques useful for the present invention.

In order to make the microorganism to produce succinic acid in significant quantities, various enzymes involved in a number of microbial metabolic pathways, including the glycolytic pathway, tricarboxylic acid cycle (also known as the Krebs cycle or TCA cycle) and glyoxylate shunt, can be manipulated using a variety of genetic engineering techniques described in the scientific and patent literature cited and incorporated by reference in the paragraph above. The details about various microbial metabolic pathways can be found in the standard biochemistry textbooks such as Principles of Biochemistry by Lehninger and Biochemistry by Lubert Stryer. The Biochemical Pathways poster by G. Michael available from Sigma Chemical Company in St. Louis, Mo., USA also provides details about various biochemical pathways within a bacterial cell.

During the aerobic growth, the microbial carbon metabolism involves glycolysis, the tricarboxylic acid cycle and oxidative phosphorylation. The reduced enzyme co-factors such as NADPH and NADH are regenerated by the operation of oxidative phosphorylation accompanied by ATP production required for cell growth. Under anaerobic growth conditions for the production of succinic acid in the preferred embodiment of the present invention, the regeneration of reduced cofactors NADPH and NADH is accomplished by directing the carbon flow into the tricarboxylic acid cycle and eliminating all of the fermentative pathways for regeneration of $NADP^+$ and $NAD^+$.

Figure 6:
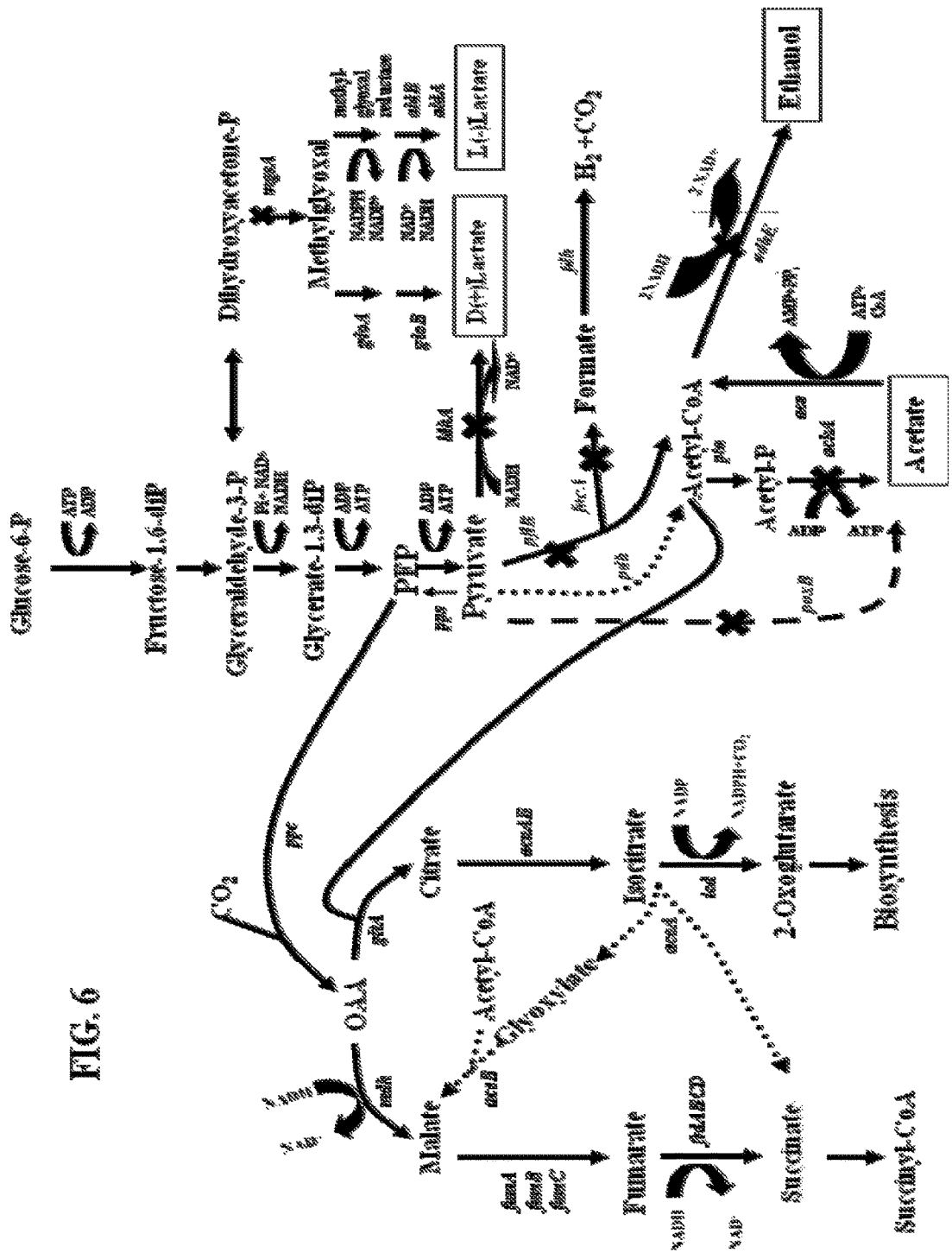
FIG. 6. Standard pathway for the fermentation of glucose-6-phosphate with associated pathways showing the genes that have been deliberately deleted in constructs engineered for succinate production. Solid arrows represent central fermentative pathways. Dashed arrow represents the microaerophilic pathway for the oxidation of pyruvate to acetate. Dotted arrows show pathways including glyoxylate bypass that normally function during aerobic metabolism. Boxed crosses represent the three initial gene deletions (ldhA, adhE, ackA) that were used to construct KJ012 and KJ017. Plain crosses mark additional genes that were deleted during the construction of KJ017 derivatives: KJ032 (ldhA, adhE, ackA, focA, pflB), KJ070 (ldhA, adhE, ackA, focA, pflB, mgsA), and KJ072 (ldhA, adhE, ackA, focA, pflB, mgsA, poxB). Genes and enzymes: ldhA, lactate dehydrogenase; focA, formate transporter; pflB, pyruvate-formate lyase; pta, phosphate acetyltransferase; ackA, acetate kinase; adhE, alcohol dehydrogenase; ppc, phosphoenolpyruvate carboxylase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; mgsA, methylglyoxal synthase; gloAB, glyoxylase I and II; poxB, pyruvate oxidase; aceA, isocitrate lyase; aceB, malate synthase; acnAB, aconitase; and acs, acetyl-CoA synthetase.
Figure 9:
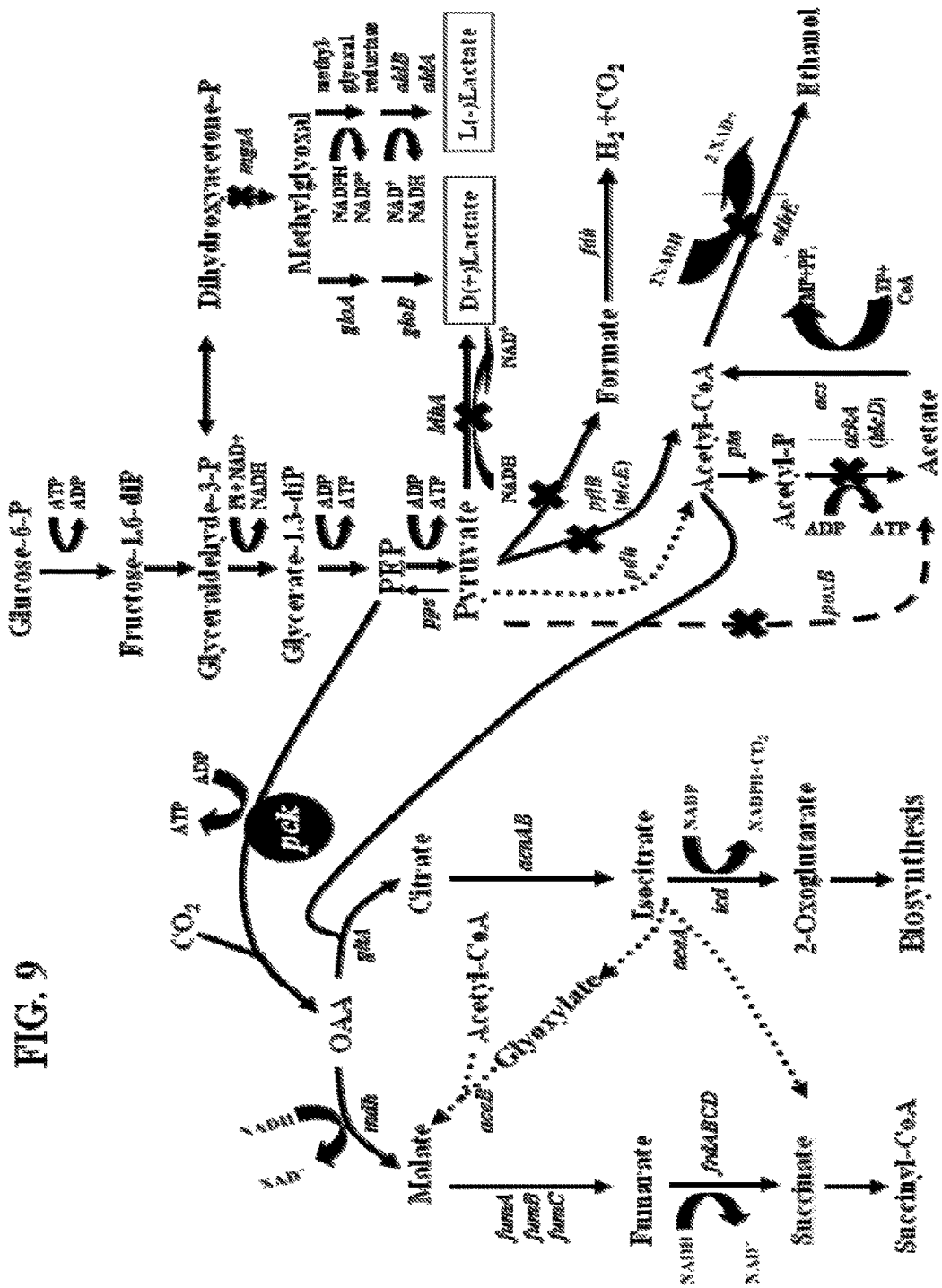
FIG. 9. Succinate production from glucose-6-phosphate in KJ073. The pck gene encoding phosphoenolpyruvate carboxykinase, the primary carboxylating enzyme involved in succinate production in this study, is shown in reverse type. Solid arrows indicate reactions expected to be functional during anaerobic fermentation of glucose. Solid crosses indicate deleted genes. Boxed crosses represent key deletions used to construct initial strain for succinate production, KJ017 (ldhA, adhE, ackA). The dashed line represents oxidation of pyruvate to acetate by PoxB, a process that is typically functional only under microaerophilic conditions. The dotted lines indicate reactions that are primarily associated with aerobic metabolism. Genes and enzymes: ldhA, lactate dehydrogenase; pflB, pyruvate-formate lyase; focA, formate transporter; pta, phosphate acetyltransferase; ackA, acetate kinase; adhE, alcohol dehydrogenase; pck, phosphoenolpyruvate carboxykinase; pdh, pyruvate dehydrogenase complex; gltA, citrate synthase; mdh, malate dehydrogenase; fumA, fumB, and fumC, fumarase isozymes; frdABCD, fumarate reductase; fdh, formate dehydrogenase; icd, isocitrate dehydrogenase; acs, acetyl-CoA synthetase; mgsA, methylglyoxal synthase; poxB, pyruvate oxidase; aldA, aldehyde dehydrogenase; and aldB, aldehyde dehydrogenase. The tdcE gene (pyruvate formate-lyase, homologous to pflB) and tcdD gene (propionate kinase, homologous to ackA) are shown in parenthesis and are typically expressed during threonine degradation.

Depending on the type of organic acid preferred, the metabolic pathways are specifically engineered so that the microorganism produces a particular organic acid of our choice. The microorganisms are capable of synthesizing a number of organic acids including lactic acid, acetic acid, malic acid, pyruvic acid, formic acid and succinic acid. Thus, in developing a biocatalyst for the production of succinic acid, the pathways for production of acetic acid, lactic acid, pyruvic acid, and formic acid are blocked and the carbon flow to succinic acid production is facilitated through manipulating one or more enzymes involved in the carbon metabolism within the cell. The list of the enzymes that are active in the microbial fermentative pathway which can be manipulated using the known genetic engineering techniques includes, but is not limited to: isocitrate synthetase (aceA); malate synthase (aceB); the glyoxylate shunt operon (aceBAK); acetate kinase-phosphotransacetylase (ackA-pta); aconitase hydratase 1 and 2 (acnA and acnB); acetyl-CoA synthetase (acs); citrate lyase (citDEF); alcohol dehydrogenase (adhE); citrate synthase (citZ); fumarate reductase (frd); lactate dehydrogenase (ldh); malate dehydrogenase (mdh); aceBAK operon repressor (iclR); phosphoenol pyruvate carboxylase (pepC); pyruvate formate lyase (pfl); pyruvate oxidase (poxB); pyruvate carboxy kinase (pck); and pyruvate carboxylase (pyc) (FIGS. 1, 6, and 9).

Glycolysis of carbon sources results in the production of phosphoenol pyruvate (PEP). PEP is further metabolized by the mixed acid pathway. As used in the present invention, the term "mixed acid pathway" refers to the flow of carbon from PEP through both the tricarboxylic acid cycle and various fermentative pathways that are operational under anaerobic conditions. Under anaerobic conditions, at least four different fermentative pathways for the metabolism of pyruvate are recognizable. The pyruvate may be reduced to lactate using NADH and thereby producing $NAD^+$ to maintain the redox balance of the cell necessary for the continuous metabolism of the carbon source. The acetyl-CoA derived from pyruvate may also be reduced to produce ethanol accompanied by the oxidation of NADH to produce $NAD^+$. Pyruvate may also be converted into formate or acetate as shown in FIG. 1A.

Within the TCA cycle, two different arms are recognized. In one arm of the TCA cycle, referred as the oxidative arm, encompassing the carbon flow from oxaloacetate to succinic acid through isocitrate, $NADP^+$ is utilized to oxidize isocitrate with the resulting formation of NADPH. In the other arm of the TCA cycle, referred as the reductive arm of the TCA cycle, encompassing the flow of carbon from oxaloacetate to succinic acid through malate and fumarate, NADH is oxidized to produce $NAD^+$ and thereby help the cell to maintain the redox balance.

In one embodiment of the present invention, the carbon flow from PEP through fermentative pathways is prevented by means of inactivating the genes coding for the enzymes involved in the fermentative pathway. The enzymes suitable for blocking the carbon flow through fermentative pathway include ldhA, pflB, adhE, pta, ackA, and poxB. The elimination of one or more of these genes is expected to reduce the carbon flow from PEP through the fermentative pathway. Inactivation of all of these six genes is expected to block the carbon flow through fermentative pathway totally. In another aspect of the present invention, the mgsA gene coding for the methylglyoxal synthase (mgsA) responsible for the conversion of methylglyoxal to lactic acid is inactivated besides the inactivation of six other genes involved in the fermentative pathway.

In yet another embodiment of the present invention, the functional homologues of the genes involved in the fermentative pathway are also inactivated besides inactivating the genes well-known to be involved in one or another fermentative pathway. A propionate kinase with acetate kinase activity is encoded by the tdcD gene which is produced only for the degradation of threonine. However, during the anaerobic growth with 10% (w/v) glucose, the expression of tdcD could functionally replace ackA. In addition, the adjacent tdcE gene in the same operon is similar to pflB and encodes α-ketobutryate formate lyase with pyruvate formate-lyase activity. In one aspect of the present invention, the tdcDE genes are inactivated to prevent the entry of carbon into fermentative pathway and to assure the flow of carbon into the TCA cycle.

In another embodiment of the present invention, besides blocking the carbon flow through fermentative pathways, the carbon flow within the TCA cycle is altered so that there is carbon flow directed towards the production of succinic acid. In one aspect of the present invention the manipulation of carbon flow within the TCA cycle is achieved by means of up-regulating the expression of one or more genes. In yet another aspect of the present invention, one or more genes functioning within the TCA cycle may be inactivated to facilitate an increased carbon flow to succinic acid.

In a preferred aspect of the present invention, the gene mdh encoding for malate dehydrogenase is up-regulated to improve the conversion of malate to fumarate and succinate. The flow of the carbon from oxaloacetate to succinic acid through malate and fumarate is referred as the reductive arm of the TCA cycle. The flow of carbon through this reductive arm of the TCA cycle from oxaloacetic acid to succinic acid would consume two moles of NADH for every mole of succinic acid produced and thereby help in maintaining the redox balance of the cell under anaerobic condition. In other words, the up-regulation of mdh would help in regenerating the $NAD^+$ required to maintain the redox balance of the cell. The up-regulation of mdh gene expression can be achieved by means of replacing the native promoter for the mdh gene with some other strong promoter sequence, or alternatively by means of mutating the promoter region of the mdh gene so that there is an increase in transcription of the mdh gene. Alternatively, additional copies of the mdh gene can be added to the strain. In a preferred embodiment of the present invention, the up-regulation of mdh gene expression is achieved by means of genetically manipulating its promoter region.

In the regular operation of the TCA cycle, succinic acid is produced through the operation of the oxidative of arm of the TCA cycle. The flow of carbon from oxaloacetate to succinic acid through citrate, cis-aconitate, isocitrate, α-ketoglutarate, and succinyl-CoA is referred as the oxidative arm of the TCA cycle. The succinic acid can also be produced through the operation of glyoxylate bypass. During the operation of glyoxylate bypass, by the action of isocitrate lyase, succinate and glyoxylate are produced from isocitrate. The succinate thus produced from the operation of the oxidative arm of the TCA cycle or from the operation of glyoxylate bypass can be acted upon by succinate dehydrogenase (sdh) to yield fumaric acid and then malic acid. Therefore, in yet another embodiment of the present invention, gene inactivation can be used to prevent the dehydrogenation of the succinate in order to increase the intracellular succinic acid production.

In yet another aspect of the present invention, the carbon flow through the glyoxylate bypass can be manipulated to achieve an increase in succinic acid production. Isocitrate lyase enzyme catalyzes the cleavage of isocitrate to glyoxylate and succinate. Isocitrate lyase is coded by the aceBAK operon. Isocitrate lyase activity is suppressed by the iclR gene. In other words, the expression of the iclR gene prevents the operation of glyoxylate shunt. In one aspect of the present invention, the iclR gene is inactivated beside the inactivation of the genes involved in the fermentative metabolism.

In yet another embodiment of the present invention, besides preventing the operation of the fermentative pathways and increasing the flow of carbon within the TCA cycle towards succinic acid production through genetic manipulations, the outward carbon flow from the TCA cycle to other metabolic pathways can also be blocked through genetic means to increase succinic acid production. For example, the flow of carbon from the TCA cycle into amino acid metabolism can be blocked in order to improve the carbon flow towards succinic acid. The aspartate aminotransferase gene (aspC) transfers the amino group from glutamic acid to oxaloacetic acid in the synthesis of aspartic acid and thereby facilitates the outward flow of carbon from the TCA cycle. In one aspect of the present invention, the inactivation of the aspC gene is followed to block the outward flow of carbon from the TCA cycle in order to improve the carbon flow from oxaloacetate towards succinic acid production either through the oxidative or reductive arm of the TCA cycle.

The other outward flow of carbon from the TCA cycle occurs from malate. The decarboxylation of malate by malic enzyme (sfcA) results in the production of pyruvate. In one aspect of the present invention, the gene coding for the sfcA gene is inactivated to curtail the outward flow of carbon from the TCA cycle. In yet another aspect of the present invention, both the aspC and sfcA genes are inactivated to prevent the outward flow of carbon from the TCA cycle so as to enhance succinic acid accumulation.

In yet another aspect of the present invention, the outward flow of carbon from the TCA cycle is prevented by inactivating the citrate lyase gene (citDEF) responsible for the cleavage of citric acid into oxaloacetate and acetate.

Besides discovering that inactivating the genes involved in the fermentative pathways and their functional analogues, preventing the carbon flow out of the TCA cycle and regulating the carbon flow towards succinic acid within the TCA cycle, could improve the succinic acid yield in the microbial fermentation, the present invention has also surprisingly discovered that the growth-coupled succinic acid yield can further be improved by genetic manipulation of carboxylating enzymes within the microbial cells. While characterizing the changes that occurred during metabolic evolution through conducting genetic and enzyme analysis, the inventors of the present invention have unexpectedly discovered that the carboxylating enzymes within the cells could be yet another target for genetic manipulation to achieve an improved succinic acid yield.

The glycolytic intermediates phosphoenol pyruvate (PEP) and pyruvic acid can be carboxylated to improve the carbon flow into the TCA cycle. Under normal conditions, carbon entry into the TCA cycle is accomplished by the action of citrate synthase, which combines the acetyl-CoA derived from pyruvate with oxaloacetate, an intermediate in the TCA cycle, to produce citric acid. By means of improving the efficiency of one or more carboxylating enzymes present within the cell, it is possible to carboxylate phosphoenol pyruvate and pyruvate to oxaloacetate, a TCA cycle intermediate (FIG. 2). The oxaloacetate thus produced from the carboxylating reaction can be further reduced through the reductive arm of the TCA cycle to produce succinic acid.

The present invention provides a method for manipulating the carboxylating enzymes present within the cell as a method to increase the succinic acid yield during anaerobic fermentative growth. It is well-known in the art that by means of introducing pyruvate carboxylase (pyc) from an exogenous source it is possible to carboxylate pyruvate to oxaloacetic acid. The microbial strains well-suited for genetic manipulation such as E. coli do not have the pyc gene. The pyc genes derived from other bacterial species such as Rhizopium elti and Lactobacillus lacti can be introduced into the genetically modified E. coli strains to improve succinic acid production.

Four different endogenous carboxylating enzymes are known in E. coli. Two of these enzymes are responsible for carboxylating phosphoenol pyruvate and two other enzymes are responsible for the carboxylation of pyruvate derived from phosphoenol pyruvate by the action of the pyruvate kinase enzyme. The enzyme phosphoenol pyruvate carboxylase (ppc) carboxylates phosphoenol pyruvate to oxaloacetate, which could enter into the reductive arm of the TCA cycle to produce succinate. The second carboxylating enzyme, phosphoenol pyruvate carboxykinase (pck), also carboxylates phosphoenol pyruvate to produce oxaloacetate, but normally catalyzes the reverse reaction as it is not expressed in the presence of glucose. The two other carboxylating enzymes, namely NADH-linked maleic enzyme (maeB) and the NADPH-linked maleic enzyme (maeA/sfcA), carboxylate pyruvic acid to malic acid. The maeB and sfcA enzymes carboxylate the pyruvate derived from phosphoenol pyruvate by the action of pyruvate kinase.

Any one of the four carboxylating enzymes present in the cell can be genetically manipulated to increase its enzymatic activity in order to improve the carbon flow from glycolytic cycle intermediates into the TCA cycle. Of the four native carboxylating enzymes present in E. coli, the PPC-catalyzed reaction is strongly favored. Energy contained in PEP is lost in this reaction with the release of inorganic phosphate. The other three carboxylating enzymes, namely pck, maeA and sfcA (maeB), are not expected to function during fermentative growth using glucose as the substrate as these three carboxylating enzymes are repressed by glucose. These three carboxylating enzymes are thought to function in the reverse direction during gluconeogenesis when the cells are oxidatively metabolizing organic acids.

In this invention, the inventors have surprisingly discovered that gluconeogenic PEP carboxykinase (PCK) can be genetically manipulated to improve the flow of carbon into the TCA cycle. The recruitment of pck as the primary pathway for succinic acid production in E. coli was surprising and is in contrast to our current understanding of the functional role of pck. Previous studies have shown that increased expression of E. coli and Actinobacillus. succinogenes pck had no effect on succinate production (Kim et al., 2004; Millard et al., 1996). A recent study has demonstrated that increased expression of E. coli pck is detrimental to growth in minimal medium, decreasing the growth rate, the rate of glucose metabolism, and the yield of succinate (Kwon et al., 2008). The advantage in improving the activity of pck lies in the fact that this enzyme, while carboxylating phosphoenol pyruvate to oxaloacetate, results in the production of a molecule of ATP for every molecule of oxaloacetate produced. An increase in the ATP yield would increase the growth rate of the cells.

The comparative analysis of phosphoenol pyruvate carboxykinase activity in a number of E. coli strains constructed during this invention has revealed that the increase in PCK enzyme activity during metabolic evolution results from an increase in the transcriptional activity of the pck gene. In those strains showing an improvement in cell growth-coupled succinate production, there is an increase in the abundance of the pck transcript. In fact, the results of the present invention have established a positive correlation between an increase in pck transcript level and an increase in PCK enzyme activity and growth-coupled succinic acid production.

The recruitment of the native gluconeogenic pck for fermentative succinate production can be achieved by any mutation that positively affects the transcription of the pck gene. An increase in the level of PCK activity can be achieved by means of expressing the pck gene in a multi-copy plasmid with a native promoter or any other promoter sequence which is known to increase the gene's expression. Another way to increase the expression of the pck gene within the cell is to integrate additional copies of the pck gene using transposons. In another embodiment of the present invention, the native promoter of the pck gene can be replaced by some other promoter elements known to enhance the level of activity. Increased expression of the pck gene can also be achieved either by mutation in the promoter region of the gene or by genetic manipulation of the regulatory elements that are known to interact with the promoter region of the pck gene. The gene coding for a regulator protein of the pck gene can be mutated or deleted or overexpressed in some way in order to increase the expression of the pck gene. The results of the present invention have indicated that a single point mutation (G to A transition at position −64 relative to the ATG start codon of the pck gene) could increase the transcription of the pck gene, accompanied by a corresponding increase in phosphoenol pyruvate carboxykinase enzyme activity. A similar increase in pck gene expression can also be achieved by genetically manipulating the genes coding for the proteins known to regulate the expression of the pck gene. For example, Cra protein has been shown to activate the expression of the pck gene in E. coli (Saier and Ramseier, 1996). Similarly the csrA system (comprising csrA, csrB, csrC, csrD, uvrY or barA) has also been reported to regulate the level of pck and other genes involved in glucose metabolism by altering mRNA stability (Babitzke and Romeo, 2007; Pernestig et al., 2003; Suzuki, K. et al., 2002).

Yet another genetic approach of the present invention to increase growth-coupled succinic acid production during the anaerobic fermentation process is concerned with the conservation of energy expended in sugar uptake by the biocatalysts.

The microorganisms take up the sugars through a set of transporter proteins located on the cytoplasmic membrane (Jojima et al., 2010). The microbial sugar transporters fall within three major categories. The largest group of sugar transporters in the bacteria is known as ATP binding cassette (ABC) transporters. As the name implies, the ABC transporters require a molecule of ATP for every molecule of sugar transported into the bacterial cell. XylFGH is an ABC transporter for the transport of xylose, a pentose sugar, into the cell. AraFGH is an ABC transporter for the transport of arabinose, yet another pentose sugar.

The second type of bacterial sugar transporters are grouped under the Major Facilitator Super family (MFS). Within the MFS sugar transporters, two different categories of transporter are recognized. MFS includes $H^+$-linked symporters, Na⁺-linked symporters-antiporters and uniporters. The uniporters are simple facilitators for sugar transport and require a molecule of ATP for every molecule of sugar transported into the cell. The trans-membrane protein Glf in *E. coli* is an example of uniporter. The H⁺ symporters require a proton and a molecule of ATP for every sugar molecule transported into the cell. The GalP protein in *E. coli* is a symporter for the transport of galactose, a hexose sugar, into the cell. GalP is a very well-characterized symporter with 12 trans-membrane loops. GalP is also reported to have the ability to transport glucose across the cell membrane. AraE is a proton-linked symporter for the transport of arabinose across the cell membrane. Similarly, XylE protein is a proton-linked symporter for the transport of xylose.

The third sugar transporter primarily responsible for the uptake of hexose sugars such as glucose is known as the phosphoenolpyruvate: carbohydrate phosphotransferase system (PTS). Transfer of the phosphoryl group from phosphoenolpyruvate (PEP) catalyzed by PTS drives the transport and phosphorylation of glucose and results in the formation of glucose 6-phosphate and pyruvic acid inside the cell. PTS-generated pyruvic acid is apparently not recycled to PEP under aerobic culture conditions where glucose is the sole source of carbon. Rather, pyruvate is oxidized by way of the tricarboxylic acid cycle to carbon dioxide. Thus, for the transport of every single molecule of glucose, a molecule of PEP is consumed. In terms of cellular bioenergetics, the transport of sugars through PTS is an energy-intensive process. Therefore, in cells growing anaerobically, where there is a need to conserve the phosphoenolpyruvate content within the cells for the production of industrially useful chemicals, it is desirable to replace the PTS with some other sugar transporters not requiring a molecule of PEP for every molecule of sugar transported into the cell.

Besides these genes directly involved in the glycolysis, tricarboxylic acid cycle and glyoxylate shunt of microbial metabolic pathways, genetic manipulation of the genes involved in the uptake of carbon compounds useful as a source of energy for the synthesis of succinic acid can also be manipulated, either to enhance the carbon uptake or to enhance the efficiency of energy utilization in organic acid production. For example the elimination of the glucose uptake by the phosphotransferase system (PTS) could help in reducing the energy spent on glucose uptake into the microbial cell. The energy conserved by manipulating the PTS can be channeled to improve the efficiency of organic acid production. The phosphotransferase system genes ptsH and ptsG can be manipulated to conserve the energy in glucose uptake and thereby improve the efficiency of succinic acid production by the microorganism. Thus, by mining the data available in the area of microbial metabolic pathways, one can delete a set of genes so as to block most of the metabolic pathways and channel the carbon flow to the production of succinic acid with great efficiency.

PTS is comprised of two cytoplasmic components, namely EI and HPr, and a membrane-bound component, EII. *E. coli* contains at least 15 different EII complexes. Each EII component is specific to a sugar type to be transported and contains two hydrophobic integral membrane domains (C and D) and two hydrophilic domains (A and B). These four domains together are responsible for the transport and phosphorylation of sugar molecules. EI protein transfers the phosphate group from PEP to HPr protein. EII protein transfers the phosphate group from phosphorylated HPr protein to the sugar molecule.

EI is encoded by the ptsI gene. HPr is encoded by the ptsH gene. The glucose-specific EII complex of enteric bacteria consists of two distinct proteins, namely EIIA$^{Glc}$, encoded by the gene crr and the membrane-associated protein EIICB-$^{Glc}$, encoded by the gene ptsG. The PTS-mediated sugar transport can be inhibited by means of deleting one of these genes coding for the proteins associated with PTS. Functional replacement of PTS by alternative phosphoenolpyruvate-independent uptake and phosphorylation activities is one of the genetic approaches for achieving significant improvements in product yield from glucose and productivity for several classes of metabolites.

With the inhibition the PTS-mediated glucose uptake, other systems for glucose uptake can be activated to assure the continued availability of glucose within the cell for the production of the industrially useful chemicals. For example, the glf gene coding for glucose permease, a glucose uniporter, has been shown to substitute for the loss of PTS-mediated glucose uptake. Similarly, the over-expression of the galP and glk genes is reported to enhance the glucose uptake and phosphorylation in the pts⁻ strain of *E. coli*. GalP is a symporter for the uptake of galactose, a hexose sugar. GalP has been reported to transport glucose in the pts⁻ strain. The significance of GalP-mediated glucose uptake is evidence by the fact that the inactivation of the galP gene in the pts⁻ mutant is found to be lethal (Yi et al., 2003). Glk is necessary to achieve the phosphorylation of the glucose molecule before it can enter into glycolysis. The expression of the GalP protein in the pts⁻ strain can be achieved either by expressing an exogenous gene under a constitutive promoter or by means of relieving the repression of the galP expression through mutations in genes coding for the repressor of the galP gene such as galS and galR.

As described above, succinic acid production using microbial catalysts can be achieved by means of genetic manipulation accompanied by metabolic evolution. The genetic changes that occur during metabolic evolution can be identified through biochemical and genetic analysis. The present invention has surprisingly discovered that mutations occurring in the genes for the phosphotransferase system and carboxylating enzymes present within the cell could positively contribute to an increase in succinic acid production. These newly discovered targets for genetic manipulation can be combined with the other targets in the glycolytic, tricarboxylic acid and fermentative pathways in several different ways to generate biocatalysts with high efficiency for succinic acid production. It is also highly desirable to identify a set of a minimal number of target genes for genetic manipulation in order to achieve the best succinic acid producing strains.

The invention also provides genetic approaches to enhance glycerol utilization in succinic acid production. The glycerol uptake is mediated by the protein coded by the glpF gene. Once taken into the cell, glycerol is oxidized by the protein coded by the gldA gene to produce dihydroxyacetone (DHA). The DHA is phosphorylated to dihydroxyacetone phosphate (DHAP) by the proteins coded by the dhaKLM operon. The phosphorylation of DHA to DHAP by the proteins coded by dhaKLM is dependent on the availability of the phosphoenol pyruvate (PEP) pool. Since the phosphorylation of DHA requires PEP, it depletes the PEP available for PCK, which directs the flow of carbon from PEP into the TCA cycle in order to assure proper redox balance required to achieve high succinic acid yield. The present invention has that preventing the flow of glycerol through the gldA and dhaKLM pathways in a bacterial cell having increased PCK enzymatic activity could enhance the succinic acid yield using glycerol as the carbon source. The present invention has also surprisingly discovered that further improvement in succinic acid yield using glycerol as the carbon source can be achieved by means of preventing the carbon flow through fermentative pathways in a bacterial cell with improved PCK enzyme activity and deletions in the gldA gene and dhaKLM operon.

The following examples are provided as way of illustrating the present invention. These examples in no way limit the scope of this invention. A person experienced in the field of industrial microbiology would be able to practice the present invention in several different embodiments without violating the spirit of the present invention.

EXPERIMENTAL SECTION

General Remarks

Strains, Media and Growth Conditions

New derivatives of E. coli C (ATCC 8739) were developed for succinate production using a unique combination of gene deletions coupled with growth-based selection. The various strains of E. coli developed in the present invention, designated NRRL B-50271, NRRL B-50272, NRRL B-50273, NRRL B-50276, NRRL B-50278, NRRL B-50279, NRRL B-50280 and NRRL B-50281, have been deposited with the Agricultural Research Culture Collection, 1815 N. University Street, Peoria, Ill. 61604, USA) under the Budapest Treaty on Mar. 17, 2009 with accession numbers as shown in Table 2.

The microbial organism of the present invention can be grown in a number of different culture media well-known in the field of microbiology. For example, the wild-type and mutant strains of E. coli are grown in Luria-Bertani (LB) medium containing 1% (w/v) tryptone, 0.5% (w/v) yeast extract, and 0.5% (w/v) NaCl. For the commercial production of the organic acid using a fermentative process involving genetically modified microorganisms as a biocatalyst, a minimal mineral salt medium supplemented with a carbon source is preferred. The use of a minimal mineral salt medium as opposed to a rich medium like LB medium reduces the cost for the production of organic acids on a commercial scale.

The minimal mineral mediums suitable for the present invention include NBS medium (Causey et al., 2007) and AM1 medium (Martinez et al., 2007). The NBS medium contains 1 mM betaine, 25.72 mM $KH_2PO_4$, 28.71 mM $K_2HPO_4$, 26.50 mM $(NH_4)2HPO_4$, 1 mM $MgSO_4.7H_2O$, 0.1 mM $CaCl_2.2H_2O$, 0.15 mM thiamine HCl, 5.92 µM $FeCl_3.6H_2O$, 0.84 µM $CoCl_2.6H_2O$, 0.59 µM $CuCl_2.2H_2O$, 1.47 µM $ZnCl_2$, 0.83 µM $Na_2MoO_4.2H_2O$, and 0.81 µM $H_3BO_3$. The AM1 medium contains 1 mM betaine, 19.92 mM $(NH_4)2HPO_4$, 7.56 mM $NH_4H_2PO_4$, 1.5 mM $MgSO_4.7H_2O$, 1.0 mM betaine KCl, 8.88 µM $FeCl_3.6H_2O$, 1.26 µM $CoCl_2.6H_2O$, 0.88 µM $CuCl_2.2H_2O$, 2.20 µM $ZnCl_2$, 1.24 µM $Na_2MoO_4.2H_2O$, 1.21 µM $H_3BO_3$ and 2.50 µM $MnCl_2.4H_2O$. The trace elements are prepared as a 1000× stock and contain the following components: 1.6 g/L $FeCl_3$, 0.2 g/L $CoCl_2.6H_2O$, 0.1 g/L $CuCl_2$, 0.2 g/L $ZnCl_2.4H_2O$, 0.2 g/L $NaMoO_4$, 0.05 g/L $H_3BO_3$, and 0.33 g/L $MnCl_2.4H_2O$.

The mineral medium for microbial production of organic acid is supplemented with a carbon source. The carbon sources useful in the present invention include but are not limited to pentose sugars like xylose, hexose sugars like glucose, fructose, and galactose and glycerol. The carbon source can also be satisfied by providing a combination of different sugars, such as a combination of glucose and xylose. The carbon source can also be derived from a hydrolysis of starch or lignocellulose. The hydrolysis of complex carbohydrates such as starch and lignocellulose can be achieved either by using thermo-chemical conversion processes or enzymatic methods well-known in the art. The preferred carbon source for the industrial production of organic acid using microbial fermentation is lignocellulosic hydrolysate derived from the hydrolysis of agricultural or forestry wastes. The lignocellulosic hydrolysate may further be fractionated to yield a hexose-enriched and a pentose-enriched fraction and those fractions can serve as the source of carbon for the commercial production of organic acids using a microbial fermentation process. The lignocellulosic hydrolysate can further be detoxified to remove certain chemicals such as furfural which are found to be toxic to a number of microbial organisms above certain concentrations.

Bacterial strains, plasmids, and primers used in this study are listed in Tables 3, 7, 9, 14 and 15 and are explained in detail at the appropriate places in the specification below. During strain construction, cultures were grown aerobically at 30, 37, or 39° C. in Luria broth (10 g $l^{-1}$ Difco tryptone, 5 g $l^{-1}$ Difco yeast extract and 5 g $l^{-1}$ NaCl) containing 2% (w/v) glucose or 5% (w/v) arabinose. No genes encoding antibiotic resistance, plasmids, or foreign genes are present in the final strains developed for succinate production. However, during the early stages of construction of the different strains, various antibiotic resistance markers were used. The antibiotics, such as ampicillin (50 mg $l^{-1}$), kanamycin (50 mg $l^{-1}$), or chloramphenicol (40 mg $l^{-1}$), were added as needed for the antibiotic selection process.

Fermentations

Seed cultures and fermentations were grown at 37° C., 100 rpm in NBS or AM1 mineral salts medium containing glucose, 100 mM $KHCO_3$ and 1 mM betaine HCl. In some experiments, corn steep liquor was used. It is a byproduct from the corn wet-milling industry. When compared to yeast extract and peptone, it is an inexpensive source of vitamins and trace elements.

For fermentative succinate production, strains were grown without antibiotics at 37° C. in NBS mineral salts medium (Causey et al., 2004) supplemented with 10% (w/v) glucose and 100 mM potassium bicarbonate unless stated otherwise. Pre-inocula for fermentation were grown by transferring fresh colonies into a 250 ml flask (100 ml NBS medium, 2% glucose). After 16 h (37° C., 120 rpm), this culture was diluted into a small fermentation vessel containing 300 ml NBS medium (10% glucose, 100 mM potassium bicarbonate) to provide an inoculum of 0.033 g cell dry wt (CDW) $l^{-1}$.

Since the accumulation of organic acids in the growth medium tends to decrease the pH of the medium, it is necessary to add appropriate neutralizing agents as required to the culture medium. The pH of the culture vessel can be continuously monitored using a pH probe, and appropriate base can be added to maintain the pH of the growth medium around neutral pH. The bases suitable for maintaining the pH of the microbial culture include, but are not limited to, NaOH, KOH, $NH_4SO_4$, $Na_2CO_3$, $NaHCO_3$, and $NH_4CO_3$. The bases suitable for this purpose can be used alone or in combination.

In certain experiments, fermentations were automatically maintained at pH 7.0 by adding base containing additional $CO_2$ (2.4 M potassium carbonate in 1.2 M potassium hydroxide). Subsequently, pH was maintained by adding a 1:1 mixture of 3M $K_2CO_3$ and 6N KOH. Fermentation vessels were sealed except for a 16 gauge needle which served as a vent for sample removal. Anaerobiosis was rapidly achieved during growth with added bicarbonate serving to ensure an atmosphere of $CO_2$.

Genetic Methods

Methods for chromosomal deletions, integration, and removal of antibiotic resistance genes have been previously described (Datsenko and Wanner, 2000; Grabar et al., 2006; Posfai et al., 1997; Zhou et al., 2006).

In the construction of bacterial strains used in the present invention, chromosomal genes were deleted seamlessly without leaving segments of foreign DNA as described previously (Jantama et al., 2008a, 2008b; Zhang et al., 2007). Red recombinase technology (Gene Bridges GmbH, Dresden, Germany) was used to facilitate chromosomal integration. Plasmids and primers used during construction are listed in Tables 3, 7, 9, 14, and 15. Plasmids and primers used in the construction of the strains KJ012, KJ017, KJ032, KJ060, KJ070, KJ071, KJ072, KJ073, and SZ204 are summarized in Table 3. Sense primers contain sequences corresponding to the N-terminus of each targeted gene (boldface type) followed by 20 bp (underlined) corresponding to the FRT-kan-FRT cassette. Anti-sense primers contain sequences corresponding to the C-terminal region of each targeted gene (boldface type) followed by 20 bp (underlined) corresponding to the cassette. Amplified DNA fragments were electroporated into E. coli strains harboring Red recombinase (pKD46). In resulting recombinants, the FRT-kan-FRT cassette replaced the deleted region of the target gene by homologous recombination (double-crossover event). The resistance gene (FRT-kan-FRT) was subsequently excised from the chromosome with FLP recombinase using plasmid pFT-A, leaving a scar region containing one FRT site. Chromosomal deletions and integrations were verified by testing for antibiotic markers, PCR analysis, and analysis of fermentation products. Generalized P1 phage transduction (Miller, 1992) was used to transfer the ΔfocA-pflB::FRT-kan-FRT mutation from strain SZ204 into strain KJ017 to produce KJ032.

Deletion of FRT Markers in the adhE, ldhA, and focA-pflB Regions

The strategy used to make sequential gene deletions and remove the FRT markers from the adhE, ldhA and focA-pflB loci has been described previously (Datsenko and Wanner, 2000; Grabar et al., 2006; Jantama et al., 2008b; Zhang et al., 2007). Plasmid pLOI4151 was used as a source of a cat-sacB cassette and Red recombinase (pKD46) was used to facilitate double-crossover, homologous recombination events. Chloramphenicol resistance was used to select for integration. Growth with sucrose was used to select for loss of sacB. With this approach, successive deletions were constructed to produce derivatives of KJ079 that eliminated all FRT sites. Primers and plasmids used in the removal of FRT markers from the adhE, ldhA and focA-pflB loci are listed in Table 3.

To remove the FRT site in the ΔadhE region, hybrid primers (WMadhEA/C) for the ΔadhE::FRT target region were designed to contain approximately 50 bp of homology to the 5' and 3' regions of the ΔadhE::FRT site and 20 bp corresponding to the cat-sacB gene from pLOI4151. These primers were used for PCR amplification of the cat-sacB cassette using pLOI4151 as a template. The resulting PCR product was used to replace the FRT site in the ΔadhE region with a cat-sacB cassette by a double-crossover, homologous recombination event with selection for resistance to chloramphenicol, to produce TG200.

The adhE gene and surrounding sequence were amplified from E. coli C using up/downadhE primers. The PCR product containing ychE'-adhE-ychG' (3.44 kb) was cloned into pCR2.1-TOPO, yielding pLOI4413. A second set of primers (IO-adhEup/down) was used to amplify the inside-out product with pLOI4413 as a template and Pfu polymerase to yield a blunt-ended product in which a 2.6 kb internal segment of adhE sequence was deleted. This inside-out PCR product was kinase-treated and self-ligated, resulting in pLOI4419. The PCR product amplified from pLOI4419 (up/downadhE primers) was used to replace the cat-sacB cassette in TG200 with the desired chromosomal sequence by another double, homologous recombination event, with sucrose selection for loss of sacB. The resulting strain was designated TG201 (KJ079 with the FRT removed from the ΔadhE region).

The FRT sites in the ΔldhA and Δ(focA-pflB) regions were removed in a manner analogous to that used to delete the adhE::FRT site. Additional primer sets (ldhAA/C and TO-ldhAup/down) used to remove the FRT site in ΔldhA are included in Table 7 together with the corresponding plasmids (pLOI4430 and pLOI4432). Strain TG202 was produced by replacing this region in TG201 with the PCR product from pLOI4151 (WMldhAA/C primers). The cat-sacB cassette in TG202 was replaced with the PCR product from pLOI4432 (ldhAA/C primers) with sucrose selection for loss of sacB to produce TG203. Primer sets (upfocA/MidpflA and IO-ycaOup/IO-midpflAdown) and corresponding plasmids (pLOI4415 and pLOI4421) used to remove the FRT site in Δ(focA-pflB) are included in Table 7. Strain TG204 was produced by replacing this region in TG203 with the PCR product from pLOI4151 (WMpflBA/C primers). The cat-sacB cassette in TG204 was replaced with the PCR product from pLOI4421 (upfocA/MidpflA primers) with sucrose selection for loss of sacB to produce KJ091. KJ091 is a derivative of KJ073 in which all FRT sites have been removed from the ΔadhE, ΔldhA and ΔfocA-pflB regions of the chromosome.

Removal of FRT Site in ackA Region and Construction of citF, sfcA, and Pta-ackA Gene Deletions To eliminate the FRT site in the ackA region of KJ073, plasmids containing sequences of the desired mutation were constructed as follows. E. coli C genomic DNA was used as the template for PCR amplification of ackA with the JMackAF1/R1 primers that bind approximately 200 bp upstream and downstream of the ackA gene. The linear product was cloned into pCR2.1-TOPO (Invitrogen, Carlsbad, Calif.) to produce pLOI4158. Plasmid pLOI4158 was then used as a template for inside-out PCR with JMack-Aup1/down1 primers and Pfu polymerase to yield a blunt-ended product that lacks an 808-bp internal segment of ackA. The PacI-flanked cat-sacB cassette (SmaI/SfoI fragment from pLOI4162) was then ligated into the blunt PCR product to produce pLOI4159. Plasmid pLOI4159 served as a template for PCR amplification (JMackAF1/R1 primers). This PCR product was used to replace the FRT site in the ackA region of KJ073 by double-crossover homologous recombination, with selection for chloramphenicol resistance. The resulting clone was designated KJ076.

Plasmid pLOI4159 was also digested with PacI to remove the cat-sacB cassette and self-ligated to produce pLOI4160, retaining the 18-bp translational stop sequence. Plasmid pLOI4160 served as a PCR template (JMackAF1/R1 primers). This amplified fragment was used to replace the cat-sacB cassette in KJ076 by double-crossover homologous recombination with selection for loss of sacB. After removal of pKD46 by growth at elevated temperature, the resulting strain was designated KJ079. In this strain, the deleted region has been replaced by the 18-bp translational stop sequence.

The strategy used above to remove the FRT site from the ackA region was employed to make sequential deletions of citF, sfcA and pta-ackA and to replace the deleted regions with the 18-bp translational stop sequence. Additional primer sets (citFup/down and citF2/3) used to construct the citF deletion are included in Table 7 together with the corresponding plasmids (pLOI4629, pLOI4630, and pLOI4631). The resulting strain was designated KJ104.

The sfcA gene was deleted from strains KJ104 and KJ110, resulting in strains designated KJ119 and KJ122, respectively. Additional primer sets (sfcAup/down and sfcA1/2) used to construct the sfcA deletions are included in Table 7 together with the corresponding plasmids (pLOI4283, pLOI4284, and pLOI4285).

The ackA-pta operon (including the synthetic translational stop sequence) was deleted from KJ122 to produce strain KJ134. Additional primer sets (ackAup/ptadown and ackA2/pta2) used to construct this deletion are included in Table 7 together with the corresponding plasmids (pLOI4710, pLOI4711, and pLOI4712). Strain KJ134 does not contain any FRT sites or foreign genes.

Figure 8:
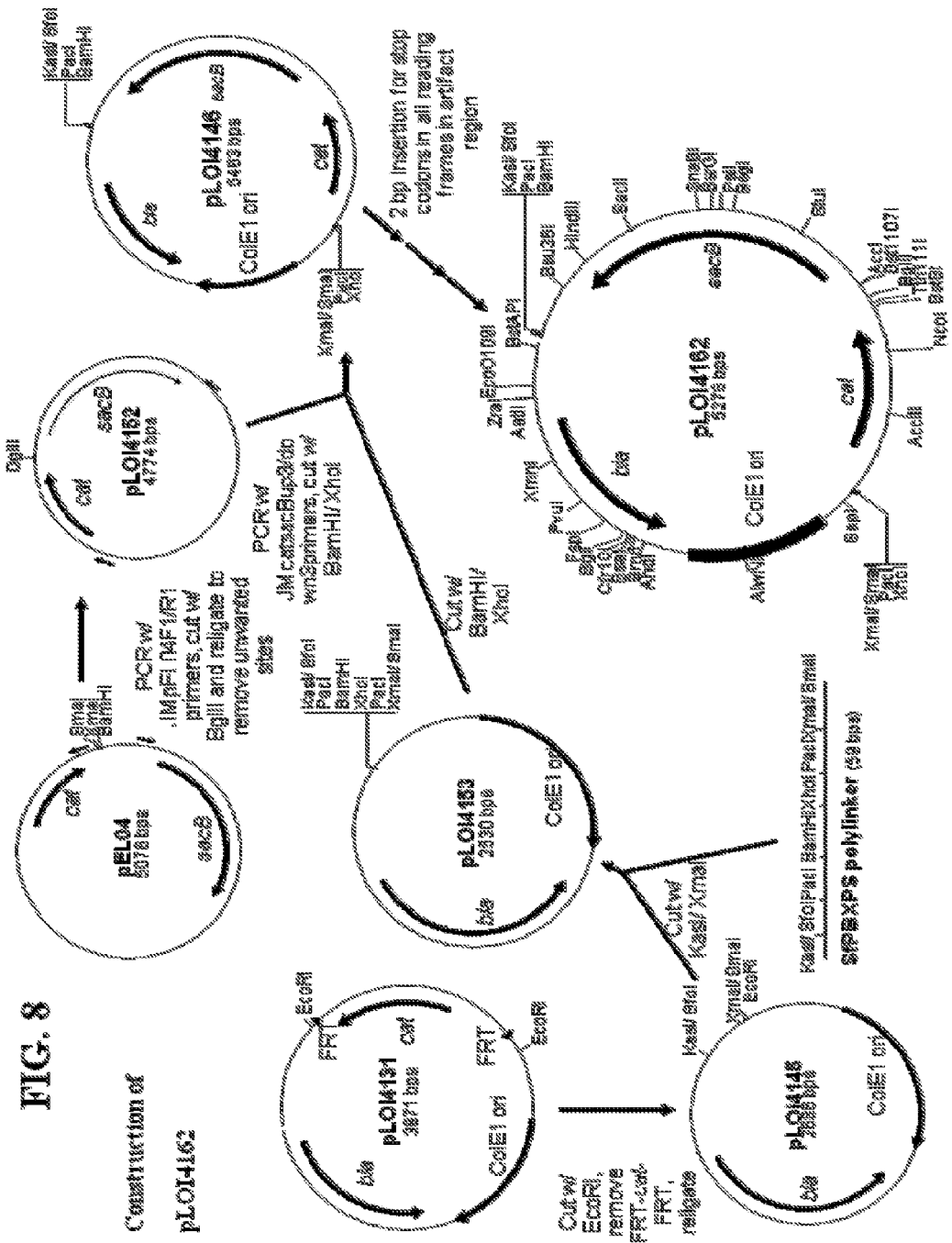
FIG. 8. Steps involved in the construction of plasmid pLOI4162. Short solid arrows associated with pEL04 and pLOI4152 represent primers used for DNA amplification.

Construction of pLOI4162 Containing a Cat-sacB Cassette for Markerless Gene Deletions To facilitate the sequential deletion of chromosomal DNA, plasmid pLOI4162 (FIG. 8) was constructed with a removable cat-sacB cassette and the option to include an 18-bp segment of synthetic DNA with stop codons in all reading frames. This plasmid is composed of synthetic sequences and parts of plasmids pLOI2228 (Martinez-Morales et al., 1999), pLOI2511 (Underwood et al., 2002), and pEL04 (Lee et al., 2001; Thomason et al., 2005). Using pEL04 as a template, inside-out PCR was performed with the JMpEL04F1/R1 primers to eliminate unwanted SmaI and BamHI sites between the cat and sacB genes. The amplified product was digested with BglII (within both primers) and self-ligated to produce pLOI4152. Plasmid pLOI4131 was constructed by ligation of the FRT-cat-FRT fragment (Klenow-treated BanI, ClaI) from pLOI2228 into compatible sites of pLOI2511 (Klenow-treated NheI, ClaI). Plasmid pLOI4131 was subsequently digested with EcoRI and self-ligated to remove the FRT-cat-FRT fragment to produce pLOI4145, retaining single KasI and XmaI sites. A polylinker segment (SfPBXPS) was prepared by annealing complementary oligonucleotides (SfPBXPSsense and SfPBXPScomp). After digestion with KasI and XmaI, this segment was ligated into corresponding sites of pLOI4145 to produce pLOI4153. The modified cat-sacB cassette in pLOI4152 was amplified by PCR using the JMcatsacBup3/down3 primer set. After digestion with BamHI and XhoI, this cassette was ligated into corresponding sites of pLOI4153 to produce pLOI4146. To create an 18-bp region (5'GCCTAATTAATTAATCCC3') (SEQ ID NO: 1) with stop codons in all six reading frames, pLOI4146 was digested with PacI and self-ligated to produce pLOI4154 (not shown), removing the cat-sacB cassette. Two additional bases (T and A) were inserted between the SfoI and PacI sites of pLOI4154 using mutagenic primers (JM4161sense/comp) and linear plasmid amplification to produce pLOI4161. Finally, the PacI digested fragment from pLOI4146 containing the cat-sacB cassette was ligated into the PacI-digested site of pLOI4161 to produce pLOI4162 (GenBank Accession No. EU531506).

Deletion of mgsA and poxB Genes

A modified method was developed to delete *E. coli* chromosomal genes using a two-step homologous recombination process (Thomason et al., 2005). With this method, no antibiotic genes or scar sequences remain on the chromosome after gene deletion. In the first recombination, part of the target gene was replaced by a DNA cassette containing a chloramphenicol resistance gene (cat) and a levansucrase gene (sacB). In the second recombination, the cat-sacB cassette was replaced with native sequences omitting the region of deletion. Cells containing the sacB gene accumulate levan during incubation with sucrose and are killed. Surviving recombinants are highly enriched for loss of the cat-sacB cassette.

A cassette was constructed to facilitate gene deletions. The cat-sacB region was amplified from pEL04 (Lee et al., 2001; Thomason et al., 2005) by PCR using the JMcatsacB primer set (Table 3), digested with NheI, and ligated into the corresponding site of pLOI3421 to produce pLOI4151. The cat-sacB cassette was amplified by PCR using pLOI4151 (template) and the cat-up2/sacB-down2 primer set (EcoRV site included in each primer), digested with EcoRV, and used in subsequent ligations.

The mgsA gene and neighboring 500 bp regions (yccT'-mgsA-helD', 1435 bp) were amplified using primer set mgsA-up/down and cloned into the pCR2.1-TOPO vector (Invitrogen) to produce plasmid pLOI4228. A 1000-fold diluted preparation of this plasmid DNA served as a template for inside-out amplification using the mgsA-1/2 primer set (both primers within the mgsA gene and facing outward). The resulting 4958 bp fragment containing the replicon was ligated to the amplified, EcoRV-digested cat-sacB cassette from pLOI4151 to produce pLOI4229. This 4958 bp fragment was also used to construct a second plasmid, pLOI4230 (phosphorylation and self-ligation). In pLOI4230, the central region of mgsA is absent (yccT'-mgsA'-mgsA"-hel).

After digestion of pLOI4229 and pLOI4230 with XmnI (within the vector), each served as a template for amplification using the mgsA-up/down primer set to produce the linear DNA fragments for integration step I (yecT'-mgsA'-cat-sacB-mgsA"-helD') and step II (yccT'-mgsA'-mgsA"-helD'), respectively. After electroporation of the step I fragment into KJ060 containing pKD46 (Red recombinase) and 2 h of incubation at 30° C. to allow expression and segregation, recombinants were selected for chloramphenicol (40 mg l$^{-1}$) and ampicillin (20 mg l$^{-1}$) resistance on plates (30° C., 18 h). Three clones were chosen, grown in Luria broth with ampicillin and 5% w/v arabinose, and prepared for electroporation. After electroporation with the step II fragment, cells were incubated at 37° C. for 4 h and transferred into a 250-ml flask containing 100 ml of modified LB (100 mM MOPS buffer added and NaCl omitted) containing 10% sucrose. After overnight incubation (37° C.), clones were selected on modified LB plates (no NaCl; 100 mM MOPS added) containing 6% sucrose (39° C., 16 h). Resulting clones were tested for loss of ampicillin and chloramphenicol resistance. Construction was further confirmed by PCR analysis. A clone lacking the mgsA gene was selected and designated KJ070.

The poxB gene was deleted from KJ071 in a manner analogous to that used to delete the mgsA gene. Additional primer sets (poxB-up/down and poxB-1/2) used to construct the poxB deletion are included in Table 3 together with the corresponding plasmids (pLOI4274, pLOI4275, and pLOI4276). The resulting strain was designated KJ072.

Construction of Gene Deletions in tdcDE and aspC

The tdcDE gene and neighboring 1000 bp regions (tdcG'-tdcFED-tdcC', 5325 bp) were amplified using tdcDEup/down primers and cloned into the pCR2.1-TOPO vector to produce plasmid pLOI4515. A 1000-fold diluted preparation of this plasmid DNA served as a template for inside-out amplification using the tdcDEF7/R7 primers (both primers within the tdcDE gene and facing outward). The resulting 6861 bp fragment containing the replicon was ligated to the amplified, SmaI/SfoI-digested cat-sacB cassette from pLOI4162 (JMcatsacBup3/down3 primers) to produce pLOI4516. This 6861 bp fragment was also used to construct a second plasmid, pLOI4517 (kinase treated, self-ligation) containing a deletion of tcdD and tdcE. The PCR fragments amplified from pLOI4516 and pLOI4517 (tdc-DEup/down primers) were used to replace the tdcDE region in KJ091. The resulting clones were tested for loss of ampicillin and chloramphenicol resistance.

The aspC gene was deleted from KJ104 in a manner analogous to that used to delete the tdcDE gene. Additional primer sets (aspCup/down and aspC1/2) used to construct the aspC deletion are included in Table 7 together with the corresponding plasmids (pLOI4280, pLOI4281, and pLOI4282). The resulting strain was designated KJ110. Neither KJ098 nor KJ110 contain any intervening sequence within the respective deleted regions (tdcDE and aspC).

Construction of Gene Deletions in gldA and dhaKLM

The E. coli strains XZ464, XZ465, and XZ466 were derived from the E. coli strain XZ632 using the genetic methods described above. The relevant characteristic of the E. coli strains XZ464, XZ465, XZ466 and XZ632 are provided in the Table 15.

Real-Time RT-PCR Analysis

Real-time RT-PCR was used to measure message RNA levels as described previously (Jarboe et al., 2008). Cells were grown in NBS medium with 5% or 10% glucose and harvested during mid-log growth by swirling in a dry ice/ethanol bath, followed by centrifugation and storage at −80° C. in RNALater (Qiagen, Valencia Calif.) until purification. RNA purification was performed with RNeasy Mini columns (Qiagen), followed by digestion with DNaseI (Invitrogen). Reverse transcription with Superscript II (Invitrogen, Carlsbad Calif.) used 50 ng total RNA as template. Real-time PCR was performed in a Bio-Rad iCycler with SYBR Green RT-PCR mix (Bio-Rad, Hercules, Calif.). RNA was checked for genomic DNA contamination by running an RT-PCR in the absence of reverse transcription. Transcript abundance was estimated using genomic DNA as a standard and expression levels were normalized by the birA gene, a transcriptional repressor (Jarboe et al., 2008). RT-PCR primers used for pck and birA are listed in Table 3.

Sequencing of pck Region

In order to know whether there was any mutation in the pck gene of KJ073, the coding region and promoter region (about 800 bp in front of coding region) of the pck gene in both KJ012 and KJ073 were amplified by PfuUltra High Fidelity DNA Polymerase (Stratagene, Wilmington, Del.). Primer set pck-FIR was used to amplify the coding region through the transcriptional terminator (Table 9). Primer set pck-2/3 was used to amplify the promoter region. DNA sequencing was provided by the University of Florida Interdisciplinary Center for Biotechnology Research (with Applied Biosystems autosequencers).

Metabolic Evolution

Cells from the pH controlled fermentations were serially transferred at 24 hours to encourage metabolic evolution though growth-based selection. The inoculum, approximately 1/100 of the volume of new media, was added directly to pre-warmed, fresh media to a starting $OD_{550}$ of 0.05. Clones with improved fermentation characteristics were isolated. The metabolic evolution strategy was applied to improve the yield of succinate production.

Analyses

Cell growth: cell mass was estimated from the optical density at 550 nm (OD 1.0=333 mg of cell dry weight $l^{-1}$) with a Bausch & Lomb Spectronic 70 spectrophotometer.

The production of the organic acid by the genetically engineered microorganism can be confirmed and quantified by using appropriate techniques well-known in the art. For example, HPLC techniques can be used to measure the quantity of the organic acid produced by the selected clone. The HPLC technology is also helpful in determining the purity of the organic acid produced by the selected clones. Organic acids and sugars were determined by using high performance liquid chromatography (Grabar et al., 2006; Zhang et al., 2007).

Succinic acid and other organic acids present in the fermentation broth were analyzed on an Agilent 1200 HPLC apparatus with a Bio-Rad Aminex HPX-87H column. Bio-Rad Microguard Cation $H^+$ was used as a guard column. The standards for HPLC analysis were prepared in 0.008N sulfuric acid. The HPLC column temperature was maintained at 50° C. Sulfuric acid at 0.008N concentration was used as a mobile phase at the flow rate of 0.6 ml/min. Quantification of various components was done by measuring their absorption at 210 nm.

Enzyme Assay

Cells were harvested by centrifugation (8,000×g for 5 min at 4° C.) during mid-log growth, washed with cold 100 mM Tris-HCl (pH 7.0) buffer, and resuspended in the same buffer (1 ml). After cellular disruption using a Fast Prep-24 (MP Biomedicals, Solon, Ohio), preparations were clarified by centrifugation (13,000×g for 15 min). Protein was measured by the BCA method (Pierce, Rockford, Ill.) using bovine serum albumin as a standard.

PEP carboxylase activity was measured as described by Canovas and Kornberg (1969). The reaction mixture contained 100 mM Tris-HCl buffer (pH 8.0), 10 mM $MgCl_2$, 1 mM DTT, 25 mM NaHCO$_3$, 0.2 mM NADH, 20 U malate dehydrogenase, and crude extract. The assay mixture was incubated for 15 min at 37° C. to activate the enzyme, after which the reaction was started by addition of 10 mM PEP.

PEP carboxykinase activity was measured as described by Van der Werf et al., (1997). The reaction mixture contained 100 mM IVIES buffer (pH 6.6), 10 mM MgCl$_2$, 75 mM NaHCO$_3$, 5 mM MnCl$_2$, 50 mM ADP, 1 mM DTT, 0.2 mM NADH, 20 U malate dehydrogenase, and crude extract. The reaction was started by addition of 10 mM PEP.

Malic enzyme activity (carboxylation direction) was measured as described by Stols and Donnelly (1997). The reaction mixture contained 100 mM Tris-HCl buffer (pH 7.5), 25 mM NaHCO$_3$, 1 mM MnCl$_2$, 1 mM DTT, 0.2 mM NADH, and crude extract. The reaction was started by addition of 25 mM pyruvate. This assay method was unsuitable for measurement of SfcA activity in wild-type *E. coli* due to the presence of lactate dehydrogenase.

The activity of β-galactosidase was measured as described by Miller (1992). In all assays, one unit of activity represents the amount of enzyme required to oxidize or reduce 1 nmol of substrate per minute.

Example 1

Construction of KJ073 Strain for Succinate Production

In the construction of a strain suitable for succinic acid production in minimal medium containing 5% glucose, both a rational design approach and metabolic evolution were followed. By inspection of FIG. 1 illustrating the generally accepted standard fermentation pathways for *E. coli*, a rational design for the metabolic engineering of strains producing succinate was devised in which insertional inactivations were made in genes encoding the terminal steps for all alternative products: lactate (ldhA), ethanol (adhE) and acetate (ackA). Results from this metabolic engineering by rational design were completely unexpected. The KJ012 (ΔldhA::FRT ΔadhE::FRT ΔackA::FRT) strain resulting from the insertional inactivation of the ldhA, adhE and ack genes grew very poorly under anaerobic conditions in mineral salts medium containing 5% glucose (278 mM) and produced acetate instead of succinate as the primary fermentation product. Counter to expectations from rational design, succinate remained as a minor product. Molar yields of succinate based on metabolized glucose were unchanged as a result of these mutations. The succinate yield was found to be 0.2 mol succinate per mol glucose both for the parent and KJ012 strains during fermentation in NBS mineral salts medium containing 5% glucose. We confirmed that NBS mineral salts medium contains all mineral nutrients needed for the growth of KJ012 by incubating under aerobic conditions (aerobic shaken flask; 5% glucose). In aerobic shaken flasks, cell yields for KJ012 were 5-fold higher than during anaerobic growth and 75% that of the *E. coli* C (parent) during anaerobic growth. These results also confirmed that all central biosynthetic pathways remain functional in KJ012.

When complex nutrients were present (Luria broth), fermentative succinate production by KJ012 increased 20-fold as compared to KJ012 in minimal salts medium and the molar yield for succinate increased 3.5-fold. Clearly, rational design based on primary pathways is better suited to academic demonstrations or to design processes intended for use with complex nutrients.

The basis for the poor growth, poor succinate production, and increase in acetate production by KJ012 during anaerobic metabolism in mineral salts medium is unknown. These are unexpected consequences that resulted from metabolic engineering using rational design based on standard pathway charts. In minimal medium, rational designs for metabolic engineering are clearly not predictable. The resulting strain, KJ012, was inferior to the parent in growth and no better than the parent for succinate production. KJ012 (ΔldhA::FRT ΔadhE::FRT ΔackA::FRT) grew poorly in comparison to the parent *E. coli* C, exhibited lower rates of succinate production, and provided no better molar yields (Table 4).

Despite these results, serial transfer of this strain was tried as a method to co-select improved growth and succinate production based on the following rationale. The primary pathway for glucose fermentation into succinate (FIG. 1A and FIG. 2A) is generally thought to use phosphoenolpyruvate carboxylase (ppc) for the carboxylation step (Unden and Kleefeld, 2004; Fraenkel, 1996; Keseler et al., 2005; Millard et al., 1996; Gottschalk, 1985; Karp et al., 2007). This carboxylating enzyme does not conserve the high energy phosphate in phosphoenolpyruvate and reduces the net ATP available for growth. Alternative pathways for succinate production can be envisioned using the repertoire of known *E. coli* genes that could increase ATP yields and could thereby increase growth (FIG. 1A; FIGS. 2B, 2C and 2D). However, none of these alternative routes have been shown to function for succinate production during fermentation with native strains of *E. coli*. Key enzymes in these alternative routes are repressed by glucose and are normally active during gluconeogenesis. Typically, levels of these gluconeogenic enzymes vary inversely with the availability of glucose and other metabolites (Goldie and Sanwal, 1980a; Wright and Sanwal, 1969; Sanwal and Smando, 1969a) and function in the reverse direction, decarboxylation (Keseler et al., 2005; Oh et al., 2002; Kao et al., 2005; Stols and Donnelly, 1997; Samuelov et al., 1991; Sanwal, 1970a; Delbaere et al., 2004; Goldie and Sanwal, 1980b; Sanwal and Smando, 1969b; Sanwal 1970b).

The key enzyme for one of these, NADH-linked malic enzyme (sfcA) (FIG. 2B), has been demonstrated to be capable of increasing succinate production in *E. coli* but required overexpression from a plasmid to do so (Stols and Donnelly, 1997). However, none of these alternative pathways would be expected to be functional in native strains of *E. coli* or KJ012 during anaerobic growth with high levels of glucose. Serial transfers of KJ012 with selection for improved growth offered an opportunity to select for mutational activation of alternative routes for succinate production (FIG. 1B) that maintained redox balance and increased ATP yields.

Figure 3A:
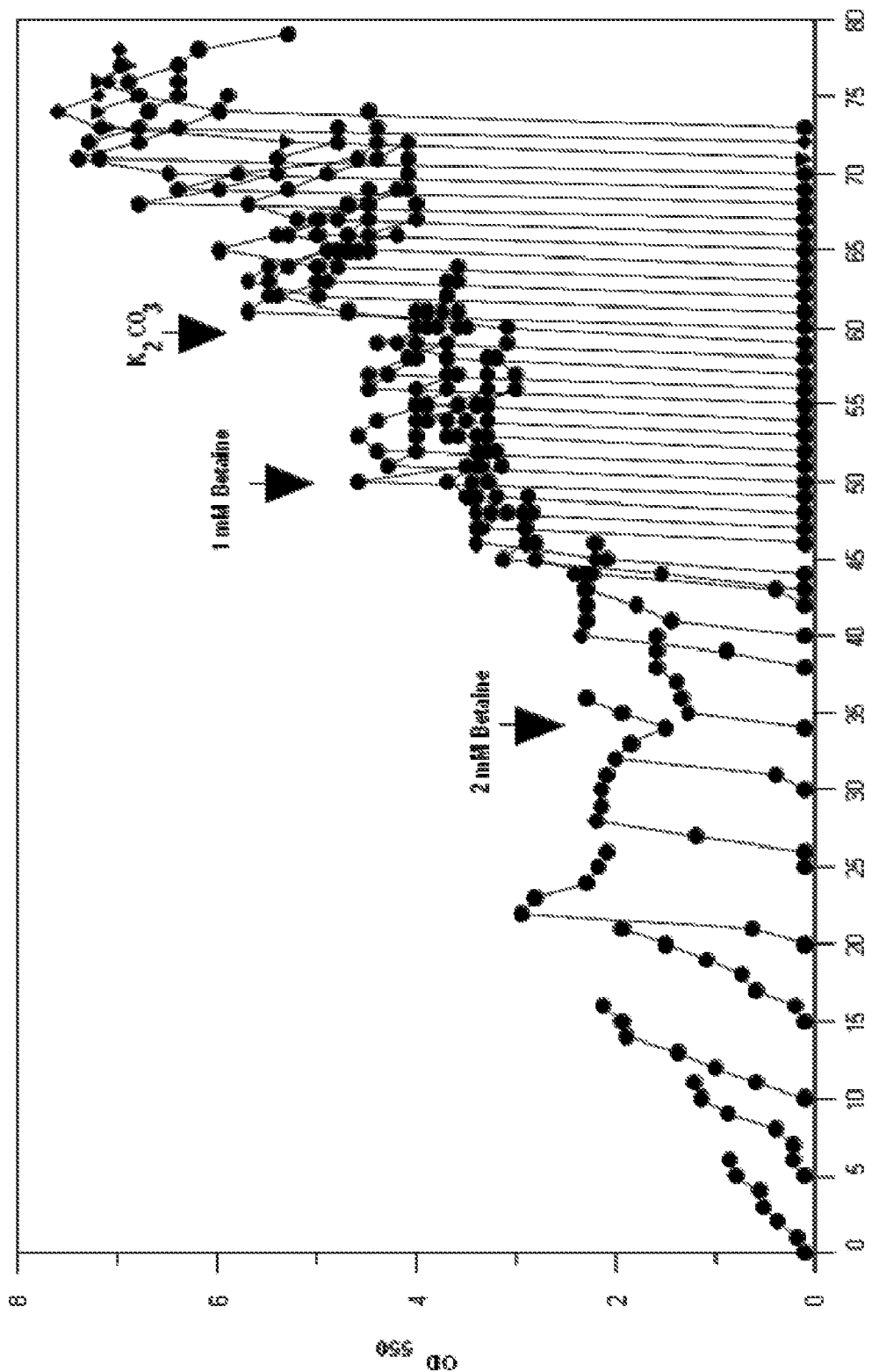
FIGS. 3A-3C. Growth during metabolic evolution of KJ012 to produce KJ017, KJ032, and KJ060. Strain KJ012 was sequentially transferred in NBS medium containing 5% (w/v) (FIG. 3A) and 10% (w/v) (FIG. 3B) glucose, respectively to produce KJ017. After deletion of focA and pflB, the resulting strain (KJ032) was initially subcultured in medium supplemented with acetate (FIG. 3C). Acetate levels were decreased and subsequently eliminated during further transfers to produce KJ060. Broken line represents fermentation by KJ017 without acetate, added for comparison. Symbol: ●=optical density at $OD_{550\ nm}$.
Figure 4A:
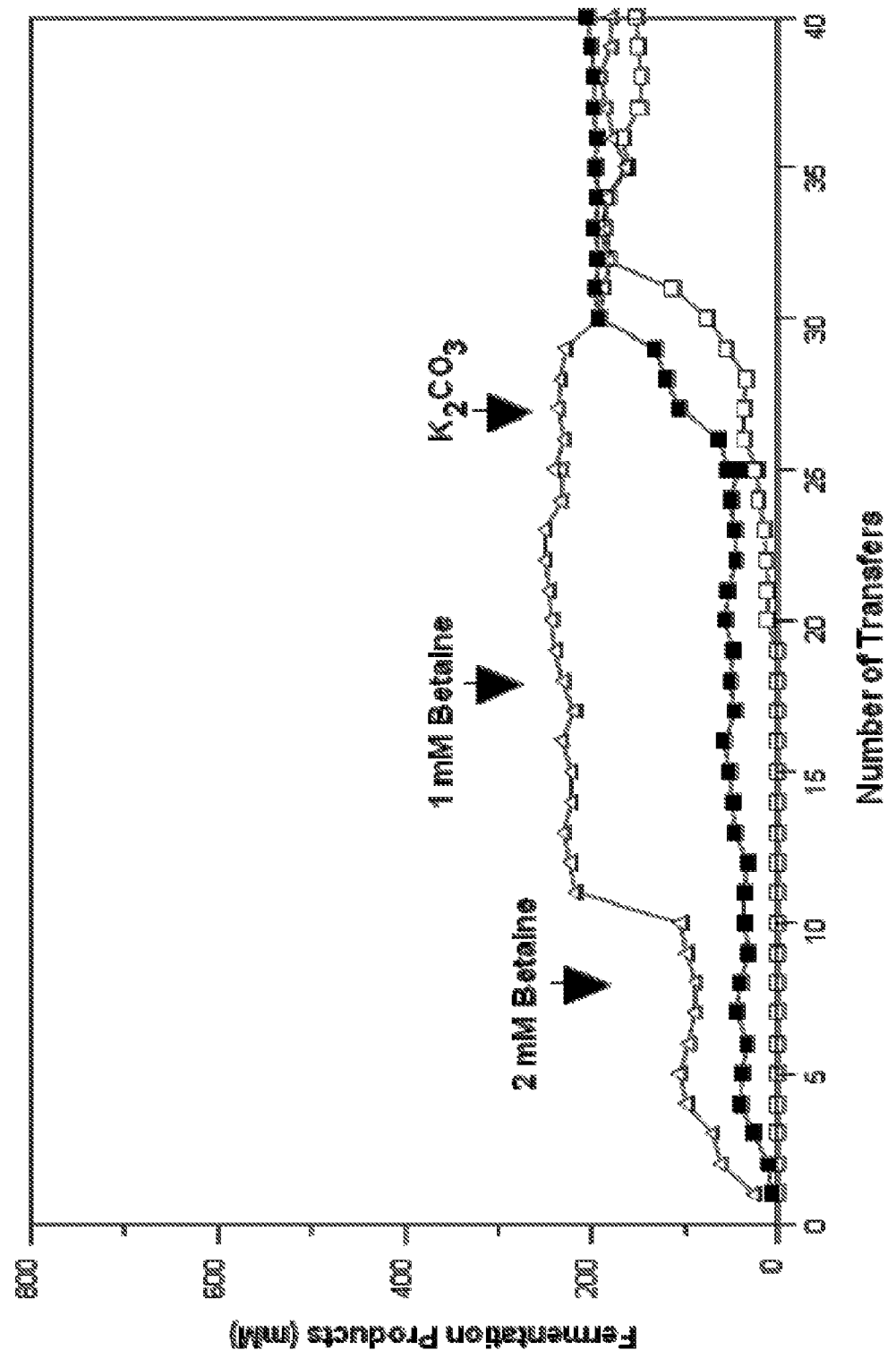
FIGS. 4A-4F. Summary of fermentation products during the metabolic evolution of strains for succinate production. Cultures were supplemented with sodium acetate as indicated. Black arrows represent the transition between fermentation conditions as indicated by text. No formate and only small amounts of lactate were detected during metabolic evolution of KJ032. No formate and lactate were detected during metabolic evolution of KJ070 and KJ072. Metabolic evolution of KJ012 to KJ017 in the medium containing 5% w/v glucose (FIG. 4A) and in the medium containing 10% w/v glucose (FIG. 4B). Metabolic evolution of KJ032 to KJ060 in a medium containing 5% w/v glucose (FIG. 4C) and 10% w/v glucose (FIG. 4D). Metabolic evolution of KJ070 to KJ071 in the medium containing 10% glucose (FIG. 4E). Metabolic evolution of KJ072 to KJ073 in the medium containing 10% glucose (FIG. 4F). Symbols for FIGS. 4A-4F: ■, succinate; □, formate; Δ, acetate; ▲, malate; ♦, lactate; and ▼, pyruvate.
Figure 4B:
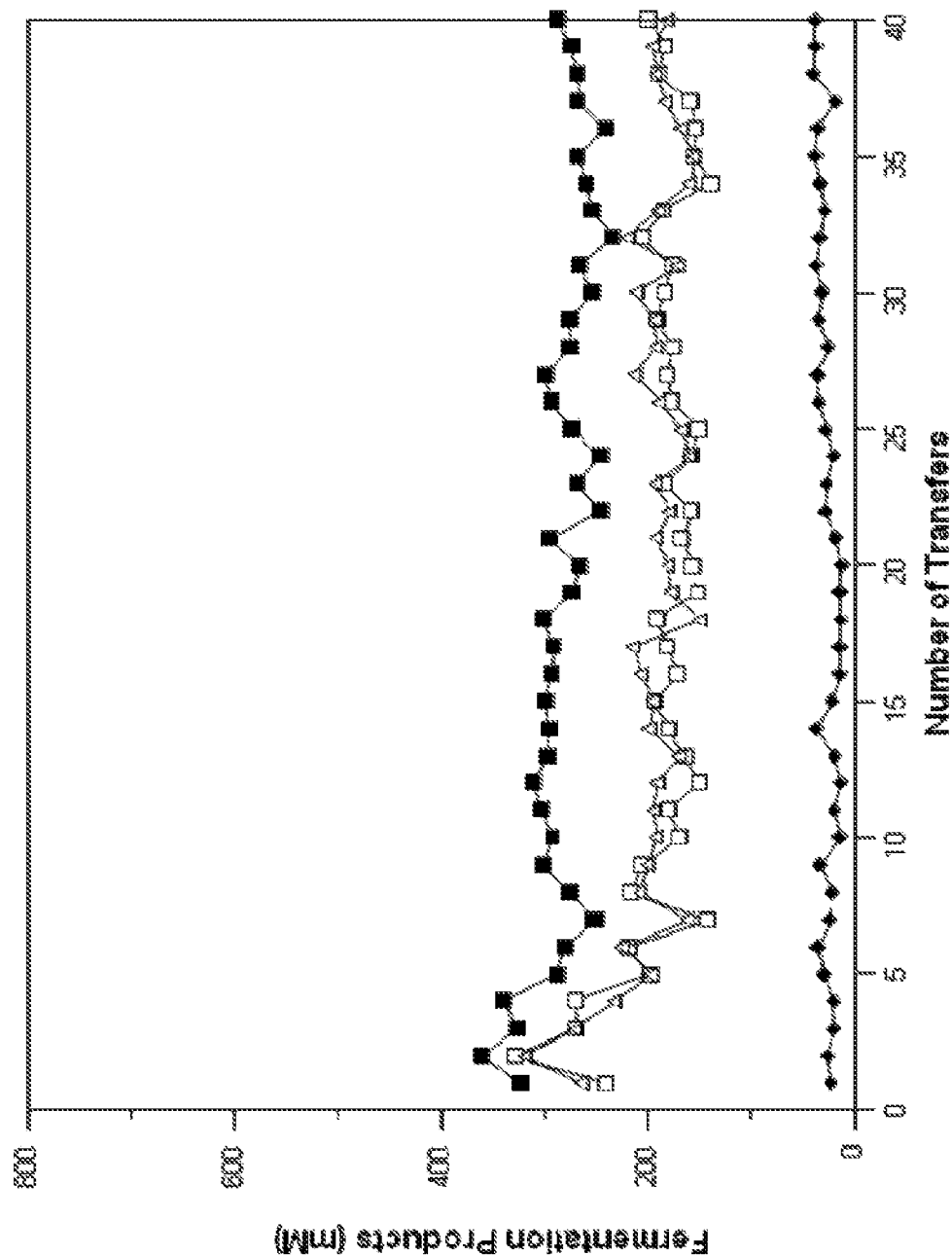
Figure 5:
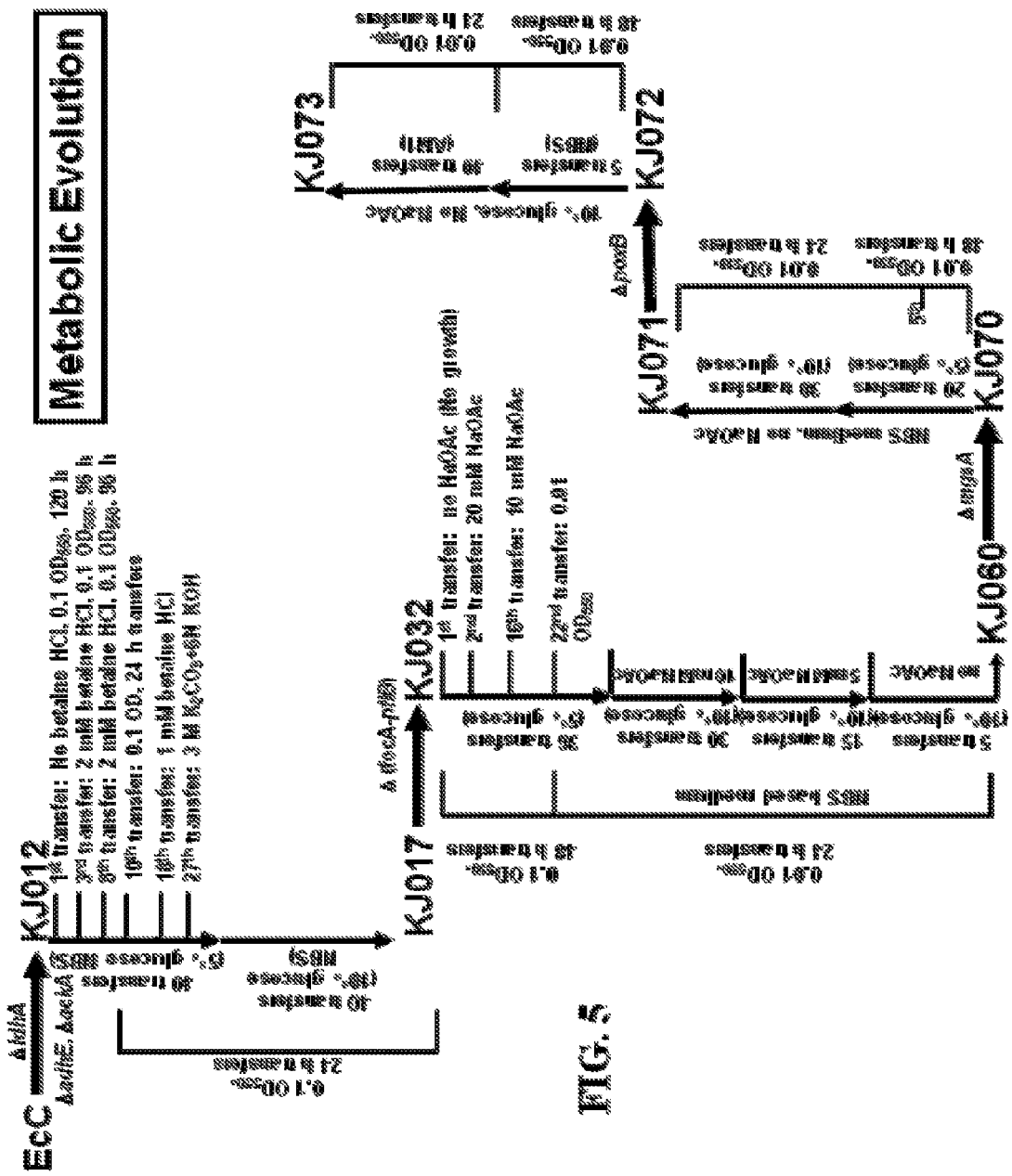
FIG. 5. Diagram summarizing steps in the genetic engineering and metabolic evolution of E. coli C as a biocatalyst for succinate production. This process represents 261 serial transfers providing over 2000 generations of growth-based selection. Clones were isolated from the final culture of each regimen and assigned strain designations, shown in parenthesis in Table 4.

Metabolic evolution of KJ012 was carried out by sequentially subculturing under various regimens using small, pH-controlled fermenters to improve the growth. KJ012 was serially transferred in NBS glucose medium under fermentative conditions as rapidly as growth permitted (FIG. 3A; FIG. 4A; FIG. 5). Growth remained slow with 4-5 days of required incubation between the first 9 transfers, then dramatically increased, allowing transfers to be made at 24-h intervals. This event was accompanied by an increase in acetate (FIG. 4A) with little improvement in succinate production. After 27 transfer (60 days), KOH was replaced with a 1:1 mixture of 3M K$_2$CO$_3$ and 6N KOH to provide additional carbon dioxide (100 mM initially added to all NBS mineral salts medium). Continuing transfers led to improvements in succinate production. A total of 40 transfers were made in 5% glucose (227 mM), followed by another 40 transfers in 10% glucose (555 mM). During the transfers in 10% glucose, succinate yields remained approximately 0.7 mol per mole of glucose metabolized with lactate, acetate, and formate as co-products (Table 4). This yield was 3-fold higher than E. coli C and KJ012 strains. A clone was isolated and designated KJ017. Selection for improvements in the growth of KJ012 to produce KJ017 co-selected for improvements in succinate production (rate, titer, and molar yield).

Succinate produced by E. coli using the pathway generally regarded as the native fermentation pathway based on phosphoenolpyruvate carboxylase (ppc) wastes the energy of phosphoenolpyruvate by producing inorganic phosphate. One ATP is lost per succinate produced by this pathway (FIG. 1; FIG. 6). Conserving this energy as ATP by using alternative enzyme systems represents an opportunity to increase cell growth and co-select for increased succinate production. Based on known genes in E. coli, three other enzyme routes for succinate production were envisioned that would conserve ATP and could thereby increase growth (FIG. 1; FIG. 6). However, all carboxylation steps in these alternative routes are thought to function in the reverse direction (decarboxylation) primarily for gluconeogenesis during growth on substrates such as organic acids (Keseler et al., 2005; Oh et al., 2002; Kao et al., 2005; Stols and Donnelly, 1997; Samuelov et al., 1991; Sanwal, 1970a; Delbaere et al., 2004; Goldie and Sanwal, 1980b; Sanwal and Smando, 1969b; Sanwal, 1970b). To test the hypothesis that growth-based selection to develop KJ017 has indeed activated one or more of these alternative routes, the activities of the four carboxylation enzymes were compared in wild-type strain ATCC 8739, KJ012 (deleted in primary fermentation pathways), and the metabolically evolved strain KJ017 (Table 5). PEP carboxylase activities were similarly low in all, 20 to 30 U (mg protein)$^{-1}$. NADH-linked malic enzyme activity (SfcA; carboxylation direction) was also low and NADPH-linked malic enzyme activity (MaeB; carboxylation direction) was undetectable. In contrast, PEP carboxykinase activity was increased by 4-fold in KJ017 as compared to KJ012, consistent with a hypothesis that selection for improved growth would co-select for increased production of succinate through increasing ATP yields, a consequence of increasing the expression of an energy-conserving route for succinate production.

Figure 3B:
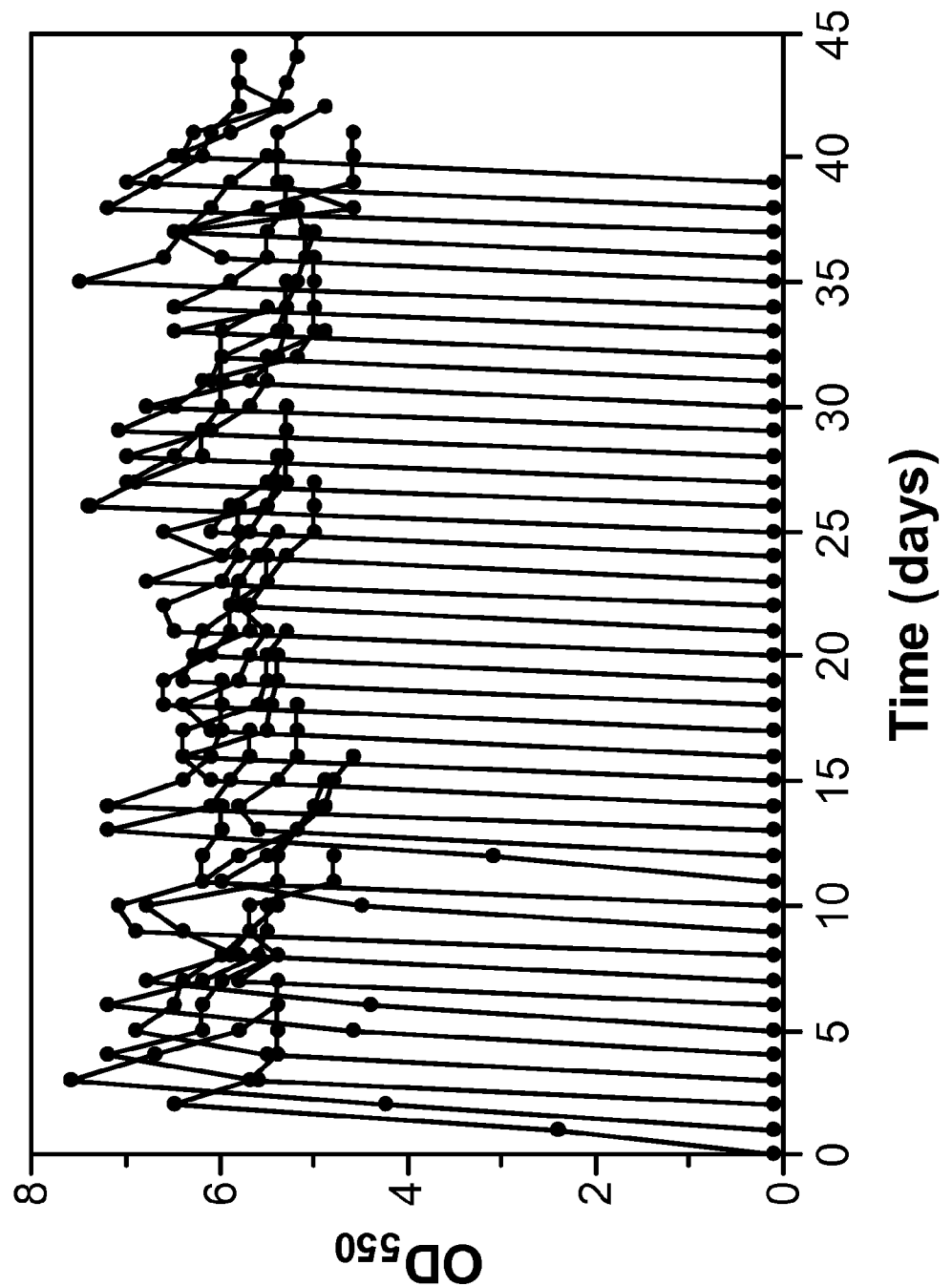

Further growth-based selections and additional gene deletions were used to construct many additional strains with further improvements in growth and succinate production (FIG. 3 and FIG. 4).

During growth with 10% (w/v) glucose, unwanted co-products (acetate, formate, and lactate) were abundant in fermentations with KJ017 (ΔldhA::FRT ΔadhE::FRT ΔackA::FRT) despite the deletion of genes encoding the primary lactate dehydrogenase (ldhA) and acetate kinase (ackA) activities (Table 4). Production of lactate and acetate could also result in higher ATP yields, a basis for growth-based selection (FIG. 1A).

Figure 3C:
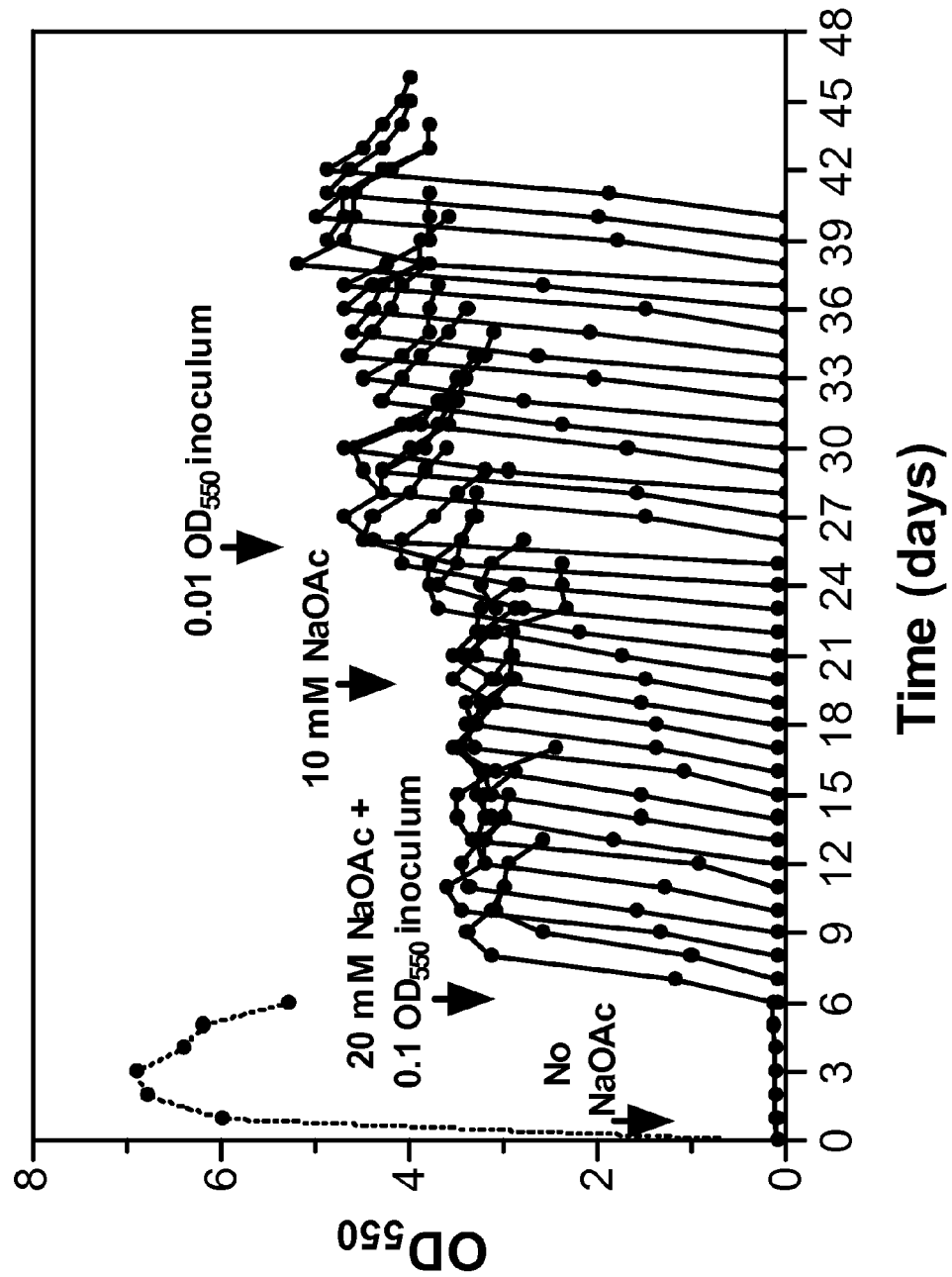
Figure 4C:
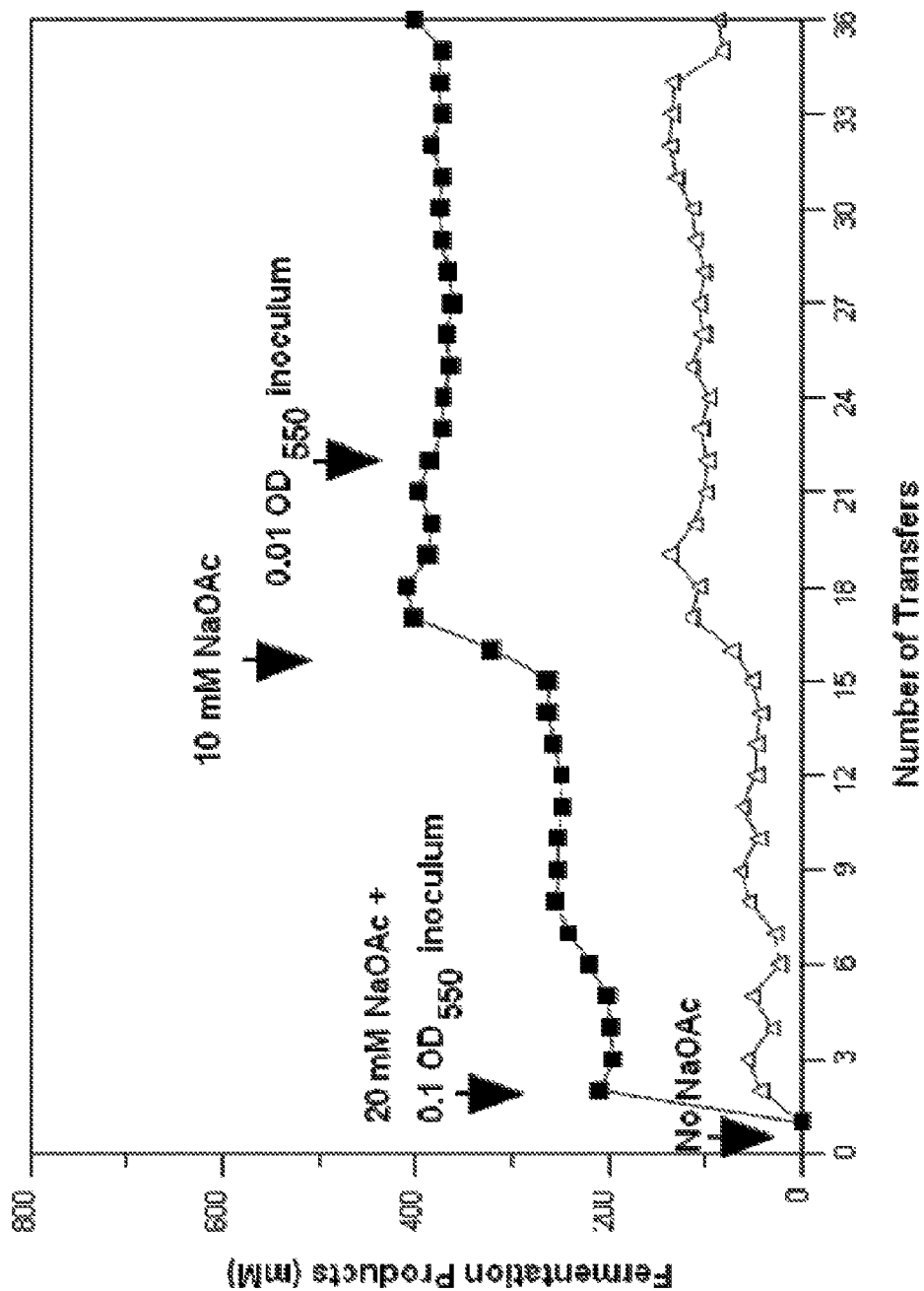
Figure 4D:
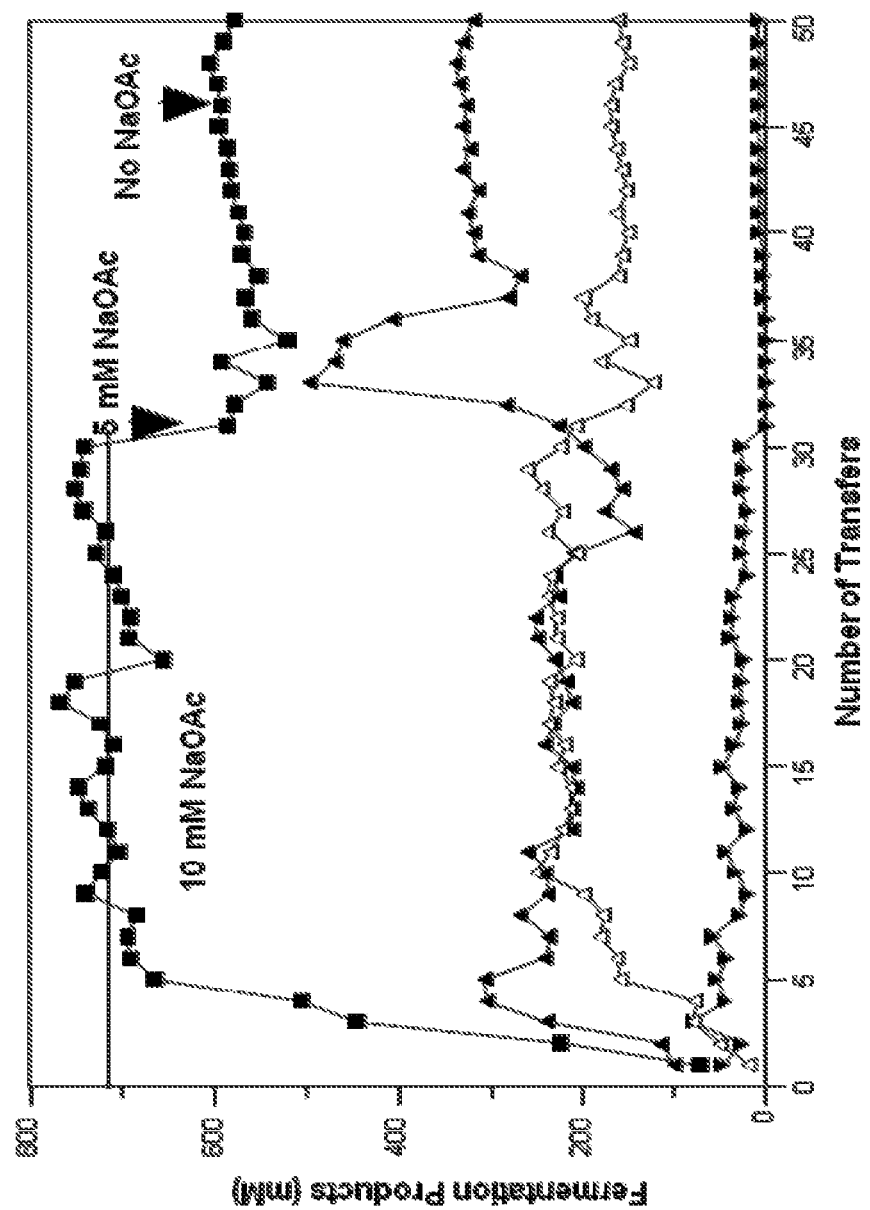

The gene encoding pyruvate formatelyase (pflB) was deleted from KJ017 to eliminate the loss of reductant as formate and an excess acetyl-CoA, a potential source of acetate. The upstream formate transporter (focA) in this operon was also deleted. As expected, this deleted strain (KJ032) did not grow without acetate, confirming that this is the primary route for acetyl-CoA production in KJ017 (FIG. 3C). Deletion of pflB is well-known to cause acetate auxotrophy under anaerobic conditions (Sawers and Bock, 1988). Growth and succinate production by KJ032 were restored by the addition of 20 mM acetate (FIG. 3C, FIG. 4C, and FIG. 5). Production of formate and acetate were substantially reduced as a result of pflB (and focA) deletion. Although this strain required acetate for growth, additional acetate was also produced during fermentation. The same phenomenon was previously reported for pflB-deleted strains during the construction of E. coli K-12 biocatalysts for pyruvate production (Causey et al., 2004). Lactate levels were also reduced in KJ032 (Table 4; FIG. 4C). Subsequent transfers were accompanied by improvements in growth and succinate production. Added acetate was reduced, inocula size was reduced, and glucose concentration was doubled (10% w/v) during subsequent transfers (FIG. 4D). After further transfers, acetate was omitted and a strain was developed that was no longer auxotrophic for acetate, presumably due to increased expression of another gene. However, succinate yields declined upon elimination of added acetate while malate and acetate levels increased. A clone was isolated from the last transfer and designated KJ060 (ΔldhA::FRT ΔadhE::FRT ΔackA::FRT ΔfocA-pflB::FRT). This strain produced 1 mole of succinate per mole of glucose metabolized in NBS mineral salts medium with 10% glucose.

Figure 4E:
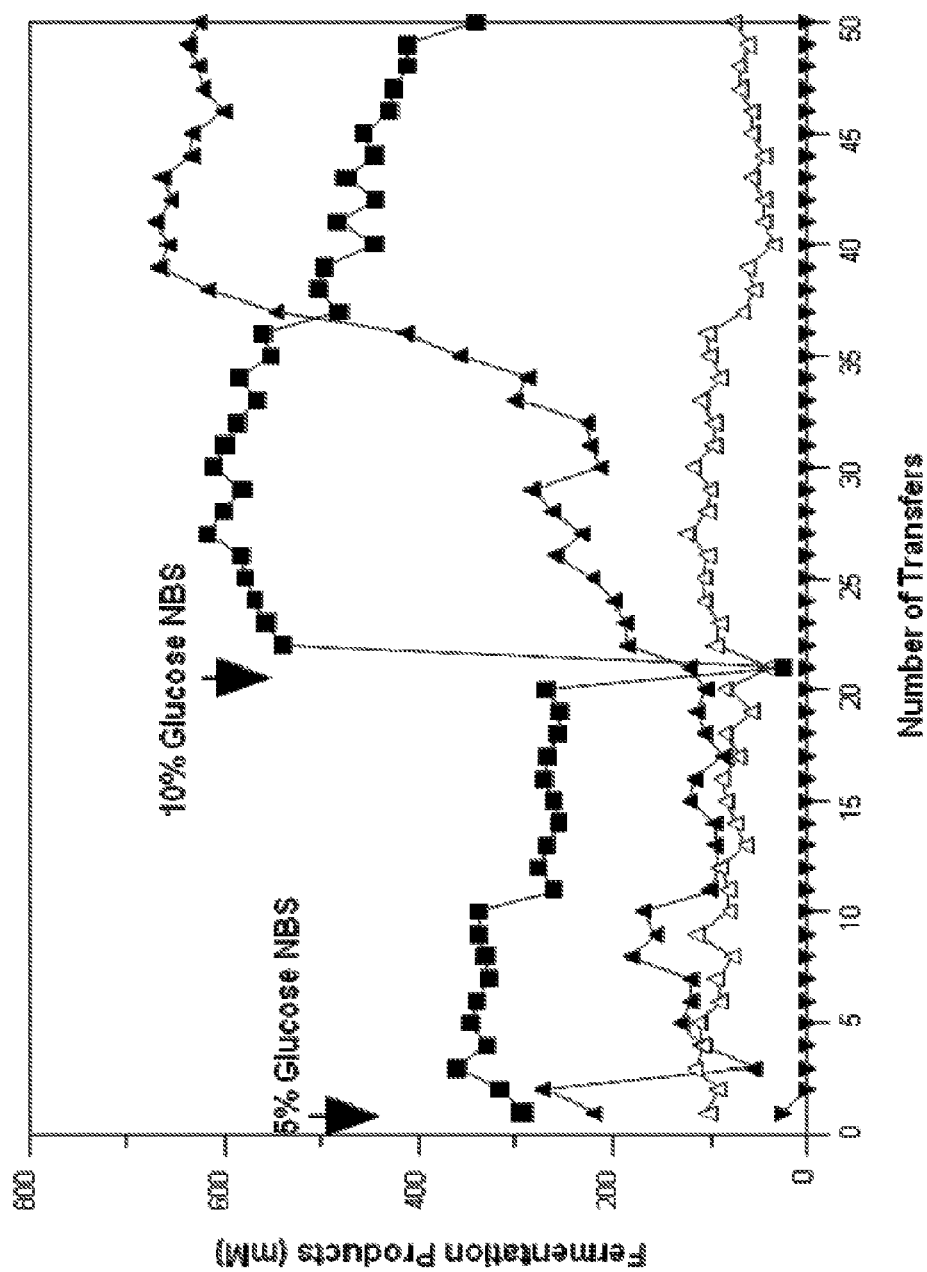

The small amount of lactate present in the fermentation broths of various strains is presumed to originate from the methylglyoxal synthase pathway (FIG. 6; Grabar et al., 2006). Although this represents a small loss of yield, lactate production by this pathway is indicative of methylglyoxal accumulation, an inhibitor of both growth and glycolysis (Egyud and Szent-Gyorgyi, 1966; Grabar et al., 2006; Hopper and Cooper, 1971). Production of methylglyoxal and lactate were eliminated by deleting the mgsA gene (methylglyoxal synthase) in KJ060 to produce KJ070 (ΔldhA::FRT ΔadhE::FRT ΔackA::FRT ΔfocA-pflB::FRT ΔmgsA). Strain KJ070 was initially subcultured in 5% (w/v) glucose (FIG. 3E, FIG. 4E, and FIG. 5). Deletion of mgsA is presumed to have increased glycolytic flux as evidenced by the accumulation of pyruvate in the medium (Table 4). This increase in glycolytic flux may also be responsible for the further decline in the succinate/malate ratio due to increased production of oxaloacetate, an allosteric inhibitor of fumarate reductase (Iverson et al., 2002; Sanwal, 1970c).

At transfer 21, glucose was doubled to 10% (w/v) and transfers continued. This higher level of glucose and subsequent transfers resulted in a new strain that was isolated from the final subculture and designated KJ071 (ΔldhA::FRT ΔadhE::FRT ΔackA::FRT ΔfocA-pflB::FRT ΔmgsA). This strain may be useful for malate production.

Although conversion of glucose to acetate is redox neutral, partitioning of carbon to acetate decreases the yield of succinate and malate. Pyruvate oxidase (poxB) represents a potential source of acetate and $CO_2$ during incubation under microaerophilic conditions (Causey et al., 2004). Although it should not function to oxidize pyruvate under anaerobic conditions, poxB was targeted for gene deletion (FIG. 6). As expected, deletion of poxB to produce KJ072 (ΔldhA::FRT ΔadhE::FRT ΔackA::FRT ΔfocA-pflB::FRT ΔmgsA ΔpoxB) did not reduce acetate production, indicating that alternative pathways are involved in acetate production. However, eliminating poxB resulted in unexpected changes in fermentation products, including an increase in succinate (Table 4, FIG. 4F). The mechanism for this improvement in succinate production is unknown but may be related to other activities of pyruvate oxidase such as acetoin production, decarboxylation, and carboligation (Ajl and Werkman, 1948; Chang and Cronan, 2000).

Figure 4F:
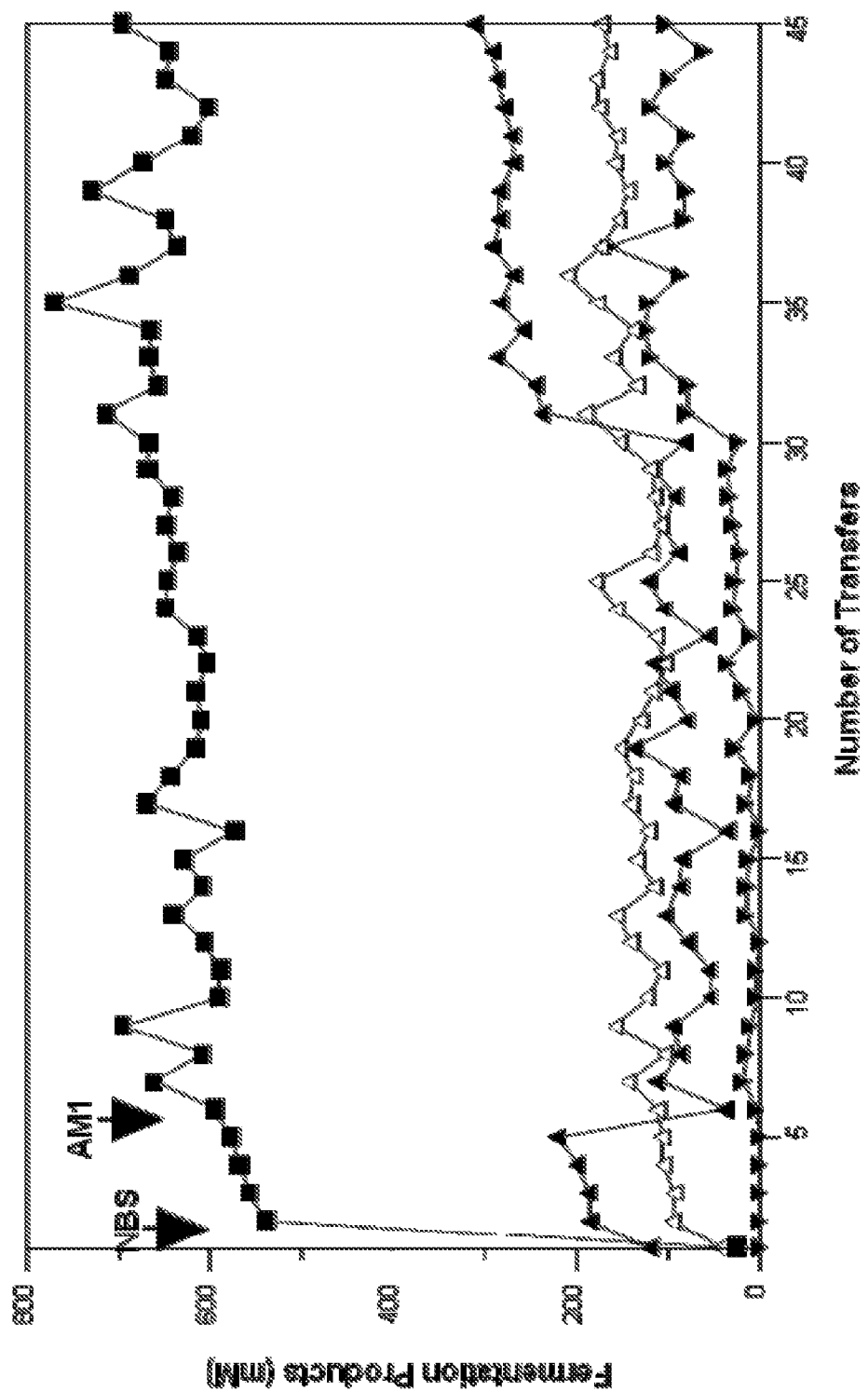

Strain KJ072 was subjected to 40 further rounds of metabolic evolution in AM1 medium, a lower salt medium, with 10% (w/v) glucose (Table 4; FIG. 4F, and FIG. 5).

Improvements in growth, cell yield and succinate production were observed during these transfers. Malate, pyruvate and acetate levels also increased. A clone was isolated from the final transfer and designated KJ073 (ΔldhA::FRT ΔadhE:: FRT ΔackA::FRT ΔpflB::FRT ΔmgsA ΔpoxB).

The KJ073 strain retained the phosphoenolpyruvate carboxykinase route for carboxylation (Table 5). In vitro activity of this strain was 45-fold higher than that of KJ012 and 10-fold higher than KJ017, providing further evidence for the tight coupling of energy conservation to succinate production and growth and further establishing the basis used for selection.

Large increases in PEP carboxykinase activity were well correlated with improvements in cell yield and succinate production (Table 5). From KJ012 to KJ017 (metabolic evolution), PEP carboxykinase activity increased 4.3-fold, cell yield increased 5.7-fold, and succinate production increased 8.8-fold. From KJ017 to KJ060 (deletion of pflB followed by metabolic evolution), PEP carboxykinase activity increased 12-fold, cell yield increased 1.3-fold, and succinate production increased 2.6-fold. From KJ060 to KJ071 (deletion of mgsA followed by metabolic evolution), PEP carboxykinase activity decreased by 92%, cell yield decreased by 45%, and succinate production decreased by 63%. From KJ071 to KJ073 (deletion of poxB followed by metabolic evolution), PEP carboxykinase activity, cell yield, and succinate production were restored to levels equivalent to KJ060.

The pck and surrounding regions were cloned from KJ012 and KJ073 and sequenced. No changes were found in the coding region. Absent post-translational modifications, the catalytic properties of the enzyme should be unchanged. A single mutation was detected in the pck promoter region, G to A at −64 bp site relative to the translation start site. This mutation was behind the transcription start site which is −139 bp site relative to the translational start site.

Previous investigators have noted that the kinetic parameters of phosphoenolpyruvate carboxylase (ppc) and phosphoenolpyruvate carboxykinase (pck) may have important effects on carboxylation and succinate production (Millard et al., 1996; Kim et al., 2004). The Km towards bicarbonate for *E. coli* phosphoenolpyruvate carboxylase (ppc) is 0.15 mM (Morikawa et al., 1980), 9-fold lower (13 mM) than *E. coli* phosphoenolpyruvate carboxykinase (pck) (Krebs and Bridger, 1980). Although overexpressing pck from *E. coli* using a multi-copy plasmid increased phosphoenolpyruvate carboxykinase activity by 50-fold, it was reported to have no effect on succinate production (Millard et al., 1996). Succinate production was also not increased when phosphoenolpyruvate carboxykinase from *Anaerobiospirillum succiniciproducens* was overexpressed in *E. coli* K12 (Kim et al., 2004). This enzyme also has a high Km (30 mM) for bicarbonate (Laivenieks et al., 1997). However, when *A. succiniciproducens* pck was overexpressed in a ppc mutant of *E. coli* K12, succinate production was increased 6.5-fold (Kim et al., 2004). In KJ017 and subsequent derivatives, phosphoenolpyruvate carboxykinase is clearly the dominant carboxylating activity even in the presence of functional native phosphoenolpyruvate carboxylase.

Results from enzyme measurements of *E. coli* C were quite surprising. The enzyme generally regarded as the dominant carboxylating activity for succinate production by native *E. coli* (phosphoenolpyruvate carboxylase; ppc) during growth (Unden and Kleefeld, 2004; Fraenkel, 1996; Keseler et al., 2005; Millard et al., 1996; Gottschalk, 1985; Karp et al., 2007) was not the most active enzyme in vitro for *E. coli* C. Thus the generally accepted metabolic pathways for *E. coli* (Unden and Kleefeld, 2004; Fraenkel, 1996; Sanchez et al., 2006; Cox et al., 2006; Vemuri et al., 2002a; Wang et al., 2006; Sanchez et al., 2005ab; Gokarn et al., 2000; Karp et al., 2007) upon which rational design of metabolic engineering and estimates of metabolic flux are typically based may not accurately reflect metabolism in all strains. Under substrate-saturating conditions in vitro, phosphoenolpyruvate carboxykinase activity was the most active. In *E. coli* K12, activities for both phosphoenolpyruvate carboxylase and phosphoenolpyruvate carboxykinase were reported to be equal in vitro (140 nm min$^{-1}$ mg$^{-1}$ cell protein; Van der Werf et al., 1997), with the former serving as the primary route to succinate.

Previous studies showed that the overexpression of a native ppc gene in *E. coli* resulted in higher specific succinate production (Millard et al., 2000), higher specific growth rate, and lower specific acetate production due to more carboxylation of PEP to replenish TCA cycle intermediates (Farmer and Liao, 1997). However, since PEP is required for the glucose transport system, overexpressing ppc also decreases the glucose uptake rate by 15-40% without significantly increasing succinate yield (per glucose) as compared to an isogenic control (Chao and Liao, 1993; Gokarn et al., 2000). This failure of the native phosphoenolpyruvate carboxylase to increase succinate yields diverted most research attention to a new metabolic design, over-expression of PYC (pyruvate carboxylase) from *Lactobacillus lactis* or *Rhizobium etli* as the carboxylating step (Vemuri et al., 2002ab; Gokarn et al., 2000; Lin et al., 2005a, 2005b, 2005c), rather than pursuing further work with the native repertoire of *E. coli* genes.

Rumen bacteria such as *Actinobacillus succinogenes* produce succinate as a primary product during glucose fermentation using the energy-conserving phosphoenolpyruvate carboxykinase for carboxylation (Kim et al., 2004; McKinlay et al., 2005; McKinlay and Vieille, 2008). Reported activities for this organism are 5-fold those of KJ017 and half of that obtained by continued growth-based selection (metabolic evolution) of KJ073. Thus, by using a combination of metabolic engineering (ldhA adhE ackA) and metabolic evolution (growth-based selection for increased efficiency of ATP production), the studies reported herein demonstrate the development of succinate-producing strains of *E. coli* that resemble a rumen organism such as *A. succinogenes* by using only the native repertoire of *E. coli* genes. Despite prior reports that over-expression of *E. coli* phosphoenolpyruvate carboxykinase (pck) is not helpful for succinate production in the absence of a mutation in phosphoenolpyruvate synthase (Chao and Liao, 1993; Kim et al., 2004; Gokarn et al., 2000; Millard et al., 1996), KJ017 and its derivatives have been metabolically evolved to use phosphoenolpyruvate carboxykinase as the primary route for succinate and malate production.

Figure 7A:
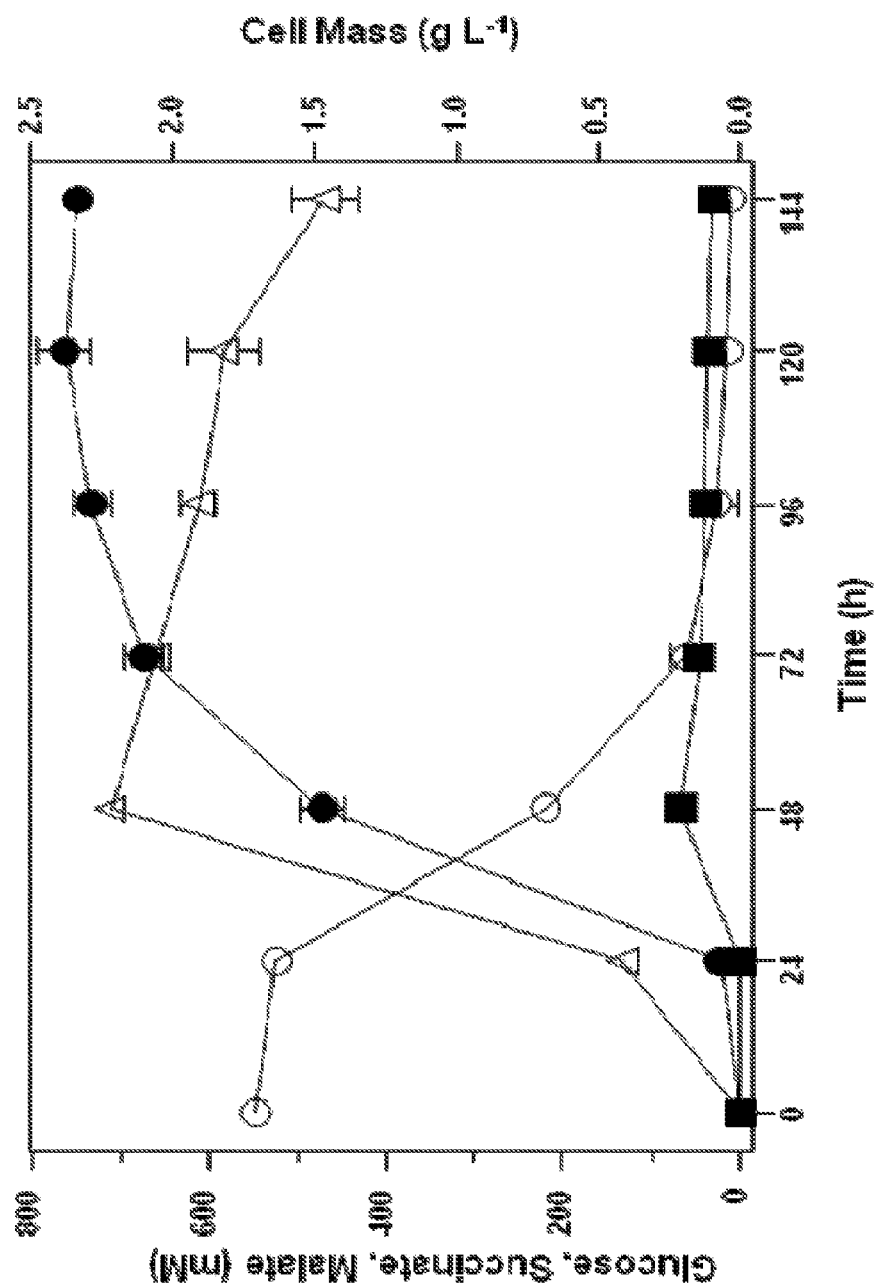
FIGS. 7A-7C. Production of succinate and malate in mineral salts media with 10% glucose (w/v) by derivatives of E. coli C.
Figure 7B:
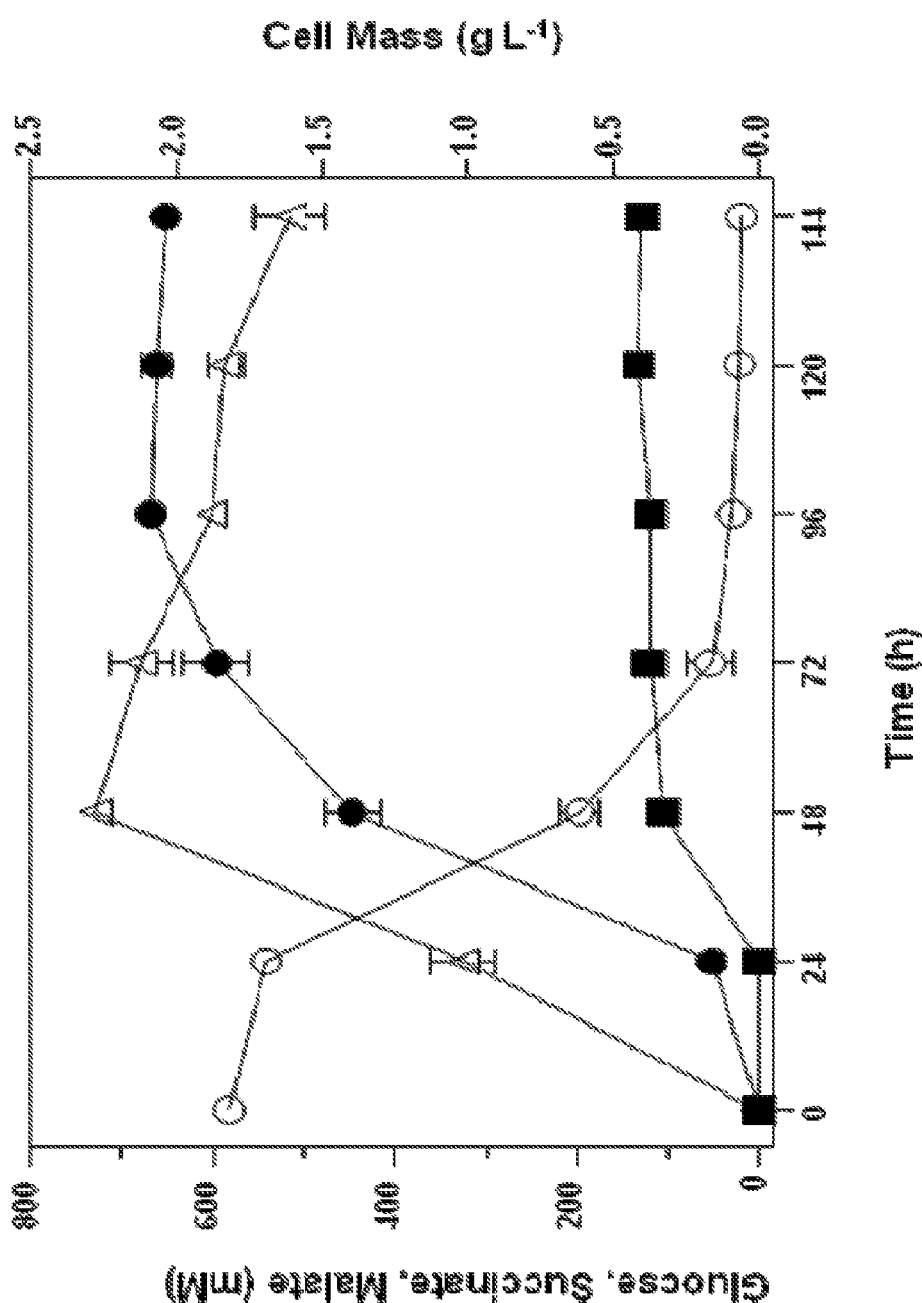
Figure 7C:
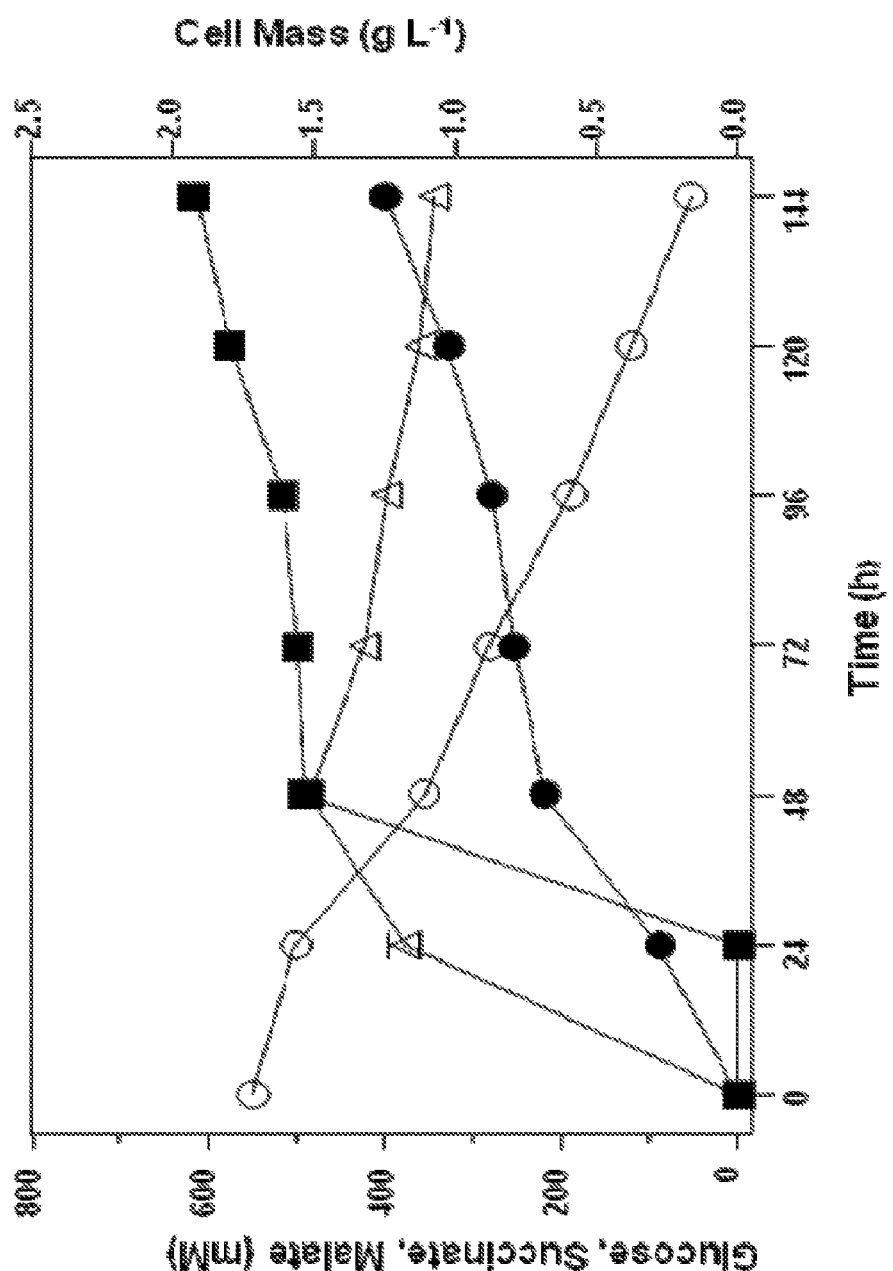

FIG. 7 shows batch fermentations with KJ060 and KJ073, the two best biocatalysts for succinate production. Although growth was completed within the initial 48 h of incubation, succinate production continued for 96 h. One-third of succinate production occurred in the absence of cell growth. These strains produced succinate titers of 668-733 mM, with a molar yield of 1.2-1.6 based on glucose metabolized. With AM1 medium, yields were typically higher than with NBS mineral salts medium. Acetate, malate, and pyruvate accumulated as undesirable co-products and detracted from the potential yield of succinate (Table 4). The maximum theoretical yield of succinate from glucose and $CO_2$ (excess) is 1.71 mol per mole glucose based on the following equation:

$C_6H_2O_6+6CO_2 \rightarrow 12C_4H_6O_4+6H_2O$.

However, there is no direct succinate pathway in *E. coli* that achieves this yield (FIG. 6).

Although this study primarily focused on the conversion of glucose to succinate; it is well known that *E. coli* has the native ability to metabolize all hexose and pentose sugars that are constituents of plant cell walls (Asghari et al., 1996; Underwood et al., 2004). Some strains of *E. coli* can also metabolize sucrose (Moniruzzaman et al., 1997). Strain KJ073 was tested for utilization of 2% sugars of hexoses and pentoses in serum tubes. In all cases, these sugars were converted primarily to succinate. Strain KJ073 also metabolized glycerol to succinate. During incubation with 2% glycerol, 143 mM glycerol was metabolized to produce 127 mM succinate with a molar yield of 0.89, or 89% of the maximum theoretical yield for succinic acid using glycerol as the carbon source for bacterial growth.

Figure 1B:
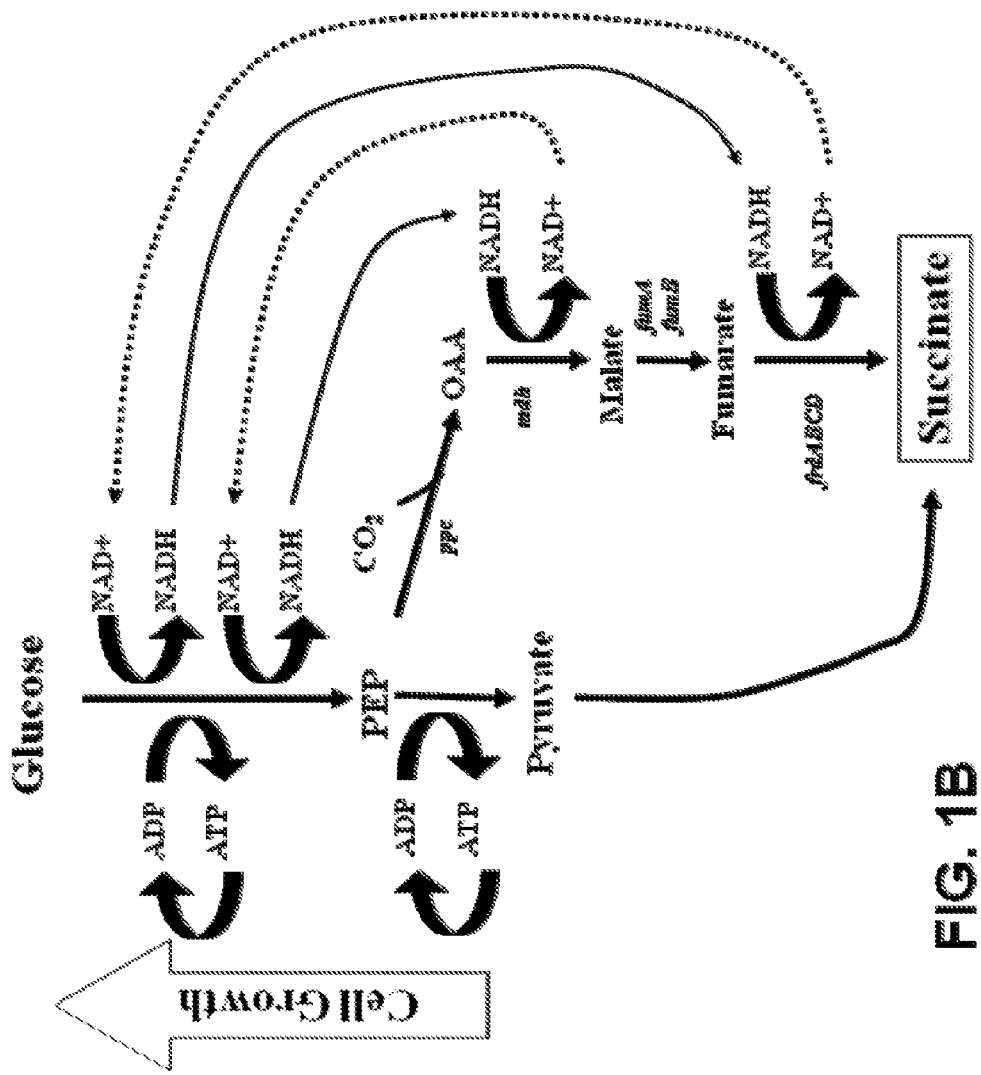

The fermentative metabolism of *E. coli* has been shown to be remarkably adaptable. Derivatives were engineered and evolved to circumvent numerous deletions of genes concerned with native fermentation pathways and increase fluxes through remaining enzymes to maintain redox balance, increase the efficiency of ATP production, and increase growth. Though much more challenging, cells can make such adaptive changes in mineral salts media while balancing carbon partitioning to provide all biosynthetic needs. After eliminating the primary routes for NADH oxidation (lactate dehydrogenase, alcohol dehydrogenase) and acetate production (acetate kinase), growth and ATP production remain linked to NADH oxidation and the production of malate or succinate for redox balance (FIG. 1B). Anaerobic growth-based selections ensure redox balance and select for increased efficiency and increased rates of ATP production, the basis for increased growth. This selection for redox balance and ATP production cannot readily distinguish between malate and succinate as end products, since the precursors of both serve as electron acceptors.

Deletion of pflB, the primary source of acetyl-CoA during anaerobic growth, resulted in an auxotrophic requirement for acetate (Sawers and Bock, 1988). This requirement was eliminated through metabolic evolution, presumably due to increased production of acetyl-CoA by other routes such as pyruvate dehydrogenase (de Graef et al., 1999). The metabolic source of the acetate or acetyl-CoA that replaced this auxotrophic need is unknown. The shift to higher succinate production after a poxB deletion was also surprising. Little change in the acetate level was observed, indicating either that this enzyme was a minor source of acetate or that it was functionally replaced by other routes for acetate production. After deletion of poxB, succinate was again produced as the dominant dicarboxylic acid. This shift in metabolic products accompanying poxB deletion was unexpected.

With the best strains for succinate production, KJ060 and KJ073, malate and acetate remained as abundant co-products (Table 4; FIGS. 4D and 4F). Elimination of these represents a further opportunity to increase yield.

All previously engineered *E. coli* developed for succinate production have used complex media and plasmids with antibiotics for maintenance. Most have achieved only low titers of succinate in simple batch fermentations, requiring more complex processes to achieve high titers (Table 1). Other investigators have also used heterologous genes and complicated processes that include sparging with gas ($CO_2$, $H_2$, $O_2$ or air) and dual aerobic and anaerobic process steps. A variety of genetic approaches have been reported that increase succinate production from glucose by recombinant *E. coli* in complex medium. This complexity of process and nutrients would be expected to increase the cost of construction, materials, purification, and waste disposal. Complex media containing vitamins, amino acids, and other macromolecular precursors may mask potential regulatory problems in metabolism and biosynthesis that were created by metabolic engineering. In our initial construct, growth and sugar metabolism were very poor in mineral salts medium but were very robust in complex medium (Luria broth). In contrast, strains KJ060 and KJ073 produced high titers of succinate (600-700 mM) in simple batch fermentations (10% sugar) using mineral salts medium without any complex nutrients or foreign genes.

Example 2

Construction of KJ134 Strain for Succinate Production

As described in Example 1 above, the central anaerobic fermentation genes in wild-type *E. coli* C were sequentially deleted by the strategy of Datsenko and Wanner (2000) with PCR products and removable antibiotic markers (by using FRT recognition sites and FLP recombinase). These constructions in combination with metabolic evolution (growth-based selection for increased efficiency of ATP production) were used to select for a mutant strain that recruited the energy-conserving phosphoenolpyruvate carboxykinase (pck) to increase growth and succinate production (FIG. 9). The resulting strain, KJ073, produced 1.2 moles of succinate per mole of metabolized glucose (Jantama et al., 2008a) and uses a succinate pathway quite analogous to the rumen bacteria, *Actinobacillus succinogenes* (van der Werf et al., 1997) and *Mannheimia succiniciproducens* (Song et al., 2007). However, methods used to construct these gene deletions left a single 82 to 85 nucleotide-long genetic scar or FRT site in the region of each deleted gene (ackA, ldhA, adhE, ackA, and focA-pflB). These FRT sites served as recognition sites for FLP recombinase (Storici et al., 1999) during removal of the antibiotic genes. All of these extraneous sequences were sequentially removed from KJ073 and replaced with native DNA with only the desired gene deletion using methods that have been described previously (Grabar et al., 2006; Zhang et al. 2007; Jantama et al., 2008b). The resulting strain, KJ091, contains specific deletions in ackA, ldhA, adhE, focA-pflB, ackA, mgsA, and poxB and lacks all FRT sites present in the KJ073 strain. The KJ091 strain is devoid of all foreign and synthetic DNA except for an 18-bp translational stop sequence within ackA. Succinate production by strain KJ091 was equivalent to that of the KJ073 strain (Table 8). This strain was used as the parent for further improvements in succinate production.

In the first step for further improvement of the KJ091 strain, attention was paid to reduce the acetate production. During the anaerobic fermentation of glucose by *E. coli*, pyruvate formate-lyase (pflB) serves as the primary source of acetyl-CoA, the precursor of acetyl-P, and acetate kinase (ackA) serves as the primary route for acetate production from acetyl-P (Karp et al., 2007; Kessler and Knappe, 1996). The abundance of acetate as a fermentation product in strains KJ073 and KJ091 was surprising since these strains contain deletions in both ackA and pflB (FIG. 9). This residual acetate at the end of fermentation represents a potential opportunity to further redirect metabolism for improved succinate yield.

Figure 10:
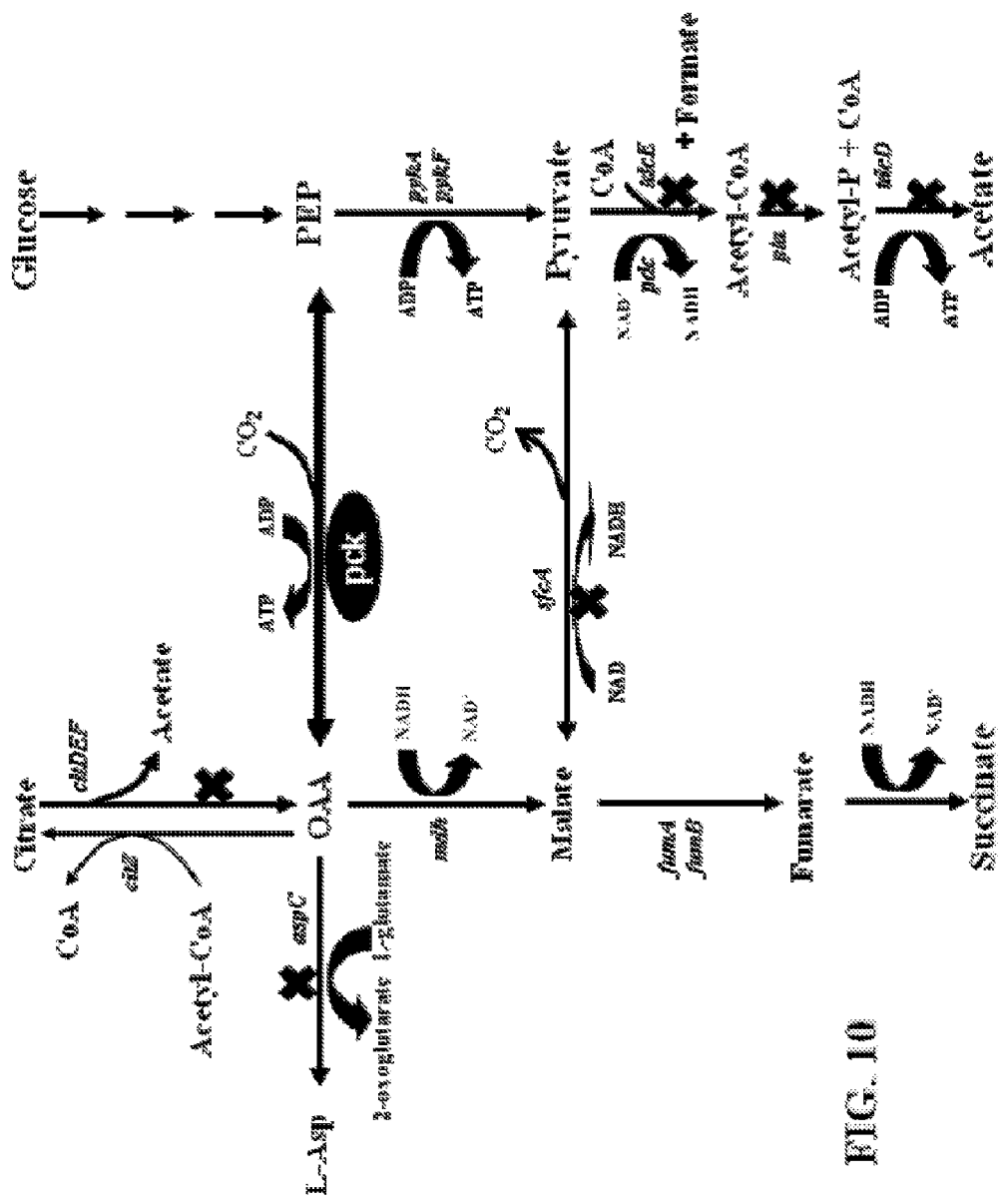
FIG. 10. Expanded portion of metabolism illustrating the pathways of additional genes that have been deleted (solid crosses). Succinate and acetate are principal products (boxed) from KJ073 fermentations. Genes and enzymes: citDEF, citrate lyase; gltA, citrate synthase; aspC, aspartate aminotransferase; pck, phosphoenolpyruvate carboxykinase; sfcA, NAD⁺-linked malic enzyme; fumA and fumB, fumarase; frdABCD, fumarate reductase; pykA and pykF, pyruvate kinase; tdcE, pyruvate formate-lyase (homologue of pflB); pta, phosphate transacetylase; and tcdD, acetate kinase (homologue of ackA).

A related enzyme with acetate kinase (and proprionate kinase) activity is encoded by tdcD but is typically produced only for the degradation of threonine (Hesslinger et al., 1998; Reed et al., 2003). It is possible that mutations occurring during selection have increased expression of tdcD as illustrated in FIG. 10. During anaerobic growth with 10% (w/v) glucose, expression of tdcD could functionally replace ackA, increasing the production of acetate from acetyl-P. The adjacent tdcE gene in the same operon is similar to pflB and encodes a pyruvate (and α-ketobutyrate) formatelyase activity that is co-expressed during threonine degradation (Hesslinger et al., 1998). It is possible that increased expression of this gene during anaerobic growth with 10% (w/v) glucose could increase the production of acetyl-CoA, the immediate precursor of acetyl-P, and waste reductant as formate (FIG. 10). Both tdcD and tdcE (adjacent) were simultaneously deleted from KJ091 to produce KJ098. Deletion of these two genes reduced acetate production by half and increased succinate yield by 10% in KJ098 in comparison to KJ091, establishing the importance of this unexpected pathway in diverting carbon flow away from succinate. The level of pyruvate produced by KJ098 also declined by 40%, an intermediate that would be predicted to increase upon elimination of two alternative routes for pyruvate metabolism, pyruvate formate-lyase activity (tdcD) and acetate kinase activity (tdcE). The significant decrease in pyruvate production is an unexpected result of tdcD/tdcE gene deletions. The mechanisms responsible for the reduction in pyruvate, and the increase in succinate which resulted from the simultaneous deletion of tdcD and tdcE are unknown.

Although KJ098 represents a significant improvement over KJ091, further reduction in acetate levels and further increases in succinate yields may be possible. Under anaerobic conditions, oxaloacetate is partitioned into the reduced product (malate) and oxidized intermediate (citrate) (FIG. 9). Citrate can be converted back to oxaloacetate and acetate by citrate lyase (citDEF) to recycle the intracellular OAA pool (FIG. 10) for other metabolic functions (Nilekani et al., 1983). Expression of significant amounts of citrate lyase is associated with growth on citrate (Lutgens and Gottschalk, 1980; Kulla and Gottschalk, 1977). Citrate lyase is a multi-enzyme complex made up of three different polypeptide chains. The α or large subunit is a citrate-ACP transferase that catalyzes the first step. The β or medium subunit is a citryl-ACP lyase that catalyzes the second step. The γ or small subunit acts as an acyl-carrier protein and also carries the prosthetic group components. All three subunits are required for the reaction to take place (Quentmeier et al., 1987). The deletion of genes encoding one or more of these subunits would eliminate citrate lyase activity and may further reduce the level of acetate during succinate production. The citF gene was deleted from KJ098 to produce KJ104. This deletion, however, had no effect on acetate production or other succinate yield (Table 8). Since deletion of citF did not cause any reduction in acetate, this intermediate is presumed to arise from other pathways. For unknown reasons, deletion of citF adversely affected the growth of KJ104 (reduced cell yield by 22%) and increased the level of pyruvate at the end of fermentation by almost 50% in comparison to KJ098. However, the succinate yield, titer, average productivity, and acetate levels with KJ104 were comparable to those with KJ098 (Table 8).

Aspartate aminotransferase (aspC) is a multifunctional enzyme that catalyzes the synthesis of aspartate, phenylalanine and other compounds by transamination. In the reaction, L-aspartate is synthesized from oxaloacetate, an intermediate from PEP carboxylation, by a transamination reaction with L-glutamate. Besides being a protein constituent, aspartate participates in several other biosynthetic pathways. About 27 percent of the cellular nitrogen has been estimated to flow through aspartate (Reitzer, 2004). Aspartate biosynthesis and succinate production share a common intracellular pool of oxaloacetate. Deletion of aspC could lead to increased succinate production but may also create an auxotrophic requirement that prevents anaerobic growth in minimal salts medium such as AM1.

This aspartate aminotransferase gene (aspC) was deleted from KJ104 to produce KJ110. Unexpectedly, the deletion of aspC had no effect on succinate yield or cell yield in KJ110 as compared to KJ104 (Table 8). Thus aspartase does not appear to divert significant levels of oxaloacetate away from succinate production in our strain. Alternative enzymes appear to be available that replace the biosynthetic needs formerly catalyzed by aspartate aminotransferase.

Significant amounts of pyruvate are present at the end of fermentation with KJ104 and other strains of E. coli engineered for succinate production (Table 8). This pyruvate represents an unwanted product and a further opportunity to increase succinate yield. This high level of pyruvate in fermentation broth could result from the decarboxylation of malate to pyruvate by malic enzyme (sfcA) as illustrated in FIG. 10. This enzyme is thought to function primarily during gluconeogenesis (Unden and Kleefeld, 2004; Stols and Donnelly, 1997; Oh et al., 2002) rather than during the anaerobic catabolism of glucose. Although reductive carboxylation of pyruvate to form malate is thermodynamically favored, the kinetic parameters of this enzyme favor dehydrogenation and decarboxylation under physiological conditions (Stols and Donnelly, 1997). Over-expression of this enzyme to carboxylate pyruvate has been previously used as a basis to construct strains for succinate production of E. coli (Stols and Donnelly, 1997).

If malic enzyme (sfcA) is carboxylating in KJ104 (and related strains) and contributing to succinate production, deletion of this gene would be expected to reduce succinate yield and increase the levels of other products such as pyruvate. Alternatively, if malic enzyme (scfA) is decarboxylating in KJ104 and diverting malate to pyruvate, deleting the gene encoding this enzyme would be expected to increase succinate yields and decrease the levels of pyruvate.

Unexpectedly, deletion of the sfcA gene from KJ104 to produce KJ119 had no measurable effect on succinate production, growth, pyruvate levels, etc. (Table 8) in comparison to KJ104. These results clearly demonstrate that malic enzyme (sfcA) is unimportant for succinate production in KJ104 and related strains. This result is in sharp contrast to the succinate-producing strains developed by Stols and Donnelly (1997) in which increased production of malic enzyme was used as the primary route for succinate production.

Although no significant benefits were observed from either an sfcA deletion or an aspC deletion in KJ104, studies were carried out to test the effect of deleting both genes in combination. This was done by deleting the sfcA gene in KJ110 to produce KJ122 and expecting to see no benefit. However, the combined deletion of both sfcA and aspC (strain KJ122) resulted in an unexpected increase in succinate yield and titer with a small reduction in acetate (Table 8), in comparison to the parent strain KJ110 and related strains (KJ104 and KJ119). The combined deletion (aspC and sfcA) in KJ122 resulted in an 18% increase in succinate yield, 24% increase in succinate titer, and 24% increase in average productivity as compared to KJ104. Although the mechanism is unknown, it is possible that single mutations were ineffective because they were compensated for in part by increased flow through the remaining enzyme activity, malic enzyme or aspartate aminotransferase (FIG. 10), dampening any potential benefit. The increase in succinate yield and titer are presumed to result from an increase in the availability of oxaloacetate, allowing a larger fraction to proceed to succinate. Malate levels also remained extremely low.

Strain KJ122 (Table 8) produced 1.5 mol succinate per mole of glucose, 88% of the maximum theoretical yield (1.71 mol per mol glucose). To produce this high level of succinate and fully reduce malate production, additional reductant was required. Although the source of this additional reductant is unknown, these results are consistent with an increase in pyruvate flow through pyruvate dehydrogenase. This enzyme is thought to function primarily during aerobic metabolism (Guest et al., 1989) but has also been reported to function at low levels during fermentation (de Graef et al., 1999).

KJ122 produced excellent succinate yields (1.5 mol mol$^{-1}$ glucose) plus smaller amounts of acetate and pyruvate. The maximum theoretical yield for succinate is 1.71 mol ma$^{-1}$ glucose and these 3-carbon intermediates represent an opportunity to further increase yield. Pyruvate is presumed to accumulate from glycolysis as a metabolic overflow and may be related to acetate accumulation. Acetyl-CoA is an allosteric regulator of many enzymes. The source of acetate and acetate kinase activity is unknown since genes encoding the two primary activities for acetate kinase (tdcD and ackA) have been deleted (FIG. 9 and FIG. 10). Assuming that the acetate is produced from acetyl-P, the product of phosphotransacetylase, a further deletion was constructed in KJ122 to inactivate the pta gene. The resulting strain, KJ134, produced near theoretical level of succinate (Table 8). In this strain, pyruvate and acetate levels were substantially reduced. Volumetric productivity was also reduced by 17%. Succinate yields with strain KJ134 are equal to or better than all other strains regardless of the complexity of fermentation processes, media, or growth conditions.

Example 3

Recruitment of gluconeogenic PEP carboxykinase (pck) for succinate production E. coli has the metabolic potential for four native carboxylation pathways that could be used to produce succinate (FIGS. 2A-2D). The carboxylation of phosphoenolpyruvate (PEP) to oxaloacetate (OAA) by phosphoenolpyruvate carboxylase (ppc) is recognized as the primary pathway for the fermentative production of succinate in E. coli (FIG. 2A). (Fraenkel, D. G., 1996; Unden and Kleefeld, 2004; Karp et al., 2007). This reaction is essentially irreversible due to the energy loss associated with the release of inorganic phosphate. The three other carboxylation reactions are normally repressed by a high concentration of glucose in the medium and also reported to function in the reverse direction for gluconeogenesis (Samuelov et al., 1991; Oh et al., 2002; Stols and Donnelly, 1997). The second and third carboxylation pathways (FIGS. 2B and 2C) use NADH-linked and NAPDH-linked malic enzymes (sfcA and maeB, respectively), to catalyze the reversible carboxylation of pyruvate to malate. Both pathways allow energy to be conserved as ATP during the pyruvate formation from PEP. The fourth pathway uses PEP carboxykinase (pck) for the reversible carboxylation of PEP to OAA with the conservation of energy as ATP (FIG. 2D). Although PEP carboxykinase (PCK) typically functions only during gluconeogenesis in E. coli, an analogous PEP carboxykinase is present at very high levels in succinate-producing rumen bacteria where it serves as the primary PEP carboxylation activity (Van der Werf et al., 1997).

E. coli strain KJ073 was metabolically engineered by both targeted gene deletion and evolution for high growth rate and succinate production (Jantama et al., 2008a). Genes encoding each of the four carboxylating enzymes (ppc, sfcA, maeB and pck) were individually deleted to identify the primary pathway for succinate production in the engineered strain KJ073 (Table 10). Deletion of the ppc gene encoding the primary carboxylating step in native E. coli (XZ320) did not alter succinate production. Deletion of the genes encoding malic enzymes (sfcA and maeB) to produce XZ341 and XZ396, respectively, also had no effect on succinate production consistent with their primary function in gluconeogenesis. Deletion of pck encoding PEP carboxykinase (XZ332), however, dramatically reduced cell growth, sugar metabolism, succinate production, and succinate yield. Complementation of the deletion mutation in strain XZ332 with the entire pck gene from strain KJ073 (plasmid pLOI4677) substantially improved succinate production to near that of KJ073 (Table 10).

Together, these results demonstrate that the gluconeogenic PEP carboxykinase was recruited during metabolic evolution to serve as the primary carboxylation reaction for fermentative succinate production in KJ073. Unlike the PEP carboxylase (FIG. 2A), PEP carboxykinase conserves energy providing an additional ATP (FIG. 2D). Since fermentative growth and ATP production are closely linked, the increase in ATP yield with PEP carboxykinase (FIG. 2D) would provide a competitive advantage during growth-based selection at the metabolic evolution steps leading to strain KJ073.

Figure 12A:
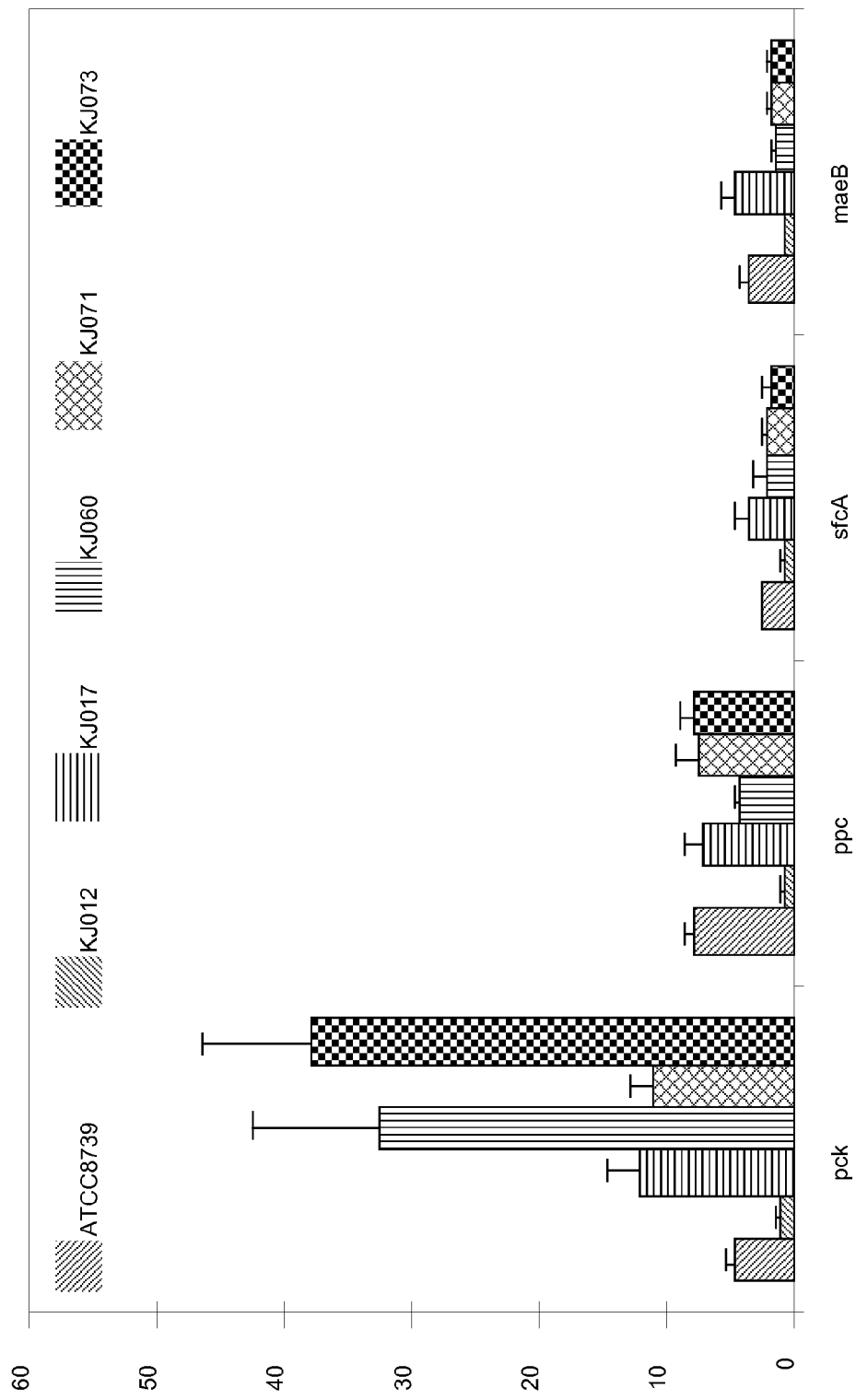
FIGS. 12A-12C. Comparison of transcript abundance of the engineered succinate-producing strains.

The increase in PEP carboxykinase activity correlated with an increase in pck mRNA abundance (Table 11; FIG. 12A). Transcript levels for ppc, sfcA and maeB were essentially unchanged while pck transcript abundance increased in KJ073 as compared to the wild-type, in excellent agreement with the enhanced PEP carboxykinase activity (Table 11).

Sequencing the pck gene revealed no difference in the coding or terminator regions of the pck gene from KJ073. However, a single point mutation (G to A transition at position −64 relative to the ATG start codon) was found in the upstream promoter region of the pck gene in KJ073 (Table 11). All six strains were sequenced to identify the origin of this mutation during strain improvement. Although PEP carboxykinase activity was 4-fold higher in KJ017 than in KJ012, the G to A mutation was absent. This point mutation in the promoter region of the pck gene in the KJ073 strain is referred as a pck* mutation (high PEP carboxykinase activity). This pck* mutation was present only in KJ060 and KJ073 strains showing high PEP carboxykinase activity and absent in KJ071. Loss of this mutation in KJ071 was accompanied by a 10-fold decrease in PEP carboxykinase activity to a level equivalent to that of KJ017.

Introduction of the pck* point mutation (G to A) into KJ017 and KJ071 increased PEP carboxykinase activity by 9-fold (Table 11). Restoring the wild-type pck gene (A to G) in strains KJ060 and KJ073 yield the strains XZ622 and XZ624, respectively. Both XZ622 and XZ624 showed decreased PEP carboxykinase activity by almost 8-fold (Table 12). Together, these results demonstrate that the increase in PCK activity that occurred during the metabolic evolution of KJ017 to produce KJ060 is due to a single nucleotide change in pck (G to A at −64 relative to the ATG start). Absence of this mutation in KJ017 suggests that the initial 4-fold increase in PEP carboxykinase activity observed in this strain is due to other yet to be defined change(s). Apparently, recruitment of the native gluconeogenic PCK for fermentative succinate production resulted from multiple mutations that affected transcription of the pck gene.

The 4-fold increase in PEP carboxykinase activity that occurred during the development of KJ017 from KJ012 did not result from a mutation in pck and may involve a mutation in a transcriptional regulator. The Cra protein has been shown to activate the expression of pck in *E. coli* (Saier and Ramseier, 1996). However, no mutation was found in the cra gene or upstream region. Deletion of cra in KJ017 (XZ626) and KJ060 (XZ627) did not affect PEP carboxykinase activity (Table 12).

The csrA system has also been reported to regulate the level of pck and other genes involved in glucose metabolism by altering mRNA stability (Pernestig et al., 2003). However, no mutation was found in the sequences of genes involved in this regulatory system (csrA, csrB, csrC, csrD, uvrY or barA).

*E. coli* PEP carboxykinase activity is subject to glucose catabolite repression (Goldie, 1984). Two Crp-binding sites have been identified in the promoter (Ramseier et al., 1995), quite distant from the point mutation in KJ060 and KJ073. Genes associated with catabolite repression (cyaA, crp) and glucose uptake by the phosphotransferase system (ptsH, ptsI, crr, ptsG) were sequenced (upstream region through terminator). Only one mutation was found, a frame-shift mutation in the carboxy-terminal region of ptsI (single base deletion at position 1,673) in strains KJ060, KJ071, and KJ073. Since this deletion was absent in KJ017, it cannot be responsible for the initial 4-fold increase in PEP carboxykinase activity in this strain (Table 12). Deletion of ptsI in KJ017 (XZ613) and in KJ060 (XZ615) did not affect PEP carboxykinase activity.

Figure 12B:
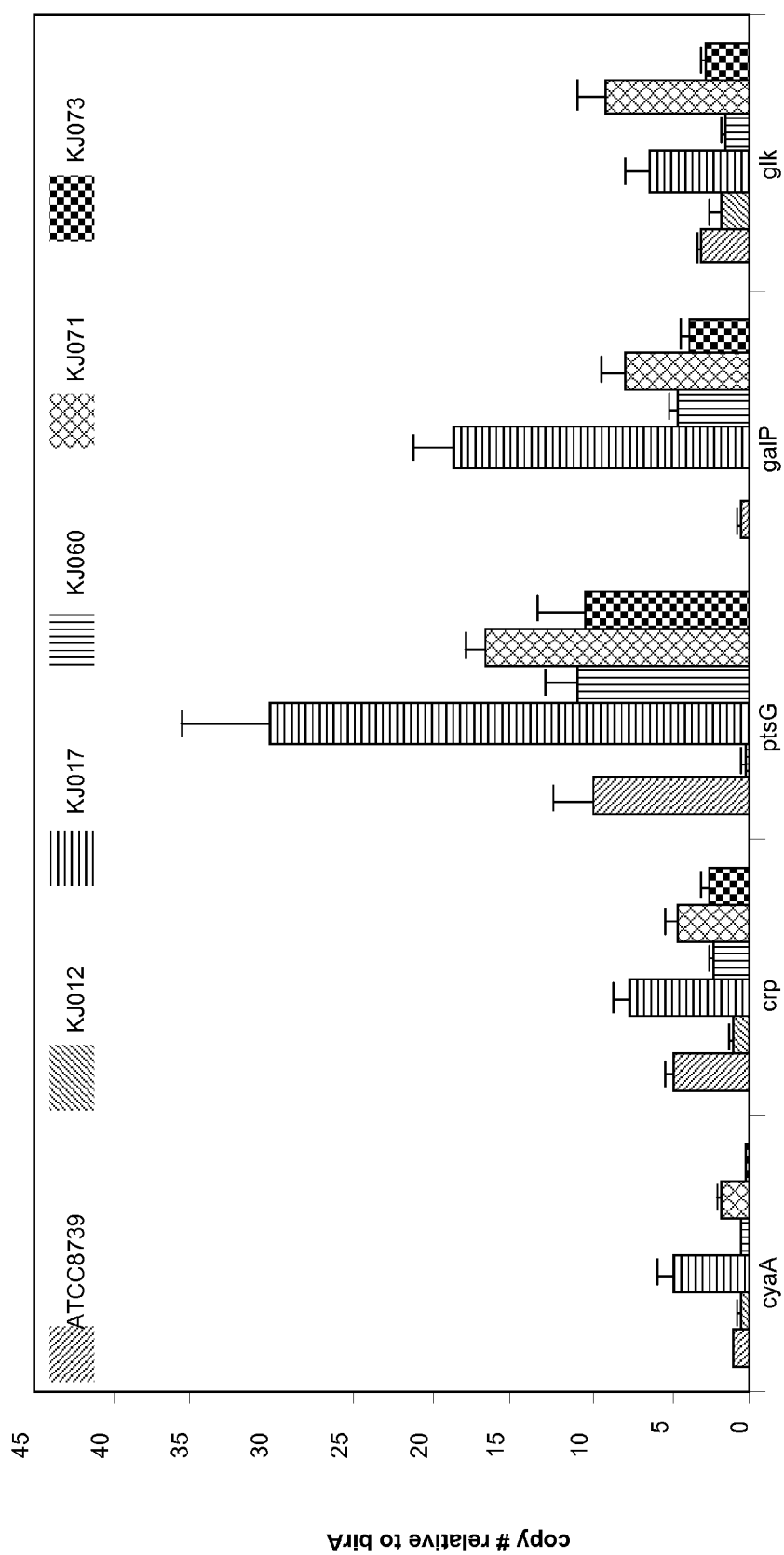
Figure 12C:
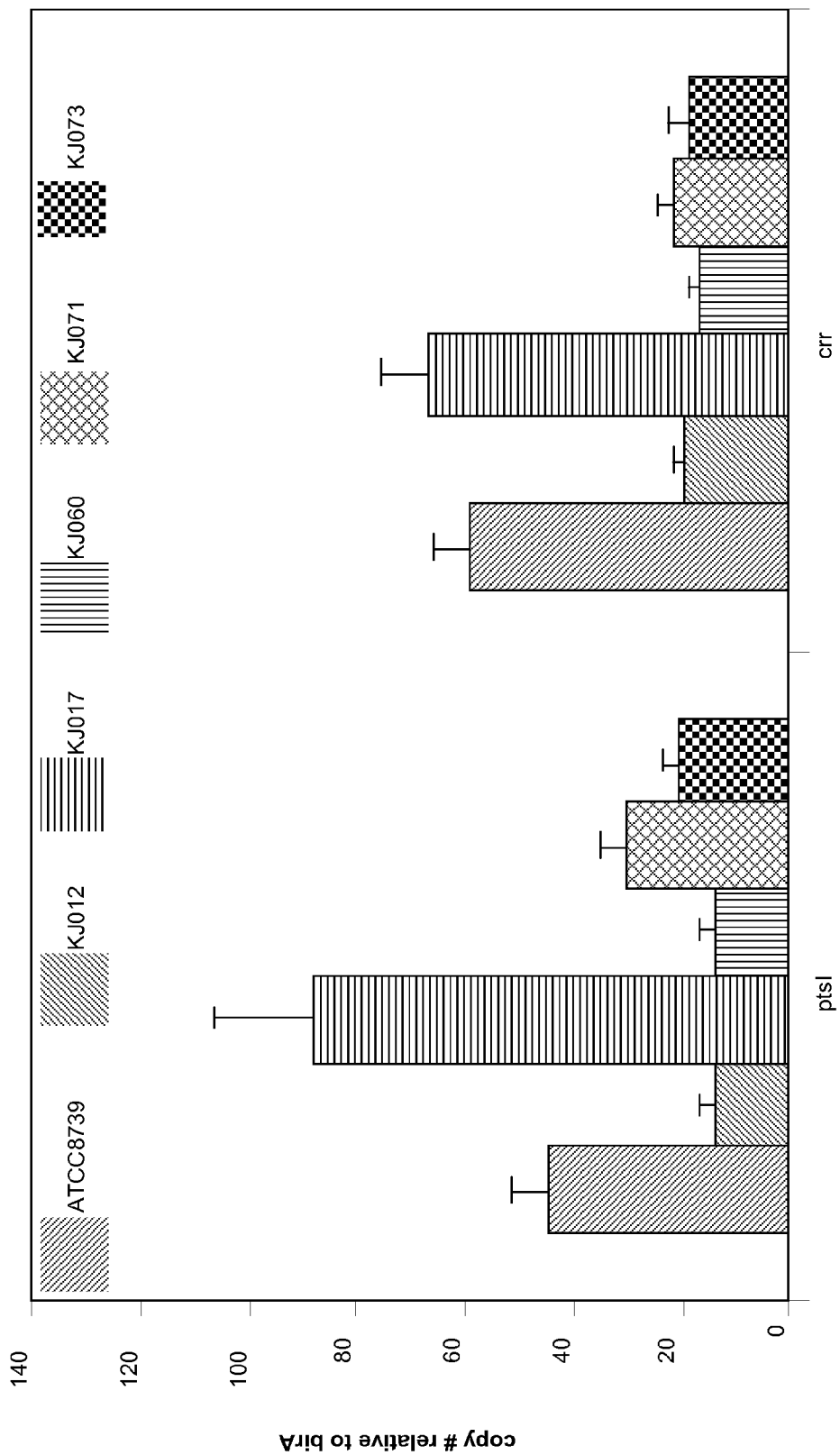

Potential changes in the catabolite repression of pck were investigated further by growing *E. coli* ATCC 8739, KJ012, KJ017, and KJ060 aerobically in LB medium with and without 5% glucose (Table 13). PEP carboxykinase activity has been reported to be maximal during the late exponential phase of growth (Goldie, 1984) and this was confirmed in our strains. In both ATCC 8739 and the starting strain for metabolic evolution (KJ012), PEP carboxykinase activities were strongly repressed (>70%) by the presence of glucose. Glucose-mediated repression was reversed by the addition of cyclic-AMP. In contrast, PEP carboxykinase activity was 4-fold higher in KJ017 than in KJ012 and was unaffected by the addition of glucose, indicating a loss of catabolite repression. PEP carboxykinase activity was even higher in KJ060 (5-fold that of KJ017) during growth in the absence of glucose, and increased further when glucose was included. In KJ060 (and KJ073), glucose catabolite repression of pck has been replaced with glucose activation (Table 13). Transcript abundance of cyaA, crp, ptsG, ptsI and crr were compared among these strains (FIGS. 12B and 12C). Transcripts for cyaA, crp, and ptsG were generally higher in KJ017, KJ060, KJ071, and KJ073 than in KJ012 and ATCC 8739. Elevated levels of these proteins could mask catabolite repression by increasing the level of cyclic-AMP.

The loss of catabolite repression in these mutants was not limited to pck expression. β-galactosidase activity was reduced by half in ATCC 8739 and KJ012 during growth with glucose (Table 13). This activity is normally repressed by glucose but was relatively unaffected in KJ017 and KJ060, consistent with general loss of Crp-mediated glucose regulation.

Deletion of the crp gene in KJ012 and KJ017 reduced the level of PEP carboxykinase activity in the resulting strains (XZ642 and XZ643, respectively) to that of the glucose-repressed parent, ATCC 8739 (Table 13). In these crp-deleted strains, PEP carboxykinase activity was not affected by the addition of glucose or cyclic AMP. Thus Crp may potentially be an essential regulatory element for the 4-fold increase in pck expression observed in KJ017 and its derivatives. This Crp-mediated 4-fold increase in pck expression together with the 10-fold increase in expression associated with the upstream pck mutation can account for the changes in the levels of PEP carboxykinase activity observed during the development of KJ060 and KJ073.

Other genes associated with cAMP-CRP regulation were also sequenced (Table 13), such as the predicted adenylate cyclase ygiF, a transcriptional co-activator for Crp sxy, the cAMP phosphodiesterase cpdA and the global regulator of carbohydrate metabolism mlc (Keseler et al., 2005; Cameron and Redfield, 2006; Imamura et al., 1996; Plumbridge, 2002). However, none of these genes associated with cAMP-CRP regulations were found to have any mutation in the upstream, coding or terminator regions.

The gene ptsI encodes PEP-protein phosphotransferase, a general (non sugar-specific) component of the phosphoenolpyruvate-dependent sugar phosphotransferase system. This major carbohydrate active-transport system catalyzes the phosphorylation of incoming sugar substrates concomitantly with their translocation across the cell membrane. PEP-protein phosphotransferase transfers the phosphoryl group from phosphoenolpyruvate (PEP) to the phosphoryl carrier protein (HPr). (See, e.g., UniProtKB, Accession Number P08839.)

A frame-shift mutation in ptsI (single base-pair deletion of position 1673 bp) was found to have occurred during the metabolic evolution of KJ060 from KJ017. To investigate the significance of this mutation, the carboxy-terminal 175 bp of ptsI was deleted in KJ017 and KJ060 to produce XZ613 and XZ615, respectively. The ptsI deletion in KJ060 (XZ615) had no effect on growth and PEP carboxykinase activities, as expected. Deletion of the ptsI carboxy-terminus in KJ017 to produce XZ613 resulted in an inability to grow on NBS mineral salts containing glucose, consistent with loss of the primary uptake system for glucose (PEP-dependent phosphotransferase system). After several days of incubation, cultures of XZ613 began to grow which are presumed to be derivatives that have activated alternative glucose transport system(s) (Karp et al., 2007).

The ptsI mutation found in KJ060, KJ071, and KJ073 would be expected to inactivate the PEP-dependent phosphotransferase system for glucose. Alternative glucose uptake systems such as GalP have been shown to restore glucose uptake in pts mutants (Wang et al., 2006; Yi et al., 2003). Expression of galP was increased by 5-fold to 20-fold in these improved strains (FIG. 12B) as compared to KJ012 and ATCC 8739, with a smaller increase in glucokinase (glk). Replacing the mutant ptsI gene in KJ060 with a functional wild-type gene (XZ616) was detrimental, dramatically reducing growth in NBS-glucose medium. This detrimental effect may result from the depletion of PEP, a required substrate for wild-type glucose transport. A functional PEP-dependent phosphotransferase system would compete with PEP carboxykinase, decreasing the PEP pool available for redox balance, ATP production, and succinate production. Thus the loss of the PEP-dependent phosphotransferase system for glucose can be viewed as a beneficial event during strain development, provided alternative transport systems such as GalP (and glucokinase) were available.

Figure 13:
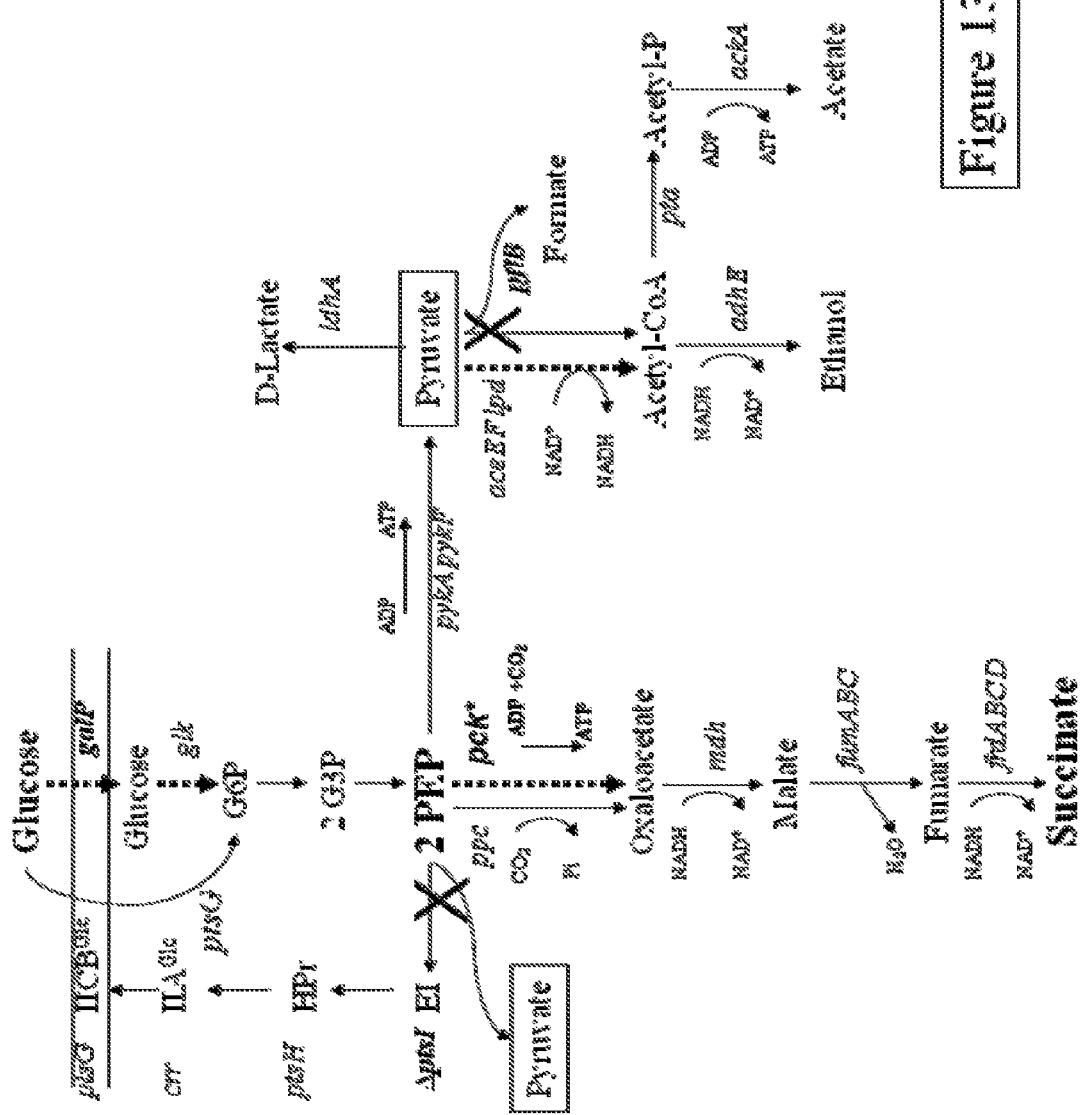

Carbon fluxes at the PEP node serve to limit the amount of succinate produced for redox balance during the anaerobic fermentation of glucose (FIG. 13). In addition, these fluxes must provide sufficient energy (ATP) for growth, maintenance, and precursors for biosynthesis. Rumen bacteria that produce succinate as the dominant product use an energy-conserving PEP carboxykinase for OAA production (FIG. 2D) (Van der Werf et al., 1997; Kim et al., 2004). Native strains of E. coli produce succinate as a minor product and use PEP carboxylase (ppc) (FIG. 2A). Unlike PEP carboxykinase, PEP carboxylase is essentially irreversible due to the energy loss associated with release of inorganic phosphate. Previous studies have shown that over-expression of the native ppc gene in E. coli resulted in higher specific succinate production (Millard et al., 1996) and higher specific growth rate due to increased carboxylation of PEP to oxaloacetate (Farmer and Liao, 1997). However, since PEP is required for the native glucose transport system, over-expressing ppc also decreased the rate of glucose uptake without significantly increasing succinate yield (Chao and Liao, 1993; Gokarn et al., 2000). This failure of the native PEP carboxylase to increase succinate yields diverted most research attention to a new metabolic design, over-expression of the pyruvate carboxylase from *Lactobacillus lactis* or *Rhizobium etli* as the carboxylating step (Sanchez et al., 2005b; Gokarn et al., 2000) and over-expression of PEP carboxykinase from *Actinobacillus succinogenes* (Kim et al., 2004) for the development of industrial biocatalysts, rather than pursuing further work with the native repertoire of E. coli genes.

Native E. coli strains have three alternative carboxylation pathways (FIGS. 2B-2D) that typically function only in the reverse direction for gluconeogenesis (Samuelov et al., 1991; Kao et al., 2005; Oh et al., 2002; Stols and Donnelly, 1997). All three would allow the conservation of energy from PEP as ATP. With succinate as the sole route for NADH oxidation, growth-based selection (metabolic evolution) resulted in strains KJ017, KJ060, KJ071, and KJ073 with improvements in growth (cell yield) and succinate production. In these strains, the gluconeogenic PEP carboxykinase (pck) was recruited to serve as the primary carboxylation activity by transcriptional activation. The recruitment of PEP carboxykinase as the primary pathway for succinate production in E. coli was surprising. Many studies have shown that increased expression of E. coli pck had no effect on succinate production (Gokarn, et al., 2001; Vemuri et al., 2002; Millard et al., 1996; Gokarn et al., 2000; Hong and Lee, 2001). A recent study demonstrated that increased expression of E. coli pck was detrimental for growth in minimal medium, decreasing the growth rate, the rate of glucose metabolism, and the yield of succinate (Kwon et al., 2008).

Increased expression of pck in E. coli resulted in increased carbon flow into the 4-carbon intermediate OAA for succinate production (redox balance), increased succinate production, and increased the net production of ATP for growth and maintenance. At least three events contributed to increased transcription of pck: 1) loss of Crp-mediated glucose-repression; 2) gain of glucose-activation; and 3) a single base change in the upstream region of pck. Each of these events provided a basis for selection through metabolic evolution by increasing the level of PEP carboxykinase, increasing the flow of carbon into succinate, and increasing the conservation of metabolic energy as ATP. The combined action of these genetic events resulted in high levels of PEP carboxykinase (>7000 U (mg protein)$^{-1}$) in KJ060 and KJ073, equivalent to rumen bacteria that have evolved to produce succinate as the primary fermentation product (VanderWerf et al., 1997).

Figure 11:
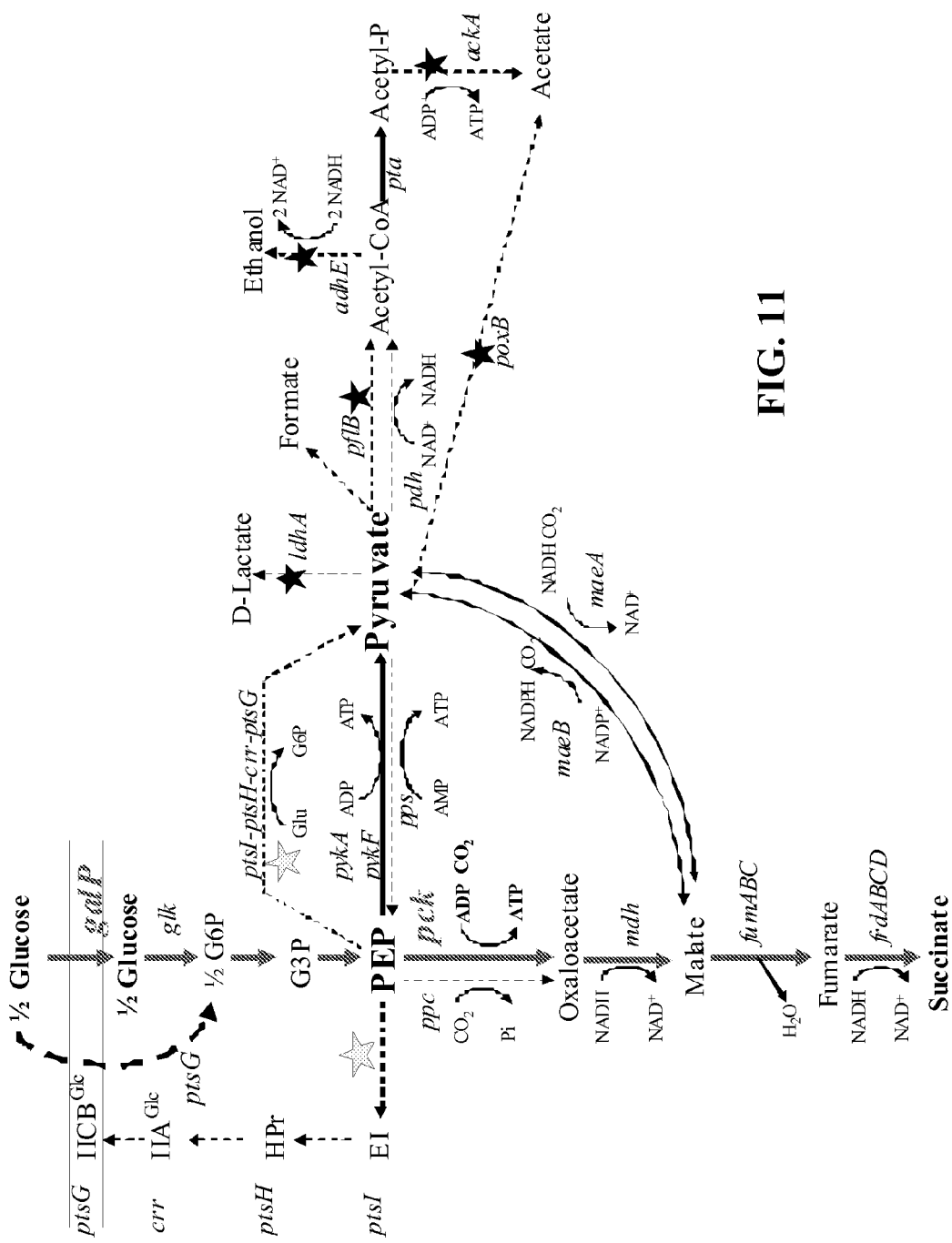
FIG. 11. Glucose fermentation in $E.$ $coli$ strains engineered for succinate production. The 5 solid stars indicate metabolic steps that have been blocked by constructing deletions. The 2 open stars indicate metabolic steps that have been blocked by mutations acquired during metabolic evolution. Dotted arrows indicate non-functional or weakly functional activities in succinate-producing mutants (KJ060 and KJ073). Bold arrows in the vertical direction indicate the primary pathway for succinate production in KJ060 and KJ073. This pathway is functionally equivalent to that of succinate-producing rumen bacteria. The two genes galP and pck were transcriptionally activated during strain development. A deletion in ptsI was acquired during growth-based selection (open star), inactivating the native glucose phosphotransferase system for uptake and phosphorylation. GalP was subsequently found to serve as the primary transporter for glucose with ATP-dependent phosphorylation by glucokinase (glk).

Additional energy-conserving changes were found in strains KJ060, KJ071, and KJ073 which may potentially assist in the recruitment of PEP carboxykinase as the primary route for fermentative succinate production. The PEP-dependent phosphotransferase system is the primary glucose uptake system in native strains of E. coli. During transport, half of the PEP produced from glucose is used for uptake and phosphorylation, limiting metabolic options for redox balance and ATP production. The improved strains contained a frame-shift mutation in ptsI that inactivated this uptake system. Expression of galP encoding a proton symporter which can transport glucose was increased by up to 20-fold. Increased expression of GalP and the native glucokinase can functionally replace the glucose phosphotransferase system by using ATP rather than PEP for phosphorylation (Wang et al., 2006; Yi et al., 2003; Flores et al., 2007). This exchange respects an energy-efficient way to increase the pool size of PEP available for carboxylation and redox balance using succinate (FIG. 11). All improved strains directed more than half of the glucose carbon into 4-carbon products (malate plus succinate) and required more than half of the PEP for redox balance. Pyruvate can be converted to PEP by ATP with the formation of PPi and AMP but energy is wasted by this process. Thus the ptsI mutation and expression of galP increased the energy efficiency of metabolizing glucose to succinate, providing a growth advantage during metabolic evolution.

Eliminating alternative routes for NADH oxidation other than the succinate, together with metabolic evolution with selection for improvements in growth, resulted in succinate-producing strains of E. coli that are the functional equivalents of succinate-producing rumen bacteria such as *Actinobacillus succinogenes* and *Mannheimia succiniciproducens* (Van der Werf et al., 1997; Kim et al., 2007; Martin, 1994; McKinlay et al., 2008). OAA is produced using an energy-conserving PEP-carboxykinase. PEP is conserved to eliminate the need for energy-expensive regeneration (2-ATP equivalents) by using glucose permeases (and glucokinase) rather than the PEP-dependent phosphotransferase system for glucose uptake. Note that among rumen bacteria producing other fermentation products, the phosphotransferase system is widely used for glucose uptake (Martin, 1994). The most promising E. coli strains for succinate production, KJ060 and KJ073, produced approximately 700 mM succinate with a yield of 1.2 mol succinate per mol glucose (Jantama et al., 2008a), comparable to the best natural succinate-producing rumen bacteria, *Actinobacillus succinogenes* (Guettler et al., U.S. Pat. No. 5,505,004).

Energy-conserving strategies that improved succinate production from glucose in E. coli could also be applied to other important problems in strain engineering. Glycerol is becoming an inexpensive feedstock due to a global increase in bio-diesel production. Being more reduced than glucose, each glycerol could be converted to succinate and maintain redox balance. However, no net ATP would be produced during glycerol metabolism to succinate using the native energy-wasting carboxylation activity, PEP carboxylase. This problem should be solved by using the energy-conserving PEP carboxykinase and allow the net formation of 1 ATP per succinate. In addition, the carboxylation product, OAA, is an important intermediate in cell metabolism that serves as a precursor for many other important fermentation products such as malic acid, fumaric acid, aspartic acid, lysine, threonine, and methionine, among others. One of

Example 4

Re-Engineering *E. coli* for Succinate Production in Mineral Salts Medium

Strains used in this study are listed in Table 16. Plasmids and primers used during construction of various strains developed during the course of this invention are listed in Table 15.

Figure 14:
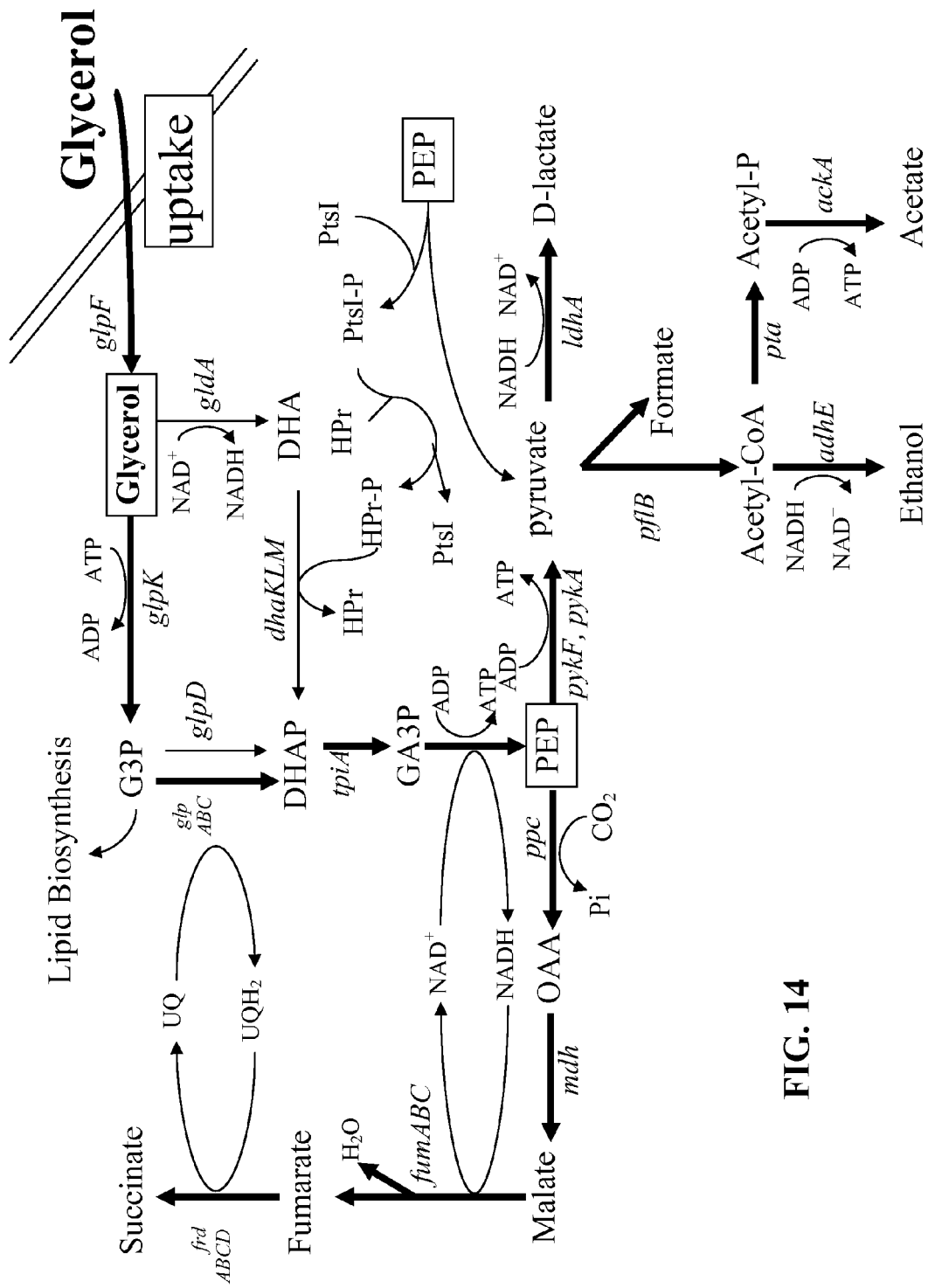
FIG. 14. Generally recognized pathways for the glycerol catabolism combined with mixed acid fermentation (anaerobic) in wild-type $E.$ $coli.$ These pathways are based on a combination of the most current reviews in EcoSal, data available in Ecocyc, and a review of primary literature (Bachler et al., 2005; Berman and Lin, 1971; Bock and Sawers, 1996; Erni et al., 2006; Gutknecht et al., 2001; Jin et al., 1983; Keseler et al., 2005; Lin, 1996; Tang et al., 1982). Bold arrows indicate the pathways generally regarded as dominant for glycerol catabolism and for mixed acid fermentation. Thin arrows show a pathway regarded as cryptic and nonfunctional in wild-type $E.$ $coli$ (Jin et al., 1983; Tang et al., 1982) involving dihydroxyacetone as an intermediate. This pathway is thought to function only in mutants in which glpK is inactive. (Jin et al., 1983; Tang et al., 1982). A thin arrow is also shown for glpD, the dehydrogenase thought to function during aerobic metabolism as a replacement for glpABC (anaerobic metabolism). Abbreviations: DHA, dihydroxyacetone; DHAP, dihydroxyacetone 3-phosphate; PEP, phosphoenolpyruvate; G3P, glycerol 3-phosphate; and GA3P, glyceraldehyde 3-phosphate. PEP is boxed to indicate a common pool.

Examination of the mixed acid pathway in *E. coli* indicates three primary routes for NADH oxidation leading to succinate, lactate, and ethanol (FIG. 14). Deleting genes that eliminated these competing routes for NADH oxidation was insufficient to direct carbon flow to succinate (Table 16). With the exception of a small increase after deletion of adhE, individual deletions of these genes decreased succinate production and yield during fermentation in NBS mineral salts medium with little effect on cell yield as compared to the parent strain (ATCC 8739). Deletion of both alternative NADH oxidation pathways (ldhA with adhE or ldhA with pflB) substantially reduced growth, succinate yield, and succinate production in NBS mineral salts medium.

Quite different results were observed in Luria broth (Table 16). A modest increase in succinate yield was found in all strains that contained a deletion in ldhA (alone or in combination). Again, growth was reduced in double mutants and triple mutants. None of these deletions were sufficient to redirect substantial amounts of glucose carbon to succinate in either mineral salts medium or complex medium. Deleted strains constructed for succinate production based on observational analysis of the native mixed acid pathway in *E. coli* were less productive than expected in complex medium, and unsuccessful in NBS mineral salts medium.

Our previous investigations (Jantama et al., 2008a; Jantama et al., 2008b) discovered a promoter mutation (G to A at −64 relative to the ATG start; denoted pck*) that increased phosphoenolpyruvate carboxykinase (PCK) activity and increased succinate production from glucose in the presence of many additional mutations. This was surprising because pck is typically repressed by glucose (Goldie, 1984) and has been shown to function primarily in gluconeogenesis during the aerobic metabolism of organic acids (Kao et al., 2005; Keseler et al., 2005; Oh et al. 2002; Unden and Kleefeld, 2004; Wu et al., 2007). To examine this further, the pck gene (ribosomal binding site, coding and terminator region) was amplified and cloned into pCR2.1-TOPO to produce pLOI4677 with pck expression under control of the lac promoter. This plasmid was transformed into ATCC 8739. Also, the native pck gene in ATCC 8739 was replaced with the mutant pck* gene to construct XZ632. Glucose fermentation was examined in both strains using NBS mineral salts medium.

Introduction of pck* resulted in a modest increase in succinate yield and production as compared to isogenic strains containing the native pck gene (Table 16). PCK activity was found to be enhanced over 8-fold both in the XZ632 stain and in the parent strain having a plasmid containing the pck* gene under the IPTG-induced promoter when compared to the parent strain. Upon chromosomal integration, the single copy of pck* was almost as effective for PCK production as the multi-copy plasmid containing the pck* gene under the IPTG-induced promoter. A modest improvement in succinate yield and production was observed for both strains with elevated PCK activity as compared to the parent ATCC 8739 strain (Table 17). However, increased PCK activity alone was insufficient to redirect glucose carbon to succinate.

The pck* mutation was tested in combination with other mutations that eliminated pathways for NADH oxidation (Table 18). The combined action of mutations to eliminate competing routes for NADH oxidation and increased PCK activity were also insufficient to substantially redirect glucose carbon to succinate.

The phosphoenolpyruvate-dependent phosphotransferase system is the primary mechanism for glucose uptake in *E. coli* and an integral part of the glucose catabolite repression system (Keseler et al., 2005; Postma et al., 1996). As described in the Example 3 above, a frame-shift mutation within the carboxyl end of ptsI (single base-pair deletion at 1673 bp position) was discovered in the succinate-producing strains KJ060, KJ071 and KJ073 as a result of metabolic evolution. This mutation would be expected to disrupt the function of the phosphotransferase system (Postma et al., 1996). In this mutant, glucose uptake was functionally replaced by galP (galactose permease) and glk (glucokinase) (Hernandez-Montalvo et al., 2003; Keseler et al., 2005). To investigate the effect of the ptsI disruption on succinate production, the carboxy-terminal 175 bp of ptsI was deleted in wild-type *E. coli* ATCC 8739 to obtain strain XZ650. Surprisingly, succinate production and yield were decreased by this mutation in comparison to the parent (Table 18).

Two approaches were used to investigate the effect of combining the ptsI truncation with high levels of PCK using the pck* mutation or the native pck over-expressed from the lac promoter (plasmid pLOI4677). In combination with the ptsI truncation, both approaches resulted in a dramatic increase in succinate production (Table 18). Strain XZ647 (pck*, ΔptsI) produced 216 mmol succinate in NBS mineral salts medium with 5% glucose with a yield of 0.89 mol succinate per mol glucose, 4.7-fold higher than wild-type *E. coli* ATCC 8739 (Table 18). With both XZ647 and XZ650 (pLOI4677), formate, ethanol and small amounts of lactate remained as minor side products. These two changes, inactivation of the phosphoenolpyruvate-dependent phosphotransferase system and elevated levels of PCK activity, represent the core changes required to effectively redirect glucose metabolism to succinate in NBS mineral salts medium without modifying any genes directly concerned with fermentative redox balance.

Further experiments confirmed that a wide variety of mutations in the phosphotransferase system increase succinate in a pck* background. Disruption of the PEP-dependent phosphotransferase system for glucose at any step increases the flow of carbon into succinate, increasing both titer and yield.

The PEP-dependent phosphotransferase system shuttles phosphate from PEP to PtsI, then PtsH, then PtsG, and then to glucose to form glucose 6-phosphate. Table 19 shows that in a strain containing the pck* mutation that increases the level of phosphoenolpyruvate carboxykinase, a second mutation in any one of the Pts genes involved in this phosphate relay system (ptsI, ptsH or ptsG) results in a similar dramatic shift in carbon flow into succinate as the dominant fermentation product. In this regard, deletion of the whole ptsI gene or a truncation of the carboxy terminus of the ptsI gene was superior to the ptsG and ptsH deletions. The truncation of the ptsI carboxyterminus produced the highest yield and titer of succinate, slightly better than the complete deletion of ptsI. Other mutations such as insertions, deletions, and frame-shifts that lead to inactive gene products would be expected to have similar effects.

Although strain XZ647 (pck* ΔptsI) produced succinate as the dominant fermentation product, significant levels of unwanted co-products (lactate, ethanol, formate, and acetate) were also produced (Table 18). Deletion of either adhE (XZ723) or pflB (XZ721) eliminated the production of ethanol. Production of acetate and formate were substantially reduced or eliminated only by deletion of pflB. The resulting strain (XZ721) produced high levels of succinate with a molar yield of over 1.2 mol succinate per mol glucose.

Succinate typically represents a minor product of glucose fermentation in *E. coli*. Most of the glucose carbon is converted to ethanol and lactate with smaller amounts of formate and acetate using alternative NADH-oxidizing pathways (FIG. 14). Derivatives of *E. coli* have been constructed to improve succinate production for more than a decade with variable success (Donnelly et al., U.S. Pat. No. 5,770,435; Gokarn et al., 2000; Gokarn et al., U.S. Pat. No. 6,455,284; Millard et al., 1996; San et al., U.S. Pat. No. 7,223,567; Sanchez et al., 2005b; Sanchez et al., 2005a; Stols and Donnelly, 1997; Vemuri et al., 2002a; Wu et al., 2007). The strategy used to construct these strains has typically focused on the elimination of competing pathways for NADH oxidation (Donnelly et al., U.S. Pat. No. 5,770,435; Gokarn et al., U.S. Pat. No. 6,455,284; San et al., U.S. Pat. No. 7,223,567; Sanchez et al., 2005b; Sanchez et al. 2005a; Vemuri et al., 2002a; Wu et al., 2007). Target genes for deletion were selected primarily based on inspection of the pathway (FIG. 14). However, successes with this strategy have been limited to complex medium and two-step (aerobic growth phase followed by anaerobic production phase) processes (Donnelly et al., U.S. Pat. No. 5,770,435; Gokarn et al., U.S. Pat. No. 6,455,284; Millard et al., 1996; San et al., U.S. Pat. No. 7,223,567; Sanchez et al., 2005b; Sanchez et al., 2005a; Vemuri et al., 2002a; Wu et al., 2007).

In complex medium such as Luria broth, most of the biosynthetic needs for growth are supplied by intermediates and building block molecules in the nutrients (yeast extract and tryptone). In this medium, deletion of genes based on observation of the fermentation pathway itself generally improved succinate production (FIG. 14; Table 16). Deletion of ldhA and all combinations of target genes including ldhA resulted in increased succinate production and increased succinate yield per glucose during fermentation in Luria broth (Table 16).

With a mineral salts medium such as NBS or AM1 broth, however, deletion of the same target genes in the mixed acid fermentation pathway was not helpful. Deletions of most were detrimental for both succinate production and succinate yield. With the exception of a small increase after the deletion of adhE, single gene deletions and combinations of gene deletions in the mixed acid fermentation pathway reduced succinate production and yields in NBS mineral salts medium (Table 17). KJ012 (ATCC 8739 ΔldhA ΔadhE ΔackA), the genetic equivalent of a strain patented for two-step (aerobic growth phase followed by anaerobic production phase) succinate production in complex medium (San et al., U.S. Pat. No. 7,223,567) produced less succinate than the wild-type parent in NBS mineral salts medium. Based on these results, we concluded that rational selection of target genes for deletion based on observations of pathways is an unreliable predictor of success for improvements in succinate production when using mineral salts medium. In mineral salts medium, carbon must be precisely partitioned between energy generation, fermentation, and the biosynthesis of building block molecules needed for cell growth.

As the results shown above indicate this invention provides a new strategy to construct strains for succinate production mineral salts medium. No mutations were required in genes encoding the *E. coli* mixed acid fermentation pathway (FIG. 14) to substantially redirect glucose carbon to succinate. In this invention, the combination of two core changes in peripheral pathways resulted in a five-fold increase in succinate yield. The two core changes that are required for succinate production are: 1) increased expression of the energy conserving (gluconeogenic) phosphoenolpyruvate carboxykinase to replace the native fermentative phosphoenolpyruvate carboxylase (energy wasting) and 2) replacement of the glucose phosphoenolpyruvate-dependent phosphotransferase system with an alternative permease such as galP and ATP-dependent phosphorylation (glk). Together, these changes increased net ATP production for growth, increased the pool of phosphoenolpyruvate available for carboxylation, and increased succinate production.

Additional mutations in genes in the mixed acid fermentation pathway, such as the deletion of pflB and others, represent opportunities for modest further increases in succinate yield and production. Note that acetyl-CoA is an essential metabolite for biosynthesis that is produced primarily by pflB during fermentative growth. This function is presumed to be replaced in pflB mutants by native expression of the pyruvate dehydrogenase complex (aceEF, lpd), an enzyme that typically serves as the dominant route for acetyl-CoA production during oxidative metabolism (Kim et al., 2007). The resulting succinate pathway in *E. coli* strains optimally engineered for succinate production in mineral salts medium (FIG. 14) is functionally similar to the native pathway that evolved in succinate-producing rumen bacteria (Kim et al., 2004; Lee et al., 2002; Lee et al., 2006; Samuelov et al., 1991; Van der Werf et al., 1997).

Example 5

Succinate Production from Glycerol

Despite the difference in redox properties and transport mechanisms for glycerol and glucose, we have discovered that the same mutations enabling the conversion of glucose into succinate in mineral salt medium can also be used to effectively redirect glycerol metabolism into succinate production at 80% of the maximum efficiency for the conversion of glycerol to succinate (0.8 mol of succinate produced per mol glycerol consumed).

Figure 15:
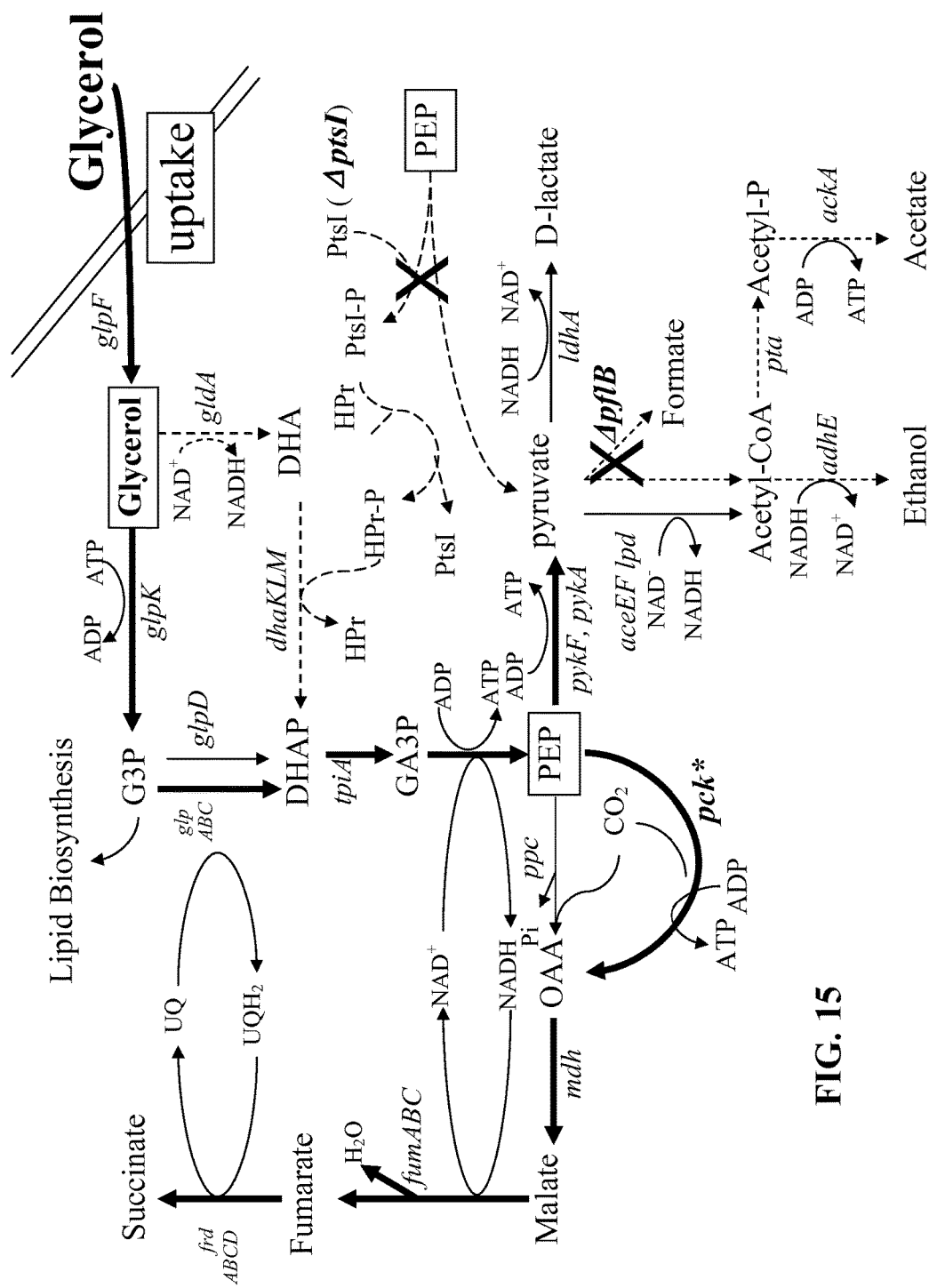
FIG. 15. Novel $E.$ $coli$ pathway for the anaerobic production of succinate from glycerol in mineral salts medium. Bold arrows indicate the primary route for the anaerobic catabolism of glycerol in strains such as XZ721 containing three core mutations for succinate production. Dotted arrows show pathways that have been blocked by mutations in pflB and ptsI. In this pathway, mutational activation of phosphoenolpyruvate carboxykinase (pck*) allows this enzyme to serve as the dominant carboxylation step for the production of oxaloacetate. Unlike the alternative carboxylating enzyme, phosphoenolpyruvate carboxylase (PPC), PCK conserves energy to produce additional ATP for biosynthesis.

During the course of these studies, we have discovered that gldA and the PEP-dependent phosphotransferase pathway previously regarded as cryptic comprise an important functional route for glycerol catabolism (FIG. 15). In both pathways, glycerol enters the cells by facilitated diffusion. Within the cell, part of the glycerol is immediately phosphorylated followed by oxidation to DHAP, the pathway that is widely regarded as the standard pathway for glycerol metabolism in *E. coli*. We have discovered that at least ⅓ of the glycerol is first reduced by gldA to DHA and subsequently phosphorylated by the PEP-dependent phosphotransferase system (ptsH, ptsI) acting within the cytoplasm to yield DHAP. DHAP serves as the common entry point to central metabolism for both uptake and activation systems.

Table 20 clearly demonstrates the effectiveness of combining the core mutations identified for succinate production with glucose for succinate production from glycerol in mineral salts medium (NBS) without the addition of complex nutrients. Although deletion of pflB alone reduced succinate production below that of the wild-type parent, the combination of the pflB deletion with the promoter mutation in pck (pck*; transcriptional activation) doubled succinate yield from 0.25 mol/mol glycerol to 0.5 mol/mol glycerol. Subsequent addition of a mutation in ptsI further increased the succinate yield to 0.8 mol of succinate/mol glycerol, 80% of the maximum theoretical yield. Similar results were also found for the deletion of other key genes (gldA, ptsH, ptsI, dhaKL, dhaM) that disrupt the use of the phosphorelay system for phosphorylation (Table 20). These results were unexpected. The resulting pathway for glycerol conversion is shown in FIG. 15.

FIG. 15 shows a combination of the generally accepted pathway for glycerol catabolism (Lin, 1996) and the mixed acid fermentation pathway (Bock and Sawers, 1996) in wild-type E. coli. In this pathway, all ATP produced would be consumed by glycerol phosphorylation if succinate is produced as a sole product. No ATP would be available for growth. Based on FIG. 15, deletion of pflB would be expected to increase succinate production by increasing the availability of reductant and intermediates. In contrast to this expectation, a decrease in succinate production was observed with the deletion of the pflB gene (Table 20). Based on this pathway, mutational activation of the pck gene that normally functions only during gluconeogenesis may be anticipated to increase the flow of phosphoenolpyruvate into succinate by competing with pyruvate kinases based solely on the prior observation in this patent application that this increase in PCK expression was beneficial for sugar fermentation into succinate; otherwise this would be unexpected. The utilization of phosphoenolpyruvate carboxykinase (pck) instead of phosphoenolpyruvate carboxylase (ppc) has the added advantage of conserving energy from phosphoenolpyruvate as an additional ATP which can be used for biosynthesis.

Although a mutation in ptsI was beneficial for the diversion of carbon from glucose to succinate, this could not have been predicted to be of any benefit since the only glycerol uptake system recognized as functional in wild-type E. coli (glpF) does not involve the phosphoenolpyruvate phosphotransferases system (Keseler et al., 2005; Lin, 1996). The only known involvement of the phosphotransferase system in glycerol metabolism is within a minor pathway thought to be inactive in wild-type E. coli. (Jin et al., 1983; Lin, 1996; Tang et al., 1982). This minor pathway first reduces intracellular glycerol to dihydroxyacetone (DHA) with GldA, then uses PtsH (ptsH) and EI (ptsI) as phosphate carriers to couple phosphoenolpyruvate to the phosphorylation of intracellular DHA to produce dihydroxyacetone-phosphate (DHAP). This pathway is thought to function only in mutant strains in which glpK is inactive (Gutknecht et al., 2001; Keseler et al., 2005). Contrary to all expectations based on the generally accepted pathways for glycerol metabolism, a mutation of ptsI significantly increased the production of succinate from glycerol. These results indicate that the glycerol dehydrogenase (gldA) and PTS phospho-relay system (phosphoenolpyruvate, PtsH, PtsI) are of unexpected importance for the catabolism of glycerol to dihydroxyacetone phosphate (DHAP) during the anaerobic fermentation of glycerol in NBS mineral salts medium. Based on the large increase in succinate yield, this dihydroxyacetone (DHA) pathway can be estimated to account for at least one-third of the glycerol flux into glycolysis. The deletion in ptsI inactivated this pathway and increased the availability of phosphoenolpyruvate for succinate production. Together, these three core mutations (pck*, ptsI, pflB) effectively and unexpectedly redirected carbon flow from glycerol to succinate at 80% of the maximum theoretical yield during anaerobic fermentation in mineral salts medium (FIG. 15). In addition, the use of this pathway results in an important increase in ATP production, facilitating growth.

TABLE 1

Comparison of succinate production by microbial biocatalysts[a]

| Organism | Medium/Condition | Succinate Titer (mM)[b] | Succinate Yield (mol/mol) | Reference |
|---|---|---|---|---|
| E. coli KJ060 (ldhA adhE ackA focA pflB) | 100 g/l glucose AM1 with 10 g/l NaHCO$_3$, simple batch fermentation, 120 h incubation, pH maintained with 1:1 mixture of 6M KOH + 3M K$_2$CO$_3$ | 733 [0.90] | 1.41 | This paper |
| E. coli KJ073 (ldhA adhE ackA focA pflB mgsA poxB) | 100 g/l glucose AM1 with 10 g/l NaHCO$_3$, simple batch fermentation, 96 h incubation, pH maintained with 1:1 mixture of 6M KOH + 3M K$_2$CO$_3$ | 668 [0.82] | 1.20 | This paper |
| E. coli KJ060 (ldhA adhE ackA focA pflB) high inoculum (200 mg CDW l$^{-1}$) | 100 g/l glucose AM1 with 10 g/l NaHCO$_3$, simple batch fermentation, 120 h incubation, pH maintained with 1:1 mixture of 6M KOH + 3M K$_2$CO$_3$ | 622 [0.61] | 1.61 | This paper |
| Actinobacillus succinogenes FZ53 | 130 g/l glucose supplemented with 15 g/l CSL and 5 g/l YE, 80 g/l MgCO$_3$, anaerobic batch fermentation, 78 h incubation | 898 [1.36] | 1.25 | Guettler et al., 1996a |
| E. coli AFP111 (pflAB, ldhA, ptsG) Rhizobium etli pyc overexpressed | 40 g/l glucose (90 g total glucose) in medium supplemented with 20 g/l tryptone, 10 g/l YE and 40 g/l MgCO$_3$, dual phase-fed batch fermentation, 76 h incubation | 841 [1.31] | 1.68 | Vemuri et al., 2002ab |

TABLE 1-continued

Comparison of succinate production by microbial biocatalysts[a]

| Organism | Medium/Condition | Succinate Titer (mM)[b] | Succinate Yield (mol/mol) | Reference |
|---|---|---|---|---|
| Anaerobiospirillum succiniciproducens ATCC 53488 | 120 g/l glucose in peptone/YE based medium, integrated membrane-bioreactor-electrodialysis with $CO_2$ sparging, 150 h incubation | 703 [0.55] | 1.35 | Meynial-Salles et al., 2007 |
| Actinobacillus succinogenes 130Z | 100 g/l glucose supplemented with 15 g/l CSL and YE, 80 g/l $MgCO_3$, anaerobic batch fermentation, $CO_2$ sparging, 39 h incubation | 678 [2.05] | 1.37 | Guettler et al., 1996b |
| E. coli HL27659k/pKK313 (iclR sdhAB ackA-pta poxB, pstG) Sorghum vulgare pepc overexpressed | 106 g/l glucose in medium supplemented with 20 g/l tryptone, 32 g/l YE and 2 g/l $NaHCO_3$, fed batch fermentation under complete aerobic condition, 59 h incubation | 499 [1.00] | 0.85 | Lin et al., 2005d |
| Anaerobiospirillum succiniciproducens ATCC 53488 | 50 g/l glucose and 10 g/l CSL, $CO_2$ sparging and 300 mM $Na_2CO_3$, batch fermentation, 24 h incubation | 426 [2.09] | 1.37 | Glassner and Datta, 1992 |
| Mannheimia succiniciproducens (ldhA pflB pta-ackA) | 63 g/L glucose in MMH3 (yeast extract based medium), fed batch fermentation, 0.25 vol/vol/min $CO_2$ sparging, 30 h incubation | 444 [1.75] | 1.16 | Lee et al., 2006 |
| Bacterial Isolate 130Z ATCC 55618 | 50 g/l glucose supplemented with 1% CSL, 0.6% YE, and 2 g/l $MgCO_3$ neutralized with 10N NaOH, 0.3 atm of $CO_2$, 29.5 h incubation | 388 [1.55] | 1.40 | Guettler et al., 1998 |
| E. coli SBS550MG (ldhA adhE iclR E.. ackA-pta), L. lactis pyc Bacillus subtilis citZ | 20 g/l glucose (100 g total glucose) LB supplemented with 1 g/l $NaHCO_3$, 200 mg/l ampicillin, and 1 mM IPTG. 100% $CO_2$ at 1 L/min STP headspace, repeated fed-batch fermentation, 95 h incubation | 339 [0.42] | 1.61[c] | Sanchez et al., 2005a; Cox et al., 2006 |
| E. coli AFP184 (pflB ldhA pts) | 102 g/l glucose supplemented with 15 g/l CSL, dual phase aerobic growth and anaerobic production, sparging with air followed by $CO_2$, 32 h incubation | 339 [1.27] | 0.72[c] | Andersson et al., 2007 |
| Actinobacillus succinogenes ATCC 55618 | 70 g/l glucose with flour hydrolysate and 5 g/l YE, anaerobic batch fermentation with 4% inoculum, 65 h incubation | 302 [0.55] | 1.18 | Du et al., 2007 |
| Anaerobiospirillum succiniciproducens ATCC 53488 | 50 g/l glucose, 2% CSL, and 25 ppm tryptophan, neutralized with 5.5M $NaCO_3$, saturated medium of 0.3 atm partial pressure of $CO_2$, 29.5 h incubation | 289 [1.16] | 1.04 | Guettler et al., 1998 |
| Succinivibrio dextrinosolvens ATCC 19716 | 15 g/l of each CSL and YE, 100 g/l glucose, and 80 g/l $MgCO_3$, batch fermentation, 36 h. | 226 [0.74] | NR | Guettler et al., 1998 |
| Corynebacterium glutamicum R | 40 g/l glucose (121 g total glucose) in Defined mineral salt medium with 400 mM $NaHCO_3$, fed batch fermentation, 6 h incubation | 195 [3.83] | 0.29 | Okino et al., 2005 |
| Prevotella ruminocola ATCC 19188 | 15 g/l of each CSL and YE, 100 g/l glucose, and 80 g/l $MgCO_3$, batch fermentation, 36 h incubation | 160 [0.52] | NR | Guettler et al., 1998 |
| E. coli SBS550MG (ldhA adhE iclR ackA-pta), L. lactis pyc Bacillus subtilis citZ | 20 g/l glucose LB supplemented with 1 g/l $NaHCO_3$, 200 mg/l ampicillin, and 1 mM IPTG. 100% $CO_2$ at 1 L/min STP headspace, batch fermentation, 24 h. incubation | 162.6 [0.80] | 1.61[c] | Sanchez et al., 2005a; Cox et al., 2006 |

TABLE 1-continued

Comparison of succinate production by microbial biocatalysts[a]

| Organism | Medium/Condition | Succinate Titer (mM)[b] | Succinate Yield (mol/mol) | Reference |
|---|---|---|---|---|
| *Mannheimia succiniciproducens* MBEL55E KCTC 0769BP | 18 g/L glucose in MH4 (YE based medium) supplemented with 119 mM NaHCO$_3$, a continuous-cell-recycle membrane reactor with the CO$_2$ partial pressure of 101.3 kPa gas (100% CO$_2$), 6 h incubation | 144 [2.83] | 1.44 | Song et al., 2007 |
| *E. coli* SBS110MG (ldhA adhE), *Lactococcus lactis* pyc | 20 g/l glucose LB supplemented with 1.5 g/l NaHCO$_3$ and 0.5 g MgCO$_3$, 200 mg/l ampicillin, and 1 mM IPTG. Dual phase with 100% CO$_2$ at 1 L/min STP headspace, 168 h incubation | 130 [0.09] | 1.24[c] | Sanchez et al., 2005a; Sanchez et al., 2006 |
| *E. coli* NZN111 (W1485 pflB ldhA), *E. coli* sfcA overexpressed | 20 g/l glucose LB supplemented with 0.5 g MgCO$_3$, 1.5 g/l NaOAc, 0.1 g/l ampicillin, and 10 μM IPTG, 44 h incubation, sealed serum tube. | 108 [0.22] | 0.98[c] | Stols et al., 1997 |
| *E. coli* JCL1208, *E. coli* ppc overexpressed | 11 g/l glucose LB supplemented with 0.15 g MgCO$_3$, 0.1 g/l carbenicillin, and 0.1 mM IPTG, 44 h incubation, anoxic CO$_2$ charging at 1 atm headspace, 18 h incubation | 91 [0.60] | 0.44[c] | Millard et al., 1996 |
| *E. coli* GJT - *Sorghum* pepC | 40 g/l glucose LB supplemented with 27.78 g/l MgCO$_3$, simple batch fermentation in sealed airtight flask | 80 [no data] | 0.42[c] | Lin et al., 2005c |
| *E. coli* HL51276k (iclR icd sdhAB ackA-pta poxB, pstG), *Sorghum* sp. pepC S8D mutation | 10.8 g/l glucose LB supplemented with 2 g/l NaHCO$_3$, 50 mg/l kanamycin, 1 mM IPTG, aerobic batch reactor, 50 h incubation | 68 [0.16] | 1.09[c] | Lin et al., 2005b |
| *E. coli* SBS880MG (ldhA adhE ΔfdhF), *L. lactis* pyc | 20 g/l glucose LB supplemented with 1.5 g/l NaHCO$_3$ and 0.5 g MgCO$_3$, 200 mg/l ampicillin, and 1 mM IPTG. Dual phase with 100% CO$_2$ headspace, 168 h incubation | 60 [0.04] | 0.94[c] | Sanchez et al., 2005b |

[a]Abbreviations: CSL, corn steep liquor; YE, yeast extract; NR, not reported.
[b]Average volumetric productivity is shown in brackets [g l$^{-1}$ h$^{-1}$] beneath succinate titer.
[c]The molar yield was calculated based on the production of succinate from metabolized sugar during both aerobic and anaerobic conditions. Biomass was generated predominantly during aerobic growth. Succinate was produced primarily during anaerobic incubation with CO$_2$, H$_2$, or a mixture of both.

TABLE 2

List of bacterial strains that have been deposited with the ARS culture collection.

| Culture | Strain Designations | Deposit Date |
|---|---|---|
| KJ012 | B-50022 | Mar. 15, 2007 |
| KJ017 | B-50023 | Mar. 15, 2007 |
| KJ032 | B-50024 | Mar. 15, 2007 |
| KJ060 | B-50025 | Mar. 15, 2007 |
| KJ070 | B-50026 | Mar. 15, 2007 |
| KJ071 | B-50027 | Mar. 15, 2007 |
| KJ072 | B-50028 | Mar. 15, 2007 |
| KJ073 | B-50029 | Mar. 15, 2007 |
| KJ091 | B-50110 | Feb. 20, 2008 |
| KJ098 | B-50111 | Feb. 20, 2008 |
| KJ104 | B-50112 | Feb. 20, 2008 |
| KJ110 | B-50113 | Feb. 20, 2008 |
| KJ119 | B-50114 | Feb. 20, 2008 |
| KJ122 | B-50115 | Feb. 20, 2008 |
| KJ134 | B-50116 | Feb. 20, 2008 |
| XZ320 | NRRL B-50267 | Mar. 17, 2009 |
| XZ332 | NRRL B-50268 | Mar. 17, 2009 |
| XZ341 | NRRL B-50269 | Mar. 17, 2009 |
| XZ396 | NRRL B-50270 | Mar. 17, 2009 |
| XZ468 | NRRL B-50271 | Mar. 17, 2009 |
| XZ469 | NRRL B-50272 | Mar. 17, 2009 |
| XZ470 | NRRL B-50273 | Mar. 17, 2009 |
| XZ613 | NRRL B-50274 | Mar. 17, 2009 |
| XZ615 | NRRL B-50275 | Mar. 17, 2009 |
| XZ616 | NRRL B-50276 | Mar. 17, 2009 |
| XZ618 | NRRL B-50277 | Mar. 17, 2009 |
| XZ620 | NRRL B-50278 | Mar. 17, 2009 |
| XZ647 | NRRL B-50279 | Mar. 17, 2009 |
| XZ721 | NRRL B-50280 | Mar. 17, 2009 |
| XZ723 | NRRL B-50281 | Mar. 17, 2009 |

TABLE 3

Escherichia coli strains, plasmids, and primers used in this study

| | Relevant Characteristics | Sources |
|---|---|---|
| *Escherichia coli* Strains | | |
| Strain C | Wild type (ATCC 8739) | ATCC |
| KJ012 | strain C, ΔldhA::FRT ΔadhE::FRT ΔackA::FRT | This study |
| KJ017 | KJ012, improved strain selected from 10% glucose, NBS | This study |
| KJ032 | KJ017, ΔldhA::FRT ΔadhE::FRT ΔackA::FRT Δ(focA-pflB)::FRT | This study |
| KJ060 | KJ032, improved strain selected from 10% glucose without initial acetate, NBS | This study |
| KJ070 | KJ060, ΔmgsA | This study |
| KJ071 | KJ070, improved strain selected from 10% glucose, NBS | This study |
| KJ072 | KJ071, ΔpoxB | This study |
| KJ073 | KJ072, improved strain selected from 10% glucose, AM1 | This study |
| SZ204 | Δ(focA-pflB)::FRT-kan-FRT | Zhou, 2003 |
| Plasmids | | |
| pKD4 | bla FRT-kan-FRT | Datsenko, 2000 |
| pKD46 | bla γ β exo (Red recombinase), temperature-conditional replicon | Datsenko, 2000 |
| pFT-A | bla flp temperature-conditional replicon and FLP recombinase | Posfai, 1997 |
| pEL04 | cat-sacB targeting cassette | Lee, 2001<br>Thomason, 2005 |
| pLOI3421 | 1.8 kbp SmaI fragment containing aac | Wood, 2005 |
| pLOI4151 | bla cat; cat-sacB cassette | This study |
| pCR2.1-TOPO | bla kan; TOPO TA cloning vector | Invitrogen |
| pLOI4228 | bla kan; yccT'-mgsA-helD' (PCR) from *E.coli* C cloned into pCR2.1-TOPO vector | This study |
| pLOI4229 | cat-sacB cassette PCR amplified from pLOI4151 (EcoRV digested) cloned into mgsA in pLOI4228 | This study |
| pLOI4230 | PCR fragment amplified from pLOI4228 (using mgsA-1/2 primers), kinase treated, then self-ligation | This study |
| pLOI4274 | bla kan; poxB (PCR) from *E.coli* C cloned into pCR2.1-TOPO vector | This study |
| pLOI4275 | cat-sacB cassette PCR amplified from pLOI4151 (EcoRV digested) cloned into poxB of pLOI4274 | This study |
| pLOI4276 | PCR fragment amplified from pLOI4274 (using poxB-1/2 primers), kinase treated, then self-ligation | This study |
| Primer sets | | |
| ldhA | 5'ATGAACTCGCCGTTTTATAGCACAAAACAGTACG<br>ACAAGAAGTACGTGTAGGCTGGAGCTGCTTC3'<br>(SEQ ID NO: 2)<br>5'TTAAACCAGTTCGTTCGGGCAGGTTTCGCCTTTT<br>TCCAGATTGCTCATATGAATATCCTCCTTAG3'<br>(SEQ ID NO: 3) | This study |

TABLE 3-continued

*Escherichia coli* strains, plasmids, and primers used in this study

| | Relevant Characteristics | Sources |
|---|---|---|
| adhE | 5'ATGGCTGTTACTAATGTCGCTGAACTTAACGCAC<br>TCGTAGAGCGT<u>GTGTAGGCTGGAGCTGCTTC</u>3'<br>(SEQ ID NO: 4)<br>5'TTAAGCGGATTTTTTCGCTTTTTTCTCAGCTTTAG<br>CCGGAGCAGC<u>CATATGAATATCCTCCTTAG</u>3'<br>(SEQ ID NO: 5) | Zhou, 2003 |
| ackA | 5'ATGTCGAGTAAGTTAGTACTGGTTCTGAACTGCG<br>GTAGTTCTTCA<u>GTGTAGGCTGGAGCTGCTTC</u>3'<br>(SEQ ID NO: 6)<br>5'TCAGGCAGTCAGGCGGCTCGCGTCTTGCGCGATA<br>ACCAGTTCTTC<u>CATATGAATATCCTCCTTAG</u>3'<br>(SEQ ID NO: 7) | Zhou, 2003 |
| focA-pflB | 5'TTACTCCGTATTTGCATAAAAACCATGCGAGTTA<br>CGGGCCTATAA<u>GTGTAGGCTGGAGCTGCTTC</u>3'<br>(SEQ ID NO: 8)<br>5'ATAGATTGAGTGAAGGTACGAGTAATAACGTCCT<br>GCTGCTGTTCT<u>CATATGAATATCCTCCTTAG</u>3'<br>(SEQ ID NO: 9) | This study |
| JMcatsacB | 5'TTAGCTAGCATGTGACGGAAGATCACTTCG3'<br>(SEQ ID NO: 10)<br>5'CCGCTAGCATCAAAGGGAAAACTGTCCATAT3'<br>(SEQ ID NO: 11) | This study |
| cat-up2/sacB-down2 | 5'AGAGAGGATATCTGTGACGGAAGATCACTTCG3'<br>(SEQ ID NO: 12)<br>5'AGAGAGGATATCGAATTGATCCGGTGGATGAC3'<br>(SEQ ID NO: 13) | This study |
| mgsA-up/down | 5'CAGCTCATCAACCAGGTCAA3'<br>(SEQ ID NO: 14)<br>5'AAAAGCCGTCACGTTATTGG3'<br>(SEQ ID NO: 15) | This study |
| mgsA-1/2 | 5'AGCGTTATCTCGCGGACCGT3'<br>(SEQ ID NO: 16)<br>5'AAGTGCGAGTCGTCAGTTCC3'<br>(SEQ ID NO: 17) | This study |
| poxB-up/down | 5'AAGCAATAACGTTCCGGTTG3'<br>(SEQ ID NO: 18)<br>5'CCACTTTATCCAGCGGTAGC3'<br>(SEQ ID NO: 19) | This study |
| poxB-1/2 | 5'GACGCGGTGATGAAGTGAT3'<br>(SEQ ID NO: 20)<br>5'TTTGGCGATATAAGCTGCAA3'<br>(SEQ ID NO: 21) | This study |
| pck-F/R | 5'TTGGCTAAGG AGCAGTGAAA TGCGCGTTA3'<br>(SEQ ID NO: 22)<br>5'CACGACAAAA GAAGGGTAAA TAAAC3'<br>(SEQ ID NO: 23) | This study |
| pck-2/3 | 5'TTGTTAACGCGCATTTCACT3'<br>(SEQ ID NO: 24)<br>5'GCGATAGCGGCTACTGTCAT3'<br>(SEQ ID NO: 25) | This study |
| pck (RT-PCR) | 5'GACGATACCACTCGCGAT3'<br>(SEQ ID NO: 26)<br>5'GTCGACAACGAACAGACGT3'<br>(SEQ ID NO: 27) | This study |
| birA (RT-PCR) | 5'ATCGTGATGGCGGAAGT3'<br>(SEQ ID NO: 28)<br>5'CTTGCGATCCTGCAGATAG3'<br>(SEQ ID NO: 29) | This study |

TABLE 4

Fermentation of glucose in mineral salts medium by mutant strains of E. coli

| Strain[a] | Culture Conditions | Media, Glucose % | Cell Yield[b] (g/L) | Succinate Yield[c] mol/mol | g/g | Av. Vol. Prod[d] (g/L/h) |
|---|---|---|---|---|---|---|
| E. coli C wild type[f] | OD$_{550}$, 0.1 mM betaine | 5%, NBS | 2.0 ± 0.2 | 0.19 ± 0.02 | 0.12 | 0.12 ± 0.01 |
| KJ012[f] | 0.1 OD$_{550}$, 0.1 mM betaine | 5% NBS | 0.3 ± 0.1 | 0.20 ± 0.01 | 0.13 | 0.04 ± 0.01 |
| KJ012 | OD$_{550}$, 0.1 mM betaine shaken flask[h] | 5% NBS + MOPS | 1.5 | 0.10 | 0.06 | 0.02 |
| KJ012 | OD$_{550}$ Luria Broth | 5% LB | 1.5 | 0.70 | 0.50 | 0.09 |
| KJ012 (ldhA, ackA, adhE) | 1$^{st}$ TF: No betaine, 0.1 OD$_{550}$, 120 h transfers | 5%, NBS | 0.3 | 0.13 | 0.09 | 0.072 |
| | 3$^{rd}$ TF: 2 mM betaine, 0.1 OD$_{550}$, 96 h transfers | 5%, NBS | 0.7 | 0.28 | 0.18 | 0.128 |
| | 40$^{th}$ TF: 1 mM betaine, 0.1 OD$_{550}$, 24 h transfers, 3M K$_2$CO$_3$ + 6N KOH | 5%, NBS | 2.3 | 0.73 | 0.48 | 0.251 |
| (KJ017) | 40$^{th}$ TF: 1 mM betaine, 0.1 OD$_{550}$, 24 h transfers, 3 M K$_2$CO$_3$ + 6N KOH | 10%, NBS | 1.7 | 0.74 | 0.49 | 0.354 |
| KJ032 (ldhA, ackA, adhE, pflB) | 2$^{nd}$ TF: 1 mM betaine, 0.1 OD$_{550}$, 48 h transfers, 20 mM NaOAc, 3M K$_2$CO$_3$ + 6N KOH | 5%, NBS | 1.0 | 1.47 | 0.97 | 0.260 |
| (KJ060) | 15$^{th}$ TF: 1 mM betaine, 0.01 OD$_{550}$, 24 h transfers, 5 mM NaOAc, 3M K$_2$CO$_3$ + 6N KOH | 10%, NBS | 1.4 | 1.07 | 0.71 | 0.736 |
| | 5$^{th}$ TF: 1 mM betaine, 0.01 OD$_{550}$, 24 h transfers, No NaOAc, 3M K$_2$CO$_3$ + 6N KOH | 10%, NBS | 1.4 | 1.04 | 0.69 | 0.711 |
| KJ070 (ldhA, ackA, adhE, focA, pflB, mgsA) | 1$^{st}$ TF: 1 mM betaine, 0.01 OD$_{550}$, 24 h TF, 3M K$_2$CO$_3$ + 6N KOH, | 5%, NBS | 1.0 | 1.06 | 0.70 | 0.361 |
| (KJ071) | 50$^{th}$ TF: 1 mM betaine, 0.01 OD$_{550}$, 24 h transfers, 3M K$_2$CO$_3$ + 6N KOH | 10%, NBS | 1.1 | 0.71 | 0.47 | 0.419 |
| KJ072 (ldhA, ackA, adhE, focA pflB, mgsA, poxB) | 2$^{nd}$ TF: 1 mM betaine, 0.01 OD$_{550}$, 24 h transfers, 3M K$_2$CO$_3$ + 6N KOH | 10%, NBS | 1.3 | 0.97 | 0.64 | 0.663 |
| (KJ073) | 6$^{th}$ TF: 1 mM betaine, 0.01 OD$_{550}$, 24 h transfers, 3M K$_2$CO$_3$ + 6N KOH | 10%, AM1 | 1.2 | 1.34 | 0.88 | 0.733 |
| | 45$^{th}$ TF: 1 mM betaine, 0.01 OD$_{550}$, 24 h transfers, 3M K$_2$CO$_3$ + 6N KOH | 10%, AM1 | 1.5 | 1.26 | 0.83 | 0.858 |
| KJ073[f] | 1mM betaine, 3M K$_2$CO$_3$ + 6N KOH, 0.01 OD$_{550}$ inoculum | 10%, AM1 | 2.3 ± 0.1 | 1.20 ± 0.09 | 0.77 ± 0.03 | 0.82 ± 0.01 |
| KJ060[f] | 1 mM betaine, 3M K$_2$CO$_3$ + 6N KOH, 0.01 OD$_{550}$ inoculum | 10%, AM1 | 2.2 ± 0.1 | 1.41 ± 0.07 | 0.92 ± 0.05 | 0.90 ± 0.04 |
| KJ060[f] | 1 mM betaine, 3M K$_2$CO$_3$ + 6N KOH, 0.60 OD$_{550}$ inoculum | 10%, AM1 | 2.2 ± 0.1 | 1.61 ± 0.12 | 1.05 ± 0.09 | 0.77 ± 0.04 |
| KJ071[f] | 1 mM betaine, 3M K$_2$CO$_3$ + 6N KOH, 0.01 OD$_{550}$ inoculum | 10%, NBS | 1.5 ± 0.0 | 0.78 ± 0.02 | 0.53 ± 0.01 | 0.33 ± 0.04 |

| Strain[a] | | Fermentation Products (mM)[e] | | | | | |
|---|---|---|---|---|---|---|---|
| | | Suc | Mal | Pyr | Ace | Lac | For |
| E. coli C wild type[f] | OD$_{550}$, 0.1 mM betaine | 49 ± 3 | —[g] | 33 ± 10 | 152 ± 30 | 98 ± 24 | 262 ± 19 |
| KJ012[f] | 0.1 OD$_{550}$, 0.1 mM betaine | 6 ± 0.4 | — | — | 26 ± 1 | — | — |
| KJ012 | OD$_{550}$, 0.1 mM betaine shaken flask[h] | 10 | — | — | 226 | — | 16 |
| KJ012 | OD$_{550}$ Luria Broth | 108 | — | — | 61 | <2 | 14 |
| KJ012 (ldhA, ackA, adhE) | 1$^{st}$ TF: No betaine, 0.1 OD$_{550}$, 120 h transfers | 6 | — | — | 26 | <2 | — |
| | 3$^{rd}$ TF: 2 mM betaine, 0.1 OD$_{550}$, 96 h transfers | 26 | — | — | 71 | <2 | — |
| | 40$^{th}$ TF: 1 mM betaine, 0.1 OD$_{550}$, 24 h transfers, 3M K$_2$CO$_3$ + 6N KOH | 204 | — | — | 179 | <2 | 151 |
| (KJ017) | 40$^{th}$ TF: 1 mM betaine, 0.1 OD$_{550}$, 24 h transfers, 3 M K$_2$CO$_3$ + 6N KOH | 288 | — | — | 181 | 38 | 199 |

TABLE 4-continued

Fermentation of glucose in mineral salts medium by mutant strains of E. coli

| Strain | Conditions | suc | mal | pyr | ace | lac | for |
|---|---|---|---|---|---|---|---|
| KJ032 (ldhA, ackA, adhE, focA, pflB) (KJ060) | 2nd TF: 1 mM betaine, 0.1 OD$_{550}$, 48 h transfers, 20 mM NaOAc, 3M K$_2$CO$_3$ + 6N KOH | 212 | — | — | 44 | — | — |
| | 15th TF: 1 mM betaine, 0.01 OD$_{550}$, 24 h transfers, 5 mM NaOAc, 3M K$_2$CO$_3$ + 6N KOH | 596 | 331 | 9 | 170 | <2 | — |
| | 5th TF: 1 mM betaine, 0.01 OD$_{550}$, 24 h transfers, No NaOAc, 3M K$_2$CO$_3$ + 6N KOH | 579 | 318 | 9 | 161 | <2 | — |
| KJ070 (ldhA, ackA, adhE, focA, pflB, mgsA) (KJ071) | 1st TF: 1 mM betaine, 0.01 OD$_{550}$, 24 h TF, 3M K$_2$CO$_3$ + 6N KOH, | 294 | 219 | 25 | 102 | — | — |
| | 50th TF: 1 mM betaine, 0.01 OD$_{550}$, 24 h transfers, 3M K$_2$CO$_3$ + 6N KOH | 341 | 626 | <2 | 76 | — | — |
| KJ072 (ldhA, ackA, adhE, focA pflB, mgsA, poxB) (KJ073) | 2nd TF: 1 mM betaine, 0.01 OD$_{550}$, 24 h transfers, 3M K$_2$CO$_3$ + 6N KOH | 539 | 186 | <2 | 95 | — | — |
| | 6th TF: 1 mM betaine, 0.01 OD$_{550}$, 24 h transfers, 3M K$_2$CO$_3$ + 6N KOH | 596 | 38 | 4 | 112 | — | — |
| | 45th TF: 1 mM betaine, 0.01 OD$_{550}$, 24 h transfers, 3M K$_2$CO$_3$ + 6N KOH | 699 | 313 | 103 | 172 | — | — |
| KJ073 [f] | 1mM betaine, 3M K$_2$CO$_3$ + 6N KOH, 0.01 OD$_{550}$ inoculum | 668 ± 8 | 118 ± 13 | 55 ± 22 | 183 ± 27 | — | — |
| KJ060 [f] | 1 mM betaine, 3M K$_2$CO$_3$ + 6N KOH, 0.01 OD$_{550}$ inoculum | 733 ± 39 | 39 ± 17 | — | 250 ± 36 | 2 ± 1 | — |
| KJ060 [f] | 1 mM betaine, 3M K$_2$CO$_3$ + 6N KOH, 0.60 OD$_{550}$ inoculum | 622 ± 8 | 17 ± 5 | 1.5 ± 1 | 180 ± 13 | 2 ± 1 | — |
| KJ071 [f] | 1 mM betaine, 3M K$_2$CO$_3$ + 6N KOH, 0.01 OD$_{550}$ inoculum | 280 ± 7 | 516 ± 14 | 58 ± 15 | 64 ± 9 | — | — |

[a] Clones were isolated from the fermentation broth at various points and assigned strain numbers, indicated by numbers in parenthesis.
[b] Cell yield estimated from optical density (3 OD$_{550\,nm}$ = 1 g l$^{-1}$ CDW).
[c] Succinate yields were calculated based on glucose metabolized.
[d] Average volumetric productivity was calculated for total incubation time.
[e] Abbreviations: suc, succinate; mal, malate; pyr, pyruvate; ace, acetate; lac, lacate; for, formate.
[f] Average of 3 or more fermentations with standard deviations.
[g] Dash indicates absence of product.
[h] Aerobic shaken flask (100 rpm); 100 ml NBS, 250-ml flask.

TABLE 5

Comparison of carboxylation enzyme activities in different strains

| | Specific activity [nmol min$^{-1}$ (mg protein)$^{-1}$] | | | | | |
|---|---|---|---|---|---|---|
| Enzyme | E.coli C | E.coli KJ012 | E.coli KJ017 | E.coli KJ073 | E.coli K12 [a] | Actinobacillus succinogenes [a] |
| PEP carboxylase | 20 ± 2 | 25 ± 2 | 17 ± 1 | 27 ± 2 | 140 | 10 |
| PEP carboxykinase | 295 ± 23 | 162 ± 11 | 700 ± 68 | 7341 ± 462 | 140 | 4,700 |
| Malic enzyme (NADH, carboxylation) | ND [b] | 5 ± 2 | 12 ± 4 | 12 ± 3 | Unknown | Unknown |
| Malic enzyme (NADPH carboxylation) | <1 | <1 | <1 | <1 | Unknown | Unknown |

[a] data was from van der Werf et al., 1997
[b] Unable to measure in wild type E. coli C due to presence of lactate dehydrogenase

TABLE 6

Composition of media (excluding carbon source).

| Component | ᵃNBS + 1 mM betaine | AM1 + 1 mM betaine |
|---|---|---|
| | Concentration (mmol L$^{-1}$) | |
| $KH_2PO_4$ | 25.72 | 0 |
| $K_2HPO_4$ | 28.71 | 0 |
| $(NH_4)_2HPO_4$ | 26.50 | 19.92 |
| $NH_4H_2PO_4$ | 0 | 7.56 |
| Total $PO_4$ | 80.93 | 27.48 |
| Total N | 53.01 | 47.39 |
| ᵇTotal K | 84.13 | 1.00 |
| $MgSO_4$ $7H_2O$ | 1.00 | 1.50 |
| $CaCl_2$ $2H_2O$ | 0.10 | 0 |
| Thiamine HCl | 0.015 | 0 |
| Betaine-KCl | 1.00 | 1.00 |

TABLE 6-continued

Composition of media (excluding carbon source).

| Component | ᵃNBS + 1 mM betaine | AM1 + 1 mM betaine |
|---|---|---|
| | (μmol L$^{-1}$)ᶜ | |
| $FeCl_3$ $6H_2O$ | 5.92 | 8.88 |
| $CoCl_2$ $6H_2O$ | 0.84 | 1.26 |
| $CuCl_2$ $2H_2O$ | 0.59 | 0.88 |
| $ZnCl_2$ | 1.47 | 2.20 |
| $Na_2MoO_4$ $2H_2O$ | 0.83 | 1.24 |
| $H_3BO_3$ | 0.81 | 1.21 |
| $MnCl_2$ $4H_2O_2$ | 0 | 2.50 |
| Total Salts | 12.5 g L$^{-1}$ | 4.1 g L$^{-1}$ |

ᵃNBS + 1 mM betaine: NBS media amended with betaine (1 mM).
ᵇCalculation includes KOH used to neutralize betaine-HCl stock.
ᶜTrace metal stock (1000X) was prepared in 120 mM HCl.

TABLE 7

Escherichia coli strains, plasmids, and primers used in herein

| Strain B | Relevant Characteristics | Sources |
|---|---|---|
| | Escherichia coli Strains | |
| KJ073 | ΔldhA::FRT ΔadhE::FRT Δ(focA-pflB)::FRT ΔackA::FRT ΔmgsA ΔpoxB | Jantama et al., 2008 |
| KJ076 | KJ073, ΔackA::cat-sacB, translational stop sequence | Disclosed herein |
| KJ079 | KJ073, ΔackA::translational stop sequence | Disclosed herein |
| TG200 | KJ079, ΔadhE::cat-sacB | Disclosed herein |
| TG201 | TG200, ΔadhE | Disclosed herein |
| TG202 | TG201, ΔldhA::cat-sacB | Disclosed herein |
| TG203 | TG202, ΔldhA | Disclosed herein |
| TG204 | TG203, Δ(focA-pflB)::cat-sacB | Disclosed herein |
| KJ091 | TG204, Δ(focA-pflB) | Disclosed herein |
| KJ098 | KJ091, ΔtdcDE | Disclosed herein |
| KJ104 | KJ098, ΔcitF | Disclosed herein |
| KJ110 | KJ104, ΔaspC | Disclosed herein |
| KJ119 | KJ104, ΔsfcA | Disclosed herein |
| KJ122 | KJ110, ΔsfcA | Disclosed herein |
| KJ134 | KJ122, ΔackA-pta | Disclosed herein |
| | Plasmids | |
| pKD46 | Bla γ β exo (red recombinase), temperature-conditional replicon | Datsenko, 2000 |

TABLE 7-continued

*Escherichia coli strains, plasmids, and primers used in herein*

| Strain B | Relevant Characteristics | Sources |
|---|---|---|
| pEL04 | cat-sacB cassette | Lee, 2001 Thomason, 2005 |
| pLOI2228 | cat; FRT-cat-FRT cassette | Martinez-Morales et al., 1999 |
| pLOI2511 | bla kan; FRT-kan-FRT cassette | Underwood et al., 2002 |
| pLOI4131 | bla; ligation of pLOI2228 (BanI digested, Klenow treated, ClaI digested FRT-cat-FRT cassette) and pLOI2511 (NheI digested, Klenow treated, ClaI digested) | Disclosed herein |
| pLOI4145 | bla; EcoRI digested pLOI4131, self-ligation | Disclosed herein |
| pLOI4146 | bla cat; ligation of cat-sacB cassette PCR amplified (using JMcatsacBup3/down3 primers) from pLOI4152, BamHI/XhoI digested and BamHI/XhoI digested pLOI4153 | Disclosed herein |
| pLOI4151 | bla cat; cat-sacB cassette | Jantama et al, 2008 |
| pLOI4152 | cat-sacB cassette; PCR amplified cassette from pEL04 (using JMpEL04F1/R1 primers), BglII digestion and self-ligation | Disclosed herein |
| pLOI4153 | bla; ligation of pLOI4145 (KasI/XmaI digested) and KasI/XmaI digested SfPBXPS polylinker (annealing of complementary oligonucleotides SfPBXPSsense/SfPBXPScomp) | Disclosed herein |
| pLOI4154 | PacI digested pLOI4146, self ligation | Disclosed herein |
| pLOI4161 | bla cat; cat-sacB cassette | Disclosed herein |
| pLOI4162 | bla cat; ligation of cat-sacB cassette (PacI digested) from pLOI4146 and PacI digested pLOI4161 | Disclosed herein |
| pCR2.1-TOPO | bla kan; TOPO TA cloning vector | Invitrogen |
| pLOI4158 | bla kan; ackA (PCR) from *E.coli* C (using JMackA-F1/R1 primers) cloned into pCR2.1-TOPO vector | Disclosed herein |
| pLOI4159 | SmaI/SfoI digested cat-sacB cassette from pLOI4162 cloned into the PCR amplified inside-out product from pLOI4158 (using JMackAup1/down1) | Disclosed herein |
| pLOI4160 | PacI digestion of pLOI4159, then self-ligated | Disclosed herein |
| pLOI4515 | bla kan; tdcG'-tdcFED-tdcC' (PCR) from *E.coli* C (using utdcDE-p/down primers) cloned into pCR2.1-TOPO vector | Disclosed herein |
| pLOI4516 | SmaI/SfoI digested cat-sacB cassette from pLOI4162 cloned into the PCR amplified inside-out product from pLOI4515 (using tdcDE-F7/R7 primers) | Disclosed herein |
| pLOI4517 | PCR fragment amplified inside-out product from pLOI415 (using tdcDE-F7/R7 primers), kinase treated, then self-ligated | Disclosed herein |
| pLOI4629 | bla kan; citF (PCR) from *E.coli* C (using citF-up2/down2 primers) cloned into pCR2.1-TOPO vector | Disclosed herein |
| pLOI4630 | SmaI/SfoI digested cat-sacB cassette from pLOI4162 cloned into the PCR amplified inside-out product from pLOI4629 (using citF-2/3 primers) | Disclosed herein |

TABLE 7-continued

*Escherichia coli* strains, plasmids, and primers used in herein

| Strain B | Relevant Characteristics | Sources |
|---|---|---|
| pLOI4631 | PacI digestion of pLOI4630, then self-ligated | Disclosed herein |
| pLOI4280 | bla kan; aspC (PCR) from *E.coli* C (using aspC-up/down primers) cloned into pCR2.1-TOPO vector | Disclosed herein |
| pLOI4281 | SmaI/SfoI digested cat-sacB cassette from pLOI4162 cloned into the PCR amplified inside-out product from pLOI4280 (using aspC-1/2 primers) | Disclosed herein |
| pLOI4282 | PCR fragment amplified inside-out product from pLOI4280 (using aspC-1/2 primers), kinase treated, then self-ligated | Disclosed herein |
| pLOI4283 | bla kan; sfcA (PCR) from *E.coli* C (using sfcA-up/down primers) cloned into pCR2.1-TOPO vector | Disclosed herein |
| pLOI4284 | SmaI/SfoI digested cat-sacB cassette from pLOI4162 cloned into the PCR amplified inside-out product from pLOI4283 (using sfcA-1/2 primers) | Disclosed herein |
| pLOI4285 | PacI digestion of pLOI4284, then self-ligated | Disclosed herein |
| pLOI4710 | bla kan; ackA-pta (PCR) from *E.coli* C (using ackA-up/pta-down primers) cloned into pCR2.1-TOPO vector | Disclosed herein |
| pLOI4711 | SmaI/SfoI digested cat-sacB cassette from pLOI4162 cloned into the PCR amplified inside-out product from pLOI4710 (using ackA-2/pta-2 primers) | Disclosed herein |
| pLOI4712 | PacI digestion of pLOI4711, then self-ligated | Disclosed herein |
| pLOI4413 | bla kan; ychE'-adhE-ychG' (PCR) from *E.coli* C (using up/down-adhE primers) cloned into pCR2.1-TOPO vector | Disclosed herein |
| pLOI4419 | PCR fragment amplified inside-out product from pLOI4413 (IO-adhE-up/down using primers), kinase treated, then self-ligated | Disclosed herein |
| pLOI4415 | bla kan; ycaO'-focA-pflB-pflA' (PCR) from *E.coli* C (using up-focA/Mid-pflA primers) cloned into pCR2.1-TOPO vector | Disclosed herein |
| pLOI4421 | PCR fragment amplified inside-out product from pLOI4415 (using IO-ycaO-up/IO-midpflB-down primers), kinase treated, then self-ligated | Disclosed herein |
| pLOI4430 | bla kan; hslJ'-ldhA-ydbH' (PCR) from *E.coli* C (using ldhA-A/C primers) cloned into pCR2.1-TOPO vector | Disclosed herein |
| pLOI4432 | PCR fragment amplified inside-out product from pLOI4424 (using IO-ldhA-up/down primers), kinase treated, then self-ligated | Disclosed herein |

Primer sets

| | | |
|---|---|---|
| JM4161 sense/comp | 5'ACCGCATCAGGCGCCTAATTAATTAATCCCGG3' (SEQ ID NO: 30)<br>5'CCGGGATTAATTAATTAGGCGCCTGATGCGGT3' (SEQ ID NO: 31) | Disclosed herein |
| JMpEL04F 1/R1 | 5'CAGCAGATCTAAGTAAATCGCGCGGGTTTG3' (SEQ ID NO: 32)<br>5'CAGCAGATCTAGCGGCTATTTAACGACCCT3' (SEQ ID NO: 33) | Disclosed herein |
| JMackA-F1/R1 | 5'GCCTGAAGGCCTAAGTAGTA3' (SEQ ID NO: 34)<br>5'GCACGATAGTCGTAGTCTGA3' (SEQ ID NO: 35) | Disclosed herein |
| JmackA up1/down1 | 5'GTTGAGCGCTTCGCTGTGAG3' (SEQ ID NO: 36)<br>5'GCCGCAATGGTTCGTGAACT3' (SEQ ID NO: 37) | Disclosed herein |

TABLE 7-continued

*Escherichia coli* strains, plasmids, and primers used in herein

| Strain B | Relevant Characteristics | Sources |
|---|---|---|
| JmcatsacB up3/down3 | 5'CTCACCTCGAGTGTGACGGAAGATCACTTCG3' (SEQ ID NO: 38)<br>5'GTGCAGGATCCATCAAAGGGAAAACTGTCCATAT3' (SEQ ID NO: 39) | Disclosed herein |
| SfPBXPS sense/comp | 5'ATGTAGGCGCCATTAATTAATGGATCCACTATCTCGAGATTAATTAATCCCGGGACTAT3' (SEQ ID NO: 40)<br>5'ATAGTCCCGGGATTAATTAATCTCGAGATAGTGGATCCATTAATTAATGGCGCCTACAT3' (SEQ ID NO: 41) | Disclosed herein |
| WMadhE A/C | 5'ATGGCTGTTACTAATGTCGCTGAACTTAACGCACTCGTAGAGCGTCGGCACGTAAGAGGTTCCAA3' (SEQ ID NO: 42)<br>5'TTAAGCGGATTTTTTCGCTTTTTTCTCAGCTTTAGCCGGAGCAGCACACTGCTTCCGGTAGTCAA3' (SEQ ID NO: 43) | Disclosed herein |
| WMldhA A/C | 5'ATGAAACTCGCCGTTTATAGCACAAAACAGTACGACAAGAAGTACGGCACGTAAGAGGTTCCAA3' (SEQ ID NO: 44)<br>5'TTAAACCAGTTCGTTCGGGCAGGTTTCGCCTTTTTCCAGATTGCTACACTGCTTCCGGTAGTCAA3' (SEQ ID NO: 45) | Disclosed herein |
| WMpflB A/C | 5'TTACTCCGTATTTGCATAAAAACCATGCGAGTTACGGGCCTATAACGGCACGTAAGAGGTTCCAA3' (SEQ ID NO: 46)<br>5'TTACATAGATTGAGTGAAGGTACGAGTAATAACGTCCTGCTGCTGTTCTACACTGCTTCCGGTAGTCAA3' (SEQ ID NO: 47) | Disclosed herein |
| tdcDE-up/down | 5'CGCCGACAGAGTAATAGGTT3' (SEQ ID NO: 48)<br>5'TGATGAGCTACCTGGTATGG3' (SEQ ID NO: 49) | Disclosed herein |
| tdcDE-F7/R7 | 5'CGATGCGGTGGCCAATTAAG3' (SEQ ID NO: 50)<br>5'GACGACGTGCTGGATTACGA3' (SEQ ID NO: 51) | Disclosed herein |
| citF-up2/down2 | 5'GGGTATTCAGGCGTTCGATA3' (SEQ ID NO: 52)<br>5'GCCCGAGAGGATGACTATGT3' (SEQ ID NO: 53) | Disclosed herein |
| citF-2/3 | 5'GGTGATCGATGTTGTGCATC3' (SEQ ID NO: 54)<br>5'CCCGTTCTTGTCGTTGAGAT3' (SEQ ID NO: 55) | Disclosed herein |
| IO-adhE-up/down | 5'GCTGCTCCGGCTAAAGCTGA3' (SEQ ID NO: 56)<br>5'ACGCTCTACGAGTGCGTTAA3' (SEQ ID NO: 57) | Disclosed herein |
| up-focA/Mid-pflB | 5'AGATCGCCAGCCGCTGCAAT3' (SEQ ID NO: 58)<br>5'AACCGTTGGTGTCCAGACAG3' (SEQ ID NO: 59) | Disclosed herein |
| IO-ycaO-up/IO-midpflB-down | 5'GCCTACATTGCGTAGGCTAT3' (SEQ ID NO: 60)<br>5'GCAGCAGGACGTTATTACTC3' (SEQ ID NO: 61) | Disclosed herein |
| ldhA-A/C | 5'ATGAAACTCGCCGTTTATAG3' (SEQ ID NO: 62)<br>5'TTAAACCAGTTCGTTGCCC3' (SEQ ID NO: 63) | Disclosed herein |
| IO-ldhA-up/down | 5'CGTTCGATCCGTATCCAAGT3' (SEQ ID NO: 64)<br>5'AGGCTGGAACTCGGACTACT3' (SEQ ID NO: 65) | Disclosed herein |
| aspC-up/down | 5'TCCATCGCTTACACCAAATC3' (SEQ ID NO: 66)<br>5'TGGGGGATGACGTGATATTT3' (SEQ ID NO: 67) | Disclosed herein |
| aspC-1/2 | 5'AGATAACATGGCTCCGCTGT3' (SEQ ID NO: 68)<br>5'AGGAGCGGCGGTAATGTTC3' (SEQ ID NO: 69) | Disclosed herein |
| sfcA-up/down | 5'CTATGCTTGATCGGCAACCT3' (SEQ ID NO: 70)<br>5'ACGATCGCCTGGTTTTAATG3' (SEQ ID NO: 71) | Disclosed herein |
| sfcA-1/2 | 5'TACCGCCGTACCTCCATCTA3' (SEQ ID NO: 72)<br>5'CGTAAGGGATATAAAGCGAACG3' (SEQ ID NO: 73) | Disclosed herein |

TABLE 7-continued

Escherichia coli strains, plasmids, and primers used in herein

| Strain B | Relevant Characteristics | Sources |
|---|---|---|
| ackA-up/pta-down | 5'CGGGACAACGTTCAAAACAT3' (SEQ ID NO: 74)<br>5'ATTGCCCATCTTCTTGTTGG3' (SEQ ID NO: 75) | Disclosed herein |
| ackA-2/pta-2 | 5'AACTACCGCAGTTCAGAACCA3' (SEQ ID NO: 76)<br>5'TCTGAACACCGGTAACACCA3' (SEQ ID NO: 77) | Disclosed herein |

TABLE 8

Fermentation of glucose in mineral salts AM1 medium by mutant strains of E. coli

| Strain | Culture Conditions | Media, Glucose (w/v) | Cell Yield$^a$ (g/L) | Succinate Yield$^b$ mol/mol | g/g | Av. Vol. Prod $^c$ (g/L/h) | Fermentation Products (mM) $^{d,e,f}$ Suc | Mal | Pyr | Ace | Lac | For |
|---|---|---|---|---|---|---|---|---|---|---|---|---|
| KJ073 | 1 mM betaine, 3M K$_2$CO$_3$ + 6N KOH (1:1) 0.01 OD$_{550}$ inoculum | 10%, AM1 | 2.3 ± 0.1 | 1.20 ± 0.09 | 0.77 ± 0.03 | 0.82 ± 0.01 | 668 ± 8 | 118 ± 13 | 55 ± 22 | 183 ± 27 | — | — |
| KJ091 | 1 mM betaine, 3M K$_2$CO$_3$ + 6N KOH (1:1) 0.01 OD$_{550}$ inoculum | 10%, AM1 | 2.2 ± 0.1 | 1.19 ± 0.02 | 0.78 ± 0.01 | 0.84 ± 0.01 | 687 ± 3 | 109 ± 3 | 72 ± 5 | 155 ± 6 | — | |
| KJ098 | 1 mM betaine, 3M K$_2$CO$_3$ + 6N KOH (1:1) 0.01 OD$_{550}$ inoculum | 10%, AM1 | 2.3 ± 0.1 | 1.30 ± 0.04 | 0.85 ± 0.02 | 0.79 ± 0.01 | 644 ± 9 | — | 42 ± 8 | 88 ± 1 | — | — |
| KJ104 | 1 mM betaine, 3M K$_2$CO$_3$ + 6N KOH (4:1) 0.01 OD$_{550}$ inoculum | 10%, AM1 | 1.8 ± 0.1 | 1.31 ± 0.01 | 0.86 ± 0.01 | 0.78 ± 0.03 | 634 ± 25 | 5 ± 1 | 78 ± 5 | 90 ± 10 | — | — |
| KJ104 | 1 mM betaine, 3M K$_2$CO$_3$ + 6N KOH (6:1) 0.01 OD$_{550}$ inoculum | 10%, AM1 | 1.9 ± 0.1 | 1.30 ± 0.01 | 0.85 ± 0.01 | 0.77 ± 0.01 | 625 ± 4 | 3 ± 2 | 94 ± 5 | 81 ± 2 | — | — |
| KJ110 | 1 mM betaine, 3M K$_2$CO$_3$ + 6N KOH (4:1) 0.01 OD$_{550}$ inoculum | 10%, AM1 | 2.0 ± 0.1 | 1.28 ± 0.02 | 0.84 ± 0.01 | 0.79 ± 0.01 | 640 ± 10 | 4 ± 1 | 76 ± 6 | 106 ± 11 | — | — |
| KJ119 | 1 mM betaine, 3M K$_2$CO$_3$ + 6N KOH (4:1) 0.01 OD$_{550}$ inoculum | 10%, AM1 | 2.0 ± 0.1 | 1.33 ± 0.07 | 0.87 ± 0.01 | 0.82 ± 0.01 | 672 ± 10 | 4 ± 0 | 64 ± 18 | 95 ± 14 | — | — |
| KJ122 | 1 mM betaine, 3M K$_2$CO$_3$ + 6N KOH (4:1) 0.01 OD$_{550}$ inoculum | 10%, AM1 | 2.3 ± 0.1 | 1.50 ± 0.02 | 0.98 ± 0.01 | 0.92 ± 0.01 | 750 ± 1 | 0 ± 0 | 122 ± 21 | 94 ± 13 | — | — |
| KJ122 | 1 mM betaine, 3M K$_2$CO$_3$ + 6N KOH (6:1) 0.01 OD$_{550}$ inoculum | 10%, AM1 | 2.0 ± 0.2 | 1.54 ± 0.02 | 1.01 ± 0.01 | 0.97 ± 0.04 | 787 ± 35 | 6 ± 3 | 59 ± 6 | 110 ± 7 | — | — |
| KJ122 | 1 mM betaine, 3M K$_2$CO$_3$ + 6N KOH (6:1) 0.15 OD$_{550}$ inoculum | 10%, AM1 | 2.1 ± 0.1 | 1.57 ± 0.09 | 1.03 ± 0.06 | 0.93 ± 0.06 | 756 ± 49 | 0 ± 0 | 124 ± 13 | 122 ± 9 | — | — |
| KJ134 | 1 mM betaine, 3M K$_2$CO$_3$ + 6N KOH (6:1) 0.01 OD$_{550}$ inoculum | 10%, AM1 | 2.3 ± 0.1 | 1.70$^g$ ± 0.03 | 1.11 ± 0.02 | 0.83 ± 0.02 | 674 ± 15 | 13 ± 2 | 22 ± 9 | 37 ± 5 | | — |

$^a$Cell yield estimated from optical density (3 OD$_{550\,nm}$ = 1 gl$^{-1}$ CDW).
$^b$Succinate yields were calculated based on glucose metabolized.
$^c$ Average volumetric productivity was calculated for total incubation time.
$^d$ Abbreviations: suc, succinate; mal, malate; pyr, pyruvate; ace, acetate; lac, lacate; for, formate.
$^e$ Ethanol (153 ± 39 mM) was present only in broth from E. coli C.
$^f$ All data represent an average of 3 or more fermentations with standard deviations.
$^g$Additional products were also found despite near theoretical yields of succinate. Based on total products, coproducts represented 11%.

TABLE 9

Sources and characteristics of *E. coli* strains and plasmids used in this study

| | Relevant characteristics | Source or reference |
|---|---|---|
| Strains | | |
| ATCC 8739 | Wild type | Lab collection |
| KJ012 | ΔackA, Δ ldhA, Δ adhE | Jantama et al. 2008 |
| KJ017 | ΔackA, Δ ldhA, ΔadhE | Jantama et al. 2008 |
| KJ060 | ΔackA, Δ ldhA, ΔadhE, ΔpflB | Jantama et al. 2008 |
| KJ071 | ΔackA, ΔldhA, ΔadhE, Δ pflB, ΔmgsA | Jantama et al. 2008 |
| KJ073 | ΔackA, ΔldhA, Δ adhE, ΔpflB, Δ mgsA, ΔpoxB | Jantama et al. 2008 |
| XZ320 | KJ073, Δppc | This study |
| XZ332 | KJ073, Δpck | This study |
| XZ341 | KJ073, ΔsfcA | This study |
| XZ396 | KJ073, ΔmaeB | This study |
| XZ613 | KJ017, ΔptsI | This study |
| XZ615 | KJ060, ΔptsI | This study |
| XZ616 | KJ060, restored ptsI to wild type | This study |
| XZ618 | KJ017, pck* | This study |
| XZ620 | KJ071, pck* | This study |
| XZ622 | KJ060, restored pck to wild type | This study |
| XZ624 | KJ073, restored pck to wild type | This study |
| XZ626 | KJ017, Δcra | This study |
| XZ627 | KJ060, Δcra | This study |
| XZ642 | KJ012, Δcrp | This study |
| XZ643 | KJ017, Δcrp | This study |
| Plasmids | | |
| pLOI4677 | bla kan; pck (including ribosomal binding site, coding and terminator fragment) from *E.coli* ATCC8739 cloned into pCR2.1-TOPO vector | This study |
| ptsI mutation change | | |
| pLOI4734 | bla kan; ptsI (ptsI-D-up/D-down) from *E.coli* ATCC8739 cloned into pCR2.1-TOPO vector | This study |
| pLOI4735 | cat-sacB cassette (SmaI-SfoI fragment of pLOI4162) cloned into ptsI of pLOI4734 | This study |
| pck mutation change | | |
| pLOI4736 | bla kan; pck-P (pck-Pro-up/Pro-down) from *E.coli* ATCC873 cloned into pCR2.1-TOPO vector | This study |

TABLE 9-continued

Sources and characteristics of *E. coli* strains and plasmids used in this study

| | Relevant characteristics | Source or reference |
|---|---|---|
| pLOI4737 | cat-sacB cassette (SmaI-SfoI fragment of pLOI4162) cloned into pck-P of pLOI4736 (pck-Pro-1/Pro-2) | This study |

Primers
pck mutation change

| | | |
|---|---|---|
| pck-Pro-up | CACGGTAGCAACAACATTGC (SEQ ID NO: 78) | This study |
| pck-Pro-down | AGAAAGCGTCGACAACGAAC (SEQ ID NO: 79) | |
| pck-Pro-1 | ATGCGCGTTAACAATGGTTT (SEQ ID NO: 80) | |
| pck-Pro-2 | ATGGATAACGTTGAACTTTC (SEQ ID NO: 81) | | ptsI mutation change

| | | |
|---|---|---|
| ptsI-D-up | CGCATTATGTTCCCGATGAT (SEQ ID NO: 82) | This study |
| ptsI-D-down | GCCTTTCAGTTCAACGGTGT (SEQ ID NO: 83) | |
| ptsI-D-1 | CGGCCCAATTTACTGCTTAG (SEQ ID NO: 84) | |
| ptsI-D-2 | ATCCCCAGCAACAGAAGTGT (SEQ ID NO: 85) | | pck sequencing

| | | |
|---|---|---|
| pck-F | TTGGCTAAGGAGCAGTGAAATGCGCGTTA (SEQ ID NO: 86) | This study |
| pck-R | CACGACAAAAGAAGGGTAAATAAAC (SEQ ID NO: 87) | |
| pck-2 | TTGTTAACGCGCATTTCACT (SEQ ID NO: 88) | |
| pck-3 | GCGATAGCGGCTACTGTCAT (SEQ ID NO: 89) | | pck* represents mutated form of pck containing, α G to A transition at −64 (ATG).
All strains are of derivatives of *E. coli* ATCC8739.

TABLE 10

Pck is critical for glucose fermentation to succinate by derivatives of KJ073

| Strain* | Genetic modification | Glucose consumed | Succinate (mM) | Yield** (mol/mol) | Acetate (mM) | Pyruvate (mM) |
|---|---|---|---|---|---|---|
| KJ073 | none | 301 | 364 | 1.21 | 113 | 3 |
| XZ320 | KJ073, Δppc | 278 | 348 | 1.25 | 100 | — |
| XZ341 | KJ073, ΔsfcA | 278 | 339 | 1.22 | 106 | — |
| XZ396 | KJ073, ΔmaeB | 278 | 337 | 1.22 | 116 | 0 |
| XZ332 | KJ073, Δpck | 92 | 42 | 0.46 | 28 | 32 |
| XZ332 (pLOI4677) | Δpck, pck over-expression | 273 | 260 | 0.95 | 78 | 32 |

*All fermentations were performed in NBS medium with 5% glucose and 100 mM potassium bicarbonate.
**Yield was calculated as mol succinate produced per mol glucose metabolized.

TABLE 11

Comparison of carboxylation enzymes in engineered E. coli strains

| Strain | Cell yield (g/L) | Succinate productivity (g/L/h) | Enzyme activity * [nmol min$^{-1}$ (mg protein)$^{-1}$] Pck | Ppc | SfcA | MaeB | pck mRNA | G to A change |
|---|---|---|---|---|---|---|---|---|
| E.coli ATCC | 2.0 | 0.12 | 295 | 20 | ND | <1 | 1.0 | No |
| KJ012‡ | 0.3 | 0.04 | 162 | 25 | 5 | <1 | 0.2 | No |
| KJ017 | 1.7 | 0.35 | 700 | 17 | 12 | <1 | 2.7 | No |
| KJ060 | 2.2 | 0.90 | 8,363 | 30 | 11 | <1 | 7.2 | Yes |
| KJ071 | 1.5 | 0.33 | 679 | 23 | 10 | <1 | 2.5 | No |
| KJ073 | 2.3 | 0.82 | 7,341 | 27 | 12 | <1 | 8.4 | Yes |
| E.coli K12** | ND | ND | 140 | 140 | ND | ND | ND | ND |
| Actinobacillus Succinogenest** | ND | ND | 4700 | 10 | ND | ND | ND | ND |

*Pck, PEP carboxykinase; Ppc, PEP carboxylase; SfcA, NADH-linked malic enzyme; MaeB, NADPH-linked malic enzyme; ND, not determined.
**Data from Vanderwerf et al., *Arch Microbiol* 167:332-342
‡Poor growth

TABLE 12

Effects of mutations in pck, ptsI, and cra on PEP carboxykinase activity.

| Strain | Genotype | PEP-carboxykinase (U/mg protein) |
|---|---|---|
| KJ017[1] | pck$^+$, ptsI$^+$, cra$^+$ | 700 |
| XZ618 | KJ017, pck* | 6,419 |
| XZ613 | KJ017, )ptsI | 614 |
| XZ626 | KJ017, )cra | 508 |
| KJ060[2§] | pck*, ptsIV, –cra$^+$ | 8,363 |
| XZ622[2] | KJ060, –pck$^+$ | 1,103 |
| XZ615 | KJ060, )ptsI | 10,309 |
| XZ627 | KJ060, )cra | 7181 |
| KJ071[1§] | ptsIV, –pck$^+$, cra$^+$ | 679 |
| XZ620 | KJ071, pck* | 6,193 |
| KJ073[2§] | pck*, ptsIV, –cra$^+$ | 7,341 |
| XZ624[2] | KJ073, –pck$^+$ | 904 |

[1]The pck in KJ017 and KJ071 was mutated (G to A) to pck* in XZ618 and XZ620, respectively.
[2]The pck* mutation in KJ060 and KJ073 was restored to wild type (A to G, –pck$^+$) in XZ622 and XZ624.
§The abbreviation ptsIV refers to a frame-shift mutation, a single base deletion in the carboxy-terminal region.

TABLE 13

Effect of glucose and cAMP on PEP carboxykinase (pck) and β-galactosidase (lacZ) activities*

| Strain | PEP carboxykinase activity[1] 5% Glu | no Glu | ratio[2] | Glu + cAMP | β-galactosidase activity (×10$^3$)[1] 5% Glu | no Glu | ratio[2] |
|---|---|---|---|---|---|---|---|
| 8739 | 141 | 476 | 3.4 | 553 | 5.0 | 15.0 | 3.0 |
| KJ012 | 146 | 462 | 3.2 | 737 | 7.9 | 19.0 | 2.4 |
| KJ017 | 587 | 624 | 1.1 | 997 | 14.2 | 19.0 | 1.3 |
| KJ060 | 5574 | 2777 | 0.5 | 4253 | 18.4 | 20.0 | 1.1 |
| XZ642 | 118 | 113 | 1.0 | 112 | — | — | — |
| XZ643 | 116 | 124 | 1.0 | 118 | — | — | — |

*Cultures were grown aerobically in shaken flasks with Luria broth.
[1] Activity is the average of two repeats and is expressed as U (mg protein)$^{-1}$.
[2] Ratio is the activity without glucose to the activity with 5% glucose.

TABLE 14

Plasmids and primers used in Example 3

Plasmids

| | |
|---|---|
| pCR2.1-TOPO | bla kan; TOPO TA cloning vector |
| pLOI4162 | bla cat; plasmid to provide cat-sacB cassette | sfcA deletion

| | |
|---|---|
| pLOI4283 | bla kan; sfcA (PCR) from ATCC 8739 cloned into pCR2.1-TOPO vector |
| pLOI4284 | cat-sacB cassette (SmaI-SfoI fragment of pLOI4162) cloned into sfcA of pLOI4284 |
| pLOI4285 | PacI digestion of pLOI4284, and self-ligated | ppc deletion

| | |
|---|---|
| pLOI4264 | bla kan; ppc (PCR) from ATCC 8739 cloned into pCR2.1-TOPO vector |
| pLOI4265 | cat-sacB cassette (SmaI-SfoI fragment of pLOI4162) cloned into ppc of pLOI4264 |
| pLOI4266 | PacI digestion of pLOI4265, and self-ligated | pck deletion

| | |
|---|---|
| pLOI4641 | bla kan; pck (PCR) from ATCC 8739 cloned into pCR2.1-TOPO vector |
| pLOI4642 | cat-sacB cassette (SmaI-SfoI fragment of pLOI4162) cloned into ppc of pLOI4641 |
| pLOI4643 | PacI digestion of pLOI4642, and self-ligated | maeB deletion

| | |
|---|---|
| pLOI4728 | bla kan; maeB (PCR) from ATCC 8739 cloned into pCR2.1-TOPO vector |
| pLOI4729 | cat-sacB cassette (SmaI-SfoI fragment of pLOI4162) cloned into maeB of pLOI4728 |
| pLOI4730 | PacI digestion of pLOI4729, and self-ligated | ptsI mutation change

| | |
|---|---|
| pLOI4734 | bla kan; ptsI (ptsI-D-up/D-down) from ATCC 8739 cloned into PCR2.1-TOPO vector |
| pLOI4735 | cat-sacB cassette (SmaI-SfoI fragment of pLOI4162) cloned into ptsI of pLOI4734 | pck mutation change

| | |
|---|---|
| pLOI4736 | bla kan; pck-P (pck-Pro-up/Pro-down) from ATCC 8739 cloned into PCR2.1-TOPO vector |
| pLOI4737 | cat-sacB cassette (SmaI-SfoI fragment of pLOI4162) cloned into pck-P of pLOI4736 (pck-Pro-1/Pro-2) |

Primers for gene deletions sfcA deletion

| | |
|---|---|
| sfcA-up | CTATGCTTGATCGGCAACCT (SEQ ID NO: 90) |
| sfcA-down | ACGATCGCCTGGTTTTAATG (SEQ ID NO: 91) |
| sfcA-1 | TACCGCCGTACCTCCATCTA (SEQ ID NO: 92) |
| sfcA-2 | CGTAAGGGATATAAAGCGAACG (SEQ ID NO: 93) |

TABLE 14-continued

Plasmids and primers used in Example 3 ppc deletion

| ppc-up | TCAAACGATGCCCAACTGTA (SEQ ID NO: 94) |
| ppc-down | TTTAATCCGCTTCGGAAAGA (SEQ ID NO: 95) |
| ppc-1 | GTCACTATTGCCGGGATTGC (SEQ ID NO: 96) |
| ppc-2 | CAATGCGGAATATTGTTCGT (SEQ ID NO: 97) | pck deletion

| pck-up | TCCGGGCAGTAGTATTTTGC (SEQ ID NO: 98) |
| pck-down | ATGGCTGGATCAAAGTCAGC (SEQ ID NO: 99) |
| pck-1 | CCTGGCGAAACTGTTTATCG (SEQ ID NO: 100) |
| pck-2 | TTGTTAACGCGCATTTCACT (SEQ ID NO: 101) | maeB deletion

| maeB-up | GCATCCTGGGGATGATAATG (SEQ ID NO: 102) |
| maeB-down | TTTCTTCGCCAGTTCCTCAC (SEQ ID NO: 103) |
| maeB-1 | AACCCAACCGCTGTAATTTTT (SEQ ID NO: 104) |
| maeB-2 | CTGGAACTGGAAATTCATGG (SEQ ID NO: 105) | pck mutation change

| pck-Pro-up | CACGGTAGCAACAACATTGC (SEQ ID NO: 106) |
| pck-Pro-down | AGAAAGCGTCGACAACGAAC (SEQ ID NO: 107) |
| pck-Pro-1 | ATGCGCGTTAACAATGGTTT (SEQ ID NO: 108) |
| pck-Pro-2 | ATGGATAACGTTGAACTTTC (SEQ ID NO: 109) | ptsI mutation change

| ptsI-D-up | CGCATTATGTTCCCGATGAT (SEQ ID NO: 110) |
| ptsI-D-down | GCCTTTCAGTTCAACGGTGT (SEQ ID NO: 111) |
| ptsI-D-1 | CGGCCCAATTTACTGCTTAG (SEQ ID NO: 112) |
| ptsI-D-2 | ATCCCCAGCAACAGAAGTGT (SEQ ID NO: 113) |

Primers for sequencing*

| pck-F | TTGGCTAAGGAGCAGTGAAATGCGCGTTA (SEQ ID NO: 114) |
| pck-R | CACGACAAAAGAAGGGTAAATAAAC (SEQ ID NO: 115) |
| pck-2 | TTGTTAACGCGCATTTCACT (SEQ ID NO: 116) |
| pck-3 | GCGATAGCGGCTACTGTCAT (SEQ ID NO: 117) |
| cra-up | GCGGTAAGCTTGATGCATTT (SEQ ID NO: 118) |
| cra-down | CTTCCCCGGTTAACAGTCCT (SEQ ID NO: 119) |
| ptsHI-up1 | TCATCGGGTGAGCGTTATTT (SEQ ID NO: 120) |
| ptsHI-down1 | TGACCGTCCAGCGTAATAGC (SEQ ID NO: 121) |
| ptsHI-up2 | CATCCTGGGCCTGAAGATTA (SEQ ID NO: 122) |
| ptsHI-down2 | AGCAATACCATCACCAACGA (SEQ ID NO: 123) |
| crr-up | CCCGCGCATTAAGAAGATTA (SEQ ID NO: 124) |
| crr-down | CTCATCAGTGGCTTGCTGAA (SEQ ID NO: 125) |

TABLE 14-continued

Plasmids and primers used in Example 3

| | |
|---|---|
| ptsG-up | GAAGAACTGGCGCAGGTAAC (SEQ ID NO: 126) |
| ptsG-down | AAGGAAACGCCGTTAATCCT (SEQ ID NO: 127) |
| cyaA-up | TCGCCATCAACTTGTCTTTG (SEQ ID NO: 128) |
| cyaA-down | AAAGGCGATGAGTGGATTTG (SEQ ID NO: 129) |
| crp-S-up | TGAGTTGCCGTCCATTAAAA (SEQ ID NO: 130) |
| crp-S-down | AATCGTAATTCGCCAAGCAT (SEQ ID NO: 131) |
| cpdA-S-up | GAAGTGTGTTCAAGCCAGCA (SEQ ID NO: 132) |
| cpdA-S-down | AGGACAATGGATTCCAGCAG (SEQ ID NO: 133) |
| ygiF-S-up | ATCAGTGTCGCTACGCAAAG (SEQ ID NO: 134) |
| ygiF-S-down | GCTGTCCTGCACAAAATCAC (SEQ ID NO: 135) |
| sxy-S-up | TTTACTTGCTGCGGATGAGA (SEQ ID NO: 136) |
| sxy-S-down | TATCTCAGCCCTCGGTGCTC (SEQ ID NO: 137) |
| csrA-up | CAGCGTTAGCCAGTGTGAAA (SEQ ID NO: 138) |
| csrA-down | ACGCCTCTTACGAGTGCTTC (SEQ ID NO: 139) |
| csrB-S-up | CTGTAGGAGATCGCCAGGAA (SEQ ID NO: 140) |
| csrB-S-down | TCTAACAAATCGTGCATTCG (SEQ ID NO: 141) |
| csrC-S-up | GCCATACGCTTTGTGAGACA (SEQ ID NO: 142) |
| csrC-S-down | AGTCACGCCCAATGGAATAG (SEQ ID NO: 143) |
| csrD-S-up1 | ATGTGCATGATGGATTGGAA (SEQ ID NO: 144) |
| csrD-S-down1 | CGGTATCCTGACCACTACGC (SEQ ID NO: 145) |
| csrD-S-up2 | GTGATTTTGCTGCGCTGTTA (SEQ ID NO: 146) |
| csrD-S-down2 | ACAAGGCGCAAAAATCATCT (SEQ ID NO: 147) |
| uvrY-s-up1 | CCTCGTCATGTTGCAATGAA (SEQ ID NO: 148) |
| uvrY-s-down1 | TATCATCGCGTAGCAAAACG (SEQ ID NO: 149) |
| barA-s-up1 | TTTTGCTTCGCTGCTGTAAA (SEQ ID NO: 150) |
| barA-s-down1 | TCAGGCACGTCGCTTTTAAT (SEQ ID NO: 151) |
| barA-s-up2 | CGCGATCACCTGAATACGAT (SEQ ID NO: 152) |
| barA-s-down2 | CTGGCTGGACGTTCGATAAC (SEQ ID NO: 153) |
| barA-s-up3 | TGGCCTATGTCGAACCAAAC (SEQ ID NO: 154) |
| mlc-s-up1 | CTGGCAAATAACCCGAATGT (SEQ ID NO: 155) |
| mlc-s-down1 | CCAGGGCATCTTTATTACGC (SEQ ID NO: 156) |
| mlc-s-up2 | TGAAACTGAAGCCTGGCACT (SEQ ID NO: 157) |

*The primers for sequencing were used to amplify the upstream, coding and terminator fragment of all genes.

TABLE 15

Sources and characteristics of E. coli strains, plasmids and primers used in this study

| | Relevant characteristics | Source or reference |
|---|---|---|
| Strains | | |
| ATCC 8739 | Wild type | Lab collection |
| KJ012 | ΔldhA, ΔadhE, ΔackA | Jantama et al., 2008a |
| XZ02 | ΔldhA | This study |
| XZ04 | ΔldhA, ΔpflB | This study |
| XZ14 | ΔldhA, ΔadhE | This study |
| XZ15 | ΔadhE | This study |
| XZ17 | ΔpflB | This study |
| XZ464 | pck*, ΔgldA | This study |
| XZ465 | pck*, ΔdhaKL | This study |
| XZ466 | pck*, ΔdhaM | This study |
| XZ468 | pck*, ΔptsH | This study |
| XZ469 | pck*, ΔptsI-W | This study |
| XZ470 | pck*, ΔptsG | This study |
| XZ629 | ΔldhA, ΔadhE, ΔackA, pck* | This study |
| XZ632 | pck* | This study |
| XZ635 | ΔldhA, pck* | This study |
| XZ638 | ΔldhA, ΔadhE, pck* | This study |
| XZ639 | ΔadhE, pck* | This study |
| XZ640 | ΔpflB, pck* | This study |
| XZ641 | ΔldhA, ΔpflB, pck* | This study |
| XZ647 | pck*, ΔptsI | This study |
| XZ650 | ΔptsI | This study |
| XZ721 | pck*, ΔptsI, ΔpflB | This study |
| XZ723 | pck*, ΔptsI, ΔadhE | This study |
| Plasmids | | |
| pLOI4162 | bla, cat sacB cassette | Jantama et al., 2008b |
| ldhA deletion | | |
| pLOI4652 | bla kan; ldhA (PCR) from E. coli cloned into pCR2.1-TOPO vector | This study |
| pLOI4653 | cat-sacB cassette cloned into ldhA of pLOI4652 | This study |
| pLOI4655 | PacI digestion of pLOI4653, and self-ligated | This study |
| pflB deletion | | |
| pLOI4667 | bla kan; pflB (PCR) from E.coli cloned into pCR2.1-TOPO vector | This study |

TABLE 15-continued

Sources and characteristics of E. coli strains, plasmids and primers used in this study

| | Relevant characteristics | Source or reference |
|---|---|---|
| pLOI4668 | cat-sacB cassette cloned into pflB of pLOI4667 | This study |
| pLOI4669 | PacI digestion of pLOI4668, and self-ligated | This study |
| *adhE deletion* | | |
| pLOI4707 | bla kan; adhE (PCR) from *E.coli* cloned into pCR2.1-TOPO vector | This study |
| pLOI4708 | cat-sacB cassette cloned into adhE of pLOI4707 | This study |
| pLOI4709 | PacI digestion of pLOI4707, and self-ligated | This study |
| *pck promoter change* | | |
| pLOI4736 | bla kan; pck-P from *E.coli* cloned into pCR2.1-TOPO vector | This study |
| pLOI4737 | cat-sacB cassette cloned into pck-P of pLOI4736 | This study |
| pLOI4752 | trc promoter cloned into pck-P of pLOI4736 | This study |
| *ptsI deletion* | | |
| pLOI4734 | bla kan; ptsI from *E.coli* cloned into pCR2.1-TOPO vector | This study |
| pLOI4735 | cat-sacB cassette cloned into ptsI of pLOI4734 | This study |
| pLOI4735B | PacI digestion of pLOI4735, and self-ligated | This study |
| *ptsG deletion* | | |
| pLOI4683 | bla kan; ptsG from *E.coli* cloned into PCR2.1-TOPO vector | This study |
| pLOI4684 | cat-sacB cassette (SmaI-SfoI fragment of pLOI4162) cloned into ptsG of pLOI4683 | This study |
| pLOI4685 | PacI digestion of pLOI4684, and self-ligated | This study |
| *gldA deletion* | | |
| pLOI4296 | bla kan; gldA from *E.coli* cloned into PCR2.1-TOPO vector | This work |
| pLOI4297 | cat-sacB cassette from pLOI4151 cloned into gldA of pLOI4296 | This work |
| pLOI4298 | PCR fragment amplified from pLOI4296 (using gldA-1/gldA-2), kinase treated, and then self-ligated | This work |
| *Primers* | | |
| *ldhA deletion* | | |
| XZ-ldhA-up | GATAACGGAGATCGGGAATG (SEQ ID NO: 158) | This study |
| XZ-ldhA-down | CTTTGGCTGTCAGTTCACCA (SEQ ID NO: 159) | This study |
| XZ-ldhA-1 | TCTGGAAAAAGGCGAAACCT (SEQ ID NO: 160) | This study |
| XZ-ldhA-2 | TTTGTGCTATAAACGGCGAGT (SEQ ID NO: 161) | This study |

TABLE 15-continued

Sources and characteristics of E. coli strains, plasmids and primers used in this study

| | Relevant characteristics | Source or reference |
|---|---|---|
| pflB deletion | | |
| PflB-up2 | TGTCCGAGCTTAATGAAAAGTT (SEQ ID NO: 162) | This study |
| PflB-down2 | CGAGTAATAACGTCCTGCTGCT (SEQ ID NO: 163) | |
| PflB-5 | AAACGGGTAACACCCCAGAC (SEQ ID NO: 164) | |
| PflB-6 | CGGAGTGTAAACGTCGAACA (SEQ ID NO: 165) | |
| adhE deletion | | |
| adhE-up | CATGCTAATGTAGCCACCAAA (SEQ ID NO: 166) | This study |
| adhE-down | TTGCACCACCATCCAGATAA (SEQ ID NO: 167) | |
| adhE-1 | TCCGGCTAAAGCTGAGAAAA (SEQ ID NO: 168) | |
| adhE-2 | GTGCGTTAAGTTCAGCGACA (SEQ ID NO: 169) | |
| pck mutation change | | |
| pck-Pro-up | CACGGTAGCAACAACATTGC (SEQ ID NO: 170) | This study |
| pck-Pro-down | AGAAAGCGTCGACAACGAAC (SEQ ID NO: 171) | |
| pck-Pro-1 | ATGCGCGTTA ACAATGGTTT (SEQ ID NO: 172) | |
| pck-Pro-2 | ATGGATAACG TTGAACTTTC (SEQ ID NO: 173) | |
| pck-P-2 | TTCACTGCTC CTTAGCCAAT (SEQ ID NO: 174) | |
| ptsI deletion | | |
| ptsI-D-up | CGCATTATGTTCCCGATGAT (SEQ ID NO: 175) | This study |
| ptsI-D-down | GCCTTTCAGTTCAACGGTGT (SEQ ID NO: 176) | |
| ptsI-D-1 | CGGCCCAATTTACTGCTTAG (SEQ ID NO: 177) | |
| ptsI-D-2 | ATCCCCAGCAACAGAAGTGT (SEQ ID NO: 178) | |
| ptsG deletion | | |
| ptsG up | GAAGAACTGGCGCAGGTAAC (SEQ ID NO: 179) | This study |
| ptsG-down | AAGGAAACGCCGTTAATCCT (SEQ ID NO: 180) | |
| ptsG-1 | CCTGAAAACCGAGATGGATG (SEQ ID NO: 181) | |
| ptsG-2 | CATCAGCGATTTACCGACCT (SEQ ID NO: 182) | |
| ptsH deletion | | |
| ptsH-D-up | ATGTTCCAGCAAGAAGTTACCATTACCGCTCCG AACGGTCTGCAC GTGTAGGCTGGAGCTGCTTC (SEQ ID NO: 183) | This study |
| ptsH-D-down | TTACTCGAGTTCCGCCATCAGTTTAACCAGATG TTCAACCGCTTT CATATGAATATCCTCCTTAG (SEQ ID NO: 184) | |
| ptsI-W deletion | | |
| ptsI-D-up | ATGATTTCAGGCATTTTAGCATCCCCGGGTATCG CTTTCGGTAAA GTGTAGGCTGGAGCTGCTTC (SEQ ID NO: 185) | This study |
| ptsI-D-down | TTAGCAGATTGTTTTTCTTCAATGAACTTGTTA ACCAGCGTCAT CATATGAATATCCTCCTTAG (SEQ ID NO: 186) | |

TABLE 15-continued

Sources and characteristics of E. coli strains, plasmids and primers used in this study

| | Relevant characteristics | Source or reference |
|---|---|---|
| | gldA deletion | |
| gldA-up | TGTATATAGCGCCGCACAAG (SEQ ID NO: 187) | This study |
| gldA-down | GATGGCAAGGTTGGTATTGG (SEQ ID NO: 188) | |
| gldA-1 | ACCAGTACGGTCAGCGTTTC (SEQ ID NO: 189) | |
| gldA-2 | ACCCGGTGATTGAATAATGC (SEQ ID NO: 190) | |
| | dhaKL deletion | |
| dhaKL-D-up | ATGAAAAAATTGATCAATGATGTGCAAGACGT ACTGGACGAACAA TGTAGGCTGGAGCTGCTTC (SEQ ID NO: 191) | This study |
| dhaKL-D-down | TTACTCTTTTGCGGCTAACGCCAACATTTGCA TCATAAACATCAC CATATGAATATCCTCCTTAG (SEQ ID NO: 192) | |
| | dhaM deletion | |
| dhaM-D-up | GTGATGGTAAACCTGGTCATAGTTTCACATA GCAGCCGACTGGGATGTAGGCTGGAGCTGCTTC (SEQ ID NO: 193) | This study |
| dhaM-D-down | TTAACCCTGACGGTTGAAACGTTGCGTTTTA ACGTCCAGCGTTAGATATGAATATCCTCCTTAG (SEQ ID NO: 194) | |

TABLE 16

The effects of inactivating alternative NADH oxidizing pathways on succinate production from glucose using NBS mineral salts medium and complex medium (Luria broth)

| Strains | Genetic modification | Media | Time (days) | Growth Cell yield (g/L) | Glue used (mmol) | Suc Yield[1] | Fermentation products (mmol)[2] | | | | | | |
|---|---|---|---|---|---|---|---|---|---|---|---|---|---|
| | | | | | | | Suc | Ace | Mal | Pyr | Lac | For | EtOH |
| ATCC 8739 | Wild type | NBS | 3 | 3.0 | 278 | 0.16 | 46 | 151 | — | — | 110 | 318 | 133 |
| XZ02 | ΔldhA | NBS | 3 | 2.9 | 278 | 0.15 (−6%) | 43 | 165 | — | — | 11 | 353 | 199 |
| XZ15 | ΔadhE | NBS | 3 | 2.7 | 278 | 0.18 (+12%) | 50 | 84 | — | — | 352 | 102 | — |
| XZ17 | ΔpflB | NBS | 3 | 2.2 | 278 | 0.09 (−44%) | 26 | 11 | — | — | 460 | — | — |
| XZ14 | ΔldhA, ΔadhE | NBS | 6 | 0.5 | 57 | 0.12 (−25%) | 6 | 48 | — | — | — | 44 | — |
| XZ04 | ΔldhA, ΔpflB | NBS | 6 | 0.5 | 39 | 0.13 (−19%) | 5 | 22 | — | — | — | 22 | 12 |
| KJ012 | ΔldhA, ΔadhE, ΔackA | NBS | 6 | 0.3 | 46 | 0.13 (−19%) | 6 | 26 | — | — | — | — | — |
| ATCC 8739 | Wild type | LB | 2 | 2.0 | 257 | 0.13 | 34 | 138 | — | — | 214 | 161 | 127 |
| XZ02 | ΔldhA | LB | 2 | 1.8 | 257 | 0.21 (+61%) | 55 | 224 | — | — | 17 | 152 | 206 |
| XZ15 | ΔadhE | LB | 2 | 1.9 | 268 | 0.11 (−15%) | 30 | 43 | — | — | 459 | — | — |
| XZ17 | ΔpflB | LB | 2 | 2.0 | 261 | 0.09 (−31%) | 24 | 8 | — | — | 469 | — | — |
| XZ14 | ΔldhA, ΔadhE | LB | 6 | 0.3 | 31 | 0.23 (+77%) | 7 | 45 | — | — | — | 17 | — |
| XZ04 | ΔldhA, ΔpflB | LB | 6 | 1.2 | 150 | 0.33 (+154%) | 48 | 9 | — | 86 | 35 | 23 | 89 |
| KJ012 | ΔldhA, ΔadhE, ΔackA | LB | 6 | 1.5 | 154 | 0.70 (+438%) | 108 | 61 | — | — | — | 14 | — |

Succinate yield was calculated as moles of succinate produced per mol glucose metabolized. The effects of inactivating alternative NADH oxidizing pathway(s) on succinate yield are shown in the parentheses. A negative sign (−) indicates a decrease in yield and a positive sign (+) indicates an increase in yield as compared to that of the wild type under the same conditions.
[2] Fermentations were carried out in either NBS mineral salts medium or Luria broth medium with 5% glucose and 100 mM potassium bicarbonate (37° C., pH 7.0, 150 rpm).
Abbreviations: Suc, succinate; Ace, acetate; Mal, malate; Pyr, pyruvate; Lac, lactate; For, formate; EtOH, ethanol.

TABLE 17

The effects of increasing PCK activity on succinate production and yield from glucose in NBS mineral salts medium

| Strains | Genetic modification[1] | Day | Growth Cell yield (g/L) | PCK activity[3] | Glu used (mmol) | Suc Yield[4] | Fermentation products (mmol) [5] | | | | | | |
|---|---|---|---|---|---|---|---|---|---|---|---|---|---|
| | | | | | | | Suc | Ace | Mal | Pyr | Lac | For | EtOH |
| ATCC 8739 | Wild type | 3 | 3.0 | 203 | 278 | 0.16 | 46 | 151 | — | — | 110 | 318 | 133 |
| ATCC 8739 | pLOI4677[2] | 3 | 2.8 | 1782 | 278 | 0.27 | 73 | 141 | — | 24 | 112 | 266 | 116 |
| XZ632 | pck* | 3 | 2.9 | 1631 | 278 | 0.22 | 61 | 161 | — | — | 88 | 302 | 152 |
| XZ635 | ΔldhA, pck* | 3 | 2.7 | 1697 | 278 | 0.22 | 60 | 151 | — | — | 13 | 327 | 178 |
| XZ639 | ΔadhE, pck* | 3 | 2.7 | 1608 | 278 | 0.25 | 70 | 80 | — | — | 329 | 99 | — |
| XZ640 | ΔpflB, pck* | 3 | 2.5 | 1623 | 278 | 0.14 | 39 | 12 | — | — | 448 | — | — |
| XZ638 | ΔldhA, ΔadhE, pck* | 6 | 0.8 | 917 | 66 | 0.24 | 16 | 71 | — | — | — | 79 | — |
| XZ641 | ΔldhA, ΔflB, pck* | 6 | 0.8 | 932 | 61 | 0.39 | 24 | 9 | — | — | — | 2 | 15 |

The abbreviation pck* denotes mutated form of pck (G to A at −64 relative to the ATG start).
The pck gene (ribosomal binding site, coding and terminator region) was over-expressed in a high-copy plasmid.
PCK activity expressed as nmol min$^{-1}$ (mg protein)$^{-1}$ Succinate yield was calculated as moles of succinate produced per mol glucose metabolized.

Fermentations were carried out in NBS mineral salts medium with 5% glucose and 100 mM potassium bicarbonate (37° C., pH 7.0, 150 rpm). Abbreviations: Suc, succinate; Ace, acetate; Mal, malate; Pyr, pyruvate; Lac, lactate; For, formate; EtOH, ethanol.

TABLE 18

Effects of combining a mutation in ptsI, mutations that disrupted the ethanol pathway, and increased expression of pck on succinate production in NBS mineral salts medium containing 5% glucose.

| Strains | Genetic modification[1] | Day | Growth Cell yield | Glu used (mmol) | Suc Yield[3] | Fermentation products (mmol) [4] | | | | | |
|---|---|---|---|---|---|---|---|---|---|---|---|
| | | | | | | Suc | Ace | Mal | Pyr | Lac | Strains | ETOH |
| ATCC 8739 | Wild type ATCC 8739 | 3 | 3.0 | 278 | 0.16 | 46 | 151 | — | — | 110 | 318 | 133 |
| XZ632 | pck* | 3 | 2.9 | 278 | 0.22 | 61 | 161 | — | — | 88 | 302 | 152 |
| XZ650 | ΔptsI | 3 | 2.6 | 259 | 0.14 | 35 | 131 | — | 28 | 130 | 273 | 119 |
| XZ647 | pck*, ΔptsI | 3 | 2.5 | 242 | 0.89 | 216 | 174 | 5 | — | 5 | 199 | 22 |
| XZ650 | ΔptsI, pLOI4677 [2] | 3 | 2.4 | 224 | 0.75 | 167 | 167 | 3 | 2 | 8 | 224 | 52 |
| XZ721 | pck*, ΔptsI, ΔpflB | 3 | 2.3 | 262 | 1.25 | 327 | 70 | — | — | 29 | — | — |
| XZ723 | pck*, ΔptsI, ΔadhE | 3 | 2.4 | 259 | 0.86 | 222 | 175 | — | — | 55 | 171 | — |

The abbreviation pck* denotes mutated form of pck (G to A at −64 relative to the ATG start).
The pck gene (ribosomal binding site, coding and terminator region) was over-expressed in a high-copy plasmid.

Succinate yield was calculated as moles of succinate produced per mol glucose metabolized.

Fermentations were carried out in NBS mineral salts medium with 5% glucose and 100 mM potassium bicarbonate (37° C., pH 7.0, 150 rpm). Abbreviations: Suc, succinate; Ace, acetate; Mal, malate; Pyr, pyruvate; Lac, lactate; For, formate; EtOH, ethanol.

TABLE 19

Effects of combining a mutation in phosphoenolpyruvate-dependent phosphotransferase pathway, and increased expression of pck on succinate production in NBS mineral salts medium containing 5% glucose

| Strains | Genetic modification [1] | Day | Growth Cell yield | Gluc used (mmol) | Suc Yield [2] | Suc | Ace | Mal | Pyr | Lac | For | EtOH |
|---|---|---|---|---|---|---|---|---|---|---|---|---|
| XZ632 | pck* | 3 | 2.9 | 278 | 0.22 | 61 | 161 | — | — | 88 | 302 | 152 |
| XZ647 | pck*, ΔptsI | 3 | 2.5 | 242 | 0.89 | 216 | 174 | 5 | — | 5 | 199 | 22 |
| XZ469 | pck*, ΔptsI-W | 3 | 3.0 | 245 | 0.84 | 206 | 143 | — | — | 3 | 164 | 31 |
| XZ468 | pck*, ΔptsH | 3 | 2.6 | 266 | 0.67 | 179 | 151 | — | — | 17 | 242 | 69 |
| XZ470 | pck*, ΔptsG | 3 | 2.5 | 269 | 0.63 | 170 | 175 | — | — | 32 | 245 | 63 |

[1] The abbreviation pck* denotes mutated form of pck (G to A at −64 relative to the ATG start). ΔptsI denotes deletion of the carboxy-terminal 175 by of ptsI gene, while ΔptsI-W denotes deletion of the whole ptsI gene.
[2] Succinate yield was calculated as mole of succinate produced per mol glucose metabolized.
[3] Fermentations were carried out in NBS medium with 5% glucose and 100 mM potassium bicarbonate at 37° C., pH 7.0, 150 rpm.
Abbreviations: Suc, succinate; Ace, acetate; Mal, malate; Pyr, pyruvate; Lac, lactate; For, formate; EtOH, ethanol.

TABLE 20

Succinate production from glycerol by engineered E. coli strains in NBS mineral salts medium

| Strains | Genetic modification | Time (Day) | Cell mass (g/l) | Glycerol used (mmol) | Suc | Suc yield | For | EtOH | Lac | Ace |
|---|---|---|---|---|---|---|---|---|---|---|
| ATCC 8739 | Wild type | 6 | 0.55 | 153 | 38 | 0.25 | 110 | 81 | — | 16 |
| XZ17 | ΔpflB | 6 | 0.3 | 48 | 5 | 0.11 | — | — | 20 | 5 |
| XZ640 | ΔpflB, pck* | 6 | 0.4 | 79 | 37 | 0.48 | — | — | 16 | 10 |
| XZ721 | ΔpflB, pck*, ΔptsI | 6 | 0.5 | 128 | 102 | 0.8 | — | — | 6 | 12 |
| XZ632 | pck* | 6 | 0.7 | 149 | 64 | 0.44 | 83 | 46 | — | 20 |
| XZ647 | pck*, ΔptsI | 6 | 0.4 | 89 | 63 | 0.71 | 25 | 5 | — | 13 |
| XZ464 | pck*, ΔgldA | 6 | 0.43 | 125 | 95 | 0.77 | 35 | 8 | — | 16 |
| XZ465 | pck*, ΔdhaK | 6 | 0.47 | 150 | 112 | 0.75 | 37 | 11 | — | 15 |
| XZ466 | pck*, ΔdhaM | 6 | 0.5 | 152 | 108 | 0.71 | 30 | 9 | — | 14 |
| XZ468 | pck*, ΔptsH | 6 | 0.5 | 125 | 85 | 0.68 | 32 | 14 | — | 10 |

[1] Fermentations were carried out in NBS medium with 5% glycerol and 100 mM potassium bicarbonate at 37° C., pH 7.0, 150 rpm.
Succinate yield was calculated based on mol of succinate produced per mol glycerol consumed.
Abbreviations: Suc, succinate; For, formate; EtOH, ethanol; Lac, lactate; Ace, acetate;

REFERENCES

All references are listed herein for the convenience of the reader. Each reference is incorporated by reference in its entirety.

U.S. Pat. No. 5,723,322
U.S. Pat. No. 5,770,435
U.S. Pat. No. 5,869,301
U.S. Pat. No. 5,143,834
U.S. Pat. No. 5,723,322
U.S. Pat. No. 5,573,931
U.S. Pat. No. 5,505,004
U.S. Pat. No. 6,455,284
U.S. Pat. No. 7,223,567

Ajl, S. J., Werkman, C. H. (1948) "Enzymatic fixation of carbon dioxide in α-ketoglutaric acid" *Proc Natl Acad Sci USA* 34:491-498.

Andersson, C., Hodge, D., Berglund, K. A., Rova, U. (2007) "Effect of different carbon sources on the production of succinic acid using metabolically engineered *Escherichia coli*" *Biotechnol Prog* 23(2):381-388.

Asghari, A., Bothast, R. J., Doran, J. B., Ingram, L. O. (1996) "Ethanol production from hemicellulose hydrolysates of agricultural residues using genetically engineered *Escherichia coli* strain KO11" *J Industrial Microbiol* 16:42-47.

Babitzke, P., Romeo, T. (2007) "CsrB sRNA family: sequestration of RNA-binding regulatory proteins" *Curr Opin Microbiol* 10:156-163.

Bachler, C., Schneider, P., Bahler, P., Lustig, A., Erni, B. (2005) "*Escherichia coli* dihydroxyacetone kinase controls gene expression by binding to transcription factor DhaR" *EMBO J* 24:283-293.

Berman, M., Lin, E. C. (1971) "Glycerol-specific revertants of a phosphoenolpyruvate phosphotransferase mutant:

suppression by the desensitization of glycerol kinase to feedback inhibition" *J Bacteriol* 105:113-120.

Berman, M., Zwaig, N., Lin, E. C. (1970) "Suppression of a pleiotropic mutant affecting glycerol dissimilation" *Biochem Biophys Res Commun* 38:272-278.

Bock, A., Sawers, G. (1996) Chapter 18, *"Fermentation,"* in Neidhardt, F. C., Curtiss III, R., Ingraham, J. L., Lin, E. C. C., Low, K. B, Magasanik, B., Reznikoff, W. S., Riley, M., Schaechter, M., Umbarger, H. E., editors. *Escherichia coli* and *Salmonella*: cellular and molecular biology. ASM Press, Washington, D.C.

Booth, I. R. (2005) Module 3.4.3, "Glycerol and methylglyoxal metabolism," in Bock, A., Curtiss III, R., Kaper, J. B., Neidhardt, F. C., Nystrom, T., Rudd, K. E., Squires, C. L., editors. EcoSal—*Escherichia coli* and *Salmonella*: cellular and molecular biology. Available at ecosal.org. ASM Press, Washington, D.C.

Cameron, A. D., Redfield, R. J. (2006) "Non-canonical CRP sites control competence regulons in *Escherichia coli* and many other gamma-proteobacteria" *Nucleic Acids Res* 34:6001-6014.

Cánovas, J. L., Kornberg, H. L. (1969) "Phosphoenolpyruvate carboxylase from *Escherichia coli*" *Methods Enzymol* 13:288-292.

Causey, T. B., Shanmugam, K. T., Yomano, L. P, Ingram, L. O. (2004) "Engineering *Escherichia coli* for efficient conversion of glucose to pyruvate" *Proc Natl Acad Sci USA* 101:2235-2240.

Chao, Y., Liao, J. C. (1993) "Alteration of growth yield by overexpression of phosphoenol pyruvate carboxylase and phosphoenolpyruvate carboxykinase in *Escherichia coli*" *Appl Environ Microbiol* 59:4261-4265.

Chang, Y. Y., Cronan, J. E., Jr. (2000) "Conversion of *Escherichia coli* pyruvate decarboxylase to an 'alpha-ketobutyrate oxidase'" *Biochem J* 352:717-724.

Chatterjee, R., Millard, C. S., Champion, K., Clark, D. P., Donnelly, M. I. (2001) "Mutation of the ptsG gene results in increased production of succinate in fermentation of glucose by *Escherichia coli*" *Appl Environ Microbiol* 67:148-154.

Cox, S. J., Levanon, S. S., Sanchez, A. M., Lin, H., Peercy, B., Bennett, G. N., San, K. Y. (2006) "Development of a metabolic network design and optimization framework incorporating implement constraints: A succinate production case study" *Metab Engin* 8:46-57.

Datsenko, K. A., Wanner, B. L. (2000) "One-step inactivation of chromosomal genes in *Escherichia coli* K-12 using PCR products" *Proc Natl Acad Sci USA* 97:6640-6645.

de Graef, M. R., Alexeeva, S., Snoep, J. L., de Mattos, M. J. T. (1999) "The steady-state internal redox state (NADH/NAD) reflects the external redox state and is correlated with catabolic adaptation in *Escherichia coli*" *J Bacteriol* 181:2351-235.

Delbaere, L. T. J., Sudom, A. M., Prasad, L., Leduc, Y., Goldie, H. (2004) "Structure/function studies of phosphoryl transfer by phosphoenolpyruvate carboxykinase" *Biochimica et Biophysica Acta* 1679:271-278.

Du, C., Lin, S. K., Koutinas, A., Wang, R., Webb, C. (2007) "Succinic acid production from wheat using a biorefining strategy" *Appl Microbiol Biotechnol* 76(6):1263-1270.

Egyud, L. G., Szent-Gyorgyi, A. (1966) "On the regulation of cell division" *Proc Natl Acad Sci USA* 56:203-207.

Erni, B., Siebold, C., Christen, S., Srinivas, A., Oberholzer, A., Baumann, U. (2006) "Small substrate, big surprise: fold, function and phylogeny of dihydroxyacetone kinases" *Cell Mol Life Sci* 63:890-900.

Farmer, W., Liao, J. C. (1997) "Reduction of aerobic acetate production by *Escherichia coli*" *Appl Environ Microbiol* 63:3205-3210.

Flores, N., Leal, L., Sigala, J. C., de Anda, R., Escalante, A., Martinez, A., Ramirez, O. T., Gosset, G., Bolivar, F. (2007) "Growth recovery on glucose under aerobic conditions of an *Escherichia coli* strain carrying a phosphoenolpyruvate: carbohydrate phosphotransferase system deletion by inactivating arcA and overexpressing the genes coding for glucokinase and galactose permease" *J Mol Microbiol Biotechnol* 13:105-116.

Fraenkel, D. G. (1996) Chapter 14, "Glycolysis," in Neidhardt, F. C., Curtiss III, R., Ingraham, J. L., Lin, E. C. C., Low, K. B, Magasanik, B., Reznikoff, W. S., Riley, M., Schaechter, M., Umbarger, H. E., editors. *Escherichia coli* and *Salmonella*: cellular and molecular biology. ASM Press, Washington, D.C.

Gokarn, R. R., Eiteman, M. A., Altman, E. (2000) "Metabolic analysis of *Escherichia coli* in the presence and absence of carboxylating enzymes phosphoenolpyruvate carboxylase and pyruvate carboxylase" *Appl Environ Microbiol* 66:1844-1850.

Gokarn, R. R., Evans, J. D., Walker, J. R., Martin, S. A., Eiteman, M. A., Altman, E. (2001) "The physiological effects and metabolic alterations caused by the expression of *Rhizobium etli* pyruvate carboxylase in *Escherichia coli*" *Appl Microbiol Biotechnol* 56:188-195.

Goldie, H. (1984) "Regulation of transcription of the *Escherichia coli* phosphoenolpyruvate carboxykinase locus: studies with pck-lacZ operon fusions" *J Bacteriol* 159:832-836.

Goldie, A. H., Sanwal, B. D. (1980a) "Genetic and physiological characterization of *Escherichia coli* mutants deficient in phosphoenolpyruvate carboxykinase activity" *J Bacteriol* 141:1115-1121.

Goldie, A. H., Sanwal, B. D. (1980b) "Allosteric control by calcium and mechanism of desensitization of phosphoenolpyruvate carboxykinase of *Escherichia coli*" *J Biol Chem* 255:1399-1405.

Gottschalk, G. (1985) Bacterial metabolism. 2nd ed. Springer-Verlag, New York.

Grabar, T. B., Zhou, S., Shanmugam, K. T., Yomano, L. P., Ingram, L. O. (2006) "Methylglyoxal bypass identified as source of chiral contamination in L(+) and D(−) lactate fermentations by recombinant *Escherichia coli*" *Biotechnol Lett* 28:1527-1535.

Guest, J. R., Angier, S. J., Russell (1989) "Structure, expression, and protein engineering in the pyruvate dehydrogenase complex of *Escherichia coli*" *Ann NY Acad Sci* 573:76-99.

Gutknecht, R., Beutler, R., Garcia-Alles, L. F., Baumann, U., Erni., B. (2001) "The dihydroxyacetone kinase of *Escherichia coli* utilizes a phosphoprotein instead of ATP as phosphoryl donor" *EMBO J* 20:2480-2486.

Hernandez-Montalvo, V., Martinez, A., Hernandez-Chavez, G., Bolivar, F., Valle, F., Gosset, G. (2003) "Expression of galP and glk in a *Escherichia coli* PTS mutant restores glucose transport and increases glycolytic flux to fermentation products" *Biotechnol Bioeng* 83:687-694.

Hesslinger, C., Fairhurst, S. A., Sawers, G. (1998) "Novel keto acid formate-lyase and propionate kinase enzymes are components of an anaerobic pathway in *Escherichia coli* that degrades L threonine to propionate" *Mol Microbiol* 127(2):477-492.

Holtman, C. K., Pawlyk, A. C., Meadow, N. D., Pettigrew, D. W. (2001) "Reverse genetics of *Escherichia coli* glycerol kinase allosteric regulation and glucose control of glycerol utilization in vivo" *J Bacteriol* 183:3336-3344.

Hong, S. H., and Lee, S. Y. (2001) "Metabolic flux analysis for succinic acid production by recombinant *Escherichia coli* with amplified malic enzyme activity" *Biotechnol Bioeng* 74:89-95.

Hopper, D. J., Cooper, R. A. (1971) "The regulation of *Escherichia coli* methylglyoxal synthase: a new control site in glycolysis" *FEBS Lett* 13:213-216.

Imamura, R., Yamanaka, K., Ogura, T., Hiraga, S., Fujita, N., Ishihama, A., Niki, H. (1996) "Identification of the cpdA gene encoding cyclic 3',5'-adenosine monophosphate phosphodiesterase in *Escherichia coli*" *J Biol Chem* 271:25423-25429.

Iverson, T. M., Luna-Chavez, C., Croal, L. R., Cecchini, G., Rees, D. C. (2002) "Crystallographic studies of the *Escherichia coli* quinol-fumarate reductase with inhibitors bound to the quinol-binding site. 2002" *J Biol Chem* 277:16124-16130.

Jantama, K., Haupt, M. J., Svoronos, S. A., Zhang, X., Moore, J. C., Shanmugam, K. T., Ingram, L. O. (2008a) "Combining metabolic engineering and metabolic evolution to develop nonrecombinant strains of *E. coli* C that produce succinate and malate" *Biotech Bioeng* 99:1140-1153.

Jantama, K., Zhang, X., Moore, J. C., Shanmugam, K. T., Svoronos, S. A., Ingram, L. O. (2008b) "Eliminating side products and increasing succinate yields in engineered strains of *Escherichia coli* C" *Biotechnol Bioeng* 101: 881-893.

Jarboe, L. R., Hyduke, D. R., Tran, L. M., Chou, K. J., Liao, J. C. (2008) "Determination of the *Escherichia coli* S-nitrosoglutathione response network using integrated biochemical and systems analysis" *J Biol Chem*. 283: 5148-5157.

Jin, R. Z., Tang, J. C., Lin, E. C. (1983) "Experimental evolution of a novel pathway for glycerol dissimilation in *Escherichia coli*" *J Mol Evol* 19:429-436.

Jojima, T., Omumasaba, C. A., Inui, M., and Yukawa, H. (2009) Sugar transporters in efficient utilization of mixed sugar substrates: current knowledge and outlook. *Appl Microbiol Biotechnol* 85: 471-480.

Kao, K. C., Tran, L. M., Liao, J. C. (2005) "A global regulatory role of gluconeogenic genes in *Escherichia coli* revealed by transcriptome network analysis" *J Biol Chem* 280:36079-36087.

Karp, P. D., Keseler, I. M., Shearer, A., Latendresse, M., Krummenacker, M., Paley, S. M., Paulsen, I. T., Collado-Vides, J., Gamma-Castro, S., Peralta-Gil, M., Santos-Zavaleta, A., Penaloza-Spinola, M., Bonavides-Martinez, C., Ingraham, J. (2007) "Multidimensional annotation of *Escherichia coli* K-12 genome" *Nucl Acids Res* 35:7577-7590.

Keseler, I. M., Collado-Vides, J., Gamma-Castro, S., Ingraham, J., Paley, S., Paulsen, I. T., Peralta-Gil, M., Karp, P. D. (2005) "Ecocyc: A comprehensive database resource for *Escherichia coli*" *Nucl Acids Res* 33:D334-D337.

Kessler, D., Knappe, J. (1996) Chapter 15, "Anaerobic dissimilation of pyruvate," in Neidhardt, F. C., Curtiss III, R., Ingraham, J. L., Lin, E. C. C., Low, K. B, Magasanik, B., Reznikoff, W. S., Riley, M., Schaechter, M., Umbarger, H. E., editors. *Escherichia coli* and *Salmonella*: cellular and molecular biology. ASM Press, Washington, D.C.

Kim, Y., Ingram, L. O., Shanmugam, K. T. (2007) "Construction of an *Escherichia coli* K-12 mutant for homoethanologenic fermentation of glucose or xylose without foreign genes" *Appl Environ Microbiol* 73:1766-1771.

Kim, P., Laivebieks, M., Vieille, C., Zeikus, J. G. (2004) "Effect of overexpression of *Actinobacillus succinogenes* phosphoenolpyruvate carboxykinase on succinate production in *Escherichia coli*" *Appl Environ Microbiol* 70:1238-1241.

Kim, T. Y., Kim, H. U., Park, J. M., Song, H., Kim, J. S., Lee, S. Y. (2007) "Genome-scale analysis of *Mannheimia succiniciproducens* metabolism" *Biotechnol Bioeng* 97:657-671.

Krebs, A., Bridger, W. A. (1980) "The kinetic properties of phosphoenolpyruvate carboxykinase of *Escherichia coli*" *Can J Biochem* 58(4): 309-318.

Kulla, H., Gottschalk, G. (1977) "Energy-dependent inactivation of citrate lyase in Enterobacter aerogenes" *J Bacteriol* 132(3): 764-770.

Kwon, Y. D., Lee, S. Y., Kim, P. (2008) "A physiology study of *Escherichia coli* overexpressing phosphoenolpyruvate carboxykinase" *Biosci Biotechnol Biochem* 72:1138-1141.

Laivenieks, M., Vieille, C., Zeikus, J. G. (1997) "Cloning, sequencing, and overexpression of the *Anaerobiospirillum succiniciproducens* phosphoenolpyruvate carboxykinase (pckA) gene" *Appl Environ Microbiol* 63(6): 2273-2280.

Lee, E-C., Yu, K., Martinez de Velasco, J., Tessarollo, L., Swing, D. A., Court, D. L., Jenkins, N. A., Copeland, N. G. (2001) "A highly efficient *Escherichia coli*-based chromosome engineering system adapted for recombinogenic targeting and subcloning of BAC DNA" *Genomics* 73: 56-65.

Lee, P. C., Lee, S. Y., Hong, S. H., Chang, H. N. (2002) "Isolation and characterization of a new succinic acid-producing bacterium, *Mannheimia succiniciproducens* MBEL55E, from bovine rumen" *Appl Microbiol Biotechnol* 58:663-668.

Lee, S. Y., Hong, S. H., Lee, S. H., Park, S. J. (2004) "Fermentative production of chemicals that can be used for polymer synthesis" *Macromol Biosci* 4:157-164.

Lee, S. J, Lee, D. Y., Kim, T. Y., Kim, B. H., Lee, J., Lee, S. Y. (2005) "Metabolic engineering of *Escherichia coli* for enhanced production of succinic acid, based on genome comparison and in silico gene knockout simulation" *Appl Environ Microbiol* 71:7880-7887.

Lee, S. J., Song, H., Lee, S. Y. (2006) "Genome-based metabolic engineering of *Mannheimia succiniciproducens* for succic acid production" *Appl Environ Microbiol* 72(3):1939-1948.

Lin, E. C. (1996) Chapter 20, "Dissimilatory Pathways for Sugars, Polyols, and Carboxylates," in Neidhardt, F. C., Curtiss III, R., Ingraham, J. L., Lin, E. C. C., Low, K. B, Magasanik, B., Reznikoff, W. S., Riley, M., Schaechter, M., Umbarger, H. E., editors. *Escherichia coli* and *Salmonella*: cellular and molecular biology. ASM Press, Washington, D.C.

Lin, E. C. (1976) "Glycerol dissimilation and its regulation in bacteria" *Annu Rev Microbiol* 30:535-578.

Lin, H., Bennett, G. N., San, K. Y. (2005a) "Chemostat culture characterization of *Escherichia coli* mutant strains metabolically engineered for aerobic succinate production: A study of the modified metabolic network based on metabolite profile, enzyme activity, and gene expression profile" *Metab Eng* 7:337-352.

Lin, H., Bennett, G. N., San, K. Y. (2005b) "Metabolic engineering of aerobic succinate production systems in

*Escherichia coli* to improve process productivity and achieve the maximum theoretical succinate yield" *Metab Eng* 7:116-127.

Lin, H., Bennett, G. N., San, K. Y. (2005c) "Effect of carbon sources differing in oxidation state and transport route on succinate production in metabolically engineered *Escherichia coli*" *J Ind Microbiol Biotechnol* 32:87-93.

Lin, H., Bennett, G. N., San, K. Y. (2005d) "Fed-batch culture of a metabolically engineered *Escherichia coli* strain designed for high-level succinate production and yield under aerobic conditions" *Biotechnol Bioeng* 90:775-779.

Lutgens, M., Gottschalk, G. (1980) "Why a co-substrate is required for the anaerobic growth of *Escherichia coli* on citrate" *J Gen Microbiol* 119: 63-70.

Martin, S. A. (1994) "Nutrient transport by ruminal bacteria: a review" *J Anim Sci* 72:3019-3031.

Martinez, A., Grabar, T. B., Shanmugam, K. T., Yomano, L. P., York, S. W., Ingram, L. O. (2007) "Low salt medium for lactate and ethanol production by recombinant *Escherichia coli*" *Biotechnol Lett* 29:397-404.

Martinez-Morales, F., Borges, A. C., Martinez, A., Shanmugam, K. T., Ingram, L. O. (1999) "Chromosomal integration of heterologous DNA in *Escherichia coli* with precise removal of markers and replicons used during construction" *J Bacteriol* 181:7143-7148.

McKinlay, J. B., Shachar-Hill, Y., Zeikus, J. G., Vieille, C. (2007) "Determining *Actinobacillus succinogenes* metabolic pathways and fluxes by NMR and GC-MS analyses of 13C-labeled metabolic product isotopomers" *Metab Eng* 9:177-192.

McKinlay, J. B., Zeikus, J. G., Vieille, C. (2005) "Insights into *Actinobacillus succinogenes* fermentative metabolism in a chemically defined growth medium" *Appl Environ Microbiol* 71(11):6651-6656.

McKinlay, J. B., Vieille, C. (2008) "$^{13}$C-metabolic flux analysis of *Actinobacillus succinogenes* fermentative metabolism at different NaHCO$_3$ and H$_2$ concentrations" *Metab Eng* 10:55-68.

McKinlay, J. B., Vieille, C., Zeikus, J. G. (2007) "Prospects for a bio-based succinate industry" *Appl Microbiol Biotechnol* 76(4):727-740.

Meynial-Salles, I., Dorotyn, S., Soucaille, P. (2007) "A new process for the continuous production of succinic acid from glucose at high yield, titer and productivity" *Biotechnol Bioeng* 99(1):129-135.

Miller, J. H. (1992) A short course in bacterial genetics: A laboratory manual and handbook for *Escherichia coli* and related bacteria. Cold Spring Harbor Press.

Millard, C. S., Chao, Y. P., Liao, J. C., Donnelly, M. I. (1996) "Enhanced production of succinic acid by overexpression of phosphoenolpyruvate carboxylase in *Escherichia coli*" *Appl Environ Microbiol* 62:1808-1810.

Morikawa, M., K. Izui, et al. (1980) "Regulation of *Escherichia coli* phosphoenolpyruvate carboxylase by multiple effectors in vivo. Estimation of the activities in the cells grown on various compounds" *J Biochem* (Tokyo) 87(2): 441-449.

Moniruzzaman, M. et al. (1997) "Isolation and molecular characterization of high-performance cellobiose-fermenting spontaneous mutants of ethanologenic *Escherichia coli* KO11 containing the *Klebsiella oxytoca casAB* operon" *Appl Environ Microbiol* 63:4633-4637.

Nilekani, S., Sivaraman, C. (1983) "Purification and properties of citrate lyase from *Escherichia coli*" *Biochemistry* 22(20):4657-63.

Oh, M. K., Rohlin, L., Kao, K. C., Liao, J. C. (2002) "Global expression profiling of acetate-grown *Escherichia coli*" *J Biol Chem* 277: 13175-13183.

Okino, S., Inui, M., Yukawa, H. (2005) "Production of organic acids by *Corynebacterium glutanicum* under oxygen deprivation" *Appl Microbiol Biotechnol* 68:475-480.

Pernestig, A. K., Georgellis, D., Romeo, T., Suzuki, K., Tomenius, H., Normakr, S., Melefors, O. (2003) "The *Escherichia coli* BarA-UvrY two-component system is needed for efficient switching between glycolytic and gluconeogenic carbon sources" *J Bacteriol* 185:843-853.

Plumbridge, J. (2002) "Regulation of gene expression in the PTS in *Escherichia coli*: the role and interactions of Mlc" *Curr Opin Microbiol* 5:187-193.

Posfai, G., Koob, M. D., Kirkpatrick, H. A., Blattner, F. C. (1997) "Versatile insertion plasmids for targeted genome manipulations in bacteria: Isolation, deletion, and rescue of the pathogenicity island LEE of the *Escherichia coli* O157:H7 genome" *J Bacteriol* 179:4426-4428.

Postma, P. W., Lengela, J. W., Jacobson, G. R. (1996) Chapter 75, "Phosphoenolpyruvate: Carbohydrate Phosphotransferase Systems," in Neidhardt, F. C., Curtiss III, R., Ingraham, J. L., Lin, E. C. C., Low, K. B, Magasanik, B., Reznikoff, W. S., Riley, M., Schaechter, M., Umbarger, H. E., editors. *Escherichia coli* and *Salmonella*: cellular and molecular biology. ASM Press, Washington, D.C.

Quentmeier, A., Holzenburg, A., Mayer, F., Antranikian, G. (1987) "Reevaluation of citrate lyase from *Escherichia coli*" *Biochim Biophys Acta* 913(1): 60-5.

Ramseier, T. M., Bledig, S., Michotey, V., Feghali, R., Saier, M. H., Jr. (1995) "The global regulatory protein FruR modulates the direction of carbon flow in *Escherichia coli*" *Mol Microbiol* 16:1157-1169.

Reed, J. L., Vo, T. D., Schilling, C. H., Palsson, B. O. (2003) "An expanded genome-scale model of *Escherichia coli* K-12 (iJR904 GSM/GPR)" *Genome Biol* 4(9):R54.

Reitzer, L. (2004) *Module* 3.6.1.3, "Biosynthesis of Glutamate, Aspartate, Asparagine, L-Alanine, and D-Alanine," in Bock, A., Curtiss III, R., Kaper, J. B., Neidhardt, F. C., Nyström, T., Rudd, K. E., Squires, C. L., editors. EcoSal—*Escherichia coli* and *Salmonella*: cellular and molecular biology. Available at ecosal.org. ASM Press, Washington, D.C.

Saier, M. H., Jr., Ramseier, T. M. (1996) "The catabolite repressor/activator (Cra) protein of enteric bacteria" *J Bacteriol* 178:3411-3417.

Samuelov, N. S., Lamed, R., Lowe, S., Zeikus, J. G. (1991) "Influence of $CO_2$—$HCO_3$ levels and pH on growth, succinate production, and enzyme-activities of *Anaerobiospirillum succiniproducens*" *Appl Environ Microbiol* 57: 3013-3019.

Sanchez, A. M., Bennett, G. N., San, K. Y. (2005a) "Novel pathway engineering design of the anaerobic central metabolic pathway in *Escherichia coli* to increase succinate yield and productivity" *Metab Eng* 7:229-239.

Sanchez, A. M., Bennett, G. N., San, K. Y. (2005b) "Efficient succinic acid production from glucose through overexpression of pyruvate carboxylase in an *Escherichia coli* alcohol dehydrogenase and lactate dehydrogenase mutant" *Biotechnol Prog* 21: 358-365.

Sanchez, A. M., Bennett, G. N., San, K. Y. (2006) "Batch culture characterization and metabolic flux analysis of succinate-producing *Escherichia coli* strains" *Metab Eng* 8: 209-226.

Sanwal, B. D., Smando, R. (1969a) "Malic enzyme of *Escherichia coli*: Possible mechanism for allosteric effects" *J Biol Chem* 244(7):1824-1830.

Sanwal, B. D., Smando, R. (1969b) "Malic enzyme of *Escherichia coli*: Diversity of the effectors controlling enzyme activity" *J Biol Chem* 244(7):1817-1823.

Sanwal, B. D. (1970a) "Allosteric controls of amphibolic pathways in bacteria" *Bacteriol Rev* 34:20-39.

Sanwal, B. D. (1970b) "Regulatory characteristics of the diphosphopyridine nucleotide-specific malic enzyme of *Escherichia coli*" *J Biol Chem* 245(5):1212-1216.

Sanwal, B. D. (1970c) "Regulatory mechanisms involving nicotinamide adenine nucleotide as allosteric effectors: A control of glucose 6-phosphate dehydrogenase" *J Biol Chem* 245(7):1625-1631.

Sawers, G., Bock, A. (1988) "Anaerobic regulation of pyruvate formate-lyase from *Escherichia coli* K-12" *J Bacteriology* 170:5330-5336.

Song, H., Lee, J. W., Choi, S., You, J. K., Hong, W. H., Lee, S. Y. (2007) "Effects of dissolved CO2 levels on the growth of *Mannheimia succiniciproducens* and succinic acid production" *Biotechnol Bioeng* 98(6): 1296-1304.

Storici, F., Coglievina, M., Bruschi, C. V. (1999) "A 2-µm DNA-based maker recycling system for multiple gene disruption in the yeast *Saccharomyces cerevisiae*" *Yeast* 15:271-283.

Stols, L., Donnelly, M. I. (1997) "Production of succinic acid through overexpression of NAD dependent malic enzyme in an *Escherichia coli* mutant" *Appl Environ Microbiol* 63:2695-2701.

Suzuki, K., Wang, X., Weilbacher, T., Pernestig, A. K., Melefors, O., Georgellis, D., Babitzke, P., Romeo, T. (2002) "Regulatory circuitry of the CsrA/CsrB and BarA/UvrY systems of *Escherichia coli*" *J Bacteriol* 184:5130-5140.

Sweet, G., Gandor, C., Voegele, R., Wittekindt, N., Beuerle, J., Truniger, V., Lin, E. C., Boos, W. (1990) "Glycerol facilitator of *Escherichia coli*: cloning of glpF and identification of the glpF product" *J Bacteriol* 172:424-430.

Tang, J. C., Forage, R. G., Lin, E. C. (1982) "Immunochemical properties of NAD+-linked glycerol dehydrogenases from *Escherichia coli* and *Klebsiella pneumoniae*" *J Bacteriol* 152:1169-1174.

Thomason, L., Court, D. L., Bubunenko, M., Constantino, N., Wilson, H., Datta, S., Oppenheim, A. (2005) "Recombineering: Genetic Engineering in Bacteria Using Homologous Recombination", sections 1.16.1-1.16.21, in F. M. Ausubel, R. Brent, R. E. Klingston, D. D. Moore, J. G. Deidman, J. A. Smith, and K. Struhl (eds.), Current Protocols in Molecular Biology. John Wiley & Sons Inc., New York.

Underwood, S. A., Buszko, M. L., Shanmugam, K. T., Ingram, L. O. (2004) "Lack of protective osmolytes limits final cell density and volumetric productivity of ethanologenic *Escherichia coli* KO11 during xylose fermentation" *Appl Environ Microbiol* 70(5): 2734-40.

Underwood, S. A., Buszko, M. L., Shanmugam, K. T., Ingram, L. O. (2002) "Genetic changes to optimize carbon partitioning between ethanol and biosynthesis in ethanologenic *Escherichia coli*" *Appl Environ Microbiol* 68(12): 6263-6272.

Unden, G. and Kleefeld, A. (2004) Module 3.4.5, "$C_4$-Dicarboxylate Degradation in Aerobic and Anaerobic Growth," in Böck, A., Curtiss III, R., Kaper, J. B., Neidhardt, F. C., Nyström, T., Rudd, K. E., Squires, C. L., eds. EcoSal—*Escherichia coli* and *Salmonella*: cellular and molecular biology. Available at ecosal.org. ASM Press, Washington, D.C.

van der Werf, M. J., Guettler, M. V., Jain, M. K., Zeikus, J. G. (1997) "Environmental and physiological factors affecting the succinate product ratio during carbohydrate fermentation by *Actinobacillus* sp. 130Z" *Arch Microbiol* 167:332-342.

Vemuri, G. N., Eiteman, M. A., Altman, E. (2002a) "Effects of growth mode and pyruvate carboxylase on succinic acid production by metabolically engineered strains of *Escherichia coli*" *Appl Environ Microbiol* 68:1715-1727.

Vemuri, G. N., Eiteman, M. A., Altman, E. (2002b) "Succinate production in dual-phase *Escherichia coli* fermentations depends on the time of transition from aerobic to anaerobic conditions" *J Ind Microbiol Biotechnol* 28:325-332.

Wang, Q., Chen, X., Yang, Y., Zhao, X. (2006) "Genome-scale in silico aided metabolic analysis and flux comparisons of *Escherichia coli* to improve succinate production" *Appl Microbiol Biotechnol* 73:887-894.

Wang, Q., Wu, C., Chen, T., Chen, X., Zhao, X. (2006) "Expression of galactose permease and pyruvate carboxylase in *Escherichia coli* ptsG mutant increases the growth rate and succinate yield under anaerobic conditions" *Biotechnol Lett* 28:89-93.

Wendisch, V. F., Bott, M., Eikmanns, B. J. (2006) "Metabolic engineering of *Escherichia coli* and *Corynebacterium glutamicum* for biotechnological production of organic acids and amino acids" *Curr Opin Microbiol* 9:1-7.

Werpy, T., Petersen, G. (2004) "Top value added chemicals from biomass," retrieved from the web, see Worldwide Website: eere.energy.gov/bioenergy/pdfs/pnn1-16983.pdf, Washington, D.C. US Department of Energy.

Wood, B. E., Yomano, L. P., York, S. W., Ingram, L. O. (2005) "Development of industrial medium required elimination of the 2,3-butanediol fermentation pathway to maintain ethanol yield in an ethanologenic strain of *Klebsiella oxytoca*" *Biotechnol Prog* 21:1366-1372.

Wright, J. A., Sanwal, B. D. (1969) "Regulatory mechanisms involving nicotinamide adenine nucleotide as allosteric effectors: Control of phosphoenolpyruvate carboxykinase" *J Biol Chem* 244(7): 1838-1845.

Wu, H., Li, Z., Zhou, L., Ye, Q. (2007) "Improved succinic acid production in the anaerobic culture of an *Escherichia coli* pflB ldhA double mutant as a result of enhanced anaplerotic activities in the preceding aerobic culture" *Appl Environ Microbiol* 73:7837-7843.

Yi, J., Draths, K. M., Li, K., Frost, J. W. (2003) "Altered glucose transport and shikimate pathway product yields in *E. coli*" *Biotechnol Prog* 19:1450-1459.

Yun, N. R., San, K. Y., Bennett, G. N. (2005) "Enhancement of lactate and succinate formation in adhE or pta-ackA mutants of NADH dehydrogenase-deficient *Escherichia coli*" *J Appl Microbiol* 99:1404-1412.

Zeikus, J. G., Jain, M. K., Elankovan, P. (1999) "Biotechnology of succinic acid production and markets for derived industrial products" *Appl Microbiol Biotechnol* 51:545-552.

Zhang, X., Jantama, K., Moore, J. C., Shanmugam, K. T., Ingram, L. O. (2007) "Production of L-alanine by metabolically engineered *Escherichia coli*" *Appl Microbiol Biotechnol* 77: 355-366.

Zhou, S., Shanmugam, K. T., Ingram, L. O. (2003) "Functional replacement of the *Escherichia coli* D-(−)-lactate dehydrogenase gene (ldhA) with the L-(+)-lactate dehydrogenase gene (ldhL) from *Pediococcus acidilactici*" *Appl Environ Microbiol* 69:2237-2244.

Zhou, S., Grabar, T. B., Shanmugam, K. T., Ingram, L. O. (2006) "Betaine tripled the volumetric productivity of D-(−)-lactate by *Escherichia coli* strain SZ132 in mineral salts medium" *Biotechnol Lett* 28:671-676.

We claim:

1. A genetically modified *E. coli* cell comprising increased levels of phosphoenol pyruvate carboxykinase (pck) gene transcripts as compared to the corresponding unmodified *E. coli* cell, wherein the genetically modified *E. coli* cell comprises one or more genetic modifications to one or more endogenous genes leading to inactivation of the one or more endogenous genes, wherein the one or more endogenous genes are selected from the group consisting of:

a) a gene encoding a glycerol dehydrogenase (gldA), b) a gene encoding a dihydroxyacetone kinase subunits K and L (dhaKL), and c) a gene encoding a dihydroxyacetone kinase subunit M (dhaM), and wherein said one or more genetic modifications leading to inactivation of the one or more genes comprise one or more of: (i) deleting the entire coding nucleotide sequence or a portion of the coding nucleotide sequence of said one or more genes, (ii) introducing a frame shift mutation into the coding nucleotide sequence of said one or more genes, (iii) introducing a missense mutation into the coding nucleotide sequence of said one or more genes or (iv) introducing a stop codon into the coding nucleotide sequence of said one or more genes.

2. The *E. coli* cell of claim 1, said cell comprising a single point mutation in the promoter region of the endogenous pck gene that increases transcription of the pck gene.

3. The *E. coli* cell of claim 2, wherein said single point mutation is a G to A transition at position −64 relative to the ATG start codon of the endogenous pck gene.

4. The *E. coli* cell of claim 1, wherein said *E. coli* cell comprises a multicopy plasmid expressing a pck gene.

5. The genetically modified *E. coli* cell of claim 1, wherein the endogenous gene is gldA.

6. The genetically modified *E. coli* cell of claim 1, wherein the endogenous gene is dhaKL.

7. The genetically modified *E. coli* cell of claim 1, wherein the endogenous gene is dhaM.

8. A method of producing succinic acid comprising:

a) culturing the genetically modified *E. coli* cell of claim 1;

b) proving a carbon source;

c) allowing the genetically modified *E. coli* cell to metabolize said carbon source; and d) isolating succinic acid.

9. The method of claim 8, wherein said genetically modified *E. coli* cell is cultured in anaerobic condition, aerobic condition, microaerobic condition or combinations thereof.

* * * * *